(12) United States Patent
Chen et al.

(10) Patent No.: US 7,045,591 B2
(45) Date of Patent: May 16, 2006

(54) SELECTIVE CYCLIC PEPTIDES WITH MELANOCORTIN-4 RECEPTOR (MC4-R) AGONIST ACTIVITY

(75) Inventors: Li Chen, Westfield, NJ (US); Adrian Wai-Hing Cheung, Glen Rock, NJ (US); Xin-Jie Chu, Livingston, NJ (US); Waleed Danho, Wayne, NJ (US); Joseph Swistok, Nutley, NJ (US); Yao Wang, Edison, NJ (US); Keith Alan Yagaloff, Broad Brook, CT (US)

(73) Assignee: Hoffmann-La Roche Inc., Nutley, NJ (US)

( * ) Notice: Subject to any disclaimer, the term of this patent is extended or adjusted under 35 U.S.C. 154(b) by 747 days.

(21) Appl. No.: 09/939,966

(22) Filed: Aug. 27, 2001

(65) Prior Publication Data
US 2002/0143141 A1 Oct. 3, 2002

Related U.S. Application Data

(60) Provisional application No. 60/229,184, filed on Aug. 30, 2000.

(51) Int. Cl.
*C07K 7/50* (2006.01)

(52) U.S. Cl. .......................... 530/317; 514/11; 514/17; 530/318; 530/328; 530/330

(58) Field of Classification Search .................. 514/11, 514/17; 530/317, 318, 328, 330
See application file for complete search history.

(56) References Cited

U.S. PATENT DOCUMENTS

| 5,811,391 A | 9/1998 | Arrhenius et al. |
| 5,858,972 A | 1/1999 | Pierschbacher et al. |

FOREIGN PATENT DOCUMENTS

WO WO 00/58361 A1 10/2000

OTHER PUBLICATIONS

Fan et al., Nature, vol. 385, pp. 165–168 (1997).
Cone et al., Rec. Prog. Hormone Research, vol. 51, pp. 287–318 (1996).
Haskell–Luevano et al., Peptides, vol. 17, No. 6, pp. 995–1002 (1996).
R. B. Merrifield, J. Amer. Chem. Soc., vol. 85, pp. 2149–2154 (1963).
Barany et al., The Peptides, Analysis, Synthesis and Biology, vol. 2, E. Gross and J. Meienhofer, Eds. Academic Press, pp. 1–284 (1980).
Kaiser et al., Anal. Biochem., 34, pp. 595–598 (1970).
Obrecht et al., Helv. Chim. Acta, vol. 75, pp. 1666–1696 (1992).
Freeman et al., J. Org. Chem., vol. 54, pp. 782–789 (1989).
Boteju et al., Tet. Lett., 33 p. 7491–7494 (1992).
Nicholas et al., J. Org. Chem. 58, pp. 766–770 (1993).
Bednarek et al., Biochem. Biophys. Res. Comm. 261, pp. 209–213 (1999).
Bednarek et al., Peptides 20, pp. 401–409 (1999).
Adan E.A., *European Journal of Pharmacology*, vol. 378, pp. 249–258 (1999).
Benoit E.A., *J. Neuroscience*, vol. 20, No. 9, pp. 3442–3448, (2000).
Bednarek, M.A., et al., Biochemical and Biophysical Research Communications, Academic Press, vol. 272, No. 1, pp. 23–28 (2000).

*Primary Examiner*—Jon P. Weber
*Assistant Examiner*—David Lukton
(74) *Attorney, Agent, or Firm*—George W. Johnston; Dennis P. Tramaloni

(57) ABSTRACT

Peptides cyclized via disulfide or lactam bridges are disclosed. The peptides exhibit melanocortin-4 receptor agonist activity and are useful for treating obesity.

76 Claims, No Drawings

SELECTIVE CYCLIC PEPTIDES WITH MELANOCORTIN-4 RECEPTOR (MC4-R) AGONIST ACTIVITY

PRIORITY TO PROVISIONAL APPLICATION(S) UNDER 35 U.S.C. § 119(e)

This application claims priority under 35 U.S.C. § 19(e) of provisional application(s) Ser. No. 60/229,184, filed Aug. 30, 2000.

BACKGROUND OF THE INVENTION

Obesity is widely recognized as a serious health problem for the developed countries, and has reached epidemic status in the United States. More than 50% of the U.S. population is considered overweight, with >25% diagnosed as clinically obese and at considerable risk for heart disease, non-insulin dependent diabetes mellitus (NIDDM), hypertension, and certain cancers. This epidemic presents a significant burden on the health care system as projected obesity treatment costs of more than $70 billion annually are expected in the U.S. alone. Strategies for treating obesity include reducing food intake or enhancing the expenditure of energy.

It has been demonstrated that, when injected into the third ventricle of the brain or intraperitoneally, a cyclic heptapeptide analog of α-melanocyte stimulating hormone (αMSH) having melanocortin-4 receptor (MC4-R) agonist activity caused long lasting inhibition of food intake in mice. This effect was reversible when co-administered with a MC4-R antagonist. (Fan, et al., Nature (1997) 385: 165–168) Therefore, agonists of MC4-R activity would be useful in treating or preventing obesity.

There are five known melanocortin receptors based on sequence homology that ranges from 35–60% homology between family members (Cone, et al., Rec. Prog. Hormone Res. (1996) 51: 287–318), but these receptors differ in their functions. For example, the MC1-R is a G-protein coupled receptor that regulates pigmentation in response to the αMSH, which is a potent agonist of MC1-R. (Cone, et al., ibid.). Agonism of the MC1-R receptor results in stimulation of the melanocytes which causes eumelanin and increases the risk for cancer of the skin. Agonism of MC1-R can also have neurological effects. Stimulation of MC2-R activity can result in carcinoma of adrenal tissue. The effects of agonism of the MC3-R and MC5-R are not yet known. All of the melanocortin receptors respond to the peptide hormone class of melanocyte stimulating hormones (MSH). These peptides are derived from pro-opiomelanocortin (POMC), a prohormone of 131 amino acids that is processed into three classes of hormones; the melanocortins (α, β and γ), adrenocorticotropin hormone (ACTH), and various endorphins (e.g. lipotropin) (Cone, et al., ibid.). Because of their different functions, simultaneous agonism of the activities of multiple melanocortin receptors has the potential of causing unwanted side effects. Therefore it is desirable that an agonist of MC4-R be more selective for the MC4-R than for one or more of the other melanocortin receptors.

Haskell-Luevano, et al. (Peptides (1996) 17(6): 995–1002) disclose peptides that contain the tripeptide (D)Phe-Arg-Trp and exhibit melanotropic (skin darkening) activity in the frog (*Rana pipiens*) skin bioassay. Haskell-Luevano, et al. (ibid.) do not disclose any compound of formula I or II described below.

Bednarek, et al. (Peptides (1999) 20: 401–409) and Bednarek, et al. (Biochem. Biophys. Res. Comm. (1999) 261: 209–213) disclose analogs of the cyclic peptide MT-II. They do not disclose any compound of formula I or II described below.

DETAILED DESCRIPTION

This invention provides a compound of the formula:

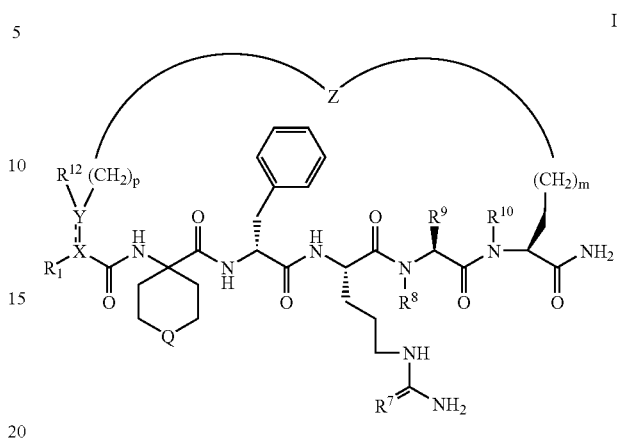

In compounds of formula I, $R^1$ and $R^{12}$ together with X and Y form a phenyl ring; or $R^1$ is hydrogen,

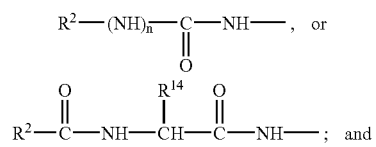

$R^{12}$ is hydrogen; with either X and Y being each C and the bond X and Y being a double bond, or with X and Y being each CH and the bond between X and Y being a single bond; $R^2$ is alkyl having from 1 to 5 carbon atoms, alkenyl having from 2 to 5 carbon atoms, or alkynyl having from 2 to 5 carbon atoms; $R^{14}$ is alkyl having from 1 to 5 carbon atoms; and n is 0 or 1, Q is

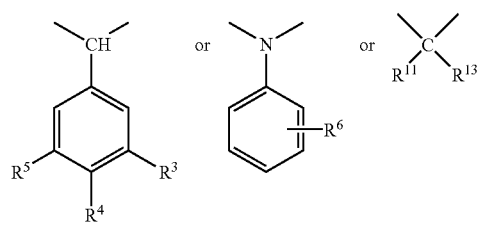

wherein $R^3$, $R^4$ and $R^5$ are independently hydrogen, halo, alkyl having from 1 to 4 carbon atoms, hydroxy or alkoxy having from 1 to 4 carbon atoms, wherein when $R^4$ is not hydrogen, $R^3$ and $R^5$ are both hydrogen; $R^6$ is hydrogen, alkyl having from 1 to 3 carbon atoms, alkoxy having from 1 to 3 carbon atoms, phenoxy, or halo; and $R^{11}$ and $R^{13}$ are each independently hydrogen, alkyl having 3 or 4 carbons, or cycloalkyl having 5 or 6 carbon atoms or $R^{11}$ and $R^{13}$ are both phenyl; $R^7$ is O or NH; $R^8$ is hydrogen or methyl. $R^9$ is

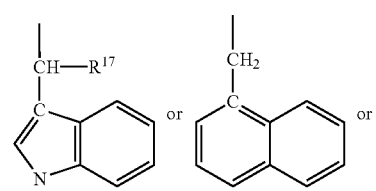

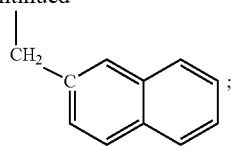

$R^{10}$ is hydrogen or methyl; p is 0 or 1; m is 0, 1, 2, or 3; Z is

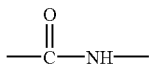

or —S—S—; and $R^{17}$ is hydrogen or lower alkyl, preferably methyl.

The dotted bond in the compound of formula I is hydrogenated when X and Y are each —CH—. On the other hand, when the dotted bond is present, Y and X taken together with $R^1$ and $R^{12}$ do not form a phenyl ring, and X and Y are both tetravalent C atoms.

This invention also provides a compound of the formula:

II

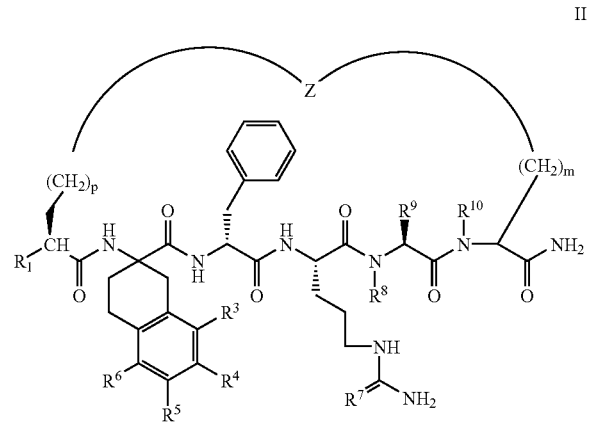

In compounds of formula II, $R^1$ is hydrogen,

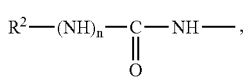

or

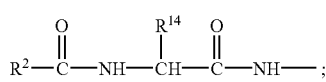

$R^2$ is alkyl having from 1 to 5 carbon atoms, alkenyl having from 2 to 5 carbon atoms, or alkynyl having from 2 to 5 carbon atoms; $R^{14}$ is alkyl having from 1 to 5 carbon atoms; and n is 0 or 1, one of $R^3$, $R^4$, $R^5$ and $R^6$ is hydrogen, halo, alkyl having from 1 to 3 carbon atoms, or alkoxy having from 1 to 3 carbon atoms, and the remainder are hydrogen. $R^7$ is O or NH. $R^8$ is hydrogen or methyl. $R^9$ is

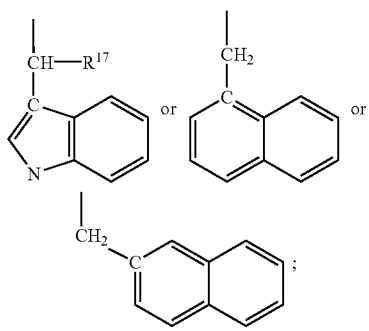

$R^{10}$ is hydrogen or methyl; p is 0 or 1; m is 0, 1, 2, or 3; Z is

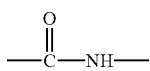

or S—S—.

The compounds of formulas I and II as well as Penta-cyclo(Asp-Lys)-Asp-Apc-(D)Phe-Ala-Trp-Lys-NH$_2$; and Penta-cyclo(Asp-Lys)-Asp-Apc-(D)Phe-Arg-(2S,3S) beta methyl-Trp-Lys-NH$_2$ are agonists of the MC4-R. It is known that agonists of MC4-R activity cause reduction of food intake in a mouse model of human obesity. Therefore these compounds are useful in the treatment or prevention of obesity.

All of the compounds of formulas I and II exemplified below as well as Penta-cyclo(Asp-Lys)-Asp-Apc-(D)Phe-Ala-Trp-Lys-NH$_2$; and Penta-cyclo(Asp-Lys)-Asp-Apc-(D)Phe-Arg-(2S,3S) beta methyl-Trp-Lys-NH$_2$ were tested for MC4-R agonist activity and MC1-R agonist activity in the in vitro assay described below in Biological Activity Example A. All of the tested compounds had an EC50 for MC4-R agonist activity of less than 500 nM, and all exhibited at least 10-fold greater MC4-R agonist activity than MC1-R agonist activity. In contrast, the compound Ac-Nle-Cyclo(Asp-Lys)-Asp-His-(D)Phe-Arg-Trp-Lys-NH$_2$ exhibited about equal MC1-R and MC4-R agonist activities.

Nomenclature and Abbreviations

The term "alkyl" means a straight chain or branched alkyl group and the term "lower alkyl" denotes an alkyl group containing from 1 to 6 carbon atoms. The term "alkenyl" means a straight chain or branched alkenyl group. The term "alkynyl" refers to a straight chain or branched alkynyl group.

The term "alkoxy" means a group of the formula alkyl-O— in which alkyl is as defined above. The term "phenoxy" means a group of the formula phenyl-O—. Except where otherwise specified, "phenyl" refers to an unsubstituted phenyl ring and "phenoxy" refers to an unsubstituted phenoxy group.

The term "halo" means a group selected from fluoro, chloro, bromo, and iodo.

Compounds of formula IA are represented as follows:

IA

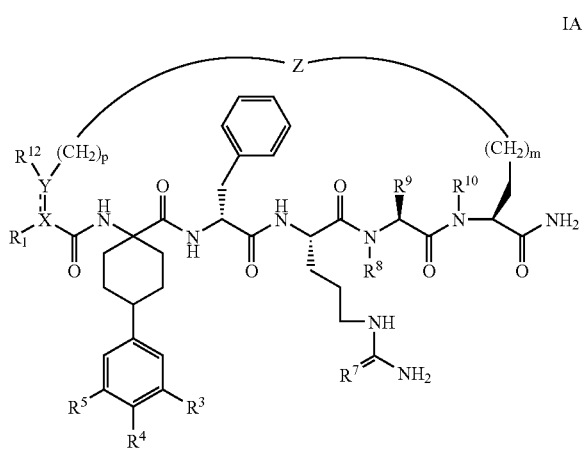

wherein $R^1$, $R^3$, $R^4$, $R^5$, $R^7$, $R^8$, $R^9$, $R^{10}$, $R^{12}$, X Y, Z and p are as above.

In the compounds of formula IA, $R^1$ and $R^{12}$ together with X and Y form a phenyl ring; or $R^1$ is hydrogen,

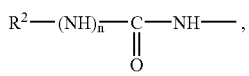

or

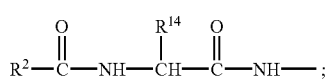

and $R^{12}$ is hydrogen, with either X and Y being each C and the bond between X and Y being a double bond, or with X and Y being each CH and the bond between X and Y being a single bond; $R^2$ is alkyl having from 1 to 5 carbon atoms, alkenyl having from 2 to 5 carbon atoms, or alkynyl having from 2 to 5 carbon atoms; $R^{14}$ is alkyl having from 1 to 5 carbon atoms; and n is 0 or 1. $R^3$, $R^4$ and $R^5$ are independently hydrogen, halo, alkyl having from 1 to 4 carbon atoms, hydroxy, or alkoxy having from 1 to 4 carbon atoms; wherein when $R^4$ is not hydrogen, $R^3$ and $R^5$ are both hydrogen. $R^7$ is O or NH. $R^8$ is hydrogen or methyl. $R^9$ is

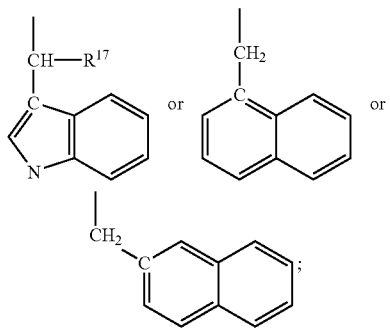

$R^{10}$ is hydrogen or methyl; p is 0 or 1; m is 0, 1, 2, or 3, Z is

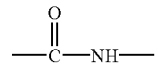

or S—S ; and $R^7$ is hydrogen or lower alkyl, preferably methyl.

The dotted bond in formula IA can be hydrogenated. When the dotted line is hydrogenated X and Y are both —CH—. On the other hand, when the dotted bond is present, Y and X taken together with $R^1$ and $R^{12}$ do not form a phenyl ring, X and Y are both the tetravalent C atoms.

In one embodiment of the compound of formula IA, X and Y are each CH and the bond between X and Y is hydrogenated to a single bond; Z is

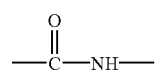

$R^7$ is O; $R^1$ is

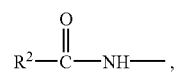

$R^2$ is alkyl having from 1 to 5 carbon atoms; and $R^{10}$ and $R^{12}$ are both hydrogen. Examples of such compounds include Penta-cyclo(Asp-Lys)-Asp-Apc-(D)Phe-Cit-Trp-Lys-NH$_2$.

In another embodiment of the compound of formula IA Z is

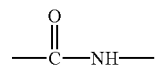

$R^7$ is NH; $R^1$ is

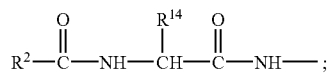

$R^2$ is alkyl; and $R^{10}$ and $R^{12}$ are both hydrogen. In a more specific embodiment, X and Y are each CH and the bond between X and Y is hydrogenated to a single bond; n is 0; and $R^9$ is

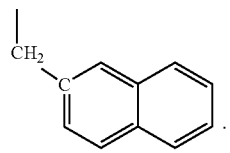

Examples of such compounds include: Penta-cyclo(Asp-Lys)-Asp-Apc-(D)Phe-Arg-(2)Nal-Lys-NH$_2$; and penta-cyclo(Asp-Lys)-Asp-Apc-(D)Phe-Arg-N-methyl(2)Nal-Lys-NH$_2$.

In another more specific embodiment of the compound of formula IA, Z is

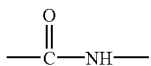

$R^7$ is NH; $R^1$ is

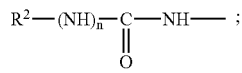

$R^2$ is alkyl; and $R^{10}$ and $R^{12}$ are both hydrogen; and $R^9$ is

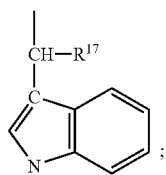

and $R^{17}$ is hydrogen or lower alyl, preferably methyl.

Such compounds include those in which X and Y are each CH and the bond between X and Y is a single bond; and one of $R^3$, $R^4$ and $R^5$ is hydrogen, halo or alkyl and the remainder are hydrogen, for example Penta-cyclo(Asp-Lys)-Asp-Apc-(D)Phe-Arg-Trp-Lys-NH$_2$; Penta-cyclo(Asp-Lys)-Asp-4-MeApc-(D)Phe-Arg-Trp-Lys-NH$_2$; Penta-cyclo(Glu-Lys)-Glu-Apc-(D)Phe-Arg-Trp-Lys-NH$_2$; Penta-cyclo(Asp-Orn)-Asp-Apc-(D)Phe-Arg-Trp-Om-NH$_2$; Penta-cyclo(Asp-Dbr)-Asp-Apc-(D)Phe-Arg-Trp-Dbr-NH$_2$; Penta-cyclo(Asp-Dpr)-Asp-Apc-(D)Phe-Arg-Trp-Dpr-NH$_2$; and Ac-cyclo(Asp-Dpr)-Asp-Apc-(D)Phe-Arg-Trp-Dpr-NH$_2$.

Another specific embodiment of the compounds of formula IA, are those compounds in which X and Y are each CH and the bond between X and Y is a single bond; and $R^1$ is

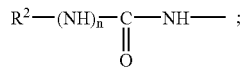

one of $R^3$, $R^4$ and $R^5$ is alkoxy, and the remainder are hydrogen; and n is 0, for example Penta-cyclo(Asp-Lys)-Asp-4-MeOApc-(D)Phe-Arg-Trp-Lys-NH$_2$; Penta-cyclo(Asp-Lys)-Asp-4-EtOApc-(D)Phe-Arg-Trp-Lys-NH$_2$; Penta-cyclo(Asp-Lys)-Asp-4-iPrOApc-(D)Phe-Arg-Trp-Lys-NH$_2$; Penta-cyclo(Asp-Lys)-Asp-3-MeOApc-(D)Phe-Arg-Trp-Lys-NH$_2$; Penta-cyclo(Asp-Lys)-Asp-4-OHApc-(D)Phe-Arg-Trp-Lys-NH$_2$; and Penta-cyclo(Asp-Lys)-Asp-4-ClApc-(D)Phe-Arg-Trp-Lys-NH$_2$.

Embodiments of compounds of formula IA include those compounds in which each of $R^1$, $R^3$, $R^4$, $R^5$, $R^8$ and $R^{10}$ is hydrogen; $R^7$ is NH; $R^9$ is

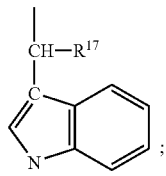

and $R^{17}$ is hydrogen or lower alkyl preferably methyl; and p is 0, for example cyclo(succinic acid-Lys)-succinic acid-Apc-(D)Phe-Arg-Trp-Lys-NH$_2$, cyclo(maleic acid-Lys)-maleic acid-Apc-(D)Phe-Arg-Trp-Lys-NH$_2$, cyclo(succinic acid-Dpr)-succinic acid-Apc-(D)Phe-Arg-Trp-Dpr-NH$_2$, cyclo(maleic acid-Dpr)-maleic acid-Apc-(D)Phe-Arg-Trp-Dpr-NH$_2$.

In another embodiment of the compound of formula IA, $R^1$ and $R^{12}$ together with X and Y form a phenyl ring. Examples of such compounds include Cyclo(phthalic acid-Lys)-phthalic acid-Apc-(D)Phe-Arg-Trp-Lys-NH$_2$; Cyclo(phthalic acid-Dpr)-phthalic acid-Apc-(D)Phe-Arg-Trp-Dpr-NH$_2$; and Ac-Nle-cyclo(Cys-Cys)-Cys-Apc-(D)Phe-Arg-Trp-Cys-NH$_2$.

Compounds of formula IB are represented by the formula:

IB

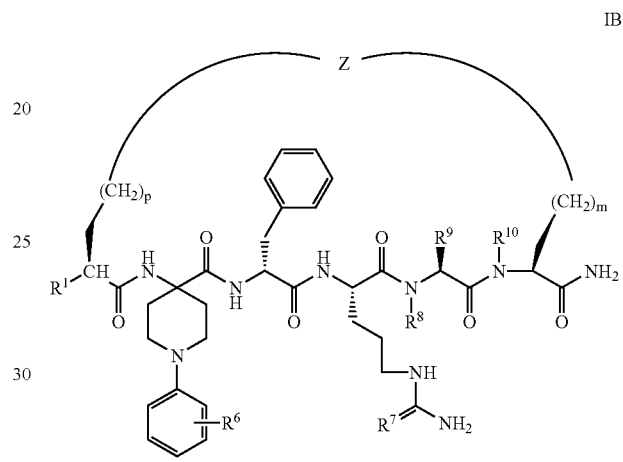

In the compounds of formula IB, $R^1$, is hydrogen,

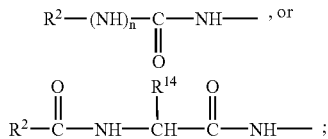

$R^2$ is alkyl having from 1 to 5 carbon atoms, alkenyl having from 2 to 5 carbon atoms, or alkynyl having from 2 to 5 carbon atoms. $R^{14}$ is alkyl having from 1 to 5 carbon atoms. N is 0 or 1. R 6 is hydrogen, alkyl having from 1 to 3 carbons, alkoxy having from 1 to 3 carbons, phenoxy, or halo; $R^7$ is O or NH. $R^8$ is hydrogen or methyl. $R^9$ is

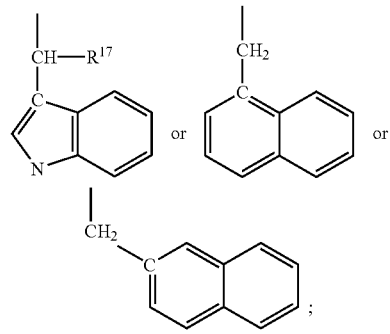

$R^{10}$ is hydrogen or methyl; p is 0 or 1; m is 0, 1, 2, or 3; Z is

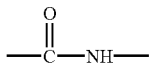

or —S—S—; and $R^{17}$ is hydrogen or lower alkyl, preferably methyl.

In an embodiment of the compounds of formula IB, i.e., compounds of formula IB1, Z is

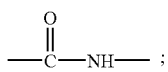

$R^7$ is NH; $R^1$ is

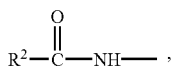

$R^2$ is alkyl; $R^8$ and $R^{10}$ are each hydrogen; and $R^9$ is

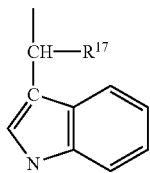

and $R^{17}$ is as above.

In a more specific embodiment of such compounds of formula IB1, $R^6$ is hydrogen or alkyl. Examples of such compounds include: Penta-cyclo(Asp-Lys)-Asp-Appc-(D)Phe-Arg-Trp-Lys-NH$_2$; Penta-cyclo(Asp-Lys)-Asp-2-MeAppc-(D)Phe-Arg-Trp-Lys-NH$_2$; Penta-cyclo(Asp-Lys)-Asp-2-iPrAppc-(D)Phe-Arg-Trp-Lys-NH$_2$; Penta-cyclo(Asp-Lys)-Asp-3-MeAppc-(D)Phe-Arg-Trp-Lys-NH$_2$; and Penta-cyclo(Asp-Lys)-Asp-4-MeAppc-(D)Phe-Arg-Trp-Lys-NH$_2$.

In another more specific embodiment of such compounds of formula IB1, $R^6$ is halo. Examples of such compounds include Penta-cyclo(Asp-Lys)-Asp-4-ClAppc-(D)Phe-Arg-Trp-Lys-NH$_2$.

In another more specific embodiment of such compounds of formula IB1, $R^6$ is alkoxy or phenoxy. Examples of such compounds include: Penta-cyclo(Asp-Lys)-Asp-4-PhOAppc-(D)Phe-Arg-Trp-Lys-NH$_2$; and Penta-(Asp-Lys)-Asp-3-MeO-Appc-(D)Phe-Arg-Trp-Lys-NH$_2$.

Compounds of formula IC are represented as follows:

IC

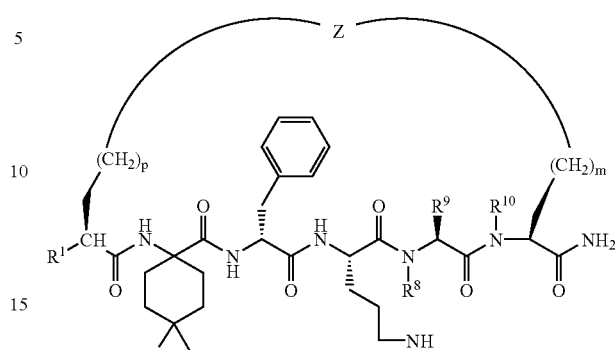

In the compounds of formula IC, $R^1$ is hydrogen or

$R^2$ is alkyl having from 1 to 5 carbon atoms, alkenyl having from 2 to 5 carbon atoms, or alkynyl having from 2 to 5 carbon atoms. $R^{14}$ is alkyl having from 1 to 5 carbon atoms. n is 0 or 1, $R^{11}$ and $R^{13}$ are each independently hydrogen, alkyl having 3 or 4 carbon atoms, cycloalkyl having 5 or 6 carbon atoms or $R^{11}$ and $R^{13}$ are both phenyl; $R^7$ is O or NH; $R^8$ is hydrogen or methyl; $R^9$ is

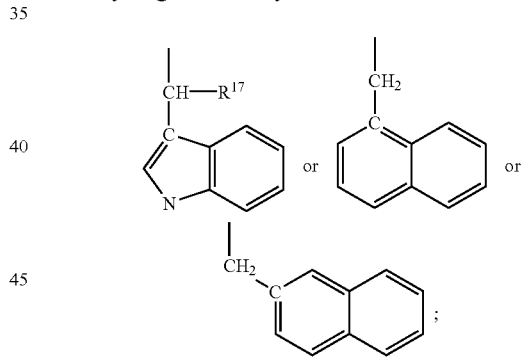

$R^{10}$ is hydrogen or methyl; p is 0 or 1; m is 0, 1, 2, or 3; and Z is

or —S—S— and $R^{17}$ is hydrogen or lower alkyl, preferably methyl.

In an embodiment of the compound of formula IC, the compound of formula IC1, Z is

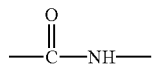

$R^7$ is NH; $R^1$ is

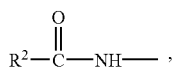

$R^2$ is alkyl; $R^8$ and $R^{10}$ are each hydrogen; and $R^9$ is

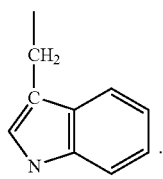

In one more specific embodiment of such compounds of formula IC1, one of $R^{11}$ and $R^{13}$ is alkyl or cycloalkyl and the other is hydrogen. Examples of such claims include: Penta-cyclo(Asp-Lys)-Asp-Achc-(D)Phe-Arg-Trp-Lys-NH$_2$; and Penta-cyclo(Asp-Lys)-Asp-Abc-(D)Phe-Arg-Trp-Lys-NH$_2$.

In another more specific embodiment of such compounds of formula IC1, one of $R^{11}$ and $R^{13}$ is phenyl and the other is hydrogen or phenyl. Examples of such compounds include Penta-cyclo(Asp-Lys)-Asp-4-Adpc-(D)Phe-Arg-Trp-Lys-NH$_2$.

In one embodiment of the compound of formula II, the compound of formula IIA, Z is

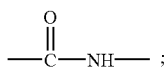

$R^1$ is

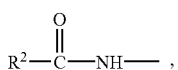

$R^2$ is alkyl;
$R^3$, $R^4$, $R^5$, $R^8$ and $R^{10}$ are each hydrogen;
$R^6$ is hydrogen, halo, alkyl having from 1 to 3 carbon atoms, or alkoxy having from 1 to 3 carbon atoms;
$R^9$ is

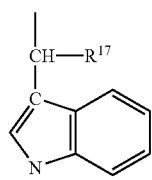

and $R^{17}$ is as above.

In one embodiment of the compounds of formula II-A, as described in the preceding paragraph, $R^7$ is NH. In a more specific embodiment, $R^7$ is NH and $R^6$ is hydrogen or alkyl. Examples of such compounds include: Penta-cyclo(Asp-Lys)-Asp-(D,L)-Atc-(D)Phe-Arg-Trp-Lys-NH$_2$; Penta-(Asp-Lys)-Asp-5-Me-(D,L)Atc-(D)Phe-Arg-Trp-Lys-NH$_2$; Penta-(Asp-Lys)-Asp-5-Et-(D,L)Atc-(D)Phe-Arg-Trp-Lys-NH$_2$; and Penta-(Asp-Lys)-Asp-5-iPr-(D,L)Atc-(D)Phe-Arg-Trp-Lys-NH$_2$.

In another specific embodiment of the compound of formula II-A, $R^7$ is NH and $R^6$ is halo. Examples of such compounds include: Penta-(Asp-Lys)-Asp-5-BrAtc-(D)Phe-Arg-Trp-Lys-NH$_2$; and Penta-(Asp-Lys)-Asp-5-ClAtc-(D)Phe-Arg-Trp-Lys-NH$_2$.

In another specific embodiment of the compound of formula II-A, $R^7$ is NH and $R^6$ is alkoxy. Penta-(Asp-Lys)-Asp-5-MeO-(D,L)Atc-(D)Phe-Arg-Trp-Lys-NH$_2$; Penta-(Asp-Lys)-Asp-5-EtO-(D,L)Atc-(D)Phe-Arg-Trp-Lys-NH$_2$; Penta-(Asp-Lys)-Asp-5-iPrO-(D,L)Atc-(D)Phe-Arg-Trp-Lys-NH$_2$.

Another embodiment of the compounds of formula II are those compounds of formula II in which Z, $R^1$ to $R^5$ and $R^8$ to $R^{10}$ are as described above, $R^7$ is O and $R^6$ is halo. Examples of such compounds include: Penta-(Asp-Lys)-Asp-5-BrAtc-(D)Phe-Cit-Trp-Lys-NH$_2$; and Penta-(Asp-Lys)-Asp-5-ClAtc-(D)Phe-Cit-Trp-Lys-NH$_2$.

In another embodiment of the compound of formula II, the compound of formula II-B are those compounds where Z is —S—S—;
$R^1$ is

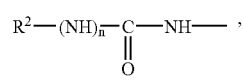

or

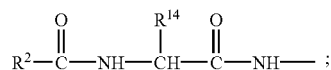

$R^3$, $R^4$, $R^5$, $R^8$ and $R^{10}$ are each hydrogen; $R^6$ is hydrogen or halo; $R^7$ is NH; and
$R^9$ is

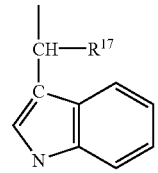

and $R^{17}$ is as above.

Examples of such compounds of formula II-B include: Ac-Nle-cyclo(Cys-Cys)-Cys-(D,L)Atc-(D)Phe-Arg-Trp-Cys-NH$_2$; and Penta-cyclo(Cys-Cys)-Cys-5-Br(D,L)Atc-(D)Phe-Arg-Trp-Cys-NH$_2$.

This invention also provides the following compounds: Penta-cyclo(Asp-Lys)-Asp-Apc-(D)Phe-Ala-Trp-Lys-NH$_2$; and Penta-cyclo(Asp-Lys)-Asp-Apc-(D)Phe-Arg-(2S,3S) beta methyl-Trp-Lys-NH$_2$.

The nomenclature used to define the peptides is that typically used in the art wherein the amino group at the N-terminus appears to the left and the carboxyl group at the C-terminus appears to the right. By natural amino acids is meant one of the naturally occurring amino acids found in proteins, i.e., Gly, Ala, Val, Leu, Ile, Ser, Thr, Lys, Arg, Asp, Asn, Glu, Gln, Cys, Met, Phe, Tyr, Pro, Trp, and His. Where the amino acid has isomeric forms, it is the L form of the amino acid that is represented unless otherwise explicitly indicated.

The following abbreviations or symbols are used to represent amino acids, protecting groups, solvents, reagents and the like.

| Symbol | Meaning |
|---|---|
| β-Ala | beta-Alanine |
| (2)-Nal | (2)-Naphthylalanine |
| Atc | 2-Aminotetraline-2-carboxylic acid |
| 5-BrAtc | 5-Bromo-2-aminotetraline-2-carboxylic acid |
| 5-ClAtc | 5-Chloro-2-aminotetraline-2-carboxylic acid |
| 5-MeOAtc | 5-Methoxy-2-aminotetraline-2-carboxylic acid |
| 5-EtOAtc | 5-Ethoxy-2-aminotetraline-2-carboxylic acid |
| 5-iPrOAtc | 5-Isopropoxy-2-aminotetraline-2-carboxylic acid |
| 5-MeAtc | 5-Methyl-2-aminotetraline-2-carboxylic acid |
| 5-EtAtc | 5-Ethyl-2-aminotetraline-2-carboxylic acid |
| 5-iPrAtc | 5-Isopropyl-2-aminotetraline-2-carboxylic acid |
| 5-DmaAtc | 5-Dimethylamino-2-aminotetraline-2-carboxylic acid |
| DBr | D-2,4-diaminobutanoic acid |
| DPr | D-2,3-diaminopropionic acid |
| Sar | Sarcosine (N-methylglycine) |
| Cit | Citrulline |
| Apc | 1-Amino-4-phenylcyclohexane-1-carboxylic acid |
| 4-HOApc | 1-Amino-4-(4-hydroxyphenyl)cyclohexane-1-carboxylic acid |
| 4-MeOApc | 1-Amino-4-(4-methoxyphenyl)cyclohexane-1-carboxylic acid |
| 3-MeOApc | 1-Amino-4-(4-methoxyphenyl)cyclohexane-1-carboxylic acid |
| 4-EtOApc | 1-Amino-4-(4-ethoxyphenyl)cyclohexane-1-carboxylic acid |
| 4-iPrOApc | 1-Amino-4-(4-isopropoxyphenyl)cyclohexane-1-carboxylic acid |
| 4-MeApc | 1-Amino-4-(4-methylphenyl)cyclohexane-1-carboxylic acid |
| 4-ClApc | 1-Amino-4-(4-chlorophenyl)cyclohexane-1-carboxylic acid |
| Appc | 4-Amino-1-phenylpiperidine-4-carboxylic acid |
| 2-MeAppc | 4-Amino-1-(2-methylphenyl)piperidine-4-carboxylic acid |
| 2-iProAppc | 4-Amino-1-(2-isopropoxyphenyl)piperidine-4-carboxylic acid |
| 3-MeAppc | 4-Amino-1-(3-methylphenyl)piperidine-4-carboxylic acid |
| 3-MeOAppc | 4-Amino-1-(3-methoxyphenyl)piperidine-4-carboxylic acid |
| 4-MeAppc | 4-Amino-1-(4-methylphenyl)piperidine-4-carboxylic acid |
| 4-ClAppc | 4-Amino-1-(4-chlorophenyl)piperidine-4-carboxylic acid |
| 4-PhOAppc | 4-Amino-1-(4-phenoxyphenyl)piperidine-4-carboxylic acid |
| Achc | 1-Amino-4-cyclohexylcyclohexane-1-carboxylic acid |
| Adpc | 1-Amino-4-diphenylcyclohexane-1-carboxylic acid |
| Abc | 1-Amino-4-tert-butylcyclohexane-1-carboxylic acid |
| 3-Amb | 3-Aminomethyl benzoic acid |
| 4-Amb | 4-Aminomethyl benzoic acid |
| 2-Aba | 2-Aminobenzoic acid |
| Bu | Butyl |
| Penta | pentanoyl |
| Fmoc | 9-Fluorenylmethoxycarbonyl |
| Pmc | 2,2,5,7,8-Pentamethylchroman-6-sulfonyl |
| Trt | Trityl (triphenylmethyl) |
| $CH_2Cl_2$ | Methylene chloride |
| $CH_3CN$ | Acetonitrile |
| DMF | Dimethylformamide |
| DIPEA | N,N-Diisopropylethylamine |
| TFA | Trifluoroacetic acid |
| HOBT | N-Hydroxybenzotriazole |
| DIC | N,N'-Diisopropylcarbodiimide |
| BOP | Benzotriazol-1-yloxy-tris-(dimethylamino)phosphonium Hexafluorophosphate |
| PyBroP | Bromo-tris-pyrrolidino-phosphonium hexafluorophosphate |
| HBTU | 2-(1H-Benzotriazole-1-yl)-1,1,3,3-tetramethyluronium Hexafluorophosphate |
| FAB-MS | Fast atom bombardment mass spectrometry |
| ES-MS | Electrospray mass spectrometry |

Setting forth the substituted amino acid, in parentheses indicates analogs of the peptide sequence. Derivatization of the N-terminal amino group, is indicated to the left of the N-terminal substitution, separated by a hyphen. That is, for example, Ac-His-(D)Phe-Arg-Trp-Gly-NH$_2$ indicates a peptide having an amino acid sequence in which an acetyl group has been substituted for hydrogen at the N-terminus. The suffixes "—OH" and "—NH$_2$" following the hyphen or the parentheses refer to the free acid and amide forms of the polypeptide, respectively.

The linear peptides, used as the precursors for the present representative compounds may be readily synthesized by any known conventional procedure for the formation of a peptide linkage between amino acids. Such conventional procedures include, for example, any solution phase procedure permitting a condensation between the free alpha amino group of an amino acid or residue thereof having its carboxyl group or other reactive groups protected and the free primary carboxyl group of another amino acid or residue thereof having its amino group or other reactive groups protected.

The process for synthesizing the linear peptides may be carried out by a procedure whereby each amino acid in the desired sequence is added one at a time in succession to another amino acid or residue thereof or by a procedure whereby peptide fragments with the desired amino acid sequence are first synthesized conventionally and then condensed to provide the desired peptide.

Such conventional procedures for synthesizing the precursor linear peptides include for example any solid phase peptide synthesis method. In such a method the synthesis of the novel compounds can be carried out by sequentially incorporating the desired amino acid residues one at a time into the growing peptide chain according to the general principles of solid phase methods [Merrifield, R. B., J. Amer. Chem. Soc. 1963, 85, 2149–2154; Barany et al. The peptides, Analysis, Synthesis and Biology, Vol. 2, Gross, E. and Meienhofer, J., Eds. Academic Press 1–284 (1980)].

Common to chemical syntheses of peptides is the protection of reactive side chain groups of the various amino acid moieties with suitable protecting groups, which will prevent a chemical reaction from occurring at that site until the protecting group is ultimately removed. Usually also common is the protection of the alpha amino group of an amino acid or fragment while that entity reacts at the carboxyl group, followed by the selective removal of the alpha amino protecting group and allow a subsequent reaction to take place at that site. While specific protecting groups have been disclosed in regard to the solid phase synthesis method, it should be noted that each amino acid can be protected by an protective group conventionally used for the respective amino acid in solution phase synthesis.

Alpha amino groups may be protected by a suitable protecting group selected from aromatic urethane-type protecting groups, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz); aliphatic urethane-type protecting groups, such as t-butyloxycarbonyl (Boc), diisopropylmethoxycarbonyl, isopropoxycarbonyl, and allyloxycarbonyl. Herein, Fmoc is the most preferred for alpha amino protection.

Guanidino groups may be protected by a suitable protecting group selected from nitro, p-toluenesulfonyl (Tos), Z, pentamethylchromanesulfonyl (Pmc), adamantyloxycarbonyl, and Boc. Pmc is the most preferred for arginine (Arg).

All solvents, isopropanol (iPrOH), methylene chloride ($CH_2Cl_2$), dimethylformamide (DMF) and N-methylpyrrolidinone (NMP) were purchased from Fisher or Burdick & Jackson and were used without additional distillation. Trifluoroacetic acid was purchased from Halocarbon or Fluka and used without further purification. Diisopropylcarbodiimide (DIC) and diisopropylethylamine (DIPEA) was purchased from Fluka or Aldrich and used without further purification. Hydroxybenzotriazole (HOBT) dimethylsulfide (DMS) and 1,2-ethanedithiol (EDT) were purchased from Sigma Chemical Co. and used without further purification. Protected amino acids were generally of the L configuration and were obtained commercially from Bachem, Advanced ChemTech, or Neosystem. Purity of these reagents was confirmed by thin layer chromatography, NMR and melting point prior to use. Benzhydrylamine resin (BHA) was a copolymer of styrene –1% divinylbenzene (100–200 or 200–400 mesh) obtained from Bachem or Advanced Chemtech. Total nitrogen content of these resins were generally between 0.3–1.2 meq/g.

High performance liquid chromatography (HPLC) was conducted on a LDC apparatus consisting of Constametric I and III pumps, a Gradient Master solvent programmer and mixer, and a Spectromonitor III variable wavelength UV detector. Analytical HPLC was performed in reversed phase mode using Vydac $C_{18}$ columns (0.4×30 cm). Preparative HPLC separations were run on Vydac columns (2×25 cm).

The linear peptides were preferably prepared using solid phase synthesis by the method generally described by Merrifield, [*J. Amer. Chem. Soc.*, 1963, 85, 2149], although other equivalent chemical synthesis known in the art could be used as previously mentioned. Solid phase synthesis is commenced from the C-terminal end of the peptide by coupling a protected alpha-amino acid to a suitable resin. Such a starting material can be prepared by attaching an alpha-amino-protected amino acid by an ester linkage to a p-benzyloxybenzyl alcohol (Wang) resin, or by an amide bond between an Fmoc-Linker, such as p-[(R, S)-α-[1-(9H-fluoren-9-yl)-methoxyformamido]-2,4-dimethyloxybenzyl]-phenoxyacetic acid (Rink linker) to a benzhydrylamine (BHA) resin. Preparation of the hydroxymethyl resin is well known in the art. Fmoc-Linker-BHA resin supports are commercially available and generally used when the desired peptide being synthesized has an unsubstituted amide at the C-terminus.

Since the compounds of the present invention are cyclic peptides, prepared by the formation of a lactam or a disulfide bond, the precursor linear peptides are assembled so as to place suitable amino acids or mimetics carrying the appropriate side chain residues in positions in the linear peptides that can ultimately be induced to undergo an intramolecular amide bond or disulfide bond formation. The lactams are formed through the coupling a side chain amino functionality of a C-terminal amino acid residue with a distal carboxylic acid residue, while the disulfide bond is formed through the oxidative coupling of two cysteine residues appropriately incorporated at the C-terminal and at or near the N-terminus of the precursor linear peptide. For example, in the preparation of the lactam peptides, in the precursor linear pentapeptides the N-cap can be used as a template to incorporate a carboxyl residue, e.g. structure X, or in the case of hexapeptides, the peptide is designed such that the N-terminal amino acid residue is chosen from one of the amino acids containing a suitably protected side chain carboxylic acid group, eg aspartic acid, glutamic acid. In the linear heptapeptides, ether aspartic acid or glutamic acid are incorporated as the penultimate residue from the N-terminus. In all the precursor linear peptides, i.e., the hepta- hexa- and pentapeptides, the C-terminal residue is chosen from natural or unnatural amino acid bearing a suitably protected basic side chain residue, capable of forming a amide bond when deprotected, for example lysine, ornithine, 2,3-diaminopropanoic acid, 2,4-diaminobutanoic acid. To form a cyclic peptide containing a disulfide bond, where the precursor is a linear hexapeptide, the peptide is designed such that an appropriately S-protected cysteine residue is incorporated as both the C and N-terminal residues, while if the precursor is a linear heptapeptide the appropriately S-protected cysteine residues are incorporated as both the C terminal residue and the penultimate N-terminal residue as in for example X.

In general, to prepare the linear peptides, the amino acids or mimetic are coupled onto the Fmoc-Linker-BHA resin using the Fmoc protected form of amino acid or mimetic, with 2–5 equivalents of amino acid and a suitable coupling reagent. After couplings, the resin may be washed and dried under vacuum. Loading of the amino acid onto the resin may be determined by amino acid analysis of an aliquot of Fmoc-amino acid resin or by determination of Fmoc groups by UV analysis. Any unreacted amino groups may be capped by reacting the resin with acetic anhydride and diisopropylethylamine in methylene chloride.

The resins are carried through several repetitive cycles to add amino acids sequentially. The alpha amino Fmoc protecting groups are removed under basic conditions. Piperidine, piperazine or morpholine (20–40% v/v) in DMF may be used for this purpose. Preferably 40% piperidine in DMF is utilized.

Following the removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. For example, appropriate reagents for such syntheses are benzotriazol-1-yloxy-tri-(dimethylamino) phosphonium hexafluorophosphate (BOP), Bromo-tris-pyrrolidino-phosphonium hexafluorophosphate (PyBroP), 2-(1H-Benzotriazole-1-yl)-1,1,3,3-tetramethyluronium hexafluorophosphate (HBTU), and diisopropylcarbodiimide (DIC). Preferred here are HBTU and DIC. Other activating agents as described by Barany and Merrifield [The Peptides, Vol. 2, J. Meienhofer, ed., Academic Press, 1979, pp 1–284] may be utilized. Various reagents such as 1-hydroxybenzotriazole (HOBT), N-hydroxysuccinimide (HOSu) and 3,4-dihydro-3-hydroxy-4-oxo-1,2,3-benzotriazine (HOOBT) may be added to the coupling mixtures in order to optimize the synthetic cycles. Preferred here is HOBT.

The protocol for a typical synthetic cycle is as follows:
Protocol 1

| | Protocol 1 | |
|---|---|---|
| Step | Reagent | Time |
| 1 | DMF | 2 × 30 sec |
| 2 | 40% piperidine/DMF | 1 min |
| 3 | 40% piperidine/DMF | 15 min |
| 4 | DMF | 2 × 30 sec |
| 5 | iPrOH | 2 × 30 sec |
| 6 | DMF | 3 × 30 sec |
| 7 | coupling | 60 min–18 hours |
| 8 | DMF | 2 × 30 sec |
| 9 | iPrOH | 1 × 30 sec |
| 10 | DMF | 1 × 30 sec |
| 11 | $CH_2Cl_2$ | 2 × 30 sec |

Solvents for all washings and couplings were measured to volumes of 10–20 ml/g resins. Coupling reactions throughout the synthesis were monitored by the Kaiser ninhydrin test to determine extent of completion [Kaiser et at. *Anal. Biochem.* 1970, 34, 595–598]. Slow reaction kinetics was observed for Fmoc-Arg (Pmc) and for couplings to secondary amines by sterically hindered acids. Any incomplete coupling reactions were either recoupled with freshly prepared activated amino acid or capped by treating the peptide resin with acetic anhydride as described above. The fully assembled peptide-resins were dried in vacuum for several hours.

For each compound, the blocking groups were removed and the linear peptide cleaved from the resin by the following procedure. Generally. The peptide-resins are treated with 100 μL ethanedithiol, 100 μL dimethylsulfide, 300 μL anisole, and 9.5 mL trifluoroacetic acid, per gram of resin, at room temperature for 120 min. The resin is filtered off and the filtrates are precipitated in chilled ethyl ether. The precipitates are centrifuged and the ether layer is decanted. The residue is washed with two or three volumes of $Et_2O$ and recentrifuged. If desired, the crude linear peptides are purified by preparative HPLC. The peptides were applied to the columns in a minimum volume of either $AcOH/H_2O$ or 0.1% $TFA/H_2O$. Gradient elution is generally started at 10% B buffer, 10%–60% B in 90 minutes, (buffer A: 0.1% $TFA/H_2O$, buffer B: 0.1% $TFA/CH_3CN$) at a flow rate of 8 mL/min. UV detection is made at 280 rm. Fractions were collected at 1.0–2.5 minute intervals and inspected by analytical HPLC. Fractions judged to be of high purity were pooled and lyophilized.

To prepare the lactams, the appropriate unpurified linear peptide is dissolved in a suitable inert solvent, for example N-methyl pyrrolidone or DMF, preferably DMF and adjusted to an apparent pH of 8.0 by the addition of a tertiary amine base, for example N-methyl morpholine, and then is treated with an amide bond forming reagent, preferably BOP. The reaction is conveniently carried out at a temperature between 40° C. and 0° C., preferably at about room temperature. Purification of the crude cyclic peptides is carried out by preparative HPLC. Gradient elution is generally started at 20% B buffer, 20%–60% B in 90 minutes, (buffer A: 0.1% $TFA/H_2O$, buffer B: 0.1% $TFA/CH_3CN$) at a flow rate of 8 mL/min. UV detection is made at 280 nm. Fractions were collected and monitored by analytical HPLC. Fractions judged to be of high purity were pooled and lyophilized.

To prepare the cyclic disulfide peptides, the purified HPLC-purified linear peptide containing two appropriately positioned cysteine residues, is dissolved at a fairly high dilution level in an suitable inert solvent mixture, for example aqueous DMSO and the solution is adjusted to pH 8.0 by the careful addition of ammonium hydroxide. Oxygen is then bubbled into the stirred solution. The reaction is conveniently carried out at a temperature between 40° C. and 0° C., preferably at about room temperature and the progress of the cyclization is monitored by analytical HPLC. After the reaction is judged to be completed, the solution is lyophillized and the crude cyclic peptide is purified by preparative HPLC. Gradient elution is generally started at 20% B buffer, 20%–60% B in 90 minutes, (buffer A: 0.1% $TFA/H_2O$, buffer B: 0.1% $TFA/CH_3CN$) at a flow rate of 8 mL/min. UV detection is made at 280 nm. Fractions were collected and monitored by analytical HPLC. Fractions judged to be of high purity were pooled and lyophilized.

Purification of the crude peptides is carried out by preparative HPLC. The peptides were applied to the columns in a minimum volume of either $AcOH/H_2O$ or 0.1% $TFA/H_2O$. Gradient elution is generally started at 10% B buffer, 10%–60% B in 90 minutes, (buffer A: 0.1% $TFA/H_2O$, buffer B: 0.1% $TFA/CH_3CN$) at a flow rate of 8 mL/min. UV detection is made at 280 nm. Fractions were collected at 1.0–2.5 minute intervals and inspected by analytical HPLC. Fractions judged to be of high purity were pooled and lyophilized.

Purity of the final products is checked by analytical HPLC on a reversed phase column as stated above. Purity of all products is judged to be approximately 95–99%. All final products were also subjected to fast atom bombardment mass spectrometry (FAB-MS) or electrospray mass spectrometry (ES-MS). All products yielded the expected parent M+H ions within acceptable limits.

The process for synthesizing the representative compounds may be carried out by a procedure whereby each amino acid in the desired sequence is added one at a time in succession to another amino acid or residue thereof or by a procedure whereby peptide fragments with the desired amino acid sequence are first synthesized conventionally and then condensed to provide the desired peptide.

Such conventional procedures for synthesizing the novel compounds of the present invention include for example any solid phase peptide synthesis method. In such a method the synthesis of the novel compounds can be carried out by sequentially incorporating the desired amino acid residues one at a time into the growing peptide chain according to the general principles of solid phase methods [Merrifield, R. B., J. Amer. Chem. Soc. 1963, 85, 2149–2154; Barany et al. The peptides, Analysis, Synthesis and Biology, Vol. 2, Gross, E. and Meienhofer, J., Eds. Academic Press 1–284 (1980)].

Common to chemical syntheses of peptides is the protection of reactive side chain groups of the various amino acid moieties with suitable protecting groups, which will prevent a chemical reaction from occurring at that site until the protecting group is ultimately removed. Usually also common is the protection of the alpha amino group of an amino acid or fragment while that entity reacts at the carboxyl group, followed by the selective removal of the alpha amino protecting group and allow a subsequent reaction to take place at that site. While specific protecting groups have been disclosed in regard to the solid phase synthesis method, it should be noted that each amino acid can be protected by an protective group conventionally used for the respective amino acid in solution phase synthesis.

Alpha amino groups may be protected by a suitable protecting group selected from aromatic urethane-type protecting groups, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz); aliphatic urethane-type protecting groups, such as t-butyloxycarbonyl (Boc), diisopropylmethoxycarbonyl, isopropoxycarbonyl, and allyloxycarbonyl. Herein, Fmoc is the most preferred for alpha amino protection.

Guanidino groups may be protected by a suitable protecting group selected from nitro, p-toluenesulfonyl (Tos), Z, pentamethylchromanesulfonyl (Pmc), adamantyloxycarbonyl, and Boc. Pmc is the most preferred for arginine (Arg).

All solvents, isopropanol (iPrOH), methylene chloride ($CH_2Cl_2$), dimethylformamide (DMF) and N-methylpyrrolidinone (NMP) were purchased from Fisher or Burdick & Jackson and were used without additional distillation. Trifluoroacetic acid was purchased from Halocarbon or Fluka and used without further purification. Diisopropylcarbodiimide (DIC) and diisopropylethylamine (DIPEA) was purchased from Fluka or Aldrich and used without further purification. Hydroxybenzotriazole (HOBT) dimethylsulfide (DMS) and 1,2-ethanedithiol (EDT) were purchased from Sigma Chemical Co. and used without further purification. Protected amino acids were generally of the L configuration and were obtained commercially from Bachem, Advanced ChemTech, or Neosystem. Purity of these reagents was confirmed by thin layer chromatography, NMR and melting point prior to use. Benzhydrylamine resin (BHA) was a copolymer of styrene –1% divinylbenzene (100–200 or 200–400 mesh) obtained from Bachem or Advanced Chemtech. Total nitrogen content of these resins were generally between 0.3–1.2 meq/g.

High performance liquid chromatography (HPLC) was conducted on a LDC apparatus consisting of Constametric I and III pumps, a Gradient Master solvent programmer and mixer, and a Spectromonitor III variable wavelength UV detector. Analytical HPLC was performed in reversed phase mode using Vydac $C_{18}$ columns (0.4×30 cm). Preparative HPLC separations were run on Vydac columns (2×25 cm).

Peptides were preferably prepared using solid phase synthesis by the method generally described by Merrifield, [*J. Amer. Chem. Soc.*, 1963, 85, 2149], although other equivalent chemical synthesis known in the art could be used as previously mentioned. Solid phase synthesis is commenced from the C-terminal end of the peptide by coupling a protected alpha-amino acid to a suitable resin. Such a starting material can be prepared by attaching an alpha-amino-protected amino acid by an ester linkage to a p-benzyloxybenzyl alcohol (Wang) resin, or by an amide bond between an Fmoc-Linker, such as p-[(R, S)-α-[1-(9H-fluoren-9-yl)-methoxyformamido]-2,4-dimethyloxybenzyl]-phenoxyacetic acid (Rink linker) to a benzhydrylamine (BHA) resin. Preparation of the hydroxymethyl resin is well known in the art. Fmoc-Linker-BHA resin supports are commercially available and generally used when the desired peptide being synthesized has an unsubstituted amide at the C-terminus.

In general, the amino acids or mimetic are coupled onto the Fmoc-Linker-BHA resin using the Fmoc protected form of amino acid or mimetic, with 2–5 equivalents of amino acid and a suitable coupling reagent. After couplings, the resin may be washed and dried under vacuum. Loading of the amino acid onto the resin may be determined by amino acid analysis of an aliquot of Fmoc-amino acid resin or by determination of Fmoc groups by UV analysis. Any unreacted amino groups may be capped by reacting the resin with acetic anhydride and diisopropylethylamine in methylene chloride.

The resins are carried through several repetitive cycles to add amino acids sequentially. The alpha amino Fmoc protecting groups are removed under basic conditions. Piperidine, piperazine or morpholine (20–40% v/v) in DMF may be used for this purpose. Preferably 40% piperidine in DMF is utilized.

Following the removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. For example, appropriate reagents for such syntheses are benzotriazol-1-yloxy-tri-(dimethylamino) phosphonium hexafluorophosphate (BOP), Bromo-tris-pyrrolidino-phosphonium hexafluorophosphate (PyBroP), 2-(1H-Benzotriazole-1-yl)-1,1,3,3-tetramethyluronium hexafluorophosphate (HBTU), and diisopropylcarbodiimide (DIC). Preferred here are HBTU and DIC. Other activating agents as described by Barany and Merrifield [The Peptides, Vol. 2, J. Meienhofer, ed., Academic Press, 1979, pp 1–284] may be utilized. Various reagents such as 1-hydroxybenzotriazole (HOBT), N-hydroxysuccinimide (HOSu) and 3,4-dihydro-3-hydroxy-4-oxo-1,2,3-benzotriazine (HOOBT) may be added to the coupling mixtures in order to optimize the synthetic cycles. Preferred here is HOBT.

The protocol for a typical synthetic cycle is as follows:

Protocol 1

| Step | Reagent | Time |
|---|---|---|
| 1 | DMF | 2 × 30 sec |
| 2 | 40% piperidine/DMF | 1 min |
| 3 | 40% piperidine/DMF | 15 min |
| 4 | DMF | 2 × 30 sec |
| 5 | iPrOH | 2 × 30 sec |
| 6 | DMF | 3 × 30 sec |
| 7 | coupling | 60 min–18 hours |
| 8 | DMF | 2 × 30 sec |
| 9 | iPrOH | 1 × 30 sec |
| 10 | DMF | 1 × 30 sec |
| 11 | $CH_2Cl_2$ | 2 × 30 sec |

Solvents for all washings and couplings were measured to volumes of 10–20 ml/g resins. Coupling reactions throughout the synthesis were monitored by the Kaiser ninhydrin test to determine extent of completion [Kaiser et at. *Anal. Biochem.* 1970, 34, 595–598]. Slow reaction kinetics was observed for Fmoc-Arg (Pmc) and for couplings to secondary amines by sterically hindered acids. Any incomplete coupling reactions were either recoupled with freshly prepared activated amino acid or capped by treating the peptide resin with acetic anhydride as described above. The fully assembled peptide-resins were dried in vacuum for several hours.

For each compound, the blocking groups were removed and the peptide cleaved from the resin by the following procedure. The peptide-resins were treated with 100 μL ethanedithiol, 100 μL dimethylsulfide, 300 μL anisole, and 9.5 mL trifluoroacetic acid, per gram of resin, at room temperature for 120 min. The resin is filtered off and the filtrates are precipitated in chilled ethyl ether. The precipitates are centrifuged and the ether layer is decanted. The residue was washed with two or three volumes of $Et_2O$ and recentrifuged. The crude products are dried under vacuum.

Purification of Crude Peptide Preparations

Purification of the crude peptides was carried out by preparative HPLC. The peptides were applied to the columns in a minimum volume of either $AcOH/H_2O$ or 0.1% $TFA/H_2O$. Gradient elution was generally started at 10% B buffer, 10%–60% B in 90 minutes, (buffer A: 0.1% TFA/$H_2O$, buffer B: 0.1% $TFA/CH_3CN$) at a flow rate of 8 mL/min. UV detection was made at 280 nm. Fractions were collected at 1.0–2.5 minute intervals and inspected by analytical HPLC. Fractions judged to be of high purity were pooled and lyophilized.

Purity of the final products was checked by analytical HPLC on a reversed phase column as stated above. Purity of all products was judged to be approximately 95–99%. All final products were also subjected to fast atom bombardment mass spectrometry (FAB-MS) or electrospray mass spectrometry (ES-MS). All products yielded the expected parent M+H ions within acceptable limits.

Utilizing the techniques described above, the compounds of this invention can be synthesized in accordance with the following reaction schemes.

Reaction Scheme A
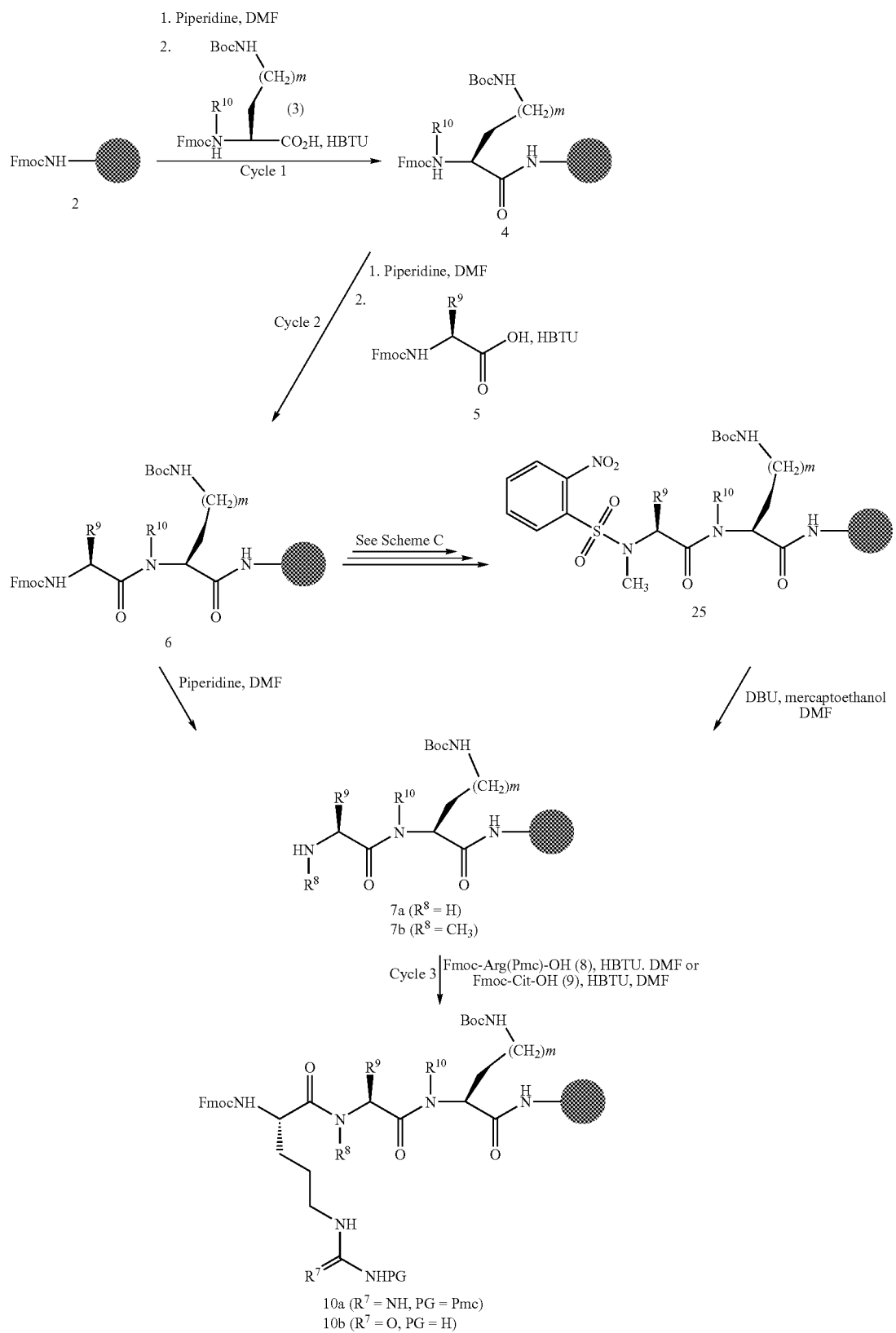
$R^8$, $R^9$, $R^{10}$ and m are as previously described.

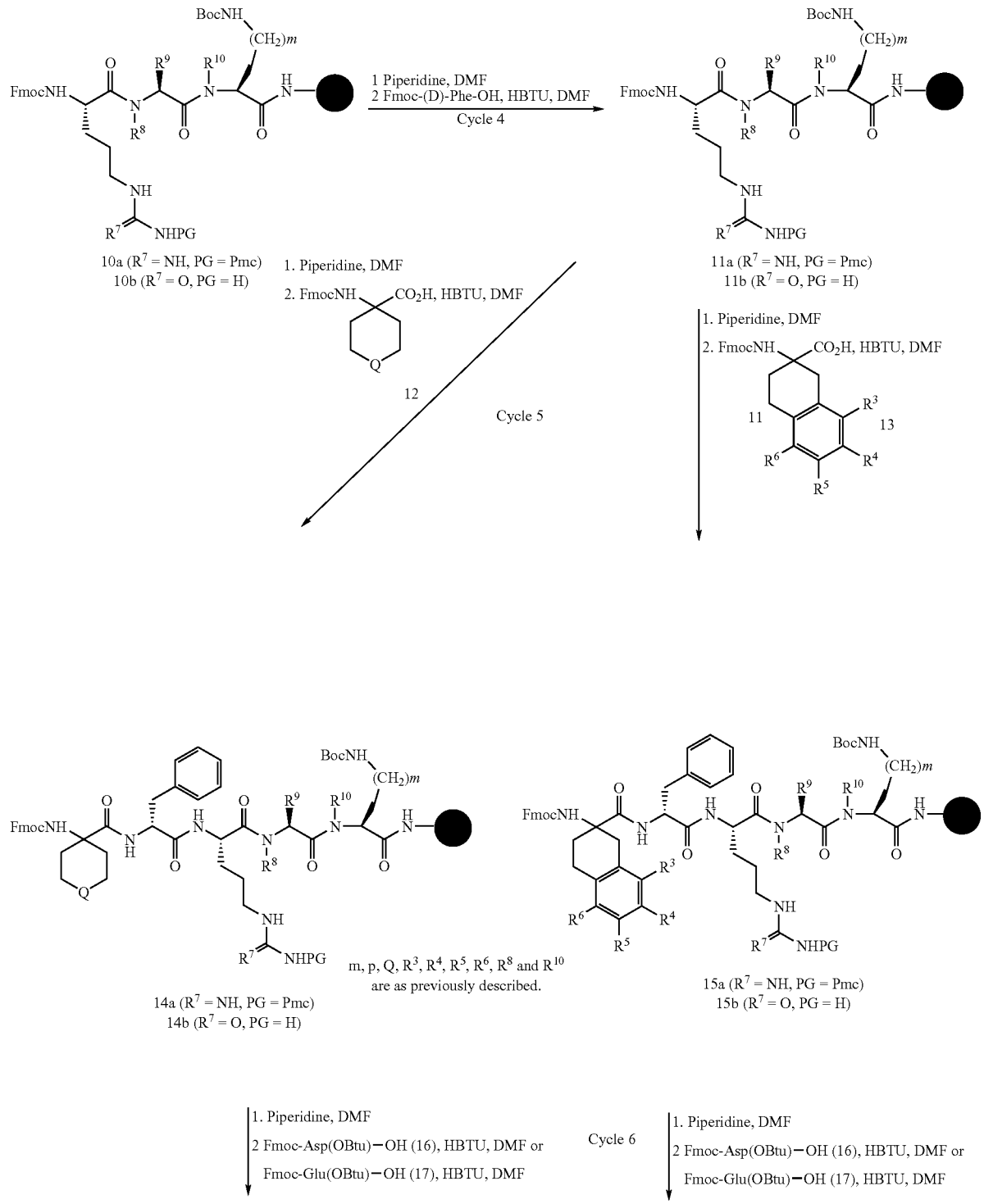

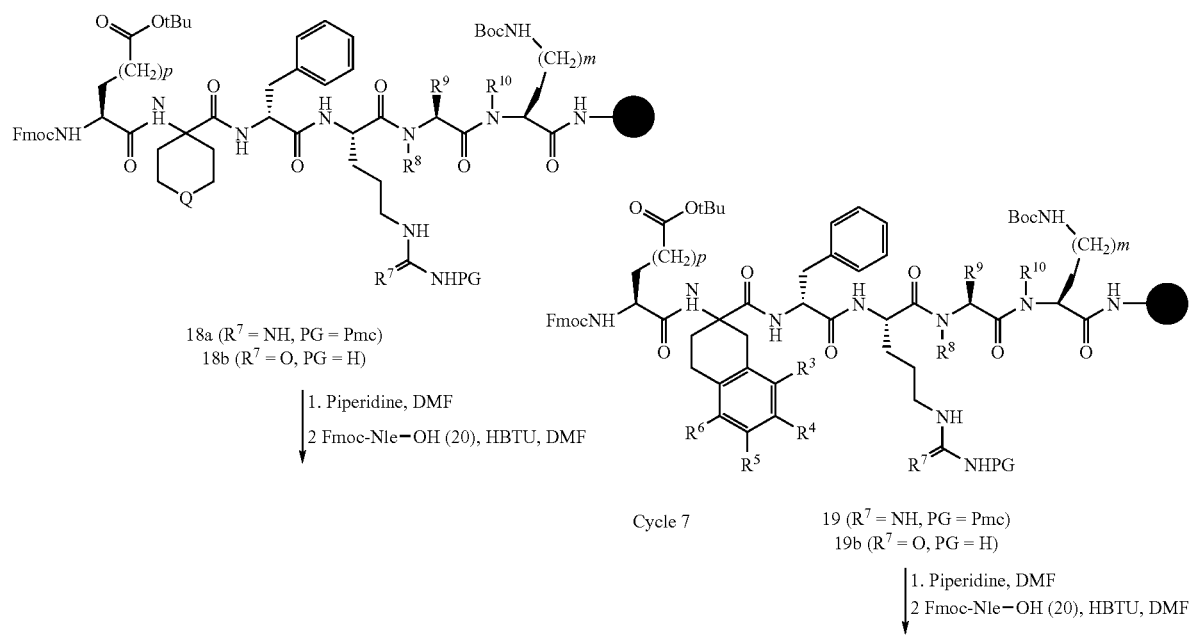
18a (R⁷ = NH, PG = Pmc)
18b (R⁷ = O, PG = H)
1. Piperidine, DMF
2. Fmoc-Nle—OH (20), HBTU, DMF
Cycle 7
19 (R⁷ = NH, PG = Pmc)
19b (R⁷ = O, PG = H)
1. Piperidine, DMF
2. Fmoc-Nle—OH (20), HBTU, DMF
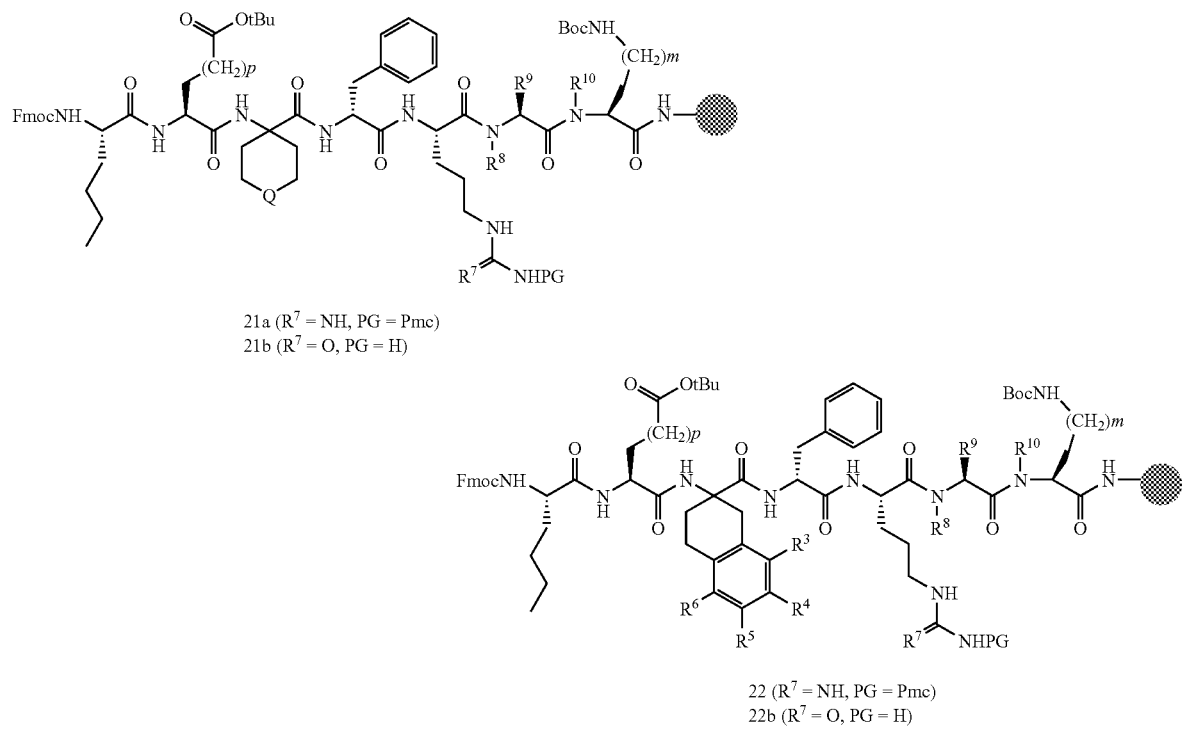
21a (R⁷ = NH, PG = Pmc)
21b (R⁷ = O, PG = H)
22 (R⁷ = NH, PG = Pmc)
22b (R⁷ = O, PG = H)

Reaction Scheme C
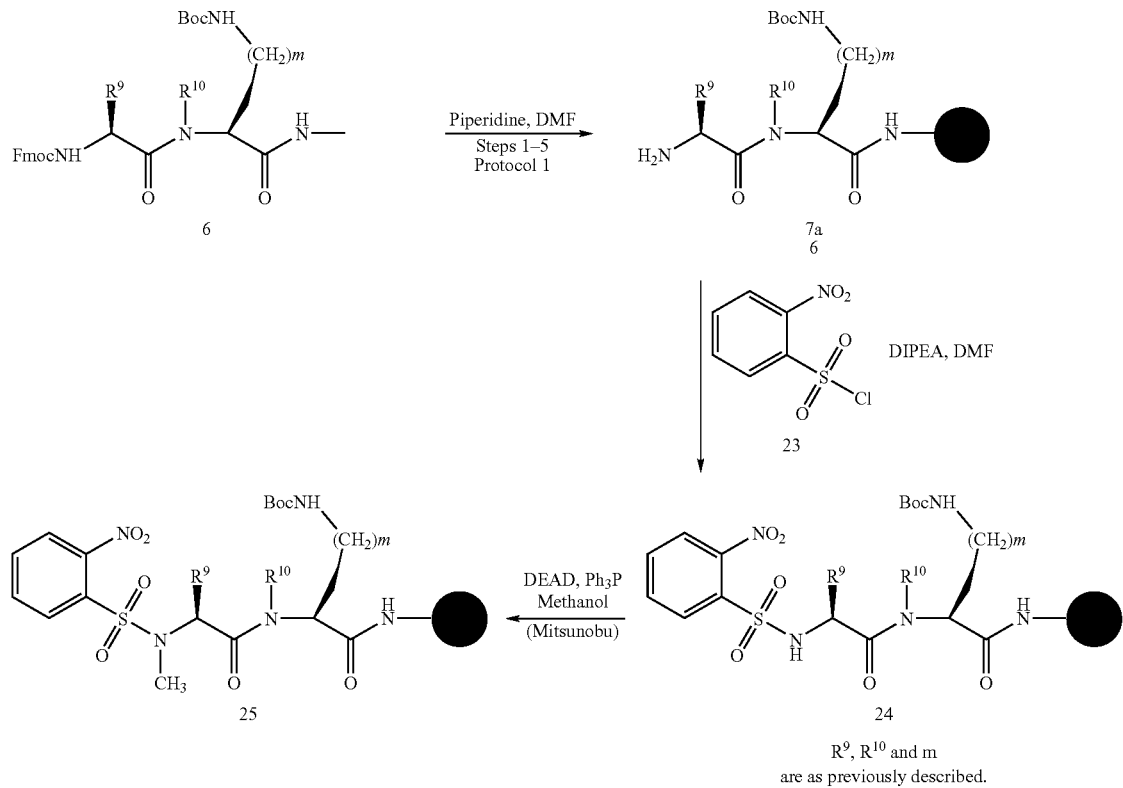
In the same manner:
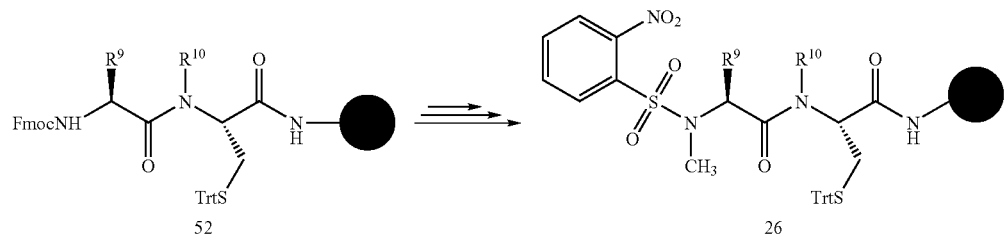
Reaction Scheme D
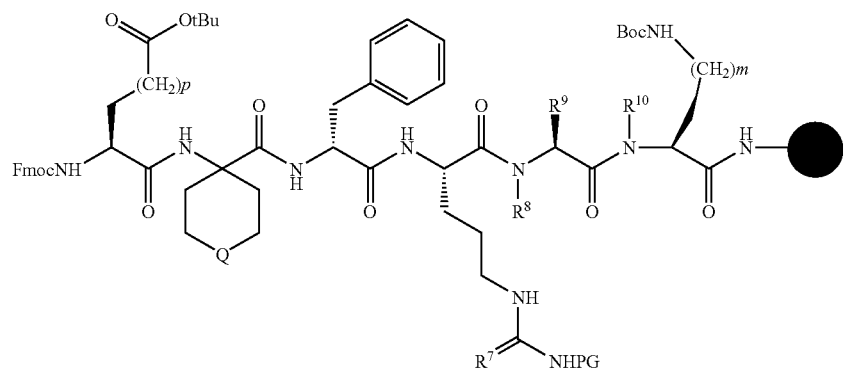

-continued
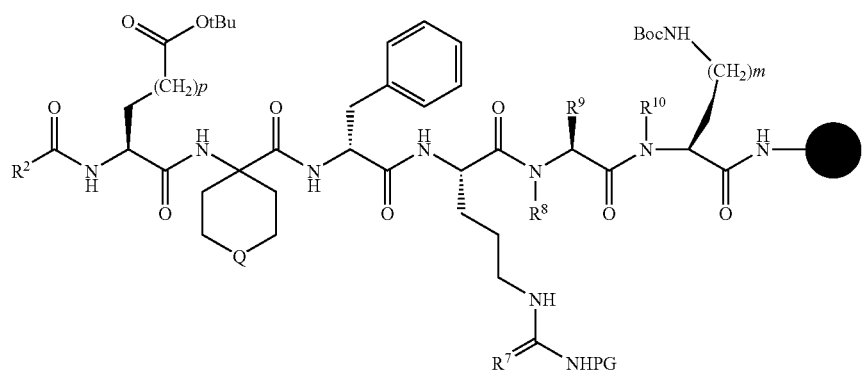
27a (R⁷ = NH, PG = Pmc)
27b (R⁷ = O, PG = H)
| 18a | R², R⁸, R⁹, R¹⁰, Q and m |
| 18b | are as previously described. |
1. Piperidine, DMF
2. R²—N=C=O, DIPEA.
   DMF or CH₂Cl₂
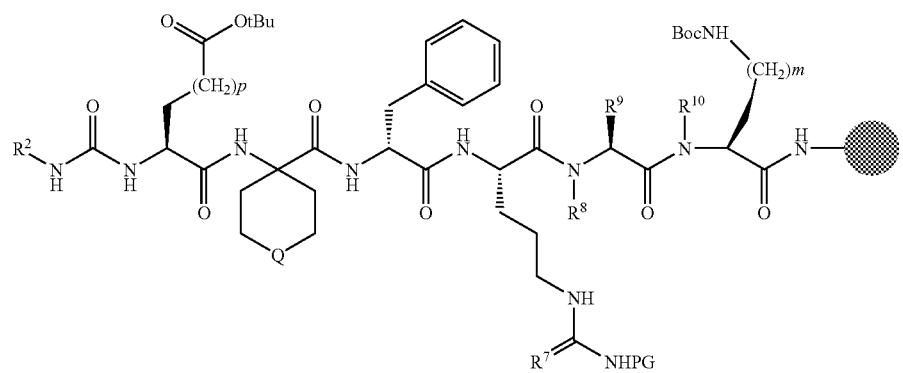
28a (R⁷ = NH, PG = Pmc)
28b (R⁷ = O, PG = H)
Reaction Scheme E
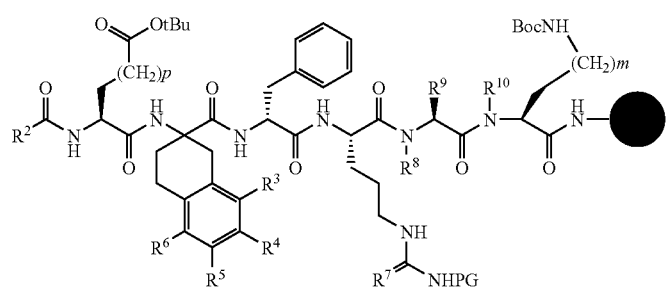
33a (R⁷ = NH, PG = Pmc)
33b (R⁷ = O, PG = H)

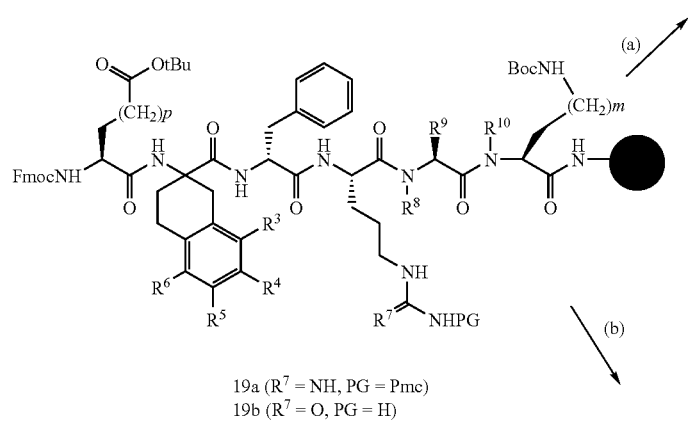
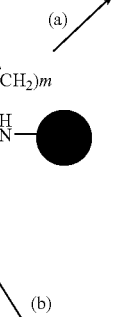
19a (R⁷ = NH, PG = Pmc)
19b (R⁷ = O, PG = H)
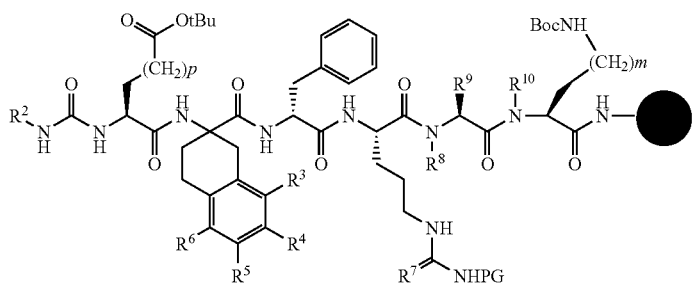
34a (R⁷ = NH, PG = Pmc)
34b (R⁷ = O, PG = H)
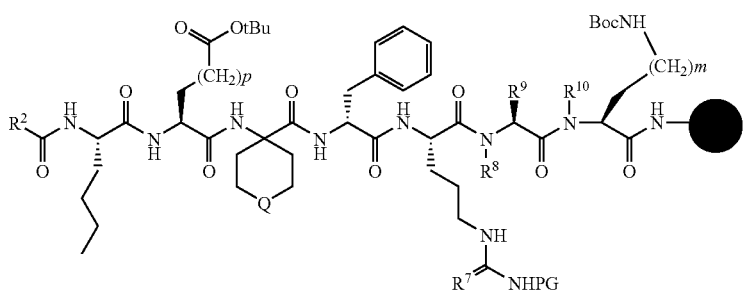
35a (R⁷ = NH, PG = Pmc)
35b (R⁷ = O, PG = H)
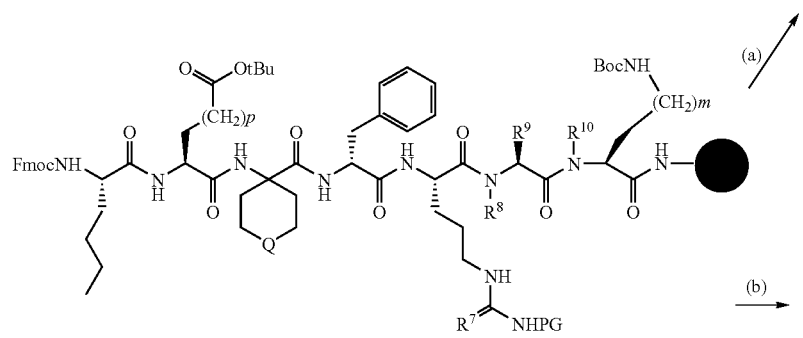
21a (R⁷ = NH, PG = Pmc)
21b (R⁷ = O, PG = H)

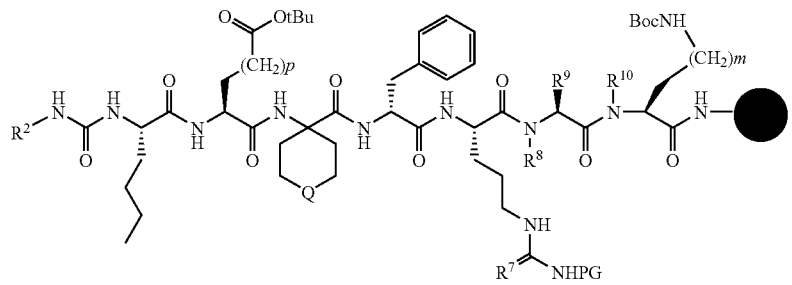
36a (R⁷ = NH, PG = Pmc)
36b (R⁷ = O, PG = H)
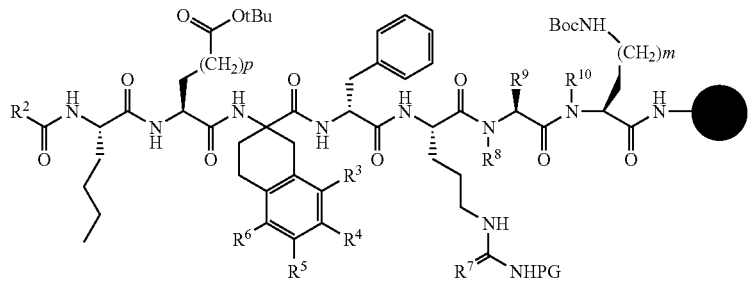
37a (R⁷ = NH, PG = Pmc)
37b (R⁷ = O, PG = H)
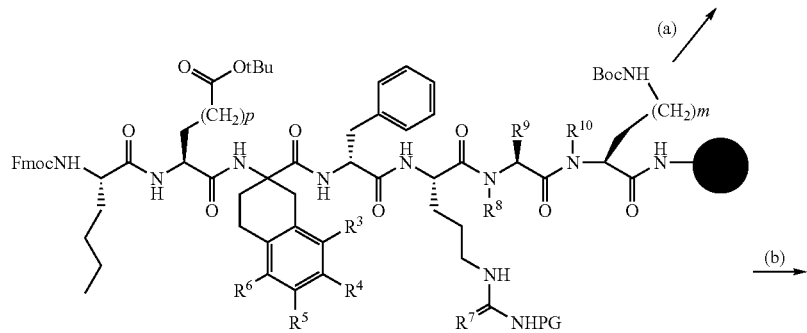
22a (R⁷ = NH, PG = Pmc)
22b (R⁷ = O, PG = H)
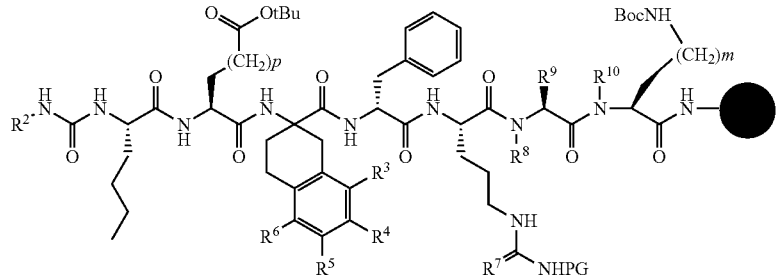
38a (R⁷ = NH, PG = Pmc)
38b (R⁷ = O, PG = H)
(a) i. piperidine/DMF ii. N-Acylation
(b) i. piperidine/DMF ii. R²—N=C=O Reaction Scheme F
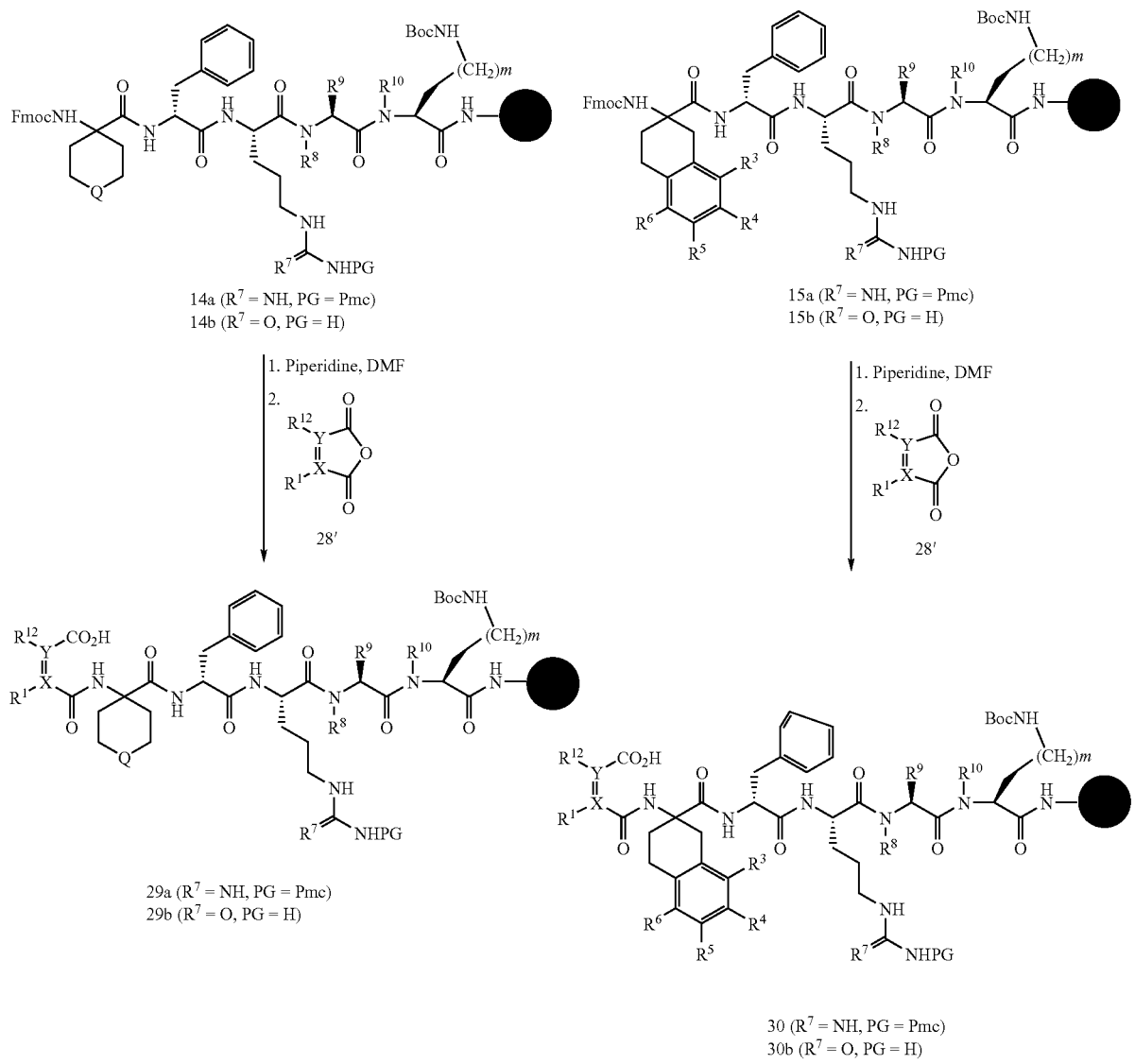
Reaction Scheme G
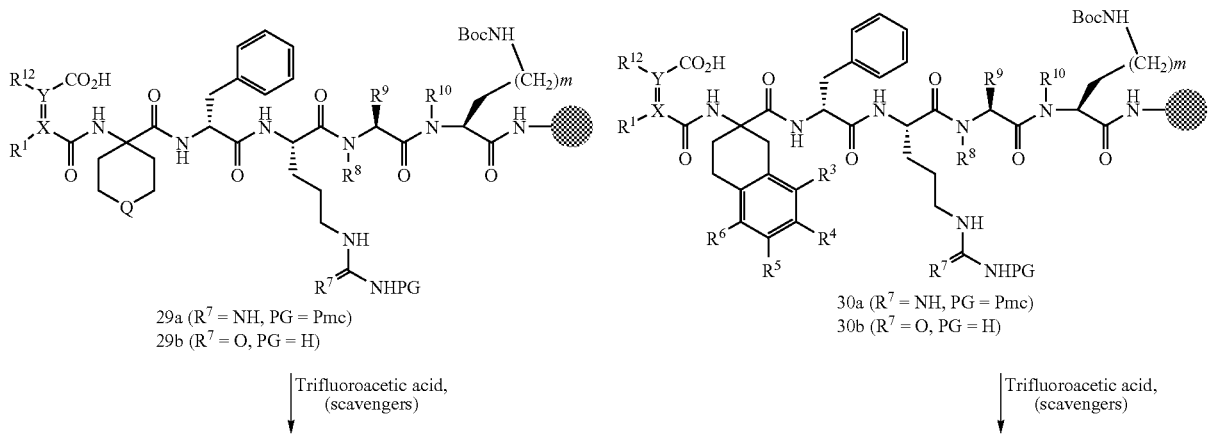

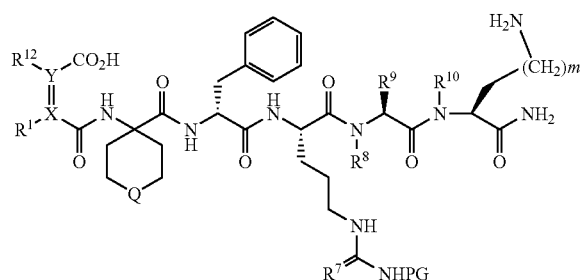
31a (R⁷ = NH, PG = Pmc)
31b (R⁷ = O, PG = H)
↓ BOP
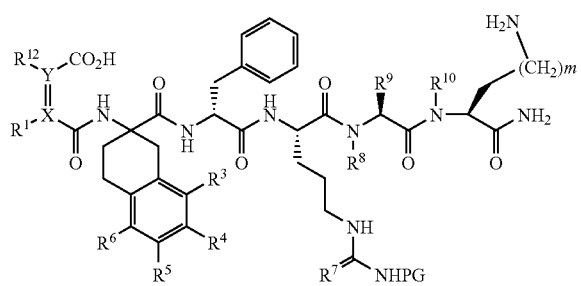
32a (R⁷ = NH, PG = Pmc)
32b (R⁷ = O, PG = H)
↓ BOP
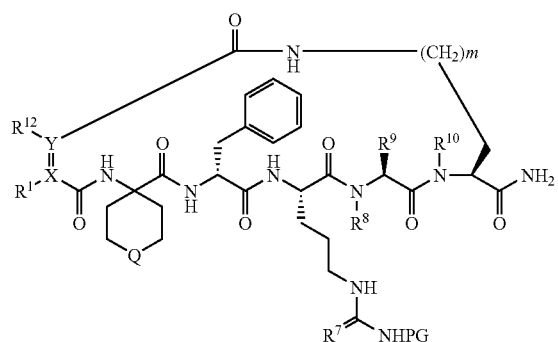
I
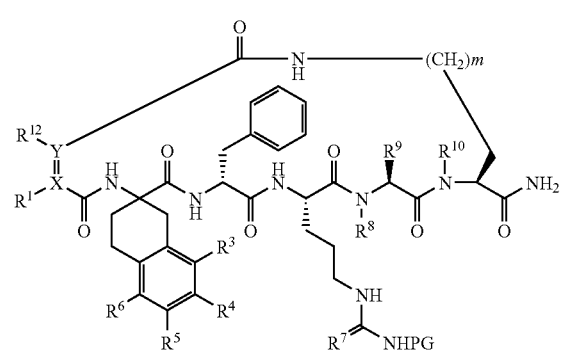
I
Reaction Scheme H
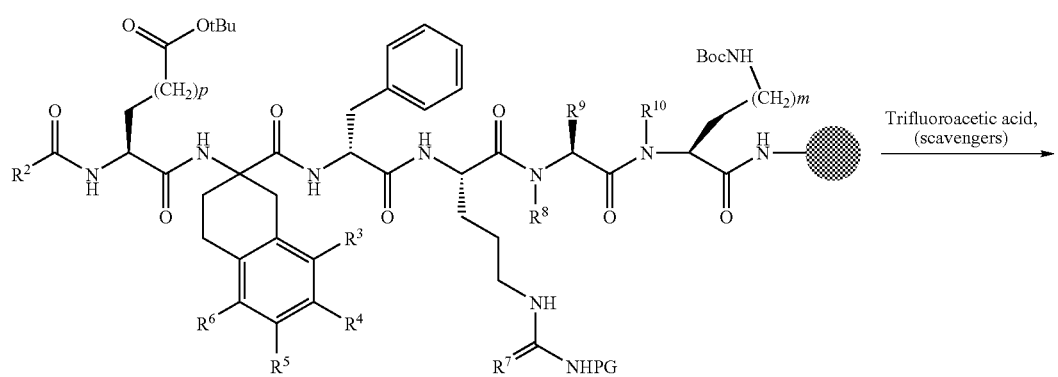
33a (R⁷ = NH, PG = Pmc)
33b (R⁷ = O, PG = H)
Trifluoroacetic acid, (scavengers) →

-continued
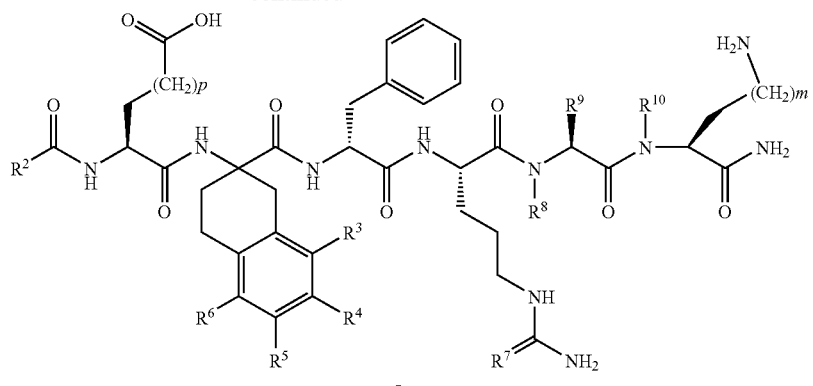
39a (R⁷ = NH)
39b (R⁷ = O)
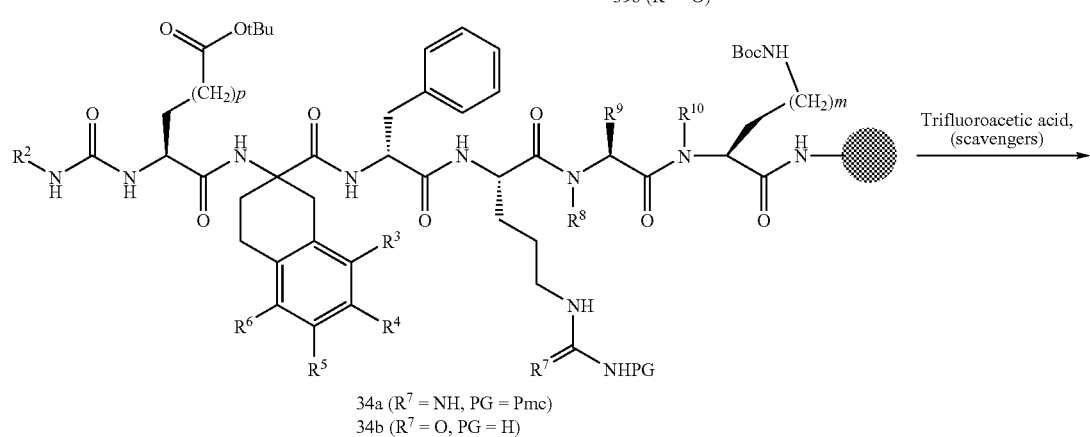
34a (R⁷ = NH, PG = Pmc)
34b (R⁷ = O, PG = H)
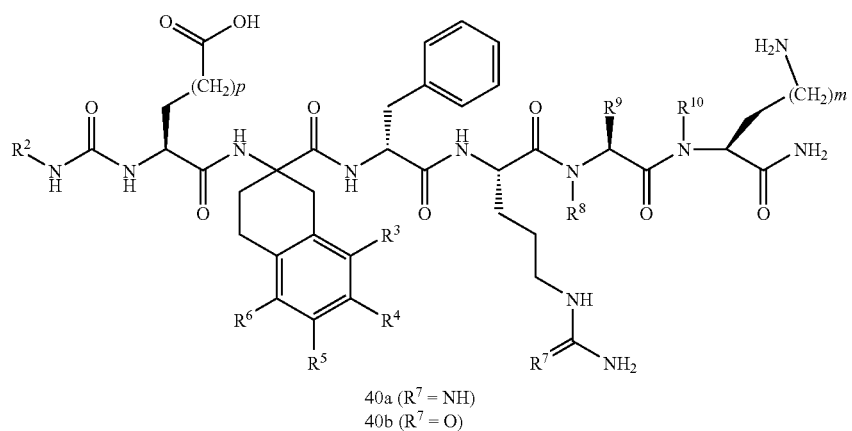
40a (R⁷ = NH)
40b (R⁷ = O)
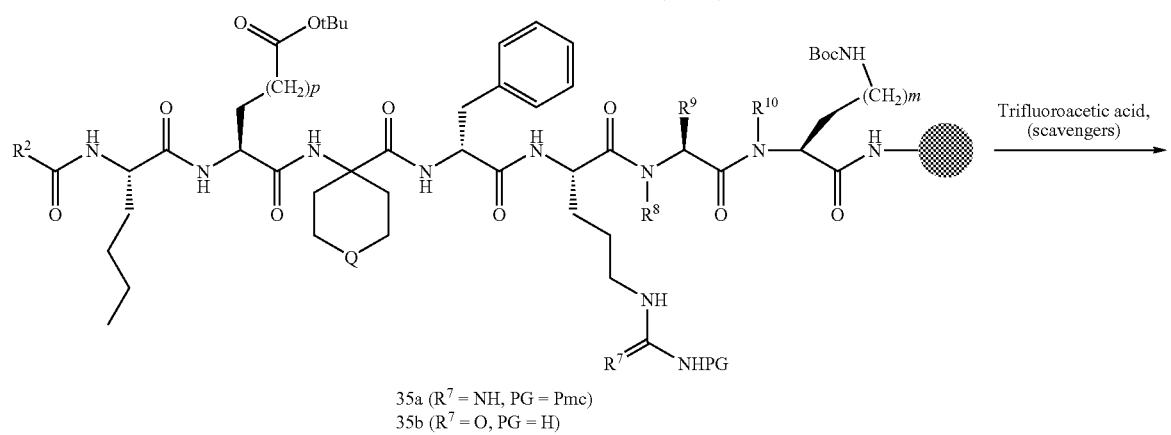
35a (R⁷ = NH, PG = Pmc)
35b (R⁷ = O, PG = H)

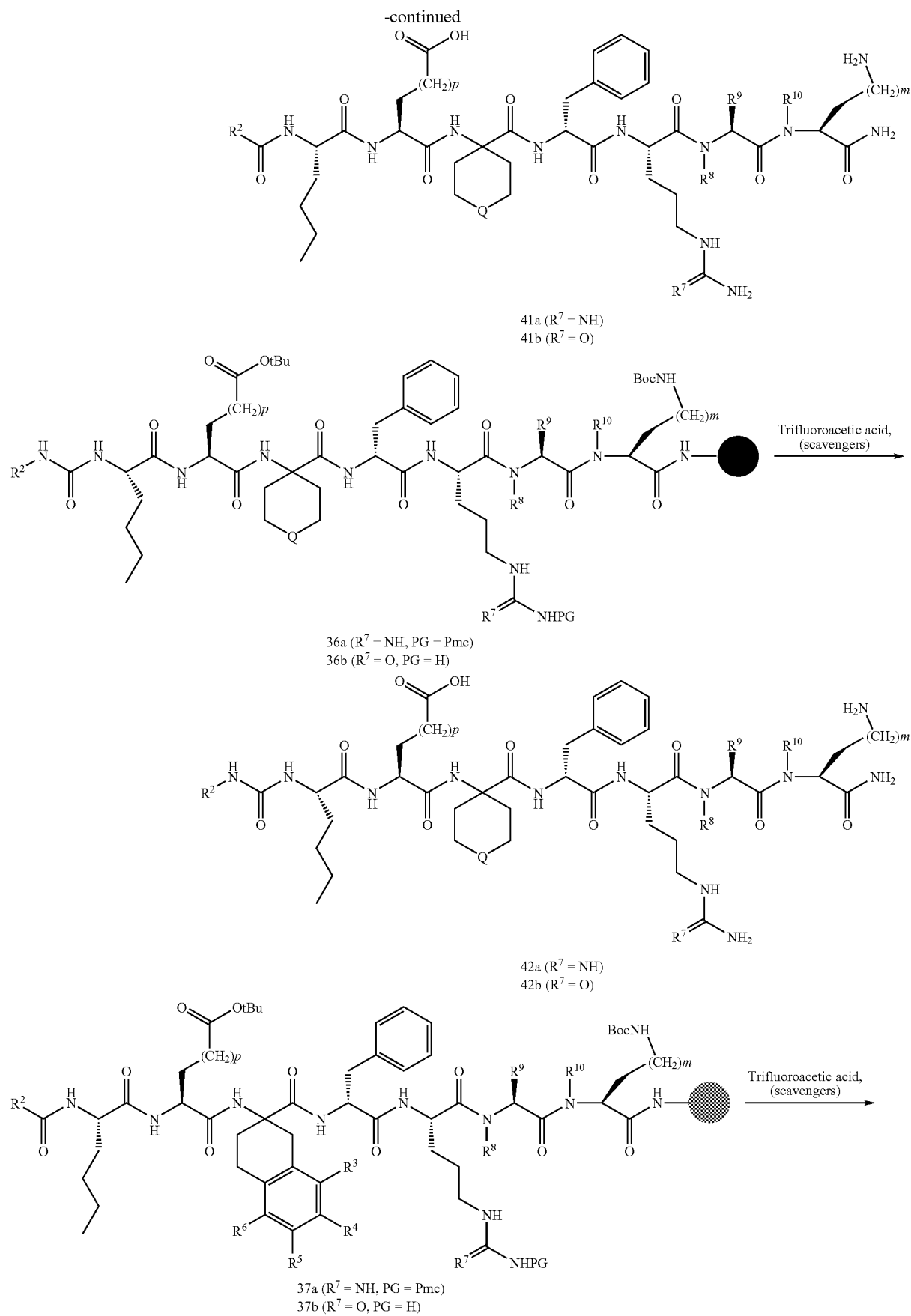

-continued
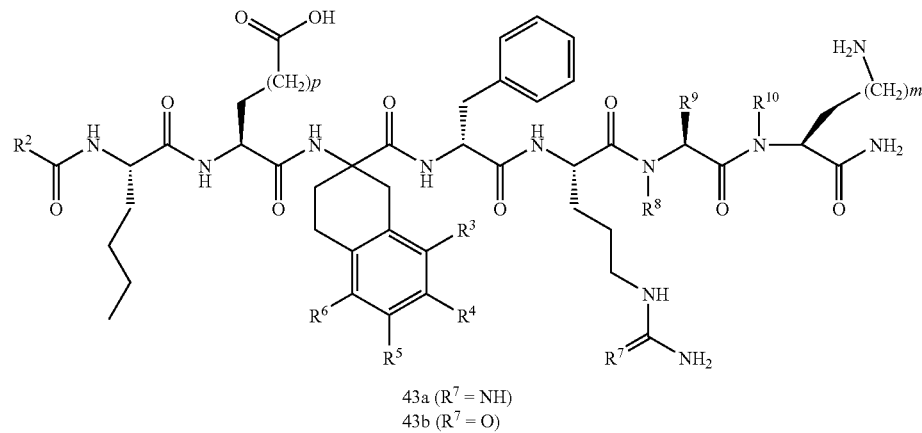
43a ($R^7$ = NH)
43b ($R^7$ = O)
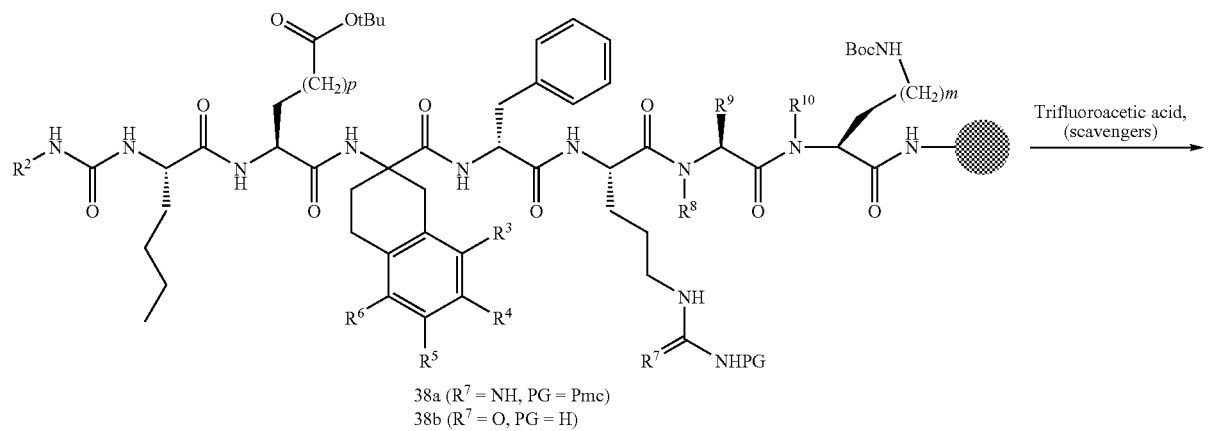
38a ($R^7$ = NH, PG = Pmc)
38b ($R^7$ = O, PG = H)
Trifluoroacetic acid, (scavengers)
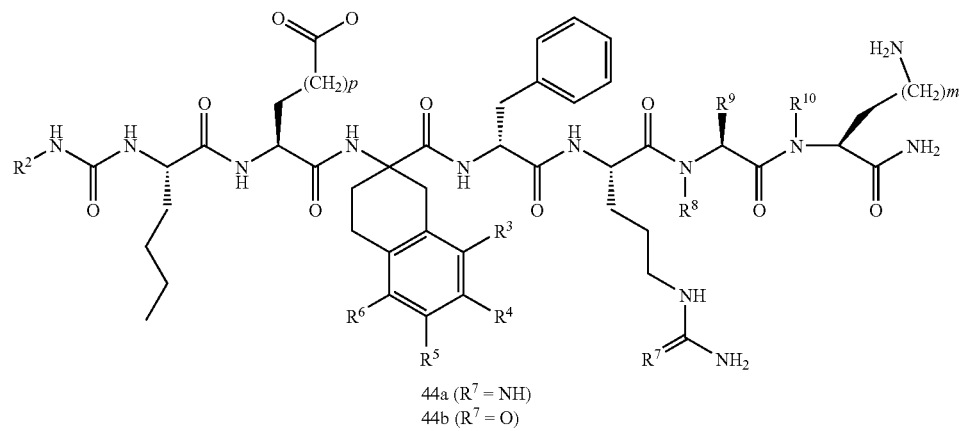
44a ($R^7$ = NH)
44b ($R^7$ = O)
$R^2$, $R^3$, $R^4$, $R^5$, $R^6$, $R^8$, $R^9$, $R^{10}$, Q, p, and m are as previously described Reaction Scheme I
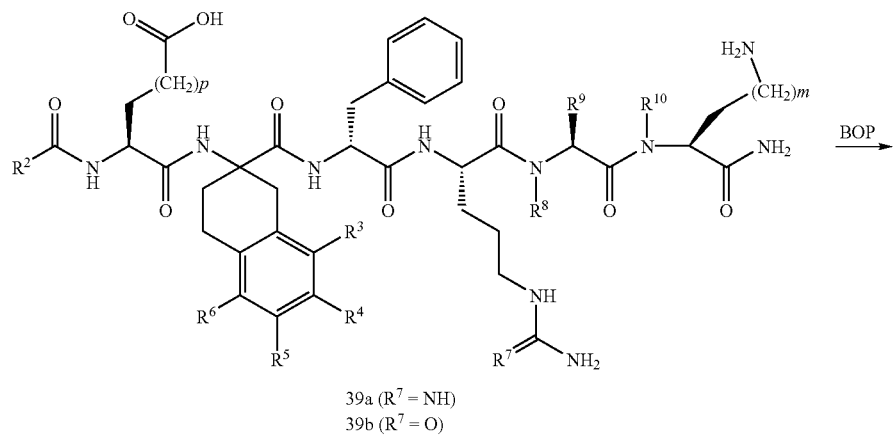
39a (R⁷ = NH)
39b (R⁷ = O)
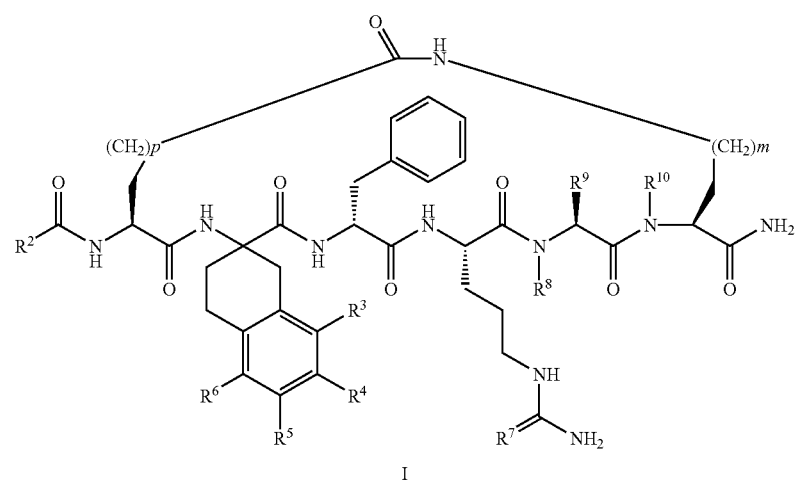
I
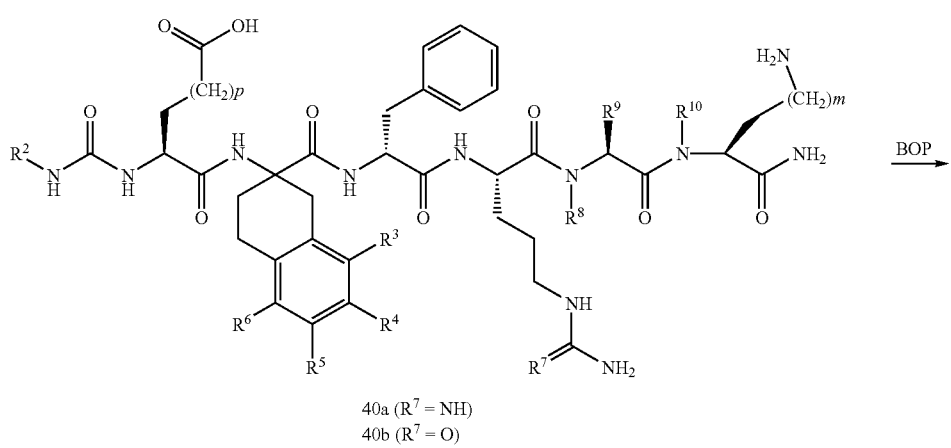
40a (R⁷ = NH)
40b (R⁷ = O)

-continued
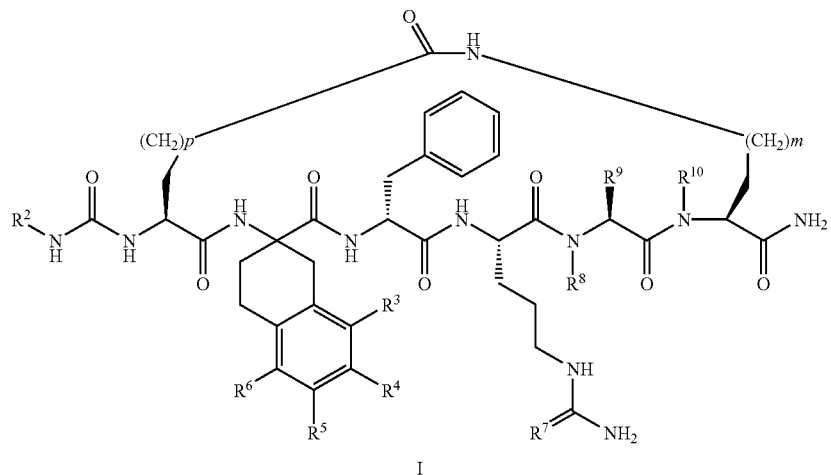
I
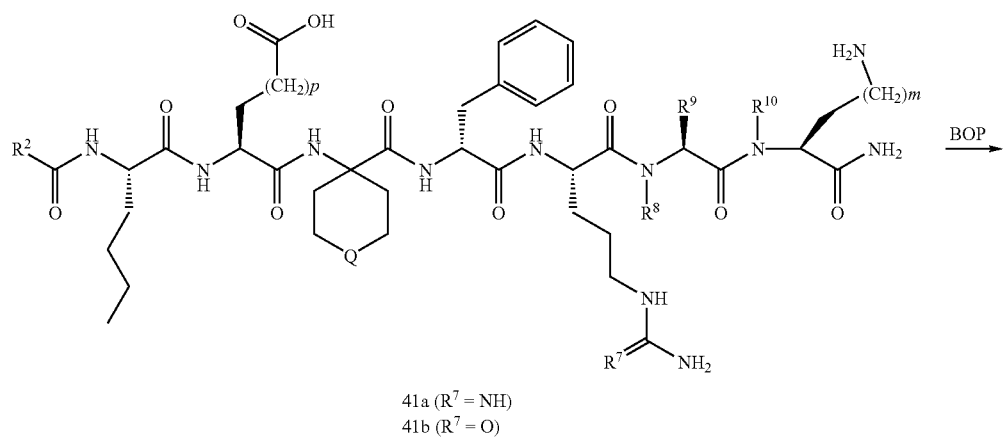
41a (R⁷ = NH)
41b (R⁷ = O)
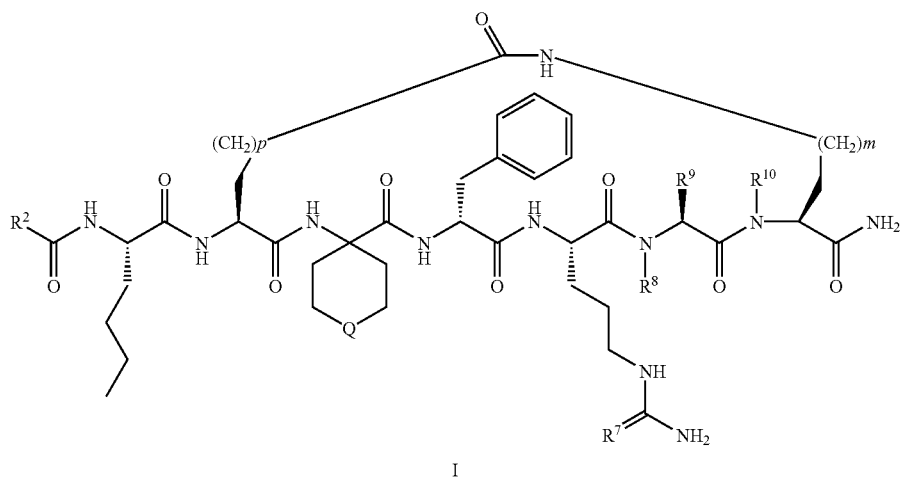
I

-continued
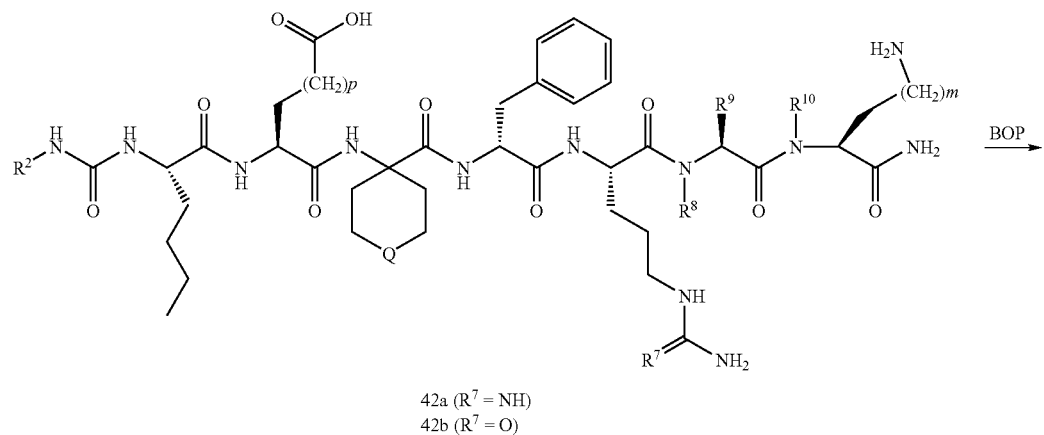
42a (R⁷ = NH)
42b (R⁷ = O)
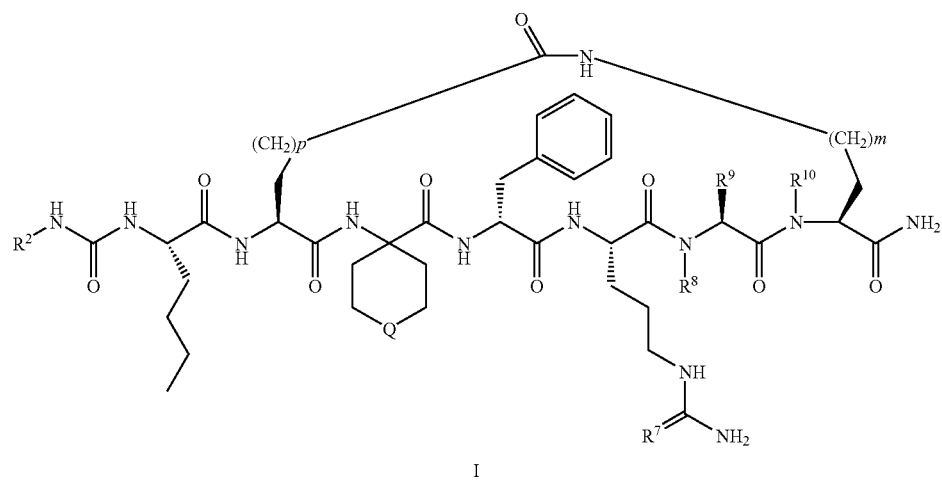
I
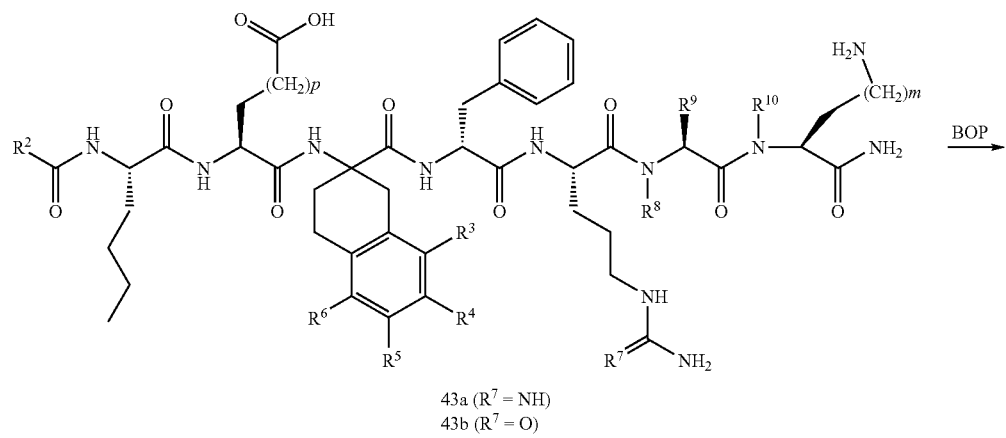
43a (R⁷ = NH)
43b (R⁷ = O)

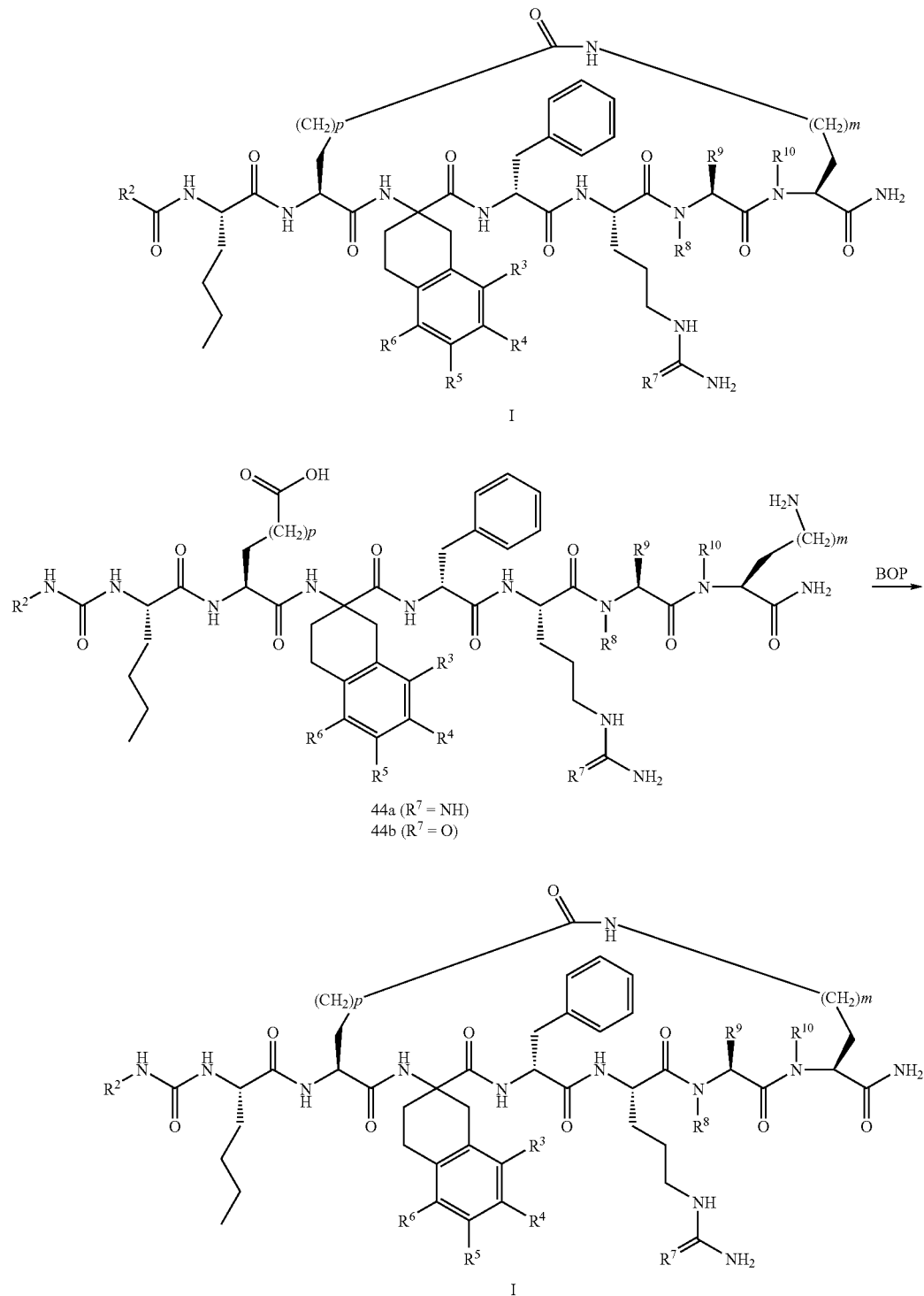
$R^2, R^3, R^4, R^5, R^6, R^8, R^9, R^{10}$, Q, p, and m are as previously described Reaction Scheme I
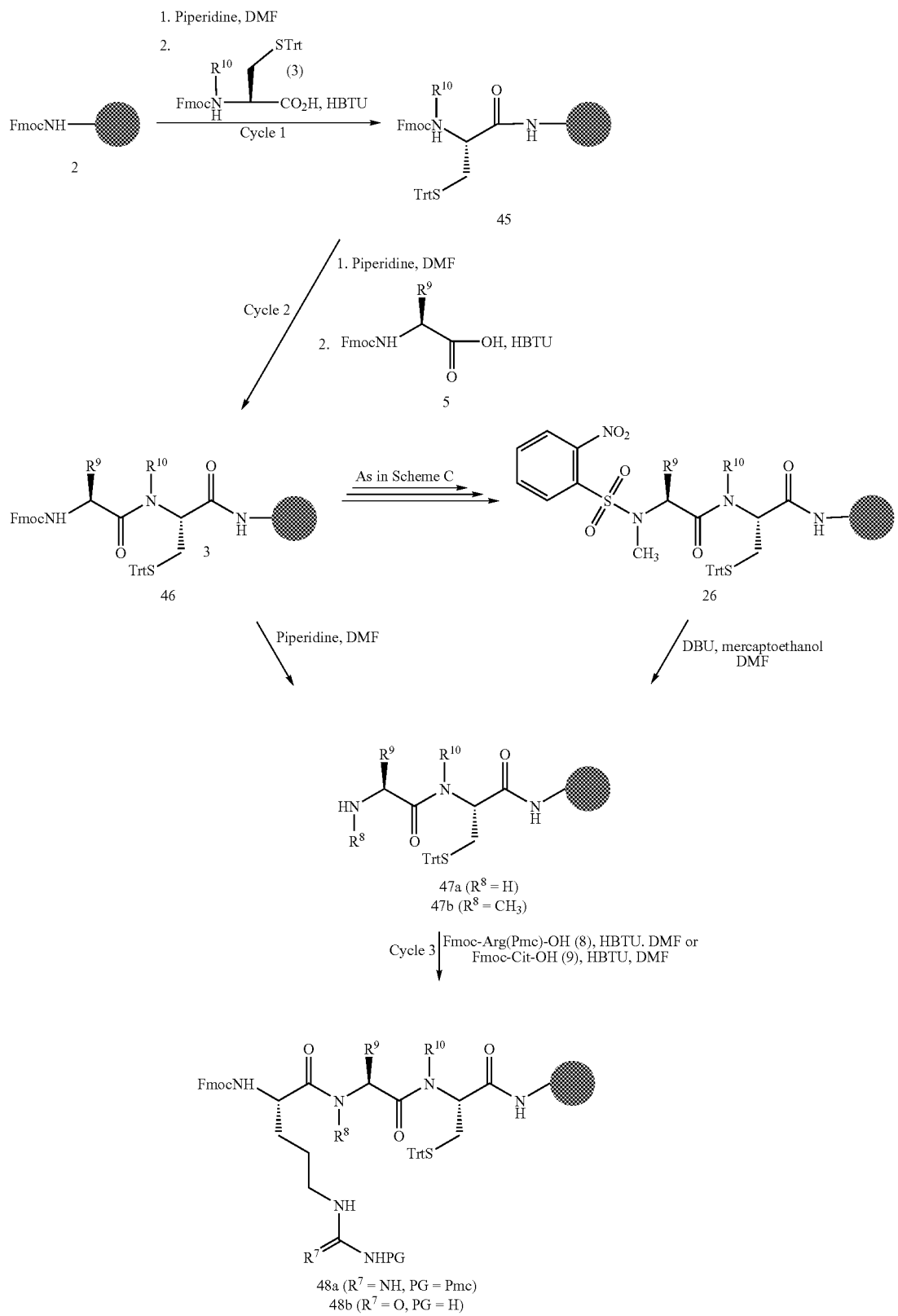
R[8], R[9], and R[10] m are as previously described.

Reaction Scheme K
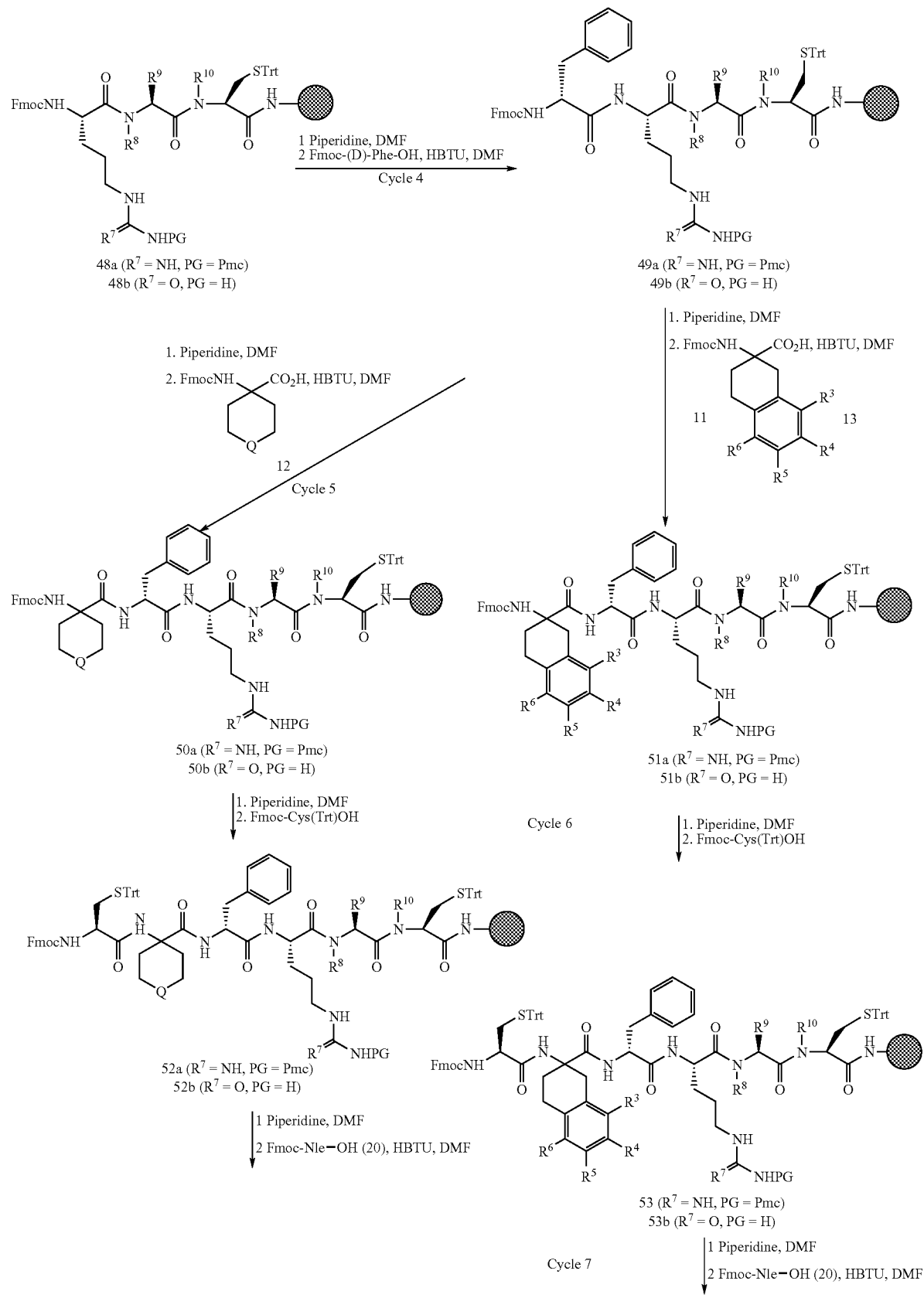

-continued
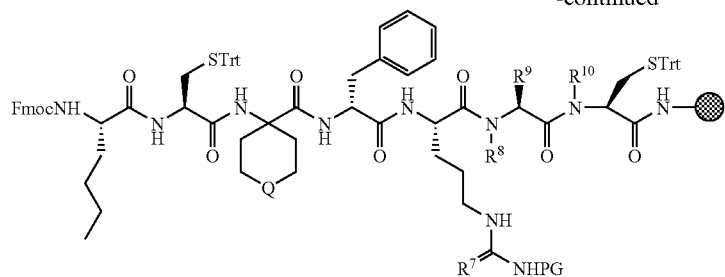
54a (R⁷ = NH, PG = Pmc)
54b (R⁷ = O, PG = H)
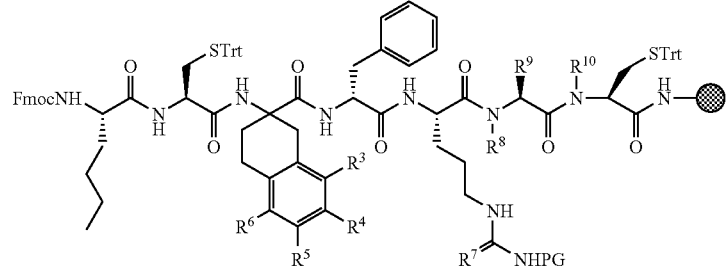
55a (R⁷ = NH, PG = Pmc)
55b (R⁷ = O, PG = H)
m, p, Q, R³, R⁴, R⁵, R⁶, R⁸ and R¹⁰ are as previously described.
Reaction Scheme L
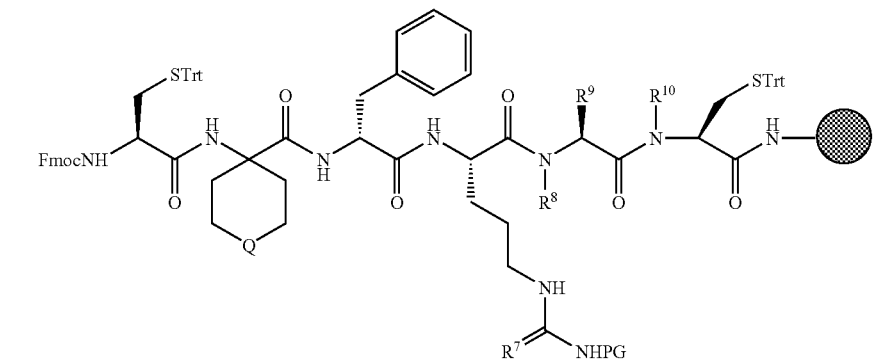
52a (R⁷ = NH, PG = Pmc)
52b (R⁷ = O, PG = H)
1. piperidine, DMF
2. N-acylation
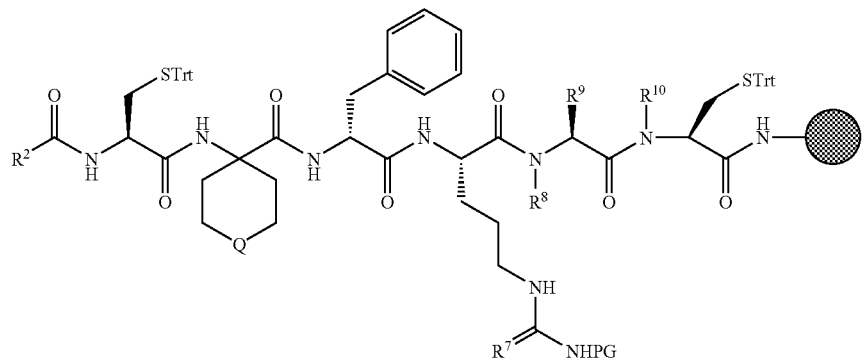
56a (R⁷ = NH, PG = Pmc)
56b (R⁷ = O, PG = H)

-continued
52a
52b
1. Piperidine, DMF
2. R² — N=C=O, DIPEA. DMF or CH₂Cl₂
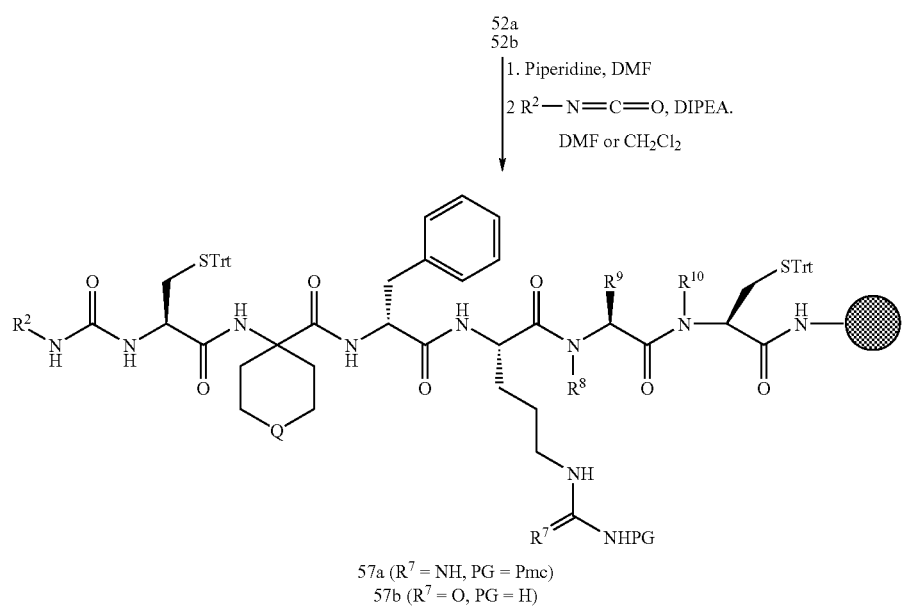
57a (R⁷ = NH, PG = Pmc)
57b (R⁷ = O, PG = H)
R², R⁸, R⁹, R¹⁰, Q and m are as previously described.
Reaction Scheme M
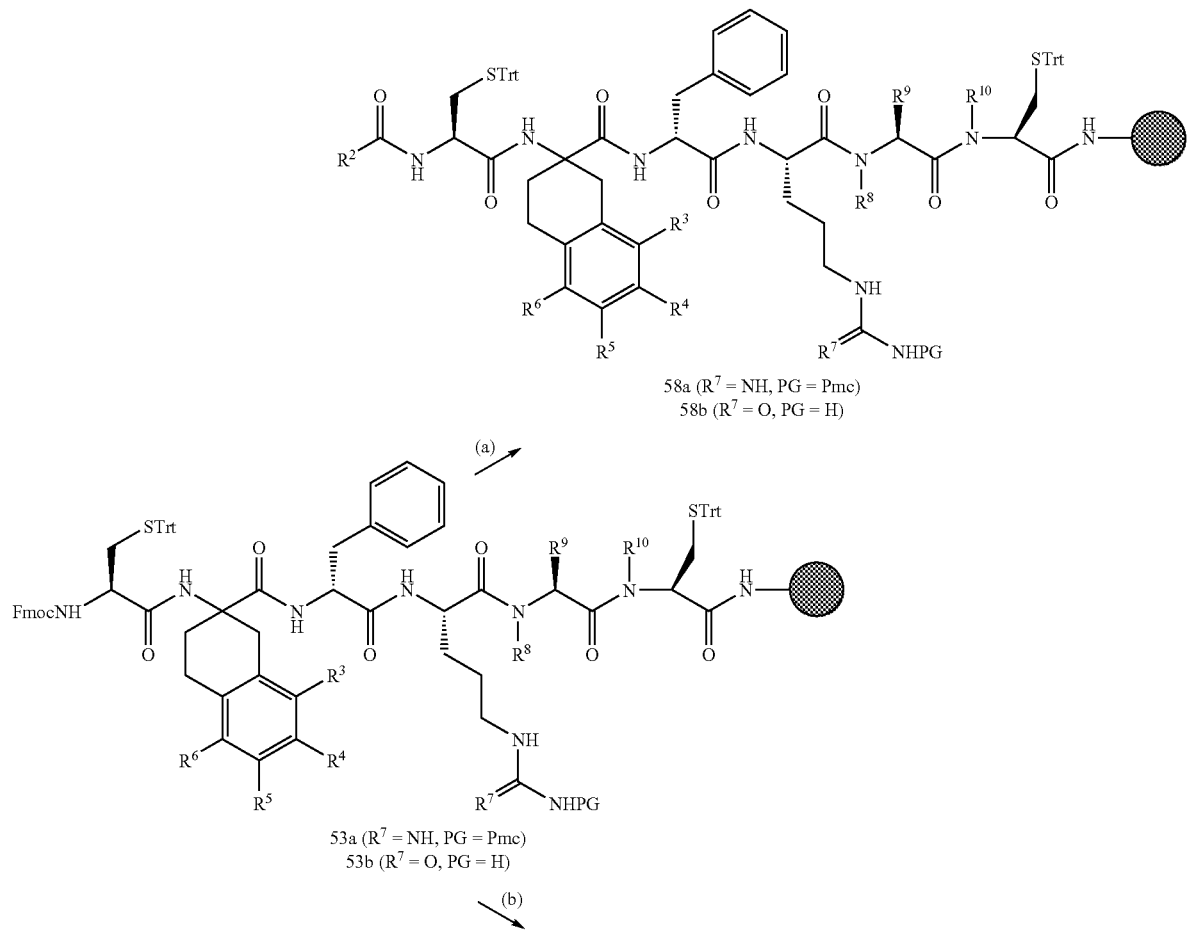
58a (R⁷ = NH, PG = Pmc)
58b (R⁷ = O, PG = H)
(a)
53a (R⁷ = NH, PG = Pmc)
53b (R⁷ = O, PG = H)
(b)

-continued
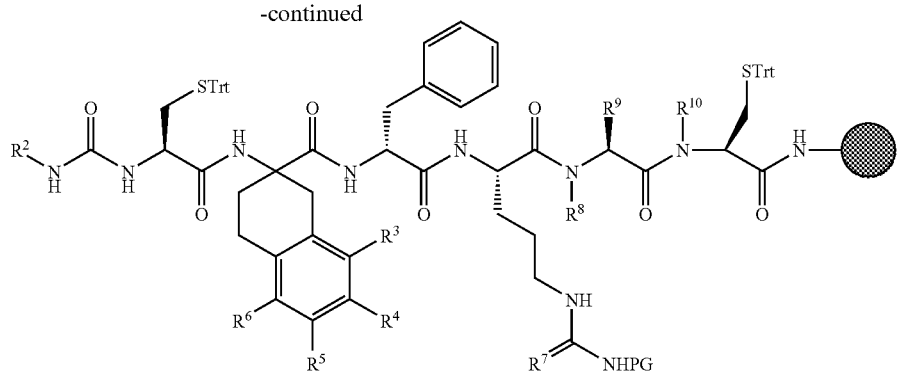
59a (R⁷ = NH, PG = Pmc)
59b (R⁷ = O, PG = H)
(a) i.piperidine, DMF ii N-Acylation
(b) i.piperidine, DMF ii R²—N=C=O
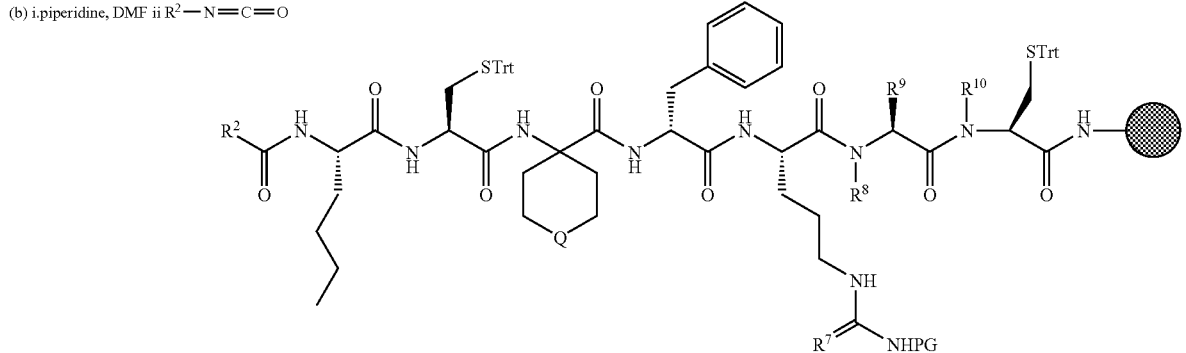
60a (R⁷ = NH, PG = Pmc)
60b (R⁷ = O, PG = H)
(a)
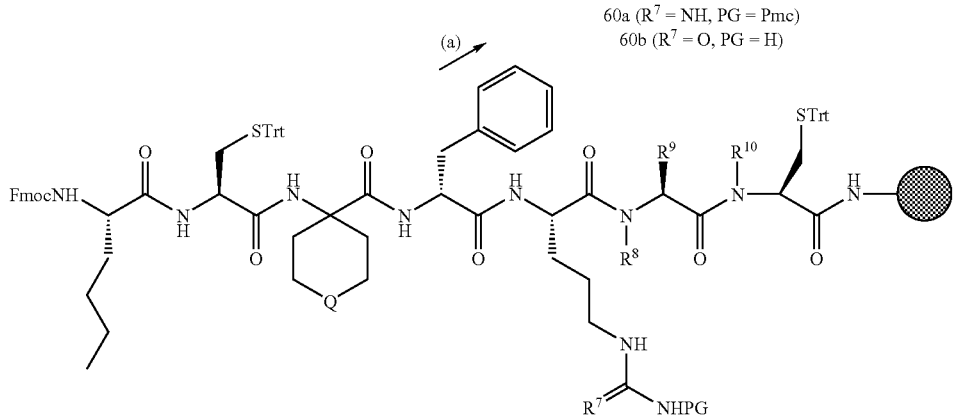
54a (R⁷ = NH, PG = Pmc)
54b (R⁷ = O, PG = H)
(b)
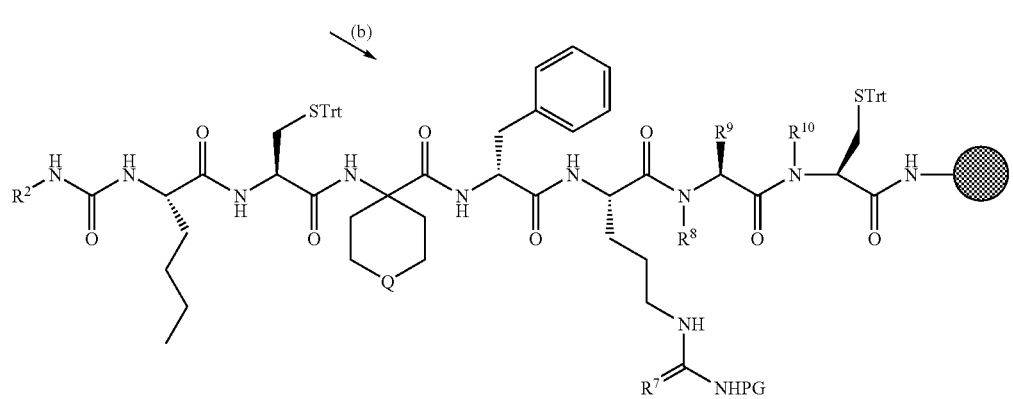
61a (R⁷ = NH, PG = Pmc)
61b (R⁷ = O, PG = H)

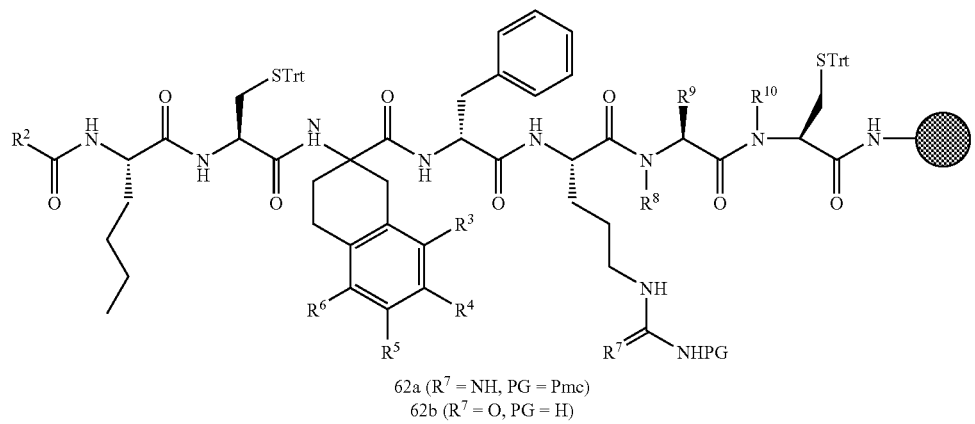
62a (R⁷ = NH, PG = Pmc)
62b (R⁷ = O, PG = H)
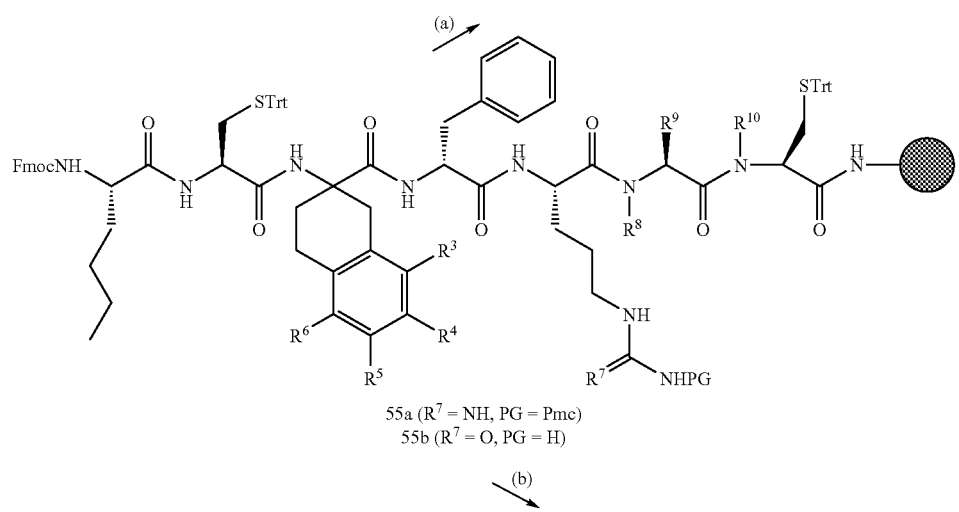
55a (R⁷ = NH, PG = Pmc)
55b (R⁷ = O, PG = H)
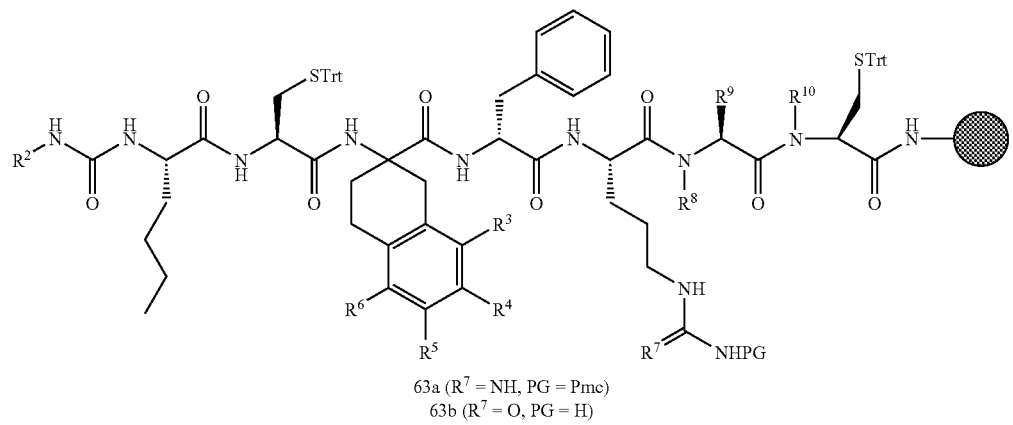
63a (R⁷ = NH, PG = Pmc)
63b (R⁷ = O, PG = H)

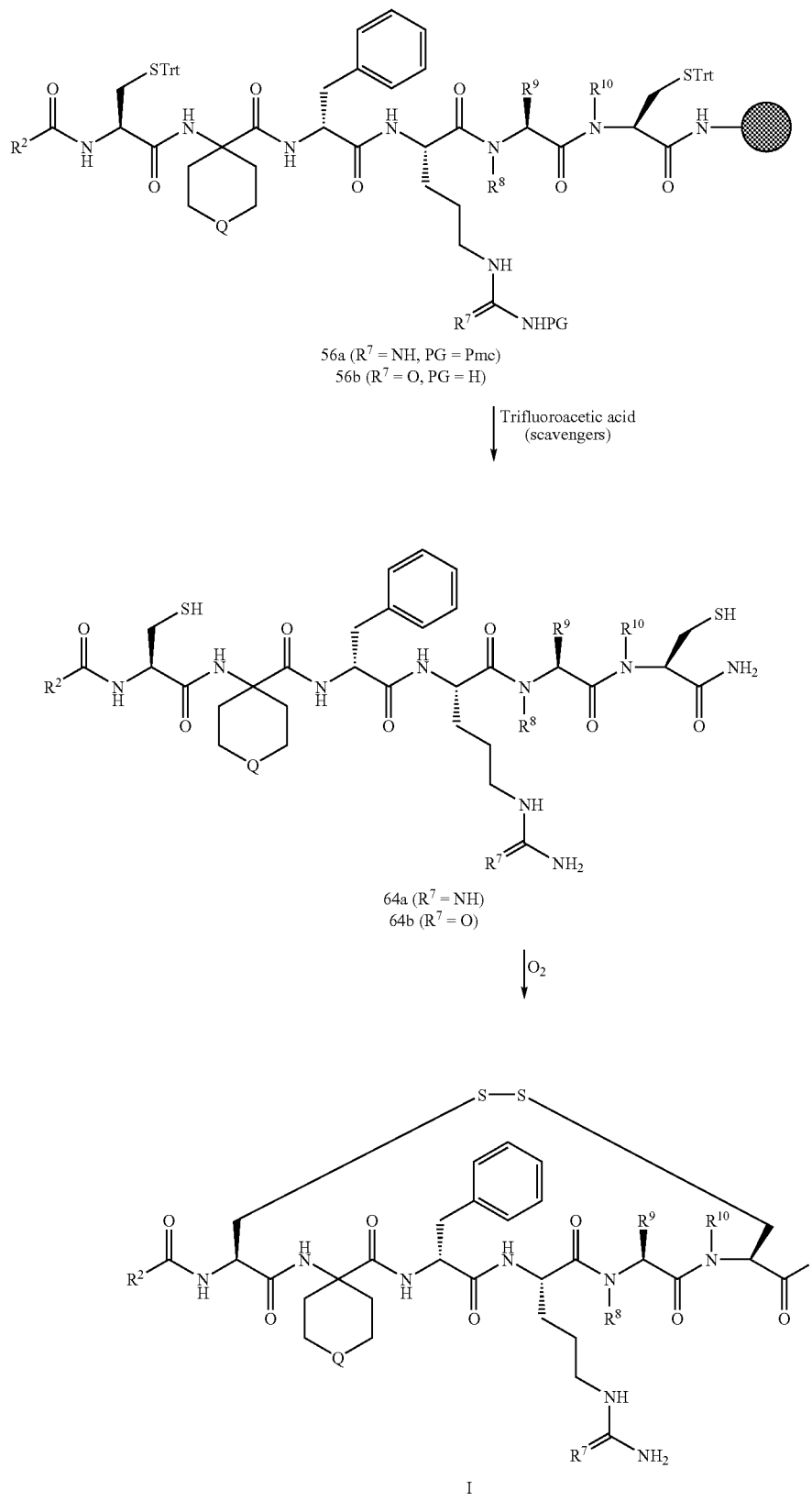
Reaction Scheme N

Reaction Scheme O
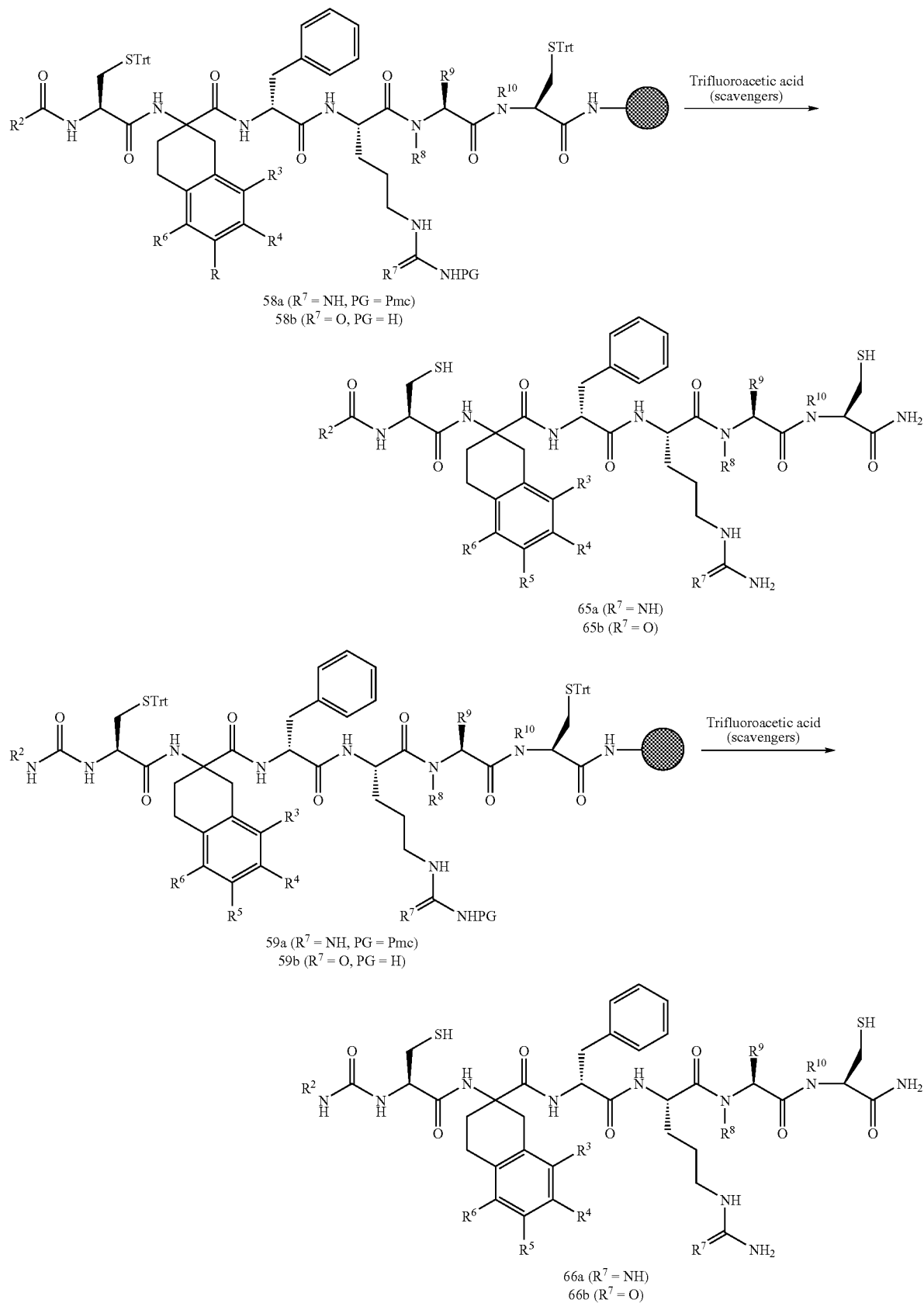

-continued
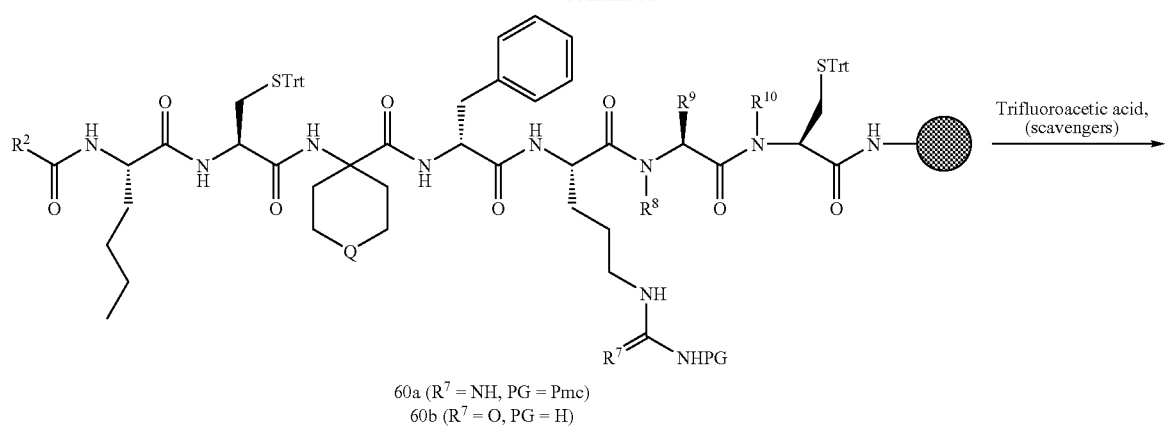
60a (R⁷ = NH, PG = Pmc)
60b (R⁷ = O, PG = H)
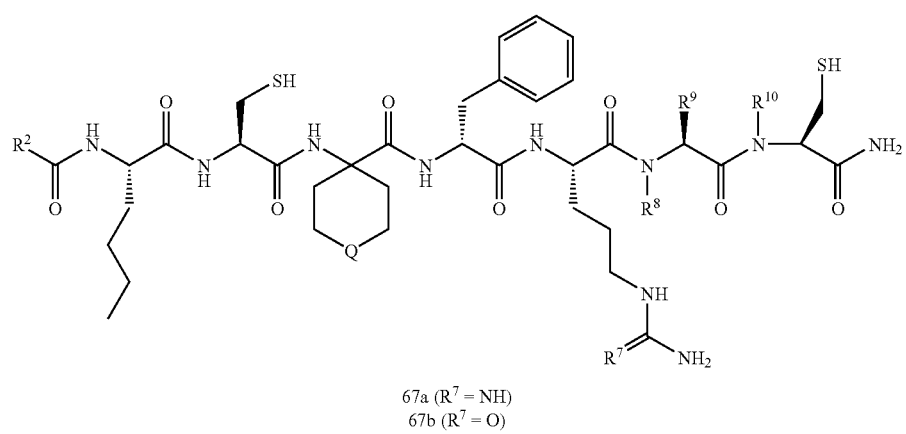
67a (R⁷ = NH)
67b (R⁷ = O)
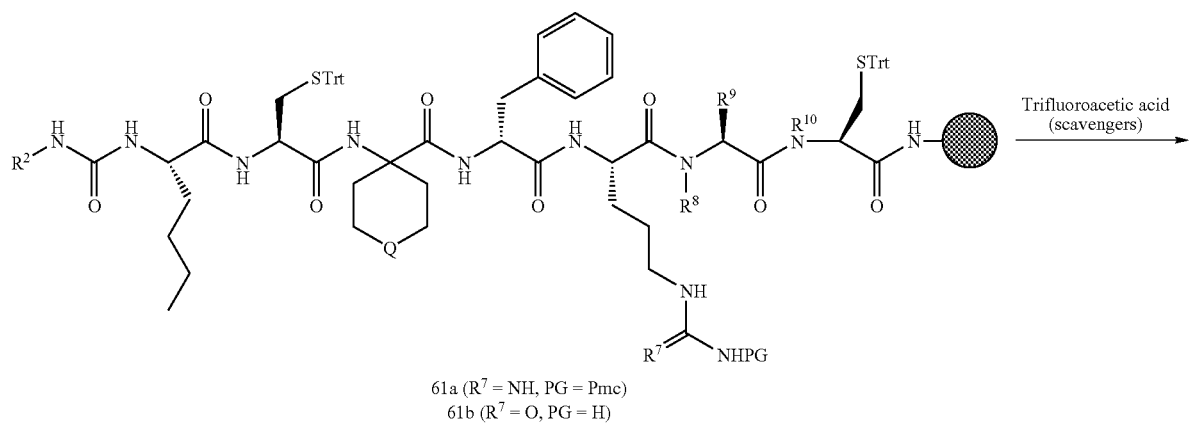
61a (R⁷ = NH, PG = Pmc)
61b (R⁷ = O, PG = H)
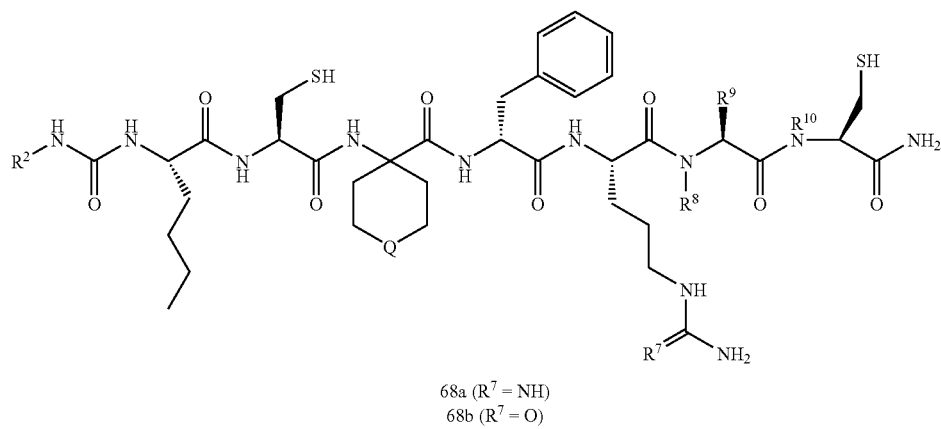
68a (R⁷ = NH)
68b (R⁷ = O)

-continued
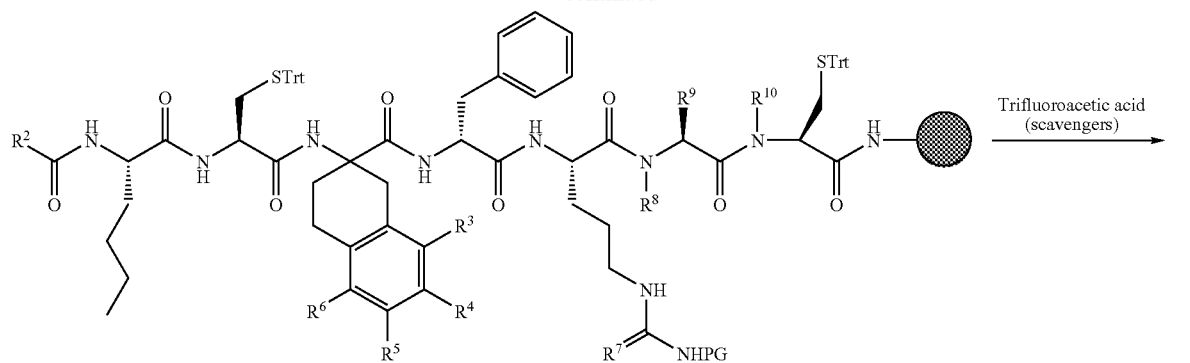
62a (R⁷ = NH, PG = Pmc)
62b (R⁷ = O, PG = H)
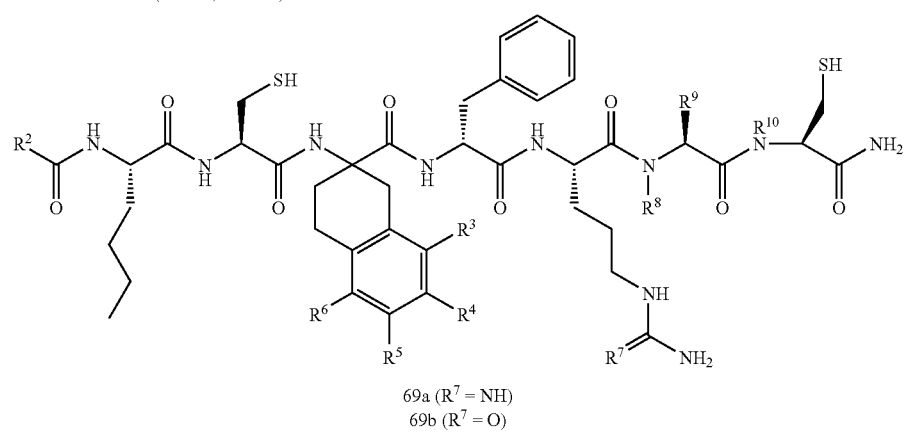
69a (R⁷ = NH)
69b (R⁷ = O)
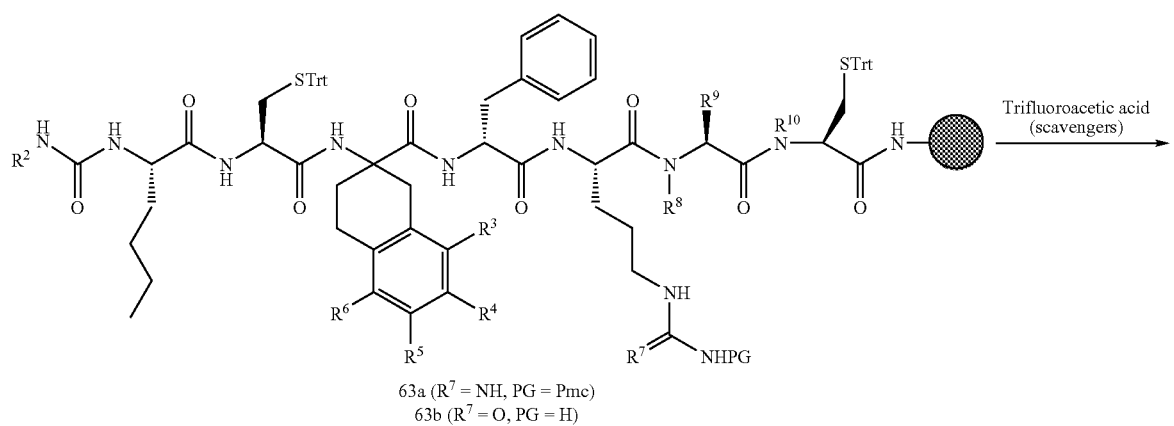
63a (R⁷ = NH, PG = Pmc)
63b (R⁷ = O, PG = H)
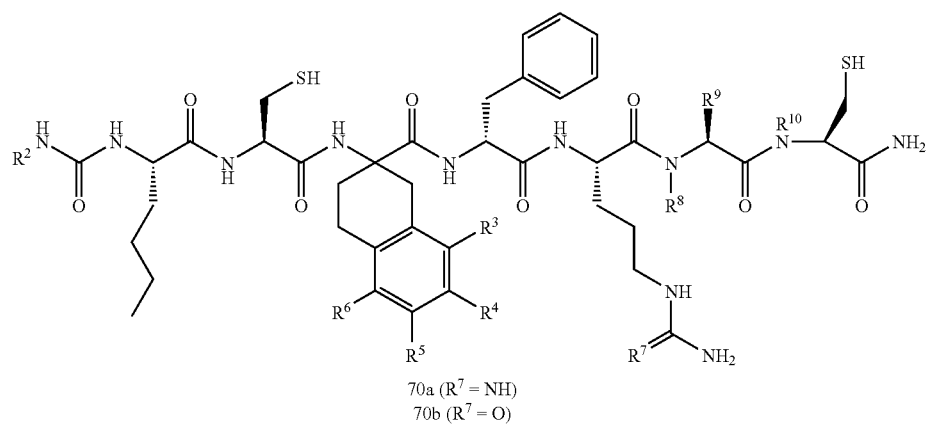
70a (R⁷ = NH)
70b (R⁷ = O)

Reaction Scheme Q
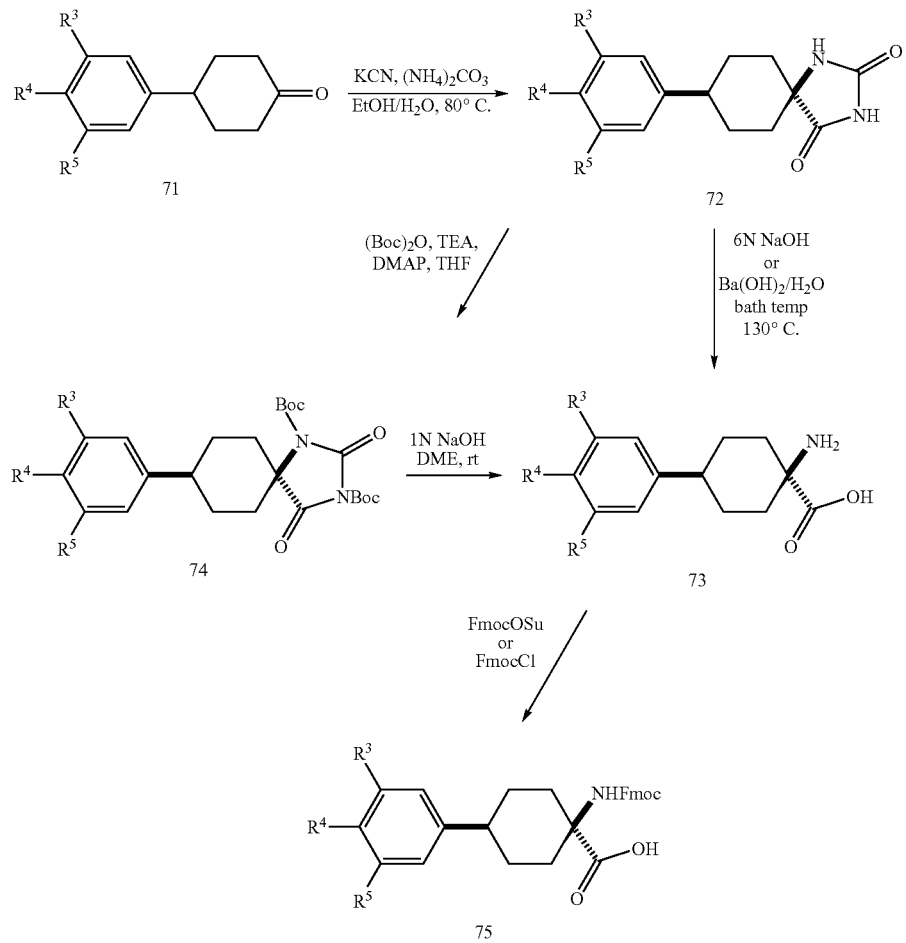
$R^3$, $R^4$, $R^5$, $R^6$ and $R^{11}$ are as previously described.
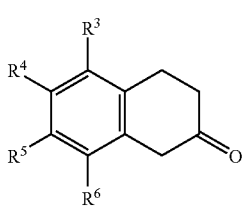

Reaction Scheme R
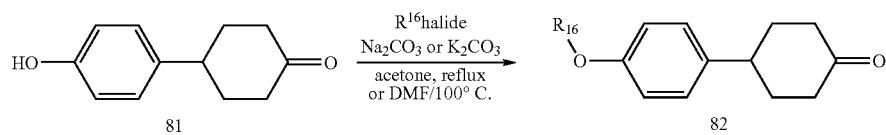
Reaction Scheme S
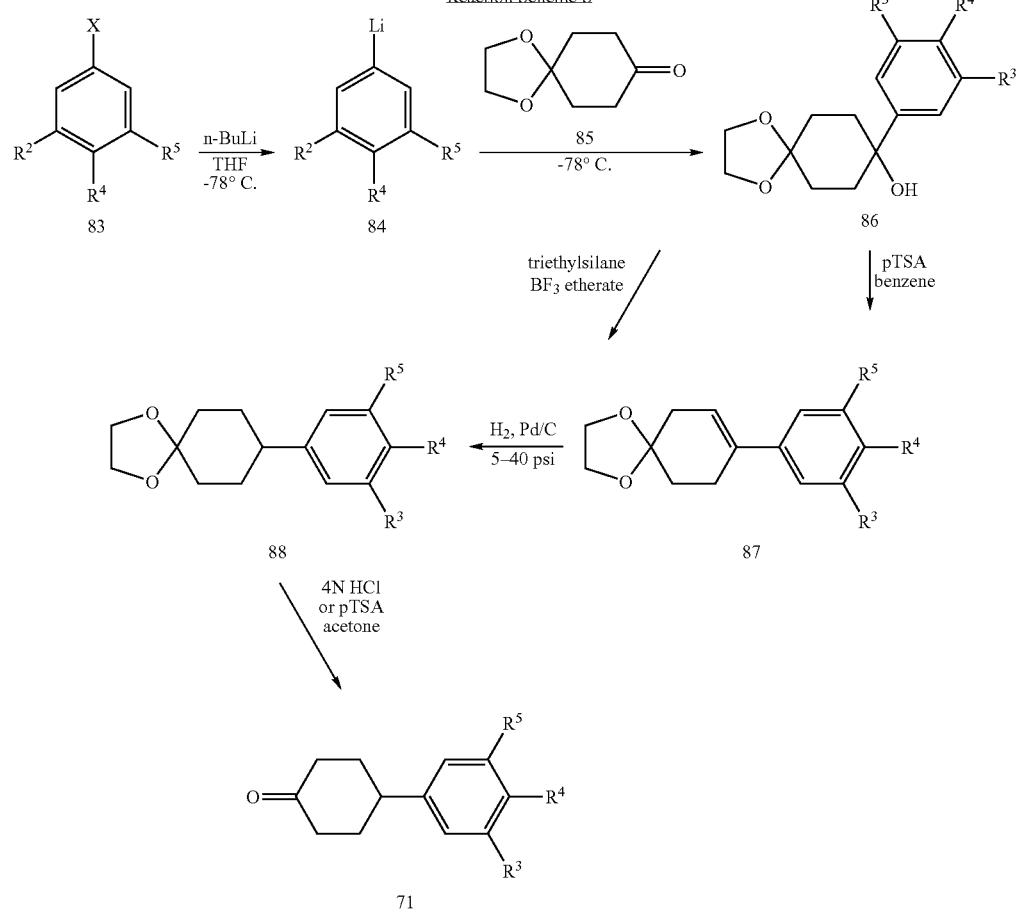
$R^3$, $R^4$ and $R^5$ are as previously described.
Reaction Scheme T
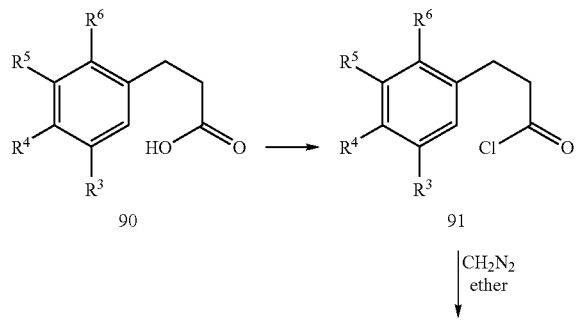

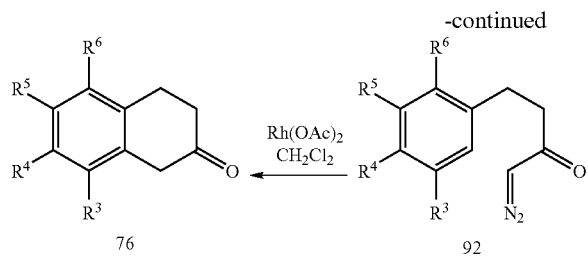

R³, R⁴, R⁵ and R⁶ are as previously described.

Reaction Scheme U

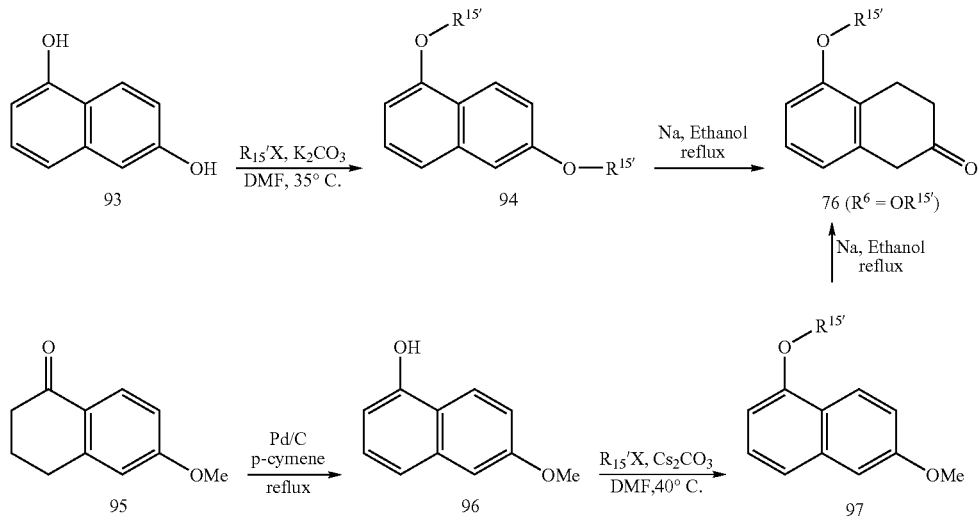

Reaction Scheme V

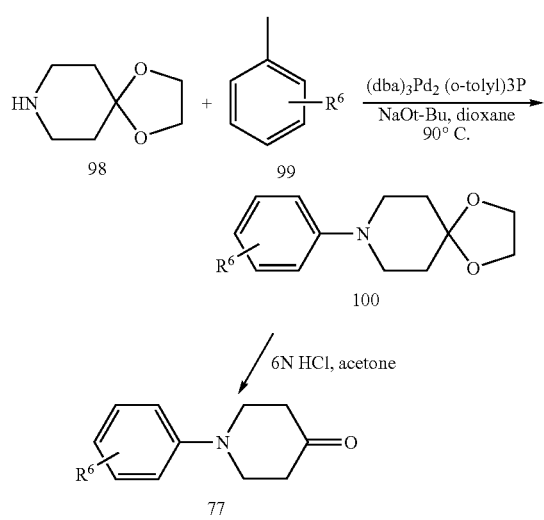

R⁶ is as previously described.

The linear peptides used herein as the penultimate intermediates in the syntheses of the cyclic peptides of the current invention (Structure 1) are prepared by using conventional solid phase peptide synthesis methodology discussed in the previous section. Each cycle consists of two procedures; the initial cleavage of the Fmoc protecting group from the terminal nitrogen in the resin bound chain followed by acylation of the amine function with an Fmoc protected amino acid. The cycle is generally carried out in accordance with the stepwise procedures outlined in Protocol 1. The deprotection is accomplished by using an organic base, for example piperazine, morpholine or piperidine, preferably piperidine in a suitable inert solvent, for example N,N-dimethylformamide (DMF) or N-methylpyrrolidone (NMP). The coupling reaction can be carried out by one of the many conditions developed for amide bond formation, for example O-benzotriazol-1-yl N,N,N',N'-tetramethyluronium hexafluorophosphate (HBTU) in the presence of an organic base, for example, diisopropylethylamine (DIPEA) in an inert solvent, for example DMF. Alternatively in the present instance, the amide group can be formed using a carbodiimide, for example, diisopropylcarbodiimide (DIC) along with an activating agent such as 1-hydroxybenzotriazole (HOBT) in a suitable inert solvent such as DMF.

In Reaction Scheme A, in the first cycle of the preparation of the linear polypeptides precursors for the cyclic peptides of Structure 1 where Z is NHCO, the Fmoc-Linker-BHA Resin represented by Structure 2 is deprotected and condensed with Fmoc-amino acids of Structure 3 to give the resin bound compounds of 4. In this syntheses of the cyclic peptides, it is required that the Fmoc-amino acid 3 contain a key structural requirement which is a suitably protected basic side chain, that when deprotected, can participate in the formation of the intramolecular amide bond. To extend the growing peptide chain, a second cycle incorporates the Fmoc-amino acids 5 to give the compounds of Structure 6. In the third cycle, treatment of the resin linked peptide 6 furnishes the intermediates of Structure 7a where R⁸ is hydrogen. The intermediates of Structure 7b where R⁸ is methyl are synthesized as shown in Scheme C.

The intermediates of Structure 7b are prepared from the compounds of Structure 7a, as shown in Scheme C. In this procedure, compounds of Structure 7a, prepared by treating compounds of Structure 6 as described in steps 1–5 of Protocol 1, are reacted with an aryl sulfonyl chloride, preferably 2-nitrobenzenesulfonyl chloride 23 to produce the compounds of Structure 24. This reaction is carried out in the presence of a proton acceptor, for example pyridine, triethylamine (TEA) or DIPEA, preferably DIPEA in a suitable inert solvent, preferably DMF. N-methylation of the formed sulfonamide group in the washed resin bound compounds of Structure 24 is accomplished under Mitsunobu conditions to produce the compound of Structure 25. In carrying out this reaction the sulfonamides of Structure 24 are reacted with methanol in the presence of diethyl azodicarboxylate (DEAD) and triphenylphosphine using methanol as solvent. After the reaction is complete, the resin bound N-methylsulfonamide of Structure 25 is washed free of residual reagents and byproducts.

In the next steps as set forth in Reaction Scheme A the 2-nitrobenzenesulfonyl residue is removed from Structure 25 by reacting 25 with 2-mercaptoethanol and the strong organic base 1,8-diazabicyclo[5.4.0]undec-7-ene (DBU) in a suitable solvent, preferably DMF, to give the resin bound intermediate of Structure 7b. The third cycle of Reaction Scheme A is completed by coupling compounds of either Structures 7a and 7b with Fmoc-Arg(Pmc)-OH (8) or Fmoc-Cit-OH (9) to give the resin bound compounds of Structure 10.

The next two cycles shown in Reaction Scheme B are carried out by first reacting peptides of Structure 10 with the amino acid Fmoc-(D)-Phe-OH to produce the compound of Structure 11 and then reacting this compound of Structure 11 with either one of the amino acid mimetics of Structure 12 or 13 to incorporate these amino acids into the resin bound peptide to give the resin bound pentapeptides of either Structures 14 and 15, depending upon which amino acid mimetics is used. The incorporation of additional amino acid containing carboxylic acid side chains into the linear pentapeptides suitable to ultimately participate in the formation of the cyclic peptides of this invention is accomplished in two ways a. As seen in Reaction Scheme B, a Fmoc amino acid with a appropriately protected acid side chain is incorporated into the resin bound pentapeptides 14 and 15. Thus in cycle 6 (Reaction Scheme B) Fmoc-Asp (OtBu)-OH (L6)-or Fmoc-Glu(OtBu)-OH (L7) is incorporated into the growing peptide chain to give the resin bound hexapeptides of Structures 18 and 19 respectively or alternatively,
  b. The resin bound pentapeptides 14 and 15 are N-capped with a cyclic anhydride of Structure 28' (Reaction Scheme F) for example, maleic anhydride or phthalic anhydride, to give the compounds of Structure 29 and 30, or alternatively,
  c. As seen in Reaction Scheme B, the resin bound hexapeptides 18 and 19 may be further reacted with an additional amino acid to form a heptapeptide before being N-capped. This is accomplished by the incorporation in the usual manner of an amino acid residue, preferably Fmoc-Nle-OH, to furnish 21 and 22.

N-capping of heptapeptide or hexapeptide produces the terminal amide function group of the compound 1. In this manner, the substitutents X, Y, $R^{12}$ and $R^1$ are produced. To N-cap the resin bound hexapeptides (18, 1) or heptapeptides (21, A2), the polypeptide is first treated with piperidine in DMF to remove the Fmoc protecting group and then is reacted with an acylating agent. As shown in Reaction Scheme D to produce the compound of Structure 1 before the formation of Z where X and Y are CH, and $R^1$ is

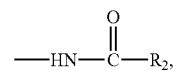

the resin bound polypeptide of Structure 18 is deprotected and N-acylated to give the resin bound amide of Structure 27 or after deprotection is reacted with an isocyanate to form the ureas of Structure 28. The N-acylation is carried out under a variety of methods well known to one skilled in the art. Among the methods used are:

(i) reaction of the terminal amino functionality with a carboxylic acid $R^2$—$CO_2H$ in a suitable solvent, such as DMF in the presence of HBTU, and an organic base, preferably DIPEA;
  (ii) reaction of the terminal amino functionality with a carboxylic acid chloride $R_2$—COCl in a suitable solvent, such as dichloromethane in the presence of an organic base, such as pyridine, TEA and DIPEA, preferably DIPEA; or
  (iii) reaction of the terminal amino functionality with a carboxylic acid anhydride of Structure 28' as shown in Reaction Scheme F. This Reaction is carried out in a suitable solvent, such as dichloromethane or DMF in the presence of an organic base, preferably DIPEA.

The N-capping reaction in Reaction Scheme D where compounds of Structure 18 are converted to ureas of Structure 28 is carried out by reacting the terminal amino group in the compounds of Structure 28 with an isocyanate $R^2$—NCO. This reaction is carried out in a suitable solvent, such as dichloromethane or DMF in the presence an organic base, preferably DIPEA. When the acylation and urea forming reactions are complete, the resin bound products 27 and 28 are washed free of residual reagents and byproducts. By using similar conditions, N-capping of the resin bound polypeptides of Structure 19, 21, and 22 is carried out by formation of the N-acylated compounds of Structures 33, 35, 37 and the ureas of Structure 34, 36 and 38 (Reaction Scheme E). However, Reaction Scheme E can be modified to provide $R^{14}$ groups other than that derived from Nle by utilizing known amino acids other than the compound of Structure 20 in Reaction Scheme B to produce compounds of Structures 21 and 22.

Reaction Schemes G and H illustrate the cleavage of remaining protecting groups in the N-capped polypeptides 29,30, 33–38 and the concomitant cleavage of the peptides from the solid support. This reaction is carried out by using a strong organic acid, preferably trifluoroacetic acid, optionally in the presence of an inert solvent such as dichloromethane and a trace (1%) of water and optionally in the presence of one or more carbocation scavengers, for example ethanedithiol, dimethyl sulfide, triethylsilane and anisole. The polypeptide cleavage solution is filtered free from the solid support, then is diluted with a suitable solvent, preferably diethyl ether, and the formed solids are collected by filtration. The solid polypeptides of Structures 39–44 produced in Reaction Scheme H may be purified by reversed phase chromatography by using a preparative C18 column.

With the appropriate functionalities thus now available to form the intramolecular amide bond, the N-capped linear polypeptides are subjected to amide forming reaction conditions well known in the art. Accordingly each in turn of the the linear peptides 31, 32 (Reaction Scheme G) and 39–44 (Reaction Scheme I) is dissolved in an inert solvent, for example DMSO, and by the addition of a tertiary amine base, for example N-methyl morpholine the solution is adjusted to an apparent pH of 8, prior to the addition of an amide forming reagent, for example BOP. The reaction is conveniently carried out at a temperature of between zero degrees and 40° C., preferably at about room temperature. The reaction is allowed to proceed until it is judged to be complete. Common methods, used by those of average skill, to monitor the progress of a reaction are for example, TLC or analytical HPLC. After removal of the reaction solvents in vacuo the crude cyclic peptides of Structure I where Z is NHCO as shown in Reaction Scheme I may be purified by reversed phase chromatography using a preparative C18 column. In this manner Compound of Structure 1 are produced where Z is NHCO Bridge.

The cyclic disulfide peptides of Structure 1 where Z is S—S are prepared by methodologies, outlined in Reaction Schemes similar to those described above in Reaction Schemes A through H for the preparation of the lactams of Structure 1 where Z is NHCO. The penultimate linear polypeptides are assembled in a like manner, with the exception that amino acids, that contain protected thiol side chain residues, for example Fmoc-Cys(Trt)-OH, are incorporated at the appropriate positions of the growing resin bound polypeptide, preferably in cycle 1 and 6. This preparation of the resin bound linear polypeptides is illustrated in Reaction Schemes J and K. As previously described and shown in Scheme L, the resin bound linear hexapeptide 52, after removal of the Fmoc protecting group group, may be N-capped either by acylation to give 56 or by reaction with an isocyanate to form the urea 57. In the same way the resin bound hexapeptide 53, and the resin bound heptapeptides 54 and 55 are converted to the corresponding N-acylated derivatives 58, 60 and 62 and the urea derivatives 59, 61 and 63 (Reaction Scheme M).

In Reaction Scheme N, the N-capped resin bound linear hexapeptide 56 is treated with a strong acid, preferably trifluoroacetic acid, optionally in the presence of an inert solvent such as dichloromethane and optionally in the presence of one or more carbocation scavengers, for example ethanedithiol, dimethyl sulfide, triethylsilane and anisole. This causes cleavage of all side chain protecting groups as well as cleavage of the linear peptide from the solid support. The reaction is conveniently carried out at a temperature of between 0° C. and 35° C., preferably at room temperature. The polypeptide cleavage solution is filtered free from the solid support, then is diluted with a suitable solvent, preferably diethyl ether, and the formed solids are collected by filtration. The solid polypeptide of Structure 64 thus produced optionally may be purified by reversed phase chromatography by using a preparative C18 column. The linear hexapeptide 64 is then treated under oxidative conditions well known to one skilled in the art, that can induce thiols to form a disulfide bond. Accordingly a dilute aqueous solution of 64 is adjusted to pH 8.0 using a moderately weak inorganic base, preferably ammonium hydroxide, and then oxygen was bubbled into the solution until the cyclization was judged to be complete, using standard methods, for example TLC or HPLC. After removal of the reaction solvents by lyophillization, the crude cyclic peptide (I; Z=S—S) prepared and isolated in this manner, may be purified by reversed phase chromatography by using a preparative C18 column.

Under similar conditions to those described hereinbefore in connection with Reaction Schemes H and I, the resin bound linear polypeptides 58–63 as shown in Reaction Schemes O and P, are deprotected and cleaved from the solid support to give the linear peptides 65–70 (Reaction Scheme 0), which are then oxidatively cyclized, as described above, to give the corresponding compounds of Structure 1 (Reaction Scheme P).

The Fmoc-amino acids used in the preparation of the peptides described above, as well as the acylating agents and isocyanates used to N-cap the polypeptides are known compounds that are commercially available. The Fmoc-amino acids 12, including its species, the compound of Structure 13, used in Reaction Scheme B, are prepared as described herein by methods that are well known to those of ordinary skill in the practice of organic chemistry. In Scheme Q, the preparation of Fmoc-amino acid species of the compound of Structure 12 from cyclic ketones is outlined. These species which are the Structure 12 and Structure 13, 79 and 80 are prepared in the same way as the species of Structure 75 as outlined in the procedure of Scheme Q. The 4-phenylcyclohexanones of Structure 71 are converted to the hydantoins of Structure 72 by treatment with ammonium carbonate and potassium cyanide. The reaction is conveniently carried out in aqueous ethanol mixture at a temperature of from 50° C. to 90° C., preferably between 80° C. and 90° C. Direct hydrolysis of the hydantoins to the amino acids of Structure 73 require a prolonged treatment with strong base, for example with 6N sodium hydroxide solution or with barium hydroxide at reflux temperature. Alternatively, compounds of Structure 72 can be converted to the bis-Boc derivatives of Structure 74. The reaction is carried out using tert-butyl dicarbonate [(Boc)$_2$O] in an inert solvent, preferably tetrahydrofuran (THF), in the presence of an organic amine base, preferably TEA and a catalyst, 4-dimethylaminopyridine (DMAP) at a temperature of from zero degrees to room temperature, preferably at room temperature. The bis-Boc hydantoins of Structure 74 are readily converted to the amino acids of Structure 73. The reaction is accomplished using 1N sodium hydroxide in an inert solvent, preferably dimethoxyethane (DME) at from zero degrees to 50° C., preferably at about room temperature. Protection of the amino functionality with an Fmoc group in a compound of Structure 73 is carried out under a variety of reaction conditions to give the compound of Structure 75 which is the Fmoc-amino acid species of the compound of Structure 12. The reaction may conveniently be performed by treatment of a solution of the amino acid 73 in a mixture of THF or dioxane, preferably dioxane and aqueous sodium carbonate with 9-fluorenylmethoxychloroformate (FmocCl) at a temperature of from zero degrees to room temperature, preferably at room temperature. Alternatively, N-(9-fluorenylmethoxycarbonyloxy)succinimide (FmocOSu) is added to a solution of the amino acid 73 in aqueous acetonitrile containing an organic tertiary amine base, preferably TEA. The reaction is run at from zero degrees to room temperature, preferably at room temperature. In another variation of the procedure, DME is evaporated from the hydrolysis mixture in the conversion of 74 to 73 and the reaction is adjusted to ~pH 11. The resulting solution of the sodium salt of 73 is then treated in situ with FmocOSu or FmocCl in dioxane at a temperature of from zero degrees to room temperature, preferably at room temperature. In the same manner, as in Reaction scheme Q, the tetralones 76, the N-aryl-4-ketopiperidines 77, and the cyclohexanone derivatives 78 can be converted to the corresponding Fmoc-amino acids of Structures 13, 79 and 80, all of which along with 73 form subgenera of Structure 12 utilized in Reaction Scheme B.

In Reaction Scheme Q, the compounds of Structure 73 where $R^4$ represents a linear or branched lower alkoxy and both $R^2$ and $R^3$ is hydrogen in the sub genus Structure 82, may be prepared by O-alkylation of the compound of Structure 81 as shown in Reaction Scheme R. Where $R^{16}$ represents an unbranched lower alkyl moiety, the alkylation is carried out by using a primary alkyl halide of Structure $R^{16}$ halide in the presence of an alkali metal carbonate, for example, sodium or potassium carbonate. The alkyl halide may be a chloro, bromo or iodo derivative, preferably an alkyl iodide. The reaction may be conveniently carried out in an inert solvent that promotes $SN_2$ displacement reactions, for example acetone, 2-butanone or N,N-dimethylformamide, preferably acetone, at a temperature of from room temperature to the reflux temperature of the solution, preferably the reflux temperature. When $R^{16}$ represents a branched lower alkyl group, e.g., 2-propyl, the alkylation of the compound of Structure 81 to produce the compound of Structure 82 is carried out by using a secondary alkyl halide of Structure $R^{16}$ halide in the presence of an alkali metal carbonate, e.g., potassium carbonate. The secondary alkyl halide is preferably a secondary alkyl iodide, for example, 2-iodopropane. The reaction may be conveniently carried out in an inert solvent, preferably N,N-dimethylformamide, at a temperature of from room temperature to the reflux temperature of the solution, preferably at about 100° C.

4-Arylcyclohexanones of Structure 71 which are the starting materials in Reaction Scheme Q can be prepared by methods that are well known to one of ordinary skill in the practice of organic chemistry. As outlined in Scheme S, treatment of the aryl halides of Structure 83, where $X^1$ represents bromo or iodo with an alkyl metal reagent, preferably t-butyl lithium, results in a transmetalation reaction to give the corresponding aryl lithium of Structure 84. The reaction is conveniently carried out at −78° C. by the addition of a solution of the alkyl lithium into a solution of a compound of Structure 83 an inert anhydrous solvent, such as diethyl ether or tetrahydrofuran, preferably tetrahydrofuran. The aryl lithium of Structure 84 produced in this manner, is then reacted in situ with a solution of the monoketal of cyclohexane-1,4-dione (85) in an suitable inert solvent, for example tetrahydrofuran, while the reaction temperature is maintained below −60° C., preferably at about −78° C. to give the carbinols of Structure 86. The compounds of Structure 87 are obtained by the dehydration of the carbinols of Structure 86. The reaction is conveniently carried out using a strong organic acid catalyst, preferably p-toluenesulfonic acid in an inert solvent, for example benzene or toluene, preferably benzene, at the reflux temperature of the solvent. The formed water is removed from the reaction mixture by means of a Dean Stark apparatus to enable the reaction to go to completion. Compounds of Structure 88 are produced by hydrogenation of the olefins of Structure 87. The reaction is conveniently carried out using a noble metal catalyst, for example palladium on carbon, in a hydrogen atmosphere in an inert solvent, for example ethanol or ethyl acetate. The hydrogenation is usually carried out at room temperature and 40 psi of hydrogen, however if the aryl ring in Structure 87 contains a group prone to hydrogenolysis, e.g., if $R^3$, $R^4$ or $R^5$ represents chloro, the reaction pressure is kept at about 5 psi. Compounds of Structure 88 may be also obtained directly from carbinols of Structure 86 by reductive elimination of the hydroxyl group. In this reaction a solution of the compound of Structure 86 ($R^3=R^4=H$ and $R^1=OMe$) in an inert solvent, for example dichloromethane, is treated with a Lewis acid, such as boron trifluoride etherate, and a reducing agent, for example triethylsilane, at a temperature of from zero degrees to room temperature. Removal of the ketal protecting group in compounds of Structure 88 gives the ketone of formula 71, which is the starting material for Reaction Scheme Q for preparing the Fmoc-amino acid species of Structure 75 of the compound of Structure 12. The reaction is conveniently carried out in acetone or 2-butanone, preferably acetone under acid catalysis, for example 4N hydrochloric acid or p-toluenesulfonic acid at from room temperature to the reflux temperature of the reaction mixture, preferably at the reflux temperature.

5-Substituted-beta-tetralones of Structure 76 shown in Reaction Scheme Q which is the starting material for preparing compound of Structure 13 are known compounds, or if they are not known they can be prepared by methods that are well known to one of ordinary skill in the field of organic chemistry. In the present instance, compounds of Structure 76 are basically prepared by two methods outlined in Reaction Schemes T and U. As shown in Scheme T, a 2-substituted hydrocinnamic acid of Structure 90 is converted to the corresponding carboxylic acid chloride of Structure 91. This conversion can be carried out by several methods, for example by treatment of the hydrocinnamic acid with oxalyl chloride, optionally in the presence of a catalytic amount of N,N-dimethylformamide, in an inert solvent, such as benzene or dichloromethane, preferably dichloromethane. The reaction may be conveniently carried out at a temperature of from zero degrees to room temperature, preferably at room temperature. Alternatively the compound of Structure 90 is reacted with an acyl chloride forming reagent such as sulfuryl chloride in an inert solvent, for example benzene or toluene, preferably toluene at a temperature between room temperature to the reflux temperature of the solution, preferably at the reflux temperature. The diazoketone of Structure 92 is prepared by treatment of the thus formed acyl halide of Structure 91 in an inert solvent, e.g., dichloromethane with an excess of a freshly prepared ethereal solution of diazomethane. The combination of reagents is conveniently carried out at ice bath temperature and the reaction is then allowed to proceed at a temperature of from zero degrees to room temperature, preferably at room temperature. As shown in Reaction Scheme T, cyclization of the diazoketone of Structure 92 to furnish the tetralone of Structure 76 is promoted by rhodium (II) acetate dimer in an inert solvent, e.g., dichloromethane. The reaction is normally carried out at from room temperature to the reflux temperature of the solution, preferably at the reflux temperature.

Compounds of Structure 76, which is a starting material in Reaction Scheme Q, wherein $R^6$ represents a linear or branched lower alkoxy group can be prepared as shown in Reaction Scheme U from compounds of Structure 93. In Reaction Scheme U, the compounds of Structure 94 where $R^{15'}$ is an unbranched lower alkyl moiety are prepared by per-O-alkylation of the naphthalenediol of Structure 93 with a primary alkyl iodide or bromide, preferably an iodide, in the presence of a base such as an alkali metal carbonate, for example, sodium or potassium carbonate. The reaction may be carried out in an inert solvent, preferably N,N-dimethylformamide at a temperature of from room temperature to 100° C., preferably at 35° C. The compounds of Structure 97 where $R^{15'}$ is a branched lower alkyl are prepared in two steps from the 2-tetralone of Structure 94. The tetralone of Structure 95 is subjected to dehydrogenation in the presence of a noble metal catalyst, such as palladium metal (10% on carbon) in a suitable high boiling solvent such as p-cymene to give the aromatized compound of Structure 96. The naphthol of Structure 96 is then O-alkylated with a secondary alkyl iodide in the presence of a base such as an alkali metal carbonate, preferably cesium carbonate to furnish the compound of Structure 97. The reaction may be conveniently carried out in an inert solvent, preferably N,N-dimethylformamide at a temperature of from room temperature to 100° C., preferably at about 40° C.

The tetralones of Structures 76 are produced by reduction of the compounds of Structures 94 and 97 under dissolving metal conditions, followed by the acid catalyzed hydrolysis of the intermediate enol ethers. The transformation is conveniently carried out by the portionwise addition of a large excess of an alkali metal, such as sodium or potassium, preferably sodium, to a boiling solution of the substrate in an lower alcohol, preferably ethanol until the starting material is consumed. The tetralones of Structures 76 are obtained by treatment of a solution of the isolated intermediate enol ethers with a strong acid catalyst, preferably p-toluenesulfonic acid. The hydrolysis may be conveniently carried out in a mixture of a lower alcohol, preferably ethanol, and water at a temperature of between room temperature and the reflux temperature of the solution, preferably at the reflux temperature.

In preparing the compounds of Structure 77, utilized in Reaction Scheme Q as starting materials in producing the compounds of formula 79 which are the Fmoc-amino acid species of the compound of Structure 12, the compound of Structure 98 is used as a starting material. This is shown in Reaction Scheme V. In Reaction Scheme V, compounds of Structure 100 can be prepared by reactions that are known per se. For example, they can be prepared by coupling the secondary amine of Structure 98 with an aryl bromide or iodide, preferably an aryl iodide of Structure 99 (Reaction Scheme V). The coupling reaction is catalyzed by a noble metal catalyst, preferably tri(dibenzylideneacetone) dipalladium, in the presence of a chelating phosphine ligand, preferably tri-o-tolylphosphine, and a hindered alkoxide base such as sodium tert-butoxide. The reaction is conveniently carried out in an inert atmosphere using an anhydrous solvent such as dioxane or toluene, preferably dioxane, at a temperature of from 60° C. to the reflux temperature, preferably at 90° C. Removal of the carbonyl protecting group in compound 100 to give compounds of Structure 77 can be carried out by a variety of methods well known in the field of organic chemistry. For example, the deprotection can be achieved by treatment of a solution of compound 100 in a low boiling ketone such as acetone or 2-butanone with an aqueous mineral acid solution, for example 6N hydrochloric acid at a temperature of from room temperature to the reflux temperature of the mixture, preferably at the reflux temperature. The compound of Structure 100 when treated in this manner with an aqueous mineral acid forms, in Reaction Scheme V, the compound of Structure 77. The compound of Structure 77, as demonstrated in the discussion of Reaction Scheme Q is the intermediate for the compound of Structure 79 which is the species of acid of Structure 12 wherein Q is

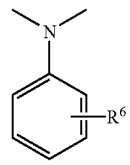

In Reaction Scheme A, amino acids of Structure 5 are known compounds where $R^9$ is

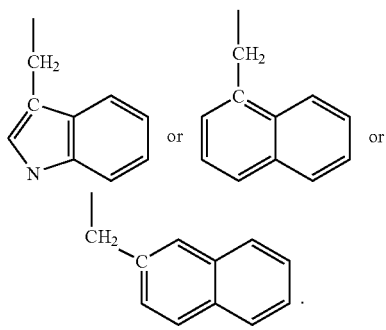

On the other hand, amino acids of Structure 5 where $R^{17}$ in $R^9$ is lower alkyl, i.e., where $R^9$ is

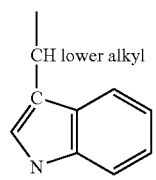

are prepared from a compound of formula 101 via Reaction Scheme V as follows:

Reaction Scheme W

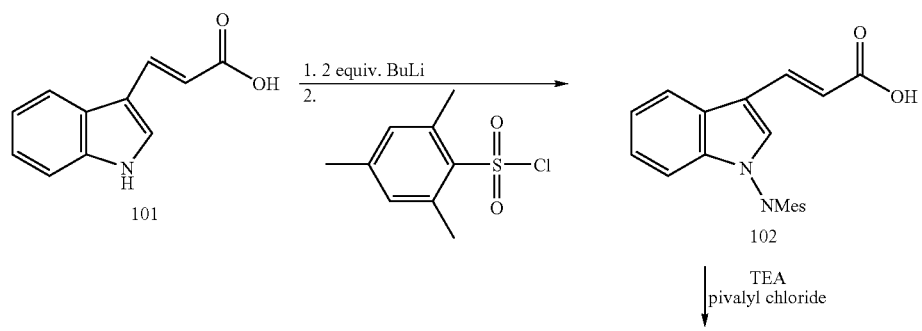

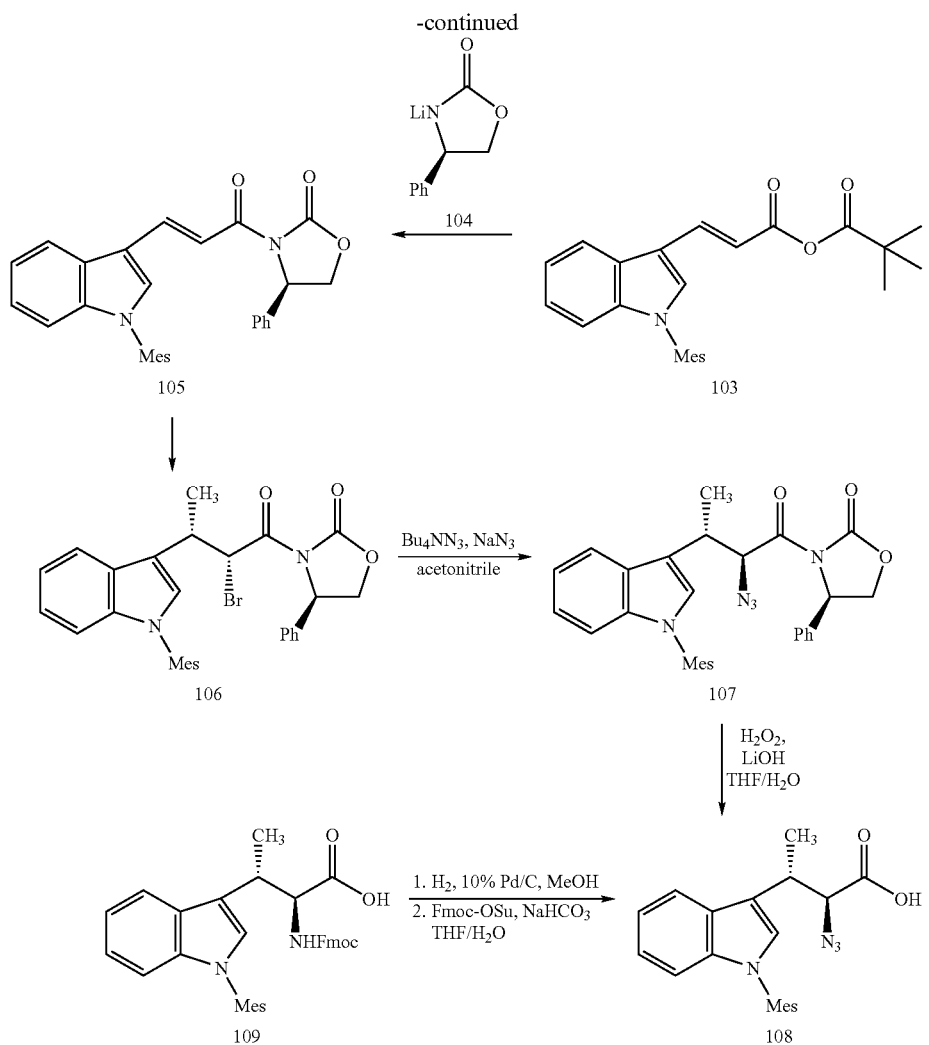

As shown in Reaction Scheme W, β-methyl(Nin-Mes) tryptophan 109 was prepared by using the method previously described by Boteju, L. W., Wenger K., and Hruby, V. J. *Tet.Lett.*, 33, 7491 (1992). In the first step the nitrogen in trans-indole-3-acrylic acid 101 is protected by conversion to the corresponding mesitylenesulfonamide 102. The reaction is carried out by treating the indole acid 101 with a excess (>2 equiv.) of a solution of an alkyl or aryl lithium reagent, for example phenyl lithium or n-butyllithium, preferably n-butyllithium in an inert solvent, preferably tetrahydrofuran, at a temperature of from −40° C. to about −100° C., most conveniently at −78° C. While the reaction is maintained at about −78° C., the formed dilithiated species is then reacted with mesitylenesulfonyl chloride to furnish the mesitylenesulfonamide 102. The N-protected indole acrylic acid 102 is then coupled with the chiral auxiliary (R)-4-phenyl-2-oxazolidinone (preparation see Nicolas et al., *J. Org Chem.* 1993, 58, 766–770.) as its N-lithiated species 104 to give the chiral acrylamide 105. The coupling was accomplished via a mixed anhydride formed from 102. To form the mixed anhydride 103, the N-protected indole acrylic acid 102 was reacted with a suitable acyl chloride, for example t-butyl chloroformate, 2,4,6 trichlorobenzoyl chloride or pivaloyl chloride, preferably pivaloyl chloride in the presence of an tertiary amine base, for example triethylamine or diisopropylethylamine, preferably triethylamine. The criteria that make possible the choice of a suitable acyl chloride to form the anhydride 103 are well established and are known by one of ordinary skill in organic chemistry. The anhydride formation is run in an inert solvent, for example tetrahydrofuran at an initial temperature of between −100° C. and 0° C., preferably at about −78° C. The reaction is allowed to go to completion at a temperature of between −78° C. and 0° C. degrees, preferably at about 0° C. The thus formed mixed anhydride 103 is then reacted in situ with a solution of N-lithiated (R)-4-phenyl-2-oxazolidinone 104, previously prepared by treating a solution of (R)-4-phenyl-2-oxazolidinone in an inert solvent, for example tetrahydrofuran, with an equimolar amount of a solution of an alkyl or aryl lithium reagent, for example phenyl lithium or n-butyllithium, preferably n-butyllithium in an inert solvent, for example, hexane at a temperature of between −100° C. and zero degrees, preferably at about −78° C. The coupling reaction which yields the chiral acrylamide 105 is carried out at an initial temperature of between −100° C. and zero degrees, preferably at about −78° C., and after all the reagents are combined the reaction is allowed to proceed at a temperature of between −78° C. and room temperature, preferably at about room temperature.

The highlight of the transformation of the chiral acrylamide 105 into 106, is the controlled generation of the two new contiguous chiral centers present in 106. The reaction involves the stereoselective 1,4-conjugate addition (Michael addition) of a methyl cuprate, formed in situ from cuprous bromide-dimethylsulfide complex and methyl magnesium bromide, to the Micheal acceptor, the α,β-unsaturated carbonyl system present in 105. The resultant metal-chelated enolate is then directly halogenated with a halogenating agent, preferably N-bromosuccinimide, to give 106. Again, as in the case of the Michael addition, the incorporation of the bromo atom is stereoselective, controlled by the bulky phenyl group on the chiral auxiliary which effectively shields the si face of both the α,β-unsaturated acyloxazolidinone system and the intermediate metal-chelated enolate from attack from incoming reagents. To prepare the methyl cuprate, a solution of methyl magnesium bromide in diethyl ether is added to a solution of cuprous bromide-dimethylsulfide (1:1) complex in an inert solvent, for example dimethyl sulfide or tetrahydrofuran, preferably a mixture thereof. The reaction is run at a temperature of between −78° C. and room temperature, preferably at −4° C. Instead of methyl magnesium bromide, any lower alkyl bromide can be added to form $R^{17}$ where $R^{17}$ is a lower alkyl group other than methyl. To this formed solution of methyl cuprate, is added in situ a solution of the α,β-unsaturated acyloxazolidinone 105 in an inert solvent, preferably tetrahydrofuran. The methyl cuprate addition is run initially at a temperature of between −30° C. and room temperature, preferably at −4° C. and then is allowed to proceed at room temperature. When it is judged that the reaction is completed (e.g. analysis by TLC or HPLC), it is then cooled to a temperature of between −100° C. and −40° C., preferably at about −78° C., whereupon a solution of a halogenating agent, preferably N-bromosuccinimide in an inert solvent, for example, tetrahydrofuran is added. The reaction is then allowed to proceed at a temperature of between 0° C. and room temperature, preferably at about room temperature to give after isolation, the bromide 106. The bromide is the displaced by azide ion with a concomitant inversion of configuration. This transformation is accomplished by reaction of the bromide 106 with tetra-butylammonium azide in the presence of excess sodium azide in an inert solvent, for example acetonitrile to give the azide 107. The reaction is conveniently run at a temperature of between 80° C. and room temperature, preferably at about room temperature. Treatment of 107 and an alkali metal hydroxide, or example sodium, potassium or lithium hydroxide, preferably lithium hydroxide in the presence of hydrogen peroxide resulted in the hydrolysis of the chiral auxilliary to give the azido acid 108. The hydrolysis reaction is run in an inert solvent, preferably water, at a temperature of between 0° C. and room temperature, preferably at about 0° C. Hydrogenation of the α-azido acid 108 gives the β-methyl(Nin-Mes) tryptophan which is immediately converted to the corresponding N(α)-Fmoc-13-methyl(Nin-Mes)tryptophan 109. The hydrogenation of 108 is carried out over a noble metal catalyst, preferably 10% Pd/C, in an inert solvent, for example a lower alkanol, preferably methanol at low pressure(<2 atmos) and at room temperature. After removal of the catalyst by filtration, the volatiles are removed and the product is dissolved in an inert solvent, for example tetrahydrofuran or water, preferably a mixture thereof, and treated with a mild inorganic base, for example an alkali metal bicarbonate, preferably sodium bicarbonate, and a Fmoc N-protecting group forming reagent, for example 9-fluorenylmethyl chloroformate (Fmoc-Cl) or 9-fluorenylmethyl-N-succinimidyl carbonate (Fmoc-OSu), preferably Fmoc-Osu to furnish 109. The reaction is conveniently run at a temperature of between 0° C. and room temperature, preferably at about room temperature. The compound of formula 109 is a species of amino acid of Structure 5 in Reaction Scheme A.

Pharmaceutical Compositions

The compounds of formulas I and II as well as Penta-cyclo(Asp-Lys)-Asp-Apc-(D)Phe-Ala-Trp-Lys-NH$_2$; and Penta-cyclo(Asp-Lys)-Asp-Apc-(D)Phe-Arg-(2S,3S) beta methyl-Trp-Lys-NH$_2$ prepared in accordance with this invention may be prepared in pharmaceutical compositions suitable for administration by injection with a suitable carrier or vehicle by methods known in the art.

Treating Obesity

The compounds prepared in accordance with this invention exhibited selective MC-4 receptor agonist activity in vitro. It is known that agonists of MC4-R activity cause reduction of food intake in a mouse model of human obesity. Therefore administration of these compounds agonizes MC4-R activity which is important in the regulation of body weight. The pharmaceutical compositions containing the compounds of this invention may be formulated at a strength effective for administration by various means to a human or animal patient experiencing undesirably elevated body weight, either alone or as part of an adverse medical condition or disease, such as type II diabetes mellitus. A variety of administrative techniques can be used. Average quantities of the active compound may vary and in particular should be based upon the recommendations and prescription of a qualified physical or veterinarian.

This invention will be better understood by reference to the following examples, which illustrate but do not limit the invention described herein. In the structures of specific compounds appearing in the Examples section, the hydrogens have generally been omitted for convenience.

EXAMPLE 1

Preparation of Fmoc-1-amino-4-phenylcyclohexane-1-carboxylic acid (Fmoc-Apc)

Step 1:

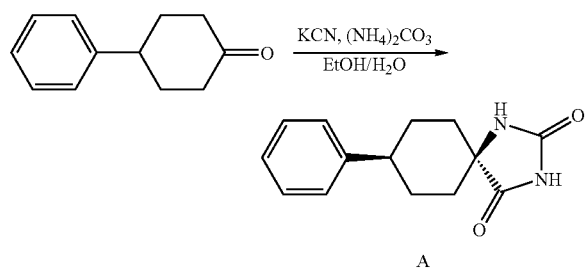

A

To a solution of 4-phenylcyclohexanone (10.0 g, 57.5 mmol) in ethanol (100 mL) and water (33 mL) in a glass pressure bottle, were added ammonium carbonate (33 g, 344 mmol, 6 equiv.) and potassium cyanide (5.6 g, 86.2 mmol, 1.5 equiv.). The mixture was heated at 80–90° C. for 24 hrs. The cooled reaction mixture was added to icy water (400 ml) and stirred vigorously for 30 min. The resulting precipitate was suction filtered, washed thoroughly with water and dried to yield the hydantoin A as a white solid (14.0 g, 100% yield). $^1$H NMR (DMSO-d$_6$): 8.63 (s, 1H), 7.23–7.36 (m, 4), 7.15 (m, 1), 2.50 (m, 1H), 2.10 (m, 1H), 1.85 (d, 1H) and 1.55–1.80 (m, 6H).

Step 2:

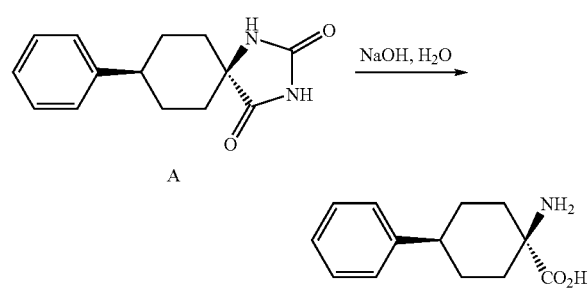

The hydantoin A (10.0 g) was suspended in aqueous NaOH (6N, 350 mL) and heated at 130° C. for 2–3 days. Upon the completion of the hydrolysis, the reaction mixture was neutralized with conc. HCl to slightly acidic (pH~6). The resulting slurry was filtered, washed with water and dried to give 1-amino-4-phenylcyclohexane carboxylic acid (APC) as a white solid (25 g, >100% yield. contaminated with inorganic salt) which was used directly for next step. Small portion of the crude product was purified on HPLC. $^1$H NMR (DMSO-d$_6$): 7.23~7.7.35 (m, 2H), 7.10–7.19 (m, 3H), 2.45 (m, 1H), 1.92–2.18 (m, 3H), 1.56–1.78 (m, 4H) and 1.20 (m, 1H); LRMS (electrospray) m/e 220 (M+1)$^+$, Calcd for $C_{13}H_{17}NO_2$, 219.

Step 3:

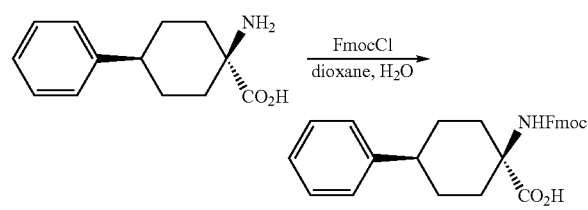

The crude 1-amino-4-phenylcyclohexane carboxylic acid (APC) from the last step (25 g) was suspended in dioxane (300 mL) and aqueous 10% Na$_2$CO$_3$ (150 ml) and stirred vigorously overnight. The reaction mixture was concentrated to remove dioxane, neutralized with 6N HCl to slightly acidic (pH 5–6) and extracted with EtOAc. The combined organic extracts were washed with brine and dried over Na$_2$SO$_4$. Removal of the solvent gave the crude product which was then purified on flash chromatography (hexane/EtOAc to CH$_2$Cl$_2$/MeOH) to give pure Fmoc-cis-APC (18.2 g, 72% overall yield for two steps) and Fmoc-trans-APC (2.1 g, 8%). Fmoc-cis-APC, $^1$H NMR(CD$_3$OD), 7.79 (d, 2H), 7.72 (d, 2H), 7.37 (t, 2), 7.24–7.32 (mn, 4), 7.14–7.23 (mn, 3), 4.37 (d, 2H), 4.24 (t, 1H), 2.55 (m, 1H), 2.28 (mn, 2H), 1.84–1.96 (mn, 2H) and 1.64–1.73 (m, 4H).

EXAMPLE 2

Preparation of Fmoc-1-amino4-(4-methoxyphenyl) cyclohexane-1-carboxylic acid (Fmoc-4-MeOApc-OH)

Step 1:

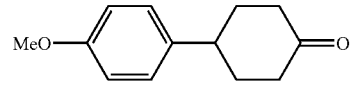

A solution of 4-(4-hydroxyphenyl)cyclohexanone (5.0 g, 26.3 mmol) in acetone (100 mL) was treated with K$_2$CO$_3$ (14.5 g, 105 mmol, 4 equiv) and iodomethane (4.9 mL, 11.2 g, 78.6 mmol, 3 equiv.). The reaction was heated at 65° C. overnight. After the solvent was removed, the residue was treated with H$_2$O and extracted with EtOAc. The organic extracts were combined and washed with brine, dried over Na$_2$SO$_4$ and concentrated in vacuum to give the spectroscopically pure 4-(4-methoxyphenyl)-cyclohexanone (5.34 g, 100%). $^1$H NMR(CDCl$_3$) 7.16 (dt, 2H), 6.87 (dt, 2H), 3.78 (s, 3H), 2.99 (tt, 1H), 2.47–2.53 (m, 4H), 2.20 (m, 2H) and 1.83–1.98 (m, 2H); MS (electrospray) m/e, 205 (M+1)$^+$, Calcd for $C_{13}H_{16}O_2$, 204.

Step 2:

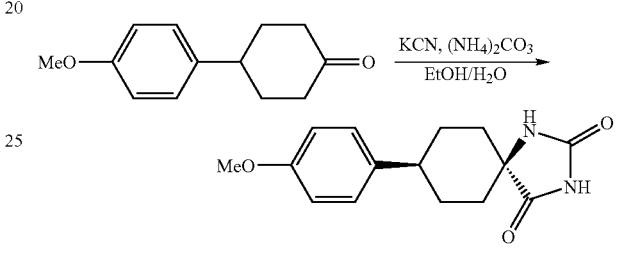

To a solution of the 4-(4-methoxyphenyl)-cyclohexanone (3.86 g, 18.9 mmol) in ethanol (50 mL) and water (15 mL) in a glass pressure bottle, were added ammonium carbonate (14.5 g, 151 mmol, 8 equiv.) and potassium cyanide (2.0 g, 30.7 mmol, 1.6 equiv.). The mixture was heated at 80–90° C. for 24 hrs. The cooled reaction mixture was added to icy water (300 ml) and stirred vigorously for 30 min. The resulting precipitate was suction filtered, washed thoroughly with water and dried to yield the hydantoin B as a white solid (4.75 g, 91% yield). MS (electrospray) m/e 273 (M–H), Calcd for $C_{15}H_{18}N_2O_3$, 274.

Step 3:

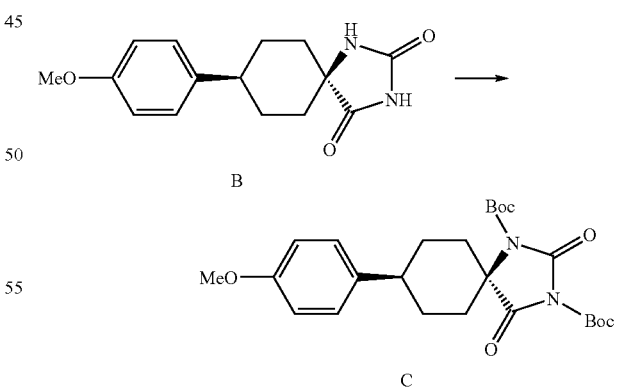

To a suspension of the hydantoin B (18.7 g, 68.25 mmol) in dry THF (450 mL) were added di-tert-butyl dicarbonate (37.2 g, 170.5 mmol, 2.5 equiv), triethylamine (10.5 mL, 7.59 g, 75.0 mmol, 1.1 equiv) and DMAP (460 mg, 3.65 mmol) in succession. About 15 minutes after the addition, the reaction turned into a clear yellow solution and was stirred overnight at room temperature. The reaction mixture was concentrated under reduced pressure to yield a solid that was then taken up in EtOAc (800 ML), washed with 1N HCl (3×50 mL), saturated aqueous $Na_2CO_3$ (2×50 mL) and brine (2×50 mL), dried over anhydrous $Na_2SO_4$ and concentrated under reduced pressure. The crude light yellow product was purified through flash chromatography (hexane/EtOAc, 90/10→70/30) to give the pure bis-Boc hydantoin C as a white solid (27.6 g, 87%). $^1$H NMR ($CDCl_3$): 7.28 (dt, 2H), 6.88 (dt, 2H), 3.79 (s, 3H), 2.14–2.24 (m, 2H), 1.59 (s, 9H) and 1.38 (s, 9H); MS (electrospray) m/e 538 (M+MeCN+Na)$^+$, Calcd for $C_{25}H_{34}N_2O_7$, 474.

Step 4:

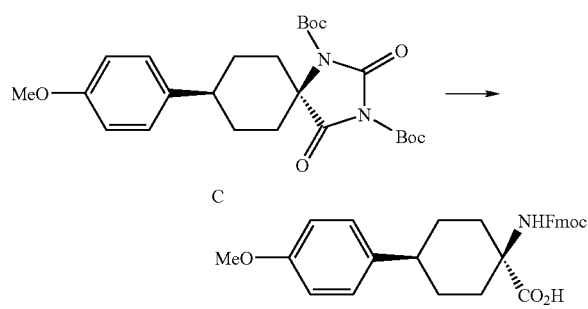

The bis-Boc hydantoin C (15.08 g, 31.78 mmol) was dissolved in DME (500 mL) to give a clear solution. To this solution was added 1N NaOH (290 mL, 290 mmol) and the reaction was stirred overnight at room temperature, giving a slightly cloudy mixture. HPLC showed completion of the reaction. The reaction mixture was concentrated under reduced pressure to remove DME and extracted with $Et_2O$. Without purification, the resulting aqueous layer containing 1-amino-4-(4-methoxyphenyl)cyclohexane carboxylic acid (4-MeOAPC) was treated with 6N HCl to adjust the pH to 11–12. To this solution (~300 mL) were added DME (300 mL) and a solution of Fmoc-OSu (16.7 g, 49.42 mmol) in DME (200 mL) and the reaction was stirred overnight at room temperature. The reaction mixture was concentrated under reduced pressure to remove DME, acidified with 3N HCl, extracted with EtOAc. The combined organic extracts were washed with brine, dried over anhydrous $Na_2SO_4$ and concentrated. The crude product was purified through flash chromatography ($CH_2Cl_2$/MeOH, 98/2→90/10) to give the pure product Fmoc-4-MeOAPC as a white solid (12.4 g, 83% yield from the bis-Boc hydantoin C). $^1$H NMR (DMSO-d$_6$), 7.88 (d, 2H), 7.76 (d, 2H), 7.40 (t, 2H), 7.30 (t, 2H), 7.11 (d, 2H), 6.85 (d, 2H), 3.71 (s, 3H); MS (electrospray) m/e 470 (M–H), Calcd for $C_{29}H_{29}NO_5$, 471.

EXAMPLE 3

Preparation of Fmoc-1-amino-4-(4-ethoxyphenyl) cyclohexane-1-carboxylic acid (Fmoc-4-EtOApc-OH)

Step 1:

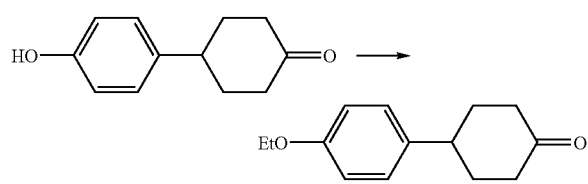

A solution of 4-(4-hydroxyphenyl)cyclohexanone (5.0 g, 26.3 mmol) in acetone (100 mL) was treated with $K_2CO_3$ (14.5 g, 105 mmol, 4 equiv) and iodoethane (10.5 mL, 20.5 g, 131 mmol, 5 equiv.). The reaction was heated at 65° C. overnight. After the solvent was removed, the residue was treated with $H_2O$ and extracted with EtOAc. The organic extracts were combined and washed with brine, dried over $Na_2SO_4$ and concentrated in vacuum to give the spectroscopically pure 4-(4-ethoxyphenyl)-cyclohexanone (5.74 g, 100%). $^1$H NMR ($CDCl_3$) 7.15 (dt, 2H), 6.86 (dt, 2H), 4.02 (q, 2H), 2.99 (tt, 1H), 2.46–2.54 (m, 4H), 2.16–2.24 (m, 2H), 1.83–2.00 (m, 2H) and 1.41 (t, 3H); MS (electrospray) m/e, 219 (M+1)$^+$, Calcd for $C_{14}H_{18}O_2$, 218.

Step 2:

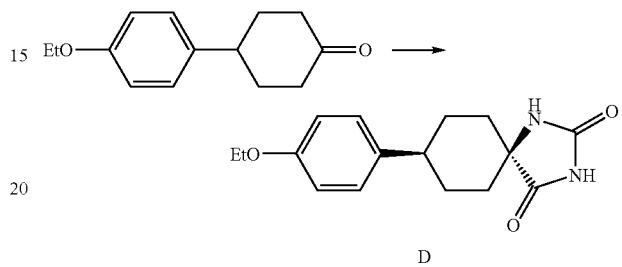

To a solution of the 4-(4-ethoxyphenyl)-cyclohexanone (4.15 g, 19.01 mmol) in ethanol (50 mL) and water (15 mL) in a glass pressure bottle, were added ammonium carbonate (14.5 g, 151 mmol, 8 equiv.) and potassium cyanide (2.05 g, 31.42 mmol, 1.6 equiv.). The mixture was heated at 80–90° C. for 19 hrs. The cooled reaction mixture was added to icy water (300 ml) and stirred vigorously for 30 min. The resulting precipitate was suction filtered, washed thoroughly with water and dried to yield the hydantoin D as a white solid (5.17 g, 94% yield). MS (electrospray) m/e 287 (M–H), Calcd for $C_{16}H_{20}N_2O_3$, 288.

Step 3:

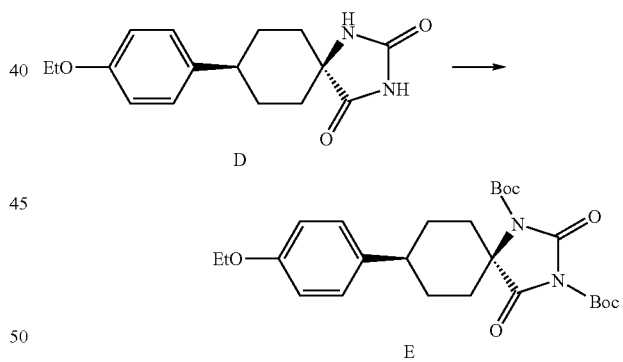

To a suspension of the hydantoin D (4.22 g, 14.65 mmol) in dry THF (100 mL) were added di-tert-butyl dicarbonate (7.98 g, 36.60 mmol, 2.5 equiv), triethylamine (2.3 mL, 1.63 g, 16.11 mmol, 1.1 equiv) and DMAP (89.4 mg, 0.73 mmol) in succession. About 15 minutes after the addition, the reaction turned into a clear yellow solution and was stirred overnight at room temperature. The reaction mixture was concentrated under reduced pressure to yield a solid that was then taken up in EtOAc (300 mL), washed with 1N HCl (3×20 mL), saturated aqueous Na2CO3 (2×20 mL) and brine (2×20 mL), dried over anhydrous $Na_2SO_4$ and concentrated under reduced pressure. The crude light yellow product was purified through flash chromatography (hexane/EtOAc, 90/10→70/30) to give the pure bis-Boc hydantoin E as a white solid (7.01 g, 98%). $^1$H NMR ($CDCl_3$): 7.27 (dt, 2H), 6.87 (dt, 2H), 4.02 (q, 2H), 1.59 (s, 9H), 1.43 (t, 3H) and 1.38 (s, 9H); MS (electrospray) m/e 999 (2M+Na)$^+$, Calcd for $C_{26}H_{36}N_2O_7$, 488.

Step 4:

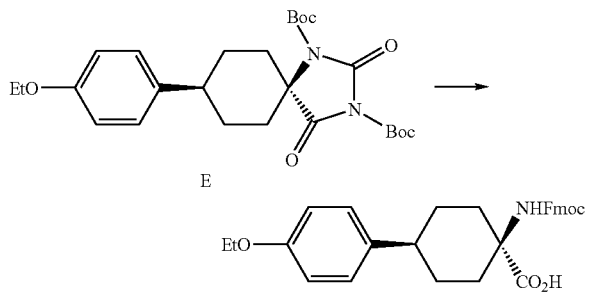

The bis-Boc hydantoin E (6.58 g, 13.46 mmol) was dissolved in DME (200 mL) to give a clear solution. To this solution was added 1N NaOH (121 mL, 121 mmol) and the reaction was stirred overnight at room temperature, giving a slightly cloudy mixture. HPLC showed completion of the reaction. The reaction mixture was concentrated under reduced pressure to remove DME and extracted with Et$_2$O. Without purification, the resulting aqueous layer containing 1-amino-4-(4-ethoxyphenyl)cyclohexane carboxylic acid (4-EtOAPC) was treated with 6N HCl to adjust the pH to 11–12. To this solution (~130 mL) were added DME (100 mL) and a solution of Fmoc-OSu (6.83 g, 20.24 mmol) in DME (30 mL) and the reaction was stirred overnight at room temperature. The reaction mixture was concentrated under reduced pressure to remove DME, acidified with 3N HCl, extracted with EtOAc. The combined organic extracts were washed with brine, dried over anhydrous Na$_2$SO$_4$ and concentrated. The crude product was purified through flash chromatography (CH$_2$Cl$_2$/MeOH, 98/2→90/10) to give the pure product Fmoc-4-EtOAPC as a white solid (5.56 g, 85% yield from the bis-Boc hydantoin E). $^1$H NMR (DMSO-d$_6$), 7.88 (d, 2H), 7.74 (d, 2H), 7.40 (td, 2H), 7.30 (td, 2H), 7.11 (d, 2H), 6.84 (d, 2H), 3.97 (q, 2H) and 1.29 (t, 3H); MS (electrospray) m/e 484 (M–H), Calcd for $C_{30}H_{31}NO_5$, 485.

EXAMPLE 4

Preparation of Fmoc-1-amino-4-(4-hydroxyphenyl)cyclohexane-1-carboxylic acid (Fmoc-4-HOApc-OH)

Step 1:

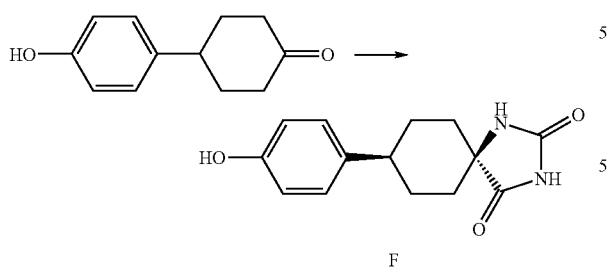

To a solution of 4-(4-hydroxyphenyl)cyclohexanone (2.00 g, 10.52 mmol) in ethanol (30 mL) and water (10 mL) in a glass pressure bottle, were added ammonium carbonate (6.17 g, 64.2 mmol, 6 equiv.) and potassium cyanide (1.07 g, 15.8 mmol, 1.5 equiv.). The mixture was heated at 80–90° C. overnight. The cooled reaction mixture was added to icy water (200 ml) and stirred vigorously for 30 min. The resulting precipitate was suction filtered, washed thoroughly with water and dried to yield the hydantoin F as a white solid (2.56 g, 94% yield). MS (electrospray) m/e 261 (M+H)$^+$, Calcd for $C_{14}H_{16}N_2O_3$, 260.

Step 2:

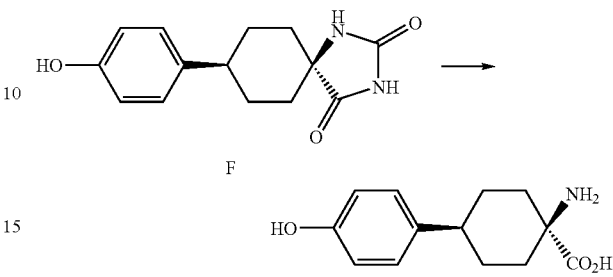

The hydantoin F (2.10 g, 8.06 mmol) was suspended in aqueous NaOH (6N, 100 mL) and heated at 130° C. for 2–3 days. Upon the completion of the hydrolysis, the reaction mixture was neutralized with conc. HCl to slightly acidic (pH~6). The resulting slurry was filtered, washed with water and dried to give 1-amino-4-(4-hydroxyphenyl)cyclohexane carboxylic acid (4-HOAPC) as a white solid (3.1 g, >100% yield. contaminated with inorganic salt). MS (electrospray) m/e 236 (M+H)$^+$, Calcd for $C_{13}H_{17}NO_3$, 235.

Step 3:

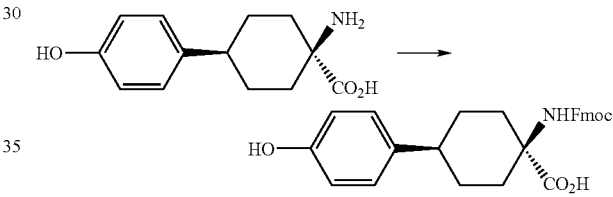

The crude 1-amino-4-(4-hydroxyphenyl)cyclohexane carboxylic acid (4-HOAPC) from the last step (3.1 g) was suspended in dioxane (100 mL) and aqueous 10% Na$_2$CO$_3$ (50 ml) and stirred vigorously overnight. The reaction mixture was concentrated to remove dioxane, neutralized with 6N HCl to slightly acidic (pH 5–6) and extracted with EtOAc. The combined organic extracts were washed with brine and dried over Na$_2$SO$_4$. Removal of the solvent gave the crude product which was purified on flash chromatography (hexane/EtOAc to CH$_2$Cl$_2$MeOH) to give pure Fmoc-4-HOAPC (2.76 g, 75% overall yield for two steps). $^1$H NMR(CD$_3$OD), 7.78 (d, 2H), 7.72 (d, 2H), 7.38 (t, 2H), 7.30 (td, 2H), 7.04 (d, 2H), 6.72 (dt, 2H), 4.38 (d, 2H), 4.25 (t, 1H), 2.46 (m, 1H), 2.24–2.34 (m, 2H) and 1.81–1.92 (m, 6H); MS (electrospray) m/e 456 (M–H), Calcd for $C_{28}H_{27}NO_5$, 457.

EXAMPLE 5

Preparation of Fmoc-1-amino-4-(4-isopropoxyphenyl)cyclohexane-1-carboxylic acid (Fmoc-4-iPrOApc-OH)

Step 1:

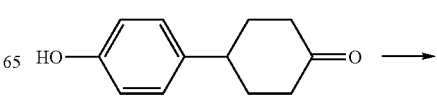

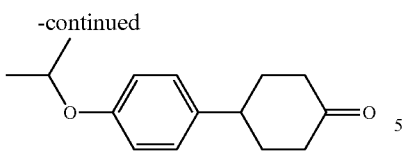
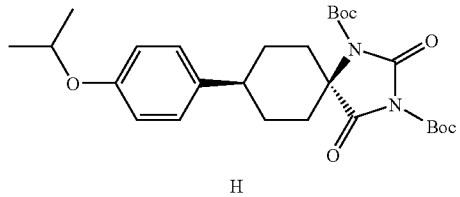

A solution of 4-(4-hydroxyphenyl)cyclohexanone (6.0 g, 31.6 mmol) in DMF (90 mL) was treated with $K_2CO_3$ (21 g, 158 mmol, 5 equiv) and 2-iodopropane (15 mL, 26.8 g, 158 mmol, 5 equiv.). The reaction was heated at 100° C. overnight. After the solvent was removed, the residue was treated with $H_2O$ and extracted with EtOAc. The organic extracts were combined and washed with brine, dried over $Na_2SO_4$ and concentrated in vacuum to give the spectroscopically pure 4-(4-isopropoxyphenyl)cyclohexanone (7.02 g, 95%). $^1H$ NMR ($CDCl_3$): 7.14 (dt, 2H), 6.84 (dt, 2H), 4.3 (septet, 1H), 2.97 (tt, 1H), 2.46–2.52 (m, 4H), 2.16–2.24 (m, 2H), 1.83–1.98 (m, 2H) and 1.33 (d, 6H).

Step 2:

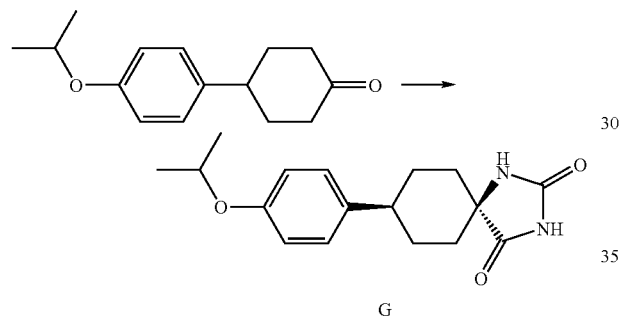

To a solution of the 4-(4-isopropoxyphenyl) cyclohexanone (5.1 g, 21.98 mmol) in ethanol (90 mL) and water (30 mL) in a glass pressure bottle, were added ammonium carbonate (12.6 g, 131 mmol, 6 equiv.) and potassium cyanide (2.14 g, 32.9 mmol, 1.5 equiv.). The mixture was heated at 80–90° C. for 24 hrs. The cooled reaction mixture was added to icy water (400 ml) and stirred vigorously for 30 min. The resulting precipitate was suction filtered, washed thoroughly with water and dried to yield hydantoin G as a white solid (6.60 g, 99% yield). $^1H$ NMR (DMSO-$d_6$): 10.60 (s, 1H), 8.65 (s, 1H), 7.18 (d, 2H), 6.80 (d, 2H), 4.52 (septet, 1H), 2.43 (m, 1H), 1.85–2.15 (m, 2H), 1.56–1.80 (m, 6H) and 1.22 (d, 6H); MS (electrospray) m/e 301 (M–H), Calcd for $C_{17}H_{22}N_2O_3$, 302.

Step 3:

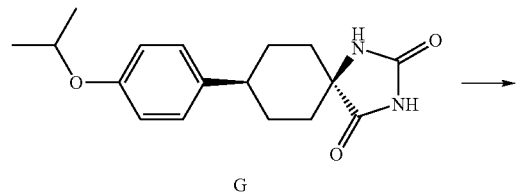

To a suspension of the hydantoin G (5.8 g, 19.20 mmol) in dry THF (180 mL) were added di-tert-butyl dicarbonate (10.46 g, 48.0 mmol, 2.5 equiv), triethylamine (2.9 mL, 2.13 g, 21.12 mmol, 1.1 equiv) and DMAP (140 mg, 1.15 mmol) in succession. About 15 minutes after the addition, the reaction turned into a clear yellow solution and was stirred overnight at room temperature. The reaction mixture was concentrated under reduced pressure to yield a solid that was then taken up in EtOAc (600 mL), washed with 1N HCl (3×40 mL), saturated aqueous $Na_2CO_3$ (2×40 mL) and brine (2×40 mL), dried over anhydrous $Na_2SO_4$ and concentrated under reduced pressure. The crude light yellow product was purified through flash chromatography (hexane/EtOAc, 90/10→80/20) to give the pure bis-Boc hydantoin H as a white solid (9.4 g, 98%). $^1H$ NMR ($CDCl_3$): 7.27 (dt, 2H), 6.87 (dt, 2H), 4.02 (q, 2H), 2.98 (t, 1H), 2.26–2.56 (m, 4H), 2.14–2.24 (m, 2H), 1.76–1.86 (m, 2H), 1.59 (s, 9H), 1.43 (t, 3H) and 1.38 (s, 9H); MS (electrospray) m/e 999 (2M+Na)$^+$, Calcd for $C_{26}H_{36}N_2O_7$, 488.

Step 4:

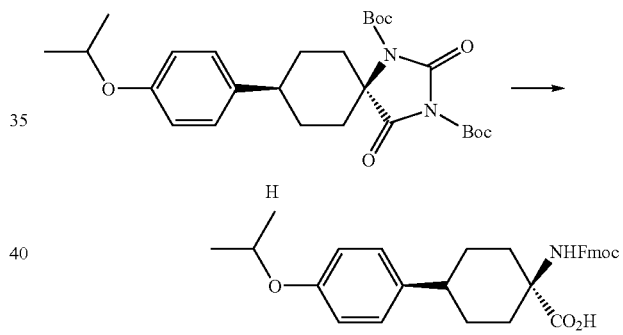

The bis-Boc hydantoin H (4.34 g, 8.64 mmol) was dissolved in DME (100 mL) to give a clear solution. To this solution was added 1N NaOH (78 mL, 78 mmol) and the reaction was stirred overnight at room temperature, giving a fairly clear mixture. HPLC showed completion of the reaction. The reaction mixture was concentrated under reduced pressure to remove DME and extracted with $Et_2O$. Without purification, the resulting aqueous layer containing 1-amino-4-(4-isopropoxyphenyl)cyclohexane carboxylic acid (4-iPrOAPC) was treated with 6N HCl to adjust the pH to 11–12. To this solution (~90 mL) were added DME (120 mL) and a solution of Fmoc-OSu (3.49 g, 10.34 mmol, 1.2 equiv) in DME (20 mL) and the reaction was stirred overnight at room temperature. The reaction mixture was concentrated under reduced pressure to remove DME, acidified with 3N HCl, extracted with EtOAc. The combined organic extracts were washed with brine, dried over anhydrous $Na_2SO_4$ and concentrated. The crude product was purified through flash chromatography (hexane/EtOAc→$CH_2Cl_2$/MeOH) to give the pure product Fmoc-4-iPrOAPC as a white solid (3.23, 75% yield from bis-Boc hydantoin H). $^1H$ NMR(DMSO-$d_6$), 7.76 (d, 2H), 7.60 (d, 2H), 7.39 (t, 2H), 7.31 (t, 2H), 7.08 (d, 2H), 6.84 (d, 2H), 4.24 (m, 1H) and 1.34 (d, 6H); MS (electrospray) m/e 498 (M−H), Calcd for C₃₁H₃₃NO₅, 499.

EXAMPLE 6

Preparation of Fmoc-1-amino-4-(4-methylphenyl)cyclohexane-1-carboxylic acid (Fmoc-4-MeApc-OH)

Step 1:

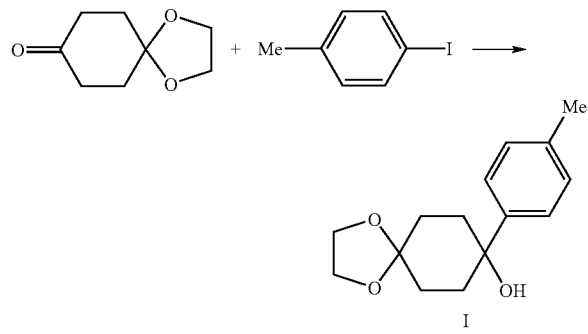

To a solution of 4-iodotoluene (10.9 g, 50.0 mmol) in dry THF (180 mL) at −78° C. was added a solution of n-BuLi (1.6 M, 31.0 mL, 50 mmol) in hexane over 20 min. The reaction was stirred for another 20 min before a solution of 1,4-cyclohexanedione mono-ethylene ketal (6.0 g, 38.46 mmol) in dry THF (100 mL) was added dropwise. After stirred for 2 h at −78° C., the reaction was quenched with aqueous NH₄Cl and extracted with EtOAc. The combined organic extracts were washed with brine, dried over Na₂SO₄, concentrated in vacuo to give the spectroscopically pure product I as a white solid (9.34 g, 98% yield). ¹H NMR (CDCl₃): 7.41 (m, 2H), 7.16 (d, 2H), 3.98 (m, 4H), 2.34 (s, 3H); MS (EI) m/e 248 (M⁺), Calcd for C₁₅H₂₀O₃, 248.

Step 2:

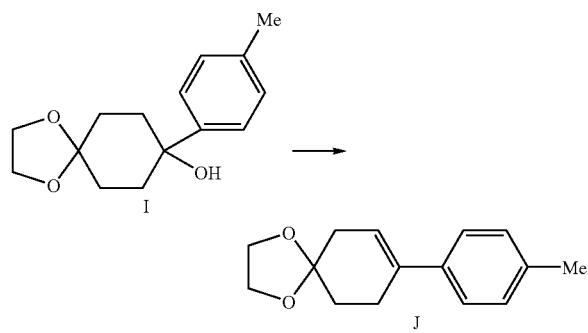

To a solution of the alcohol I (⁹·¹⁰ g, 36.65 mmol) in dry benzene (200 mL) in a flask equipped with a Dean-Stark trap, was added p-toluenesulfonic acid monohydrate (650 mg) and the reaction was heated at 100° C. for 3 hrs. The reaction was cooled to rt, diluted with EtOAc (500 mL) and washed with aqueous Na₂CO₃ (50 mL), brine (3×50 mL), dried over Na₂SO₄ and concentrated under reduced pressure to give the spectroscopically pure product J (8.36 g, 100 yield), which was used for next step without purification. MS (EI) m/e 230 (M⁺), 190 (M-OCH₂CH₂O ), Calcd for C₁₅H₁₈O₂, 230.

Step 3:

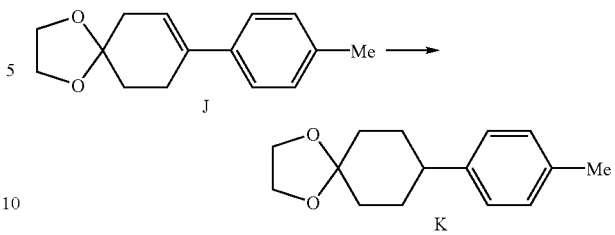

To a solution of the olefin J (7.49 g) in EtOAc (180 mL) was added Pd/C (5 wt % on carbon, 800 mg) and the reaction was run under 40 psi of hydrogen for 3 hrs at room temperature. The catalyst was filtered off and the filtrate was concentrated to give the spectroscopically pure product K as a colorless oil (7.40 g, 100% yield). MS (EI) m/e 232 (M⁺), 188 (M-OCH₂CH₂), Calcd for C₁₅H₂₀O₂, 232.

Step 4:

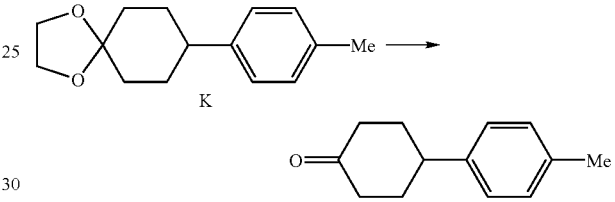

A solution of the ketal K (6.90 g) in acetone (140 mL) was treated with 4N HCl (60 mL) and heated at 65° C. for 4 hrs. Solvent was removed and the residue was diluted with EtOAc and neutralized with 4N HCl. The aqueous was extracted with EtOAc. The combined organic extracts were washed with brine, dried and concentrated. The resulting crude 4-(4-methylphenyl)cyclohexanone was used for next step without purification (5.57 g, quantitative yield). MS (EI) m/e 188 (M⁺), Calcd for C₁₃H₁₆O, 188.

Step 5:

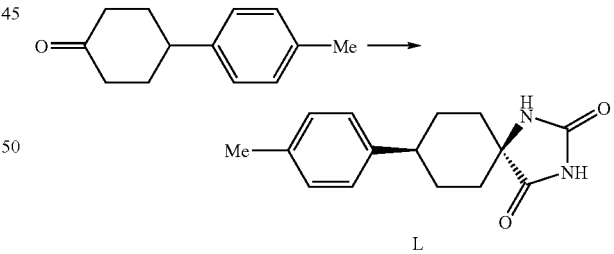

To a solution of 4-(4-methylphenyl)cyclohexanone (5.32 g, 28.3 mmol) in ethanol (90 mL) and water (30 mL) in a glass pressure bottle, were added ammonium carbonate (16.3 g, 169.8 mmol, 6 equiv.) and potassium cyanide (3.68 g, 56.5 mmol, 2 equiv.). The mixture was heated at 80–90° C. overnight. The cooled reaction mixture was added to icy water (400 ml) and stirred vigorously for 30 min. The resulting precipitate was suction filtered, washed thoroughly with water and dried to yield the hydantoin L as a white solid (6.3 g, 86% yield). MS (electrospray) m/e 517 (2M+H), Calcd for C₁₅H₁₈CN₂O₂, 258

Step 6:

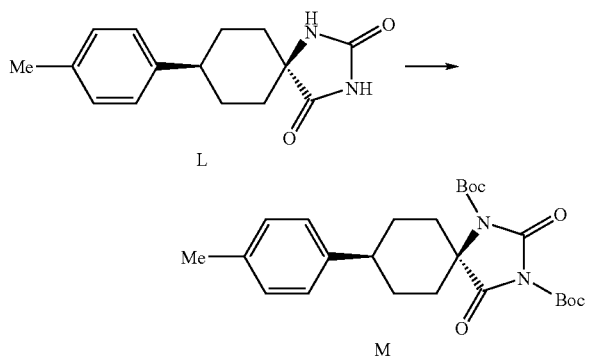

To a suspension of the hydantoin L (5.82 g, 22.55 mmol) in dry THF (250 mL) were added di-tert-butyl dicarbonate (12.3 g, 56.4 mmol, 2.5 equiv), triethylamine (3.5 mL, 2.5 g, 24.7 mmol, 1.1 equiv) and DMAP (275 mg, 2.25 mmol) in succession. The reaction turned into a clear yellow solution and was stirred overnight at room temperature. The reaction mixture was concentrated under reduced pressure to yield a solid that was then taken up in EtOAc (500 mL), washed with 1N HCl (3×50 mL), saturated aqueous $Na_2CO_3$ (2×50 mL) and brine (2×50 mL), dried over anhydrous $Na_2SO_4$ and concentrated under reduced pressure. The crude light yellow product was purified through flash chromatography (hexane/EtOAc, 90/10→70/30) to give the pure bis-Boc hydantoin M as a white solid (10.03 g, 100% yield). $^1$H NMR (CDCl$_3$): 7.26 (d, 2H), 6.87 (d, 2H), 3.00 (m, 1H), 2.32 (s, 3H), 1.59 (s, 9H) and 1.37 (s, 9H).

Step 7:

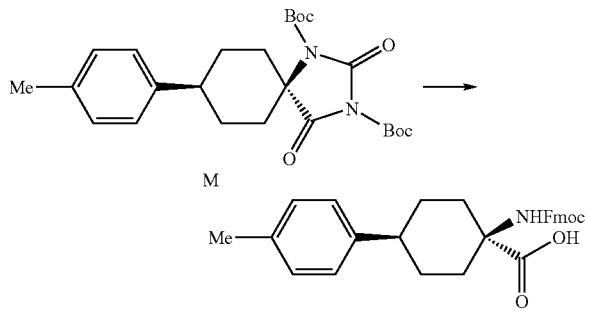

The bis-Boc hydantoin M (6.40 g, 13.97 mmol) was dissolved in DME (200 mL) to give a clear solution. To this solution was added 1N NaOH (120 mL, 120 mmol) and the reaction was stirred overnight at room temperature, giving a slightly cloudy mixture. HPLC showed completion of the reaction. The reaction mixture was concentrated under reduced pressure to remove DME and extracted with $Et_2O$. Without purification, the resulting aqueous layer containing 1-amino-4-(4-methylphenyl)cyclohexane carboxylic acid (4-MeAPC) was treated with 6N HCl to adjust the pH to 11–12. To this solution (~140 mL) were added DME (240 mL) and a solution of Fmoc-OSu (5.10 g, 15.13 mmol, 1.1 equiv) in DME (40 mL) and the reaction was stirred overnight at room temperature. The reaction mixture was concentrated under reduced pressure to remove DME, acidified with 3N HCl, extracted with EtOAc. The combined organic extracts were washed with brine, dried over anhydrous $Na_2SO_4$ and concentrated. The crude product was purified through flash chromatography ($CH_2Cl_2$/MeOH, 98/2→90/10) to give the pure product Fmoc-4-MeAPC as a white solid (4.35 g, 69% yield from bis-Boc hydantoin M). $^1$H NMR (DMSO-d$_6$): 7.88 (d, 2H), 7.75 (d, 2H), 7.24–7.43 (m, 4H), 7.02–7.14 (m, 4H), 4.25 (m, 3H), 2.24 (s, 3H).

EXAMPLE 7

Preparation of Fmoc-1-amino-4-(4-chlorophenyl) cyclohexane-1-carboxylic acid (Fmoc-4-ClApc-OH)

Step 1:

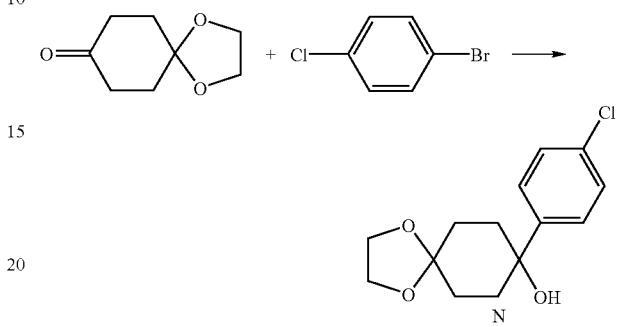

A solution of 4-chlorophenylbromide (7.5 g, 39.2 mmol) in dry THF (180 mL) was cooled to −78° C. and treated dropwise with a solution of n-BuLi (1.6 M, 25 mL, 40 mmol) in hexane over 20 min. The reaction was stirred for a further 30 min before a solution of 1,4-cyclohexanedione mono-ethylene ketal (6.0 g, 38.46 mmol) in dry THF (100 mL) was added dropwise. After stirred for 1 hr at −78° C., the reaction was quenched with aqueous $NH_4Cl$ and extracted with EtOAc. The combined organic extracts were washed with brine, dried over $Na_2SO_4$, concentrated in vacuo to give the spectroscopically pure product N as a white solid (9.40 g, 91% yield). $^1$H NMR (CDCl$_3$): 7.45 (m 2H), 7.31 (m, 2H), 3.99 (m, 4H), 2.02–2.20 (m, 4H), 1.75–1.82 (m, 2H), 1.66–1.73 (m, 2H), 1.54 (s, 1H); MS (EI) m/e 268 (M$^+$), 251 (M-OH), 250 (M-H$_2$O ), Calcd for $C_{14}H_{17}ClO_3$, 268.

Step 2:

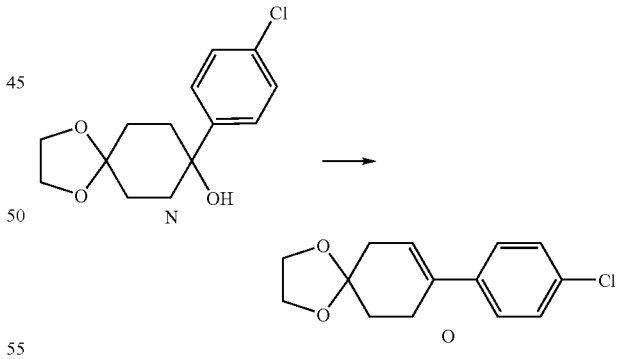

To a solution of the alcohol N (6.78 g, 25.30 mmol) in dry benzene (120 mL) in a flask equipped with a Dean-Stark trap, was added p-toluenesulfonic acid monohydrate (960 mg) and the reaction was heated at reflux for 3 hrs. The reaction was cooled to rt, diluted with EtOAc (500 mL) and washed with aqueous $Na_2CO_3$ (50 mL), brine (3×50 mL), dried over $Na_2SO_4$ and concentrated under reduced pressure to give the spectroscopically pure product O (6.30 g, 100 yield), which was used for next step without purification. MS (EI) m/e 250 (M$^+$), 190 (M-OCH$_2$CH$_2$O ), Calcd for $C_{14}H_{15}ClO_2$, 250.

Step 3:

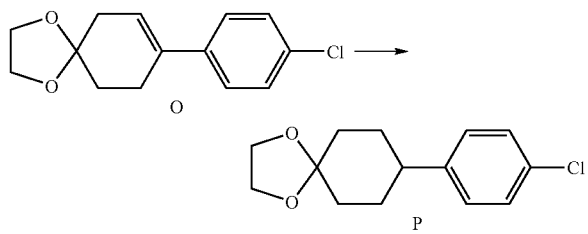

To a solution of the olefin O (6.11 g) in EtOAc (120 mL) was added Pd/C (5 wt % on carbon, 600 mg) and the reaction was run under 5 psi of hydrogen for 3 hrs at room temperature. The catalyst was filtered off and the filtrate was concentrated to give the spectroscopically pure product P as a colorless oil (6.10 g, 100% yield). MS (EI) m/e 252(M+), Calcd for $C_{14}H_{17}ClO_2$, 252.

Step 4:

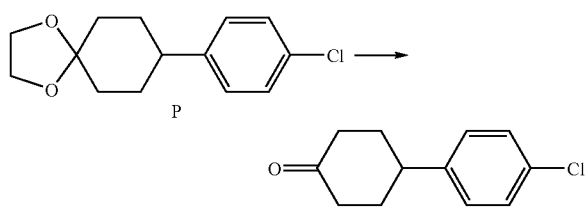

A solution of the ketal P (5.81 g, 23.06 mmol) in acetone (200 mL) was treated with p-toluenesulfonic acid monohydrate (876 mg) and heated at 60° C. overnight. Solvent was removed and the residue was taken up in EtOAc, washed with aqueous $Na_2CO_3$ solution, brine, dried and concentrated to give the crude product as a yellow oil (5.38 g, >100% yield). Purification through flash chromatography (heaxane/EtOAc, 80/20→60/40) provided 4-(4-chlorophenyl)cyclohexanone as a light yellow oil (4.54 g, 95% yield). MS (EI) m/e 208 (M+), Calcd for $C_{12}H_{13}ClO_2$, 208.

Step 5:

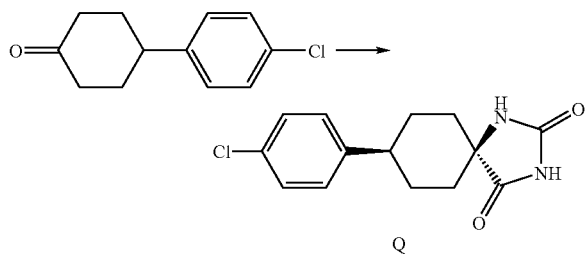

To a solution of 4-(4-chlorophenyl)cyclohexanone (4.26 g, 20.48 mmol) in ethanol (90 mL) and water (30 mL) in a glass pressure bottle, were added ammonium carbonate (13.8 g, 144 mmol, 7 equiv) and potassium cyanide (3.56 g, 54.77 mmol, 2.5 equiv). The mixture was heated at 80–90° C. overnight. The cooled reaction mixture was added to icy water (400 ml) and stirred vigorously for 30 min. The resulting precipitate was suction filtered, washed thoroughly with water and dried to yield the hydantoin Q as a white solid (5.58 g, 98% yield). MS (electrospray) m/e 277 (M−H), Calcd for $C_{14}H_{15}ClN_2O_2$, 278.

Step 6:

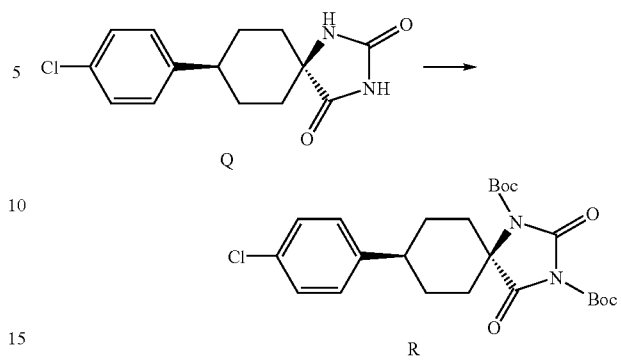

To a suspension of the hydantoin Q (5.15 g, 18.5 mmol) in dry THF (250 mL) were added di-tert-butyl dicarbonate (10.1 g, 46.3 mmol, 2.5 equiv), triethylamine (2.8 mL, 2.07 g, 20.45 mmol, 1.1 equiv) and DMAP (226 mg, 1.85 mmol) in succession. The reaction turned into a clear yellow solution and was stirred overnight at room temperature. The reaction mixture was concentrated under reduced pressure to yield a solid that was then taken up in EtOAc (500 mL), washed with 1N HCl (3×50 mL), saturated aqueous $Na_2CO_3$ (2×50 mL) and brine (2×50 mL), dried over anhydrous $Na_2SO_4$ and concentrated under reduced pressure. The crude light yellow product was purified through flash chromatography (hexane/EtOAc, 90/10→70/30) to give the pure bis-Boc hydantoin R as a white solid (8.05 g, 91% yield). MS (electrospray) m/e 542 (M+Ma+MeCN), Calcd for $C_{24}H_{31}ClN_2O_6$, 478.

Step 7:

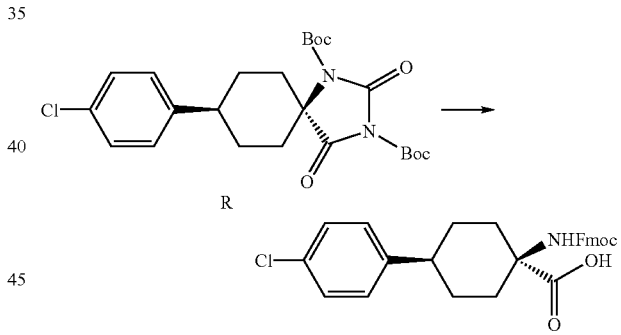

The bis-Boc hydantoin R (6.41 g, 13.97 mmol) was dissolved in DME (200 mL) to give a clear solution. To this solution was added 1N NaOH (120 mL, 120 mmol) and the reaction was stirred overnight at room temperature, giving a slightly cloudy mixture. HPLC showed completion of the reaction. The reaction mixture was concentrated under reduced pressure to remove DME and extracted with $Et_2O$. Without purification, the resulting aqueous layer containing 1-amino-4-(4-chlorophenyl)cyclohexane carboxylic acid (4-ClAPC) was treated with 6N HCl to adjust the pH to 11–12. To this solution (~180 mL) were added DME (240 mL) and a solution of Fmoc-OSu (5.31 g, 15.74 mmol, 1.1 equiv) in DME (30 mL) and the reaction was stirred overnight at room temperature. The reaction mixture was concentrated under reduced pressure to remove DME, acidified with 3N HCl, extracted with EtOAc. The combined organic extracts were washed with brine, dried over anhydrous $Na_2SO_4$ and concentrated. The crude product was purified through flash chromatography ($CH_2Cl_2$/MeOH, 98/2→90/

10) to give the pure product Fmoc-4-ClAPC as a white solid (5.04 g, 76% yield from the bis-Boc hydantoin). $^1$H NMR (DMSO-d$_6$), 7.88 (d, 2H), 7.74 (d, 2H), 7.19–7.42 (m, 8H), 4.20–4.31 (m, 3H); MS (electrospray) m/e 474 (M–H), Calcd for $C_{28}H_{26}ClNO_4$, 475.

EXAMPLE 8

Preparation of Fmoc-1-amino-4-(3-methoxyphenyl) cyclohexane-1-carboxylic acid (Fmoc-3-MeOApc-OH)

Step 1:

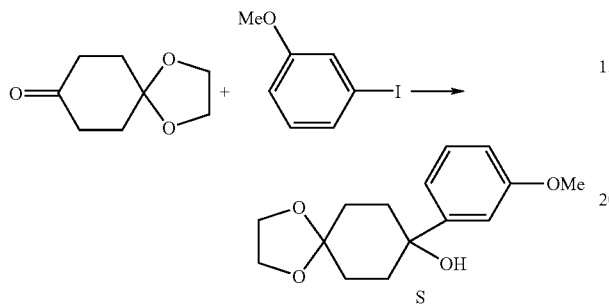

To a solution of 3-iodoanisole (11.7, 50.0 mmol, 1.3 equiv) in dry THF (180 mL) at –78° C. was added a solution of n-BuLi (1.6 M, 31.0 mL, 50 mmol, 1.3 equiv) in hexane over 25 min. The reaction was stirred for another 30 min before a solution of 1,4-cyclohexanedione mono-ethylene ketal (6.0 g, 38.46 mmol) in dry THF (100 mL) was added dropwise. After stirred for 2 h at –78° C., the reaction was quenched with aqueous NH$_4$Cl and extracted with EtOAc. The combined organic extracts were washed with brine, dried over Na$_2$SO$_4$, concentrated in vacuo to give the spectroscopically pure product S as a white solid (9.34 g, 98% yield). $^1$H NMR (CDCl$_3$): 7.26 (dd, 1H), 7.06–7.11 (m, 2H), 6.79 (dd, 1H), 3.98 (m, 4H), 3.81 (s, 3H).

Step 2:

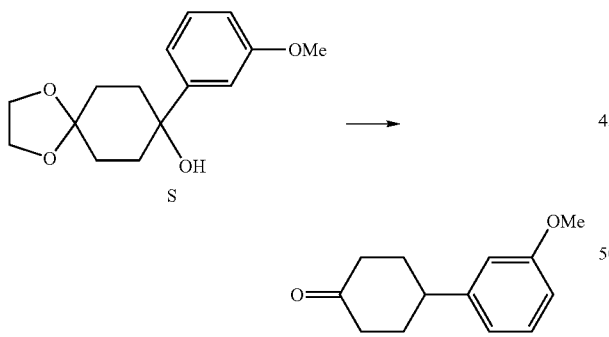

To a stirred solution of the alcohol S (5.6 g, 21.21 mmol) in dry CH$_2$Cl$_2$ (200 mL) under a nitrogen atmosphere at salt-ice bath temperature, were added in succession triethylsilane (10.2 mL, 7.4 g, 63.63 mmol, 3 equiv) and boron trifluoride etherate (21.5 mL, 24.1 g, 169.7 mmol, 8 equiv). The reaction mixture was then allowed to warm to room temperature and stirred for 3 hrs before washed with 10% aqueous K$_2$CO$_3$ solution and H$_2$O, dried over Na$_2$SO$_4$, and concentrated in vacuo to give the deoxygenation compound as an oil (4.91 g), which was sufficiently pure for direct use. This crude intermediate was dissolved in acetone (130 mL) and treated with 4N HCl (60 mL) and heated at 65° C. for 4 hrs. Solvent was removed under reduced pressure and the residue was diluted with EtOAc and neutralized with 4N NaOH solution. The aqueous layer was extracted with EtOAc and the combined organic extracts were washed with brine, dried and concentrated. The resulting residue was purified by flash chromatography on silica gel (80/20→60/40) to give 4-(3-methoxyphenyl)cyclohexanone (3.67 g, 85% overall yield) as a yellow oil. $^1$H NMR (CDCl$_3$): 7.25 (dt, 1H), 6.75–6.86 (m, 3H), 3.81 (s, 3H), 3.00 (tt, 1H); MS (EI) m/e 204 (M+), Calcd for $C_{13}H_{16}O_2$, 204.

Step 3:

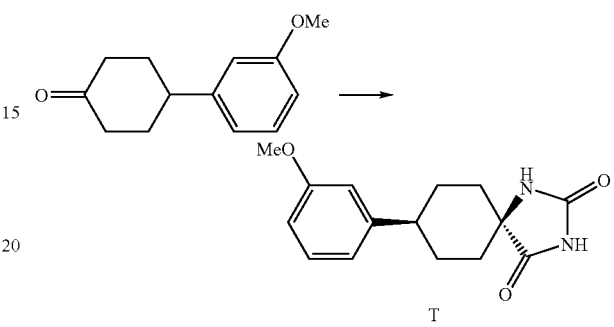

To a solution of 4-(3-methoxyphenyl)cyclohexanone (3.10 g, 15.20 mmol) in ethanol (60 mL) and water (20 mL) in a glass pressure bottle, were added ammonium carbonate (8.75 g, 91.20 mmol, 6 equiv.) and potassium cyanide (1.98 g, 30.40 mmol, 2 equiv.). The mixture was heated at 80–90° C. overnight. The cooled reaction mixture was added to icy water (300 ml) and stirred vigorously for 30 min. The resulting precipitate was suction filtered, washed thoroughly with water and dried to yield the hydantoin T as a white solid (4.08 g, 98% yield). $^1$H NMR (DMSO-d$_6$): 7.11 (d, 1H), 6.70–6.94 (m, 3H), 3.72 (s, 3H); MS (electrospray) m/e 316 (M+MeCN+H), Calcd for $C_{15}H_{18}N_2O_3$, 274.

Step 4:

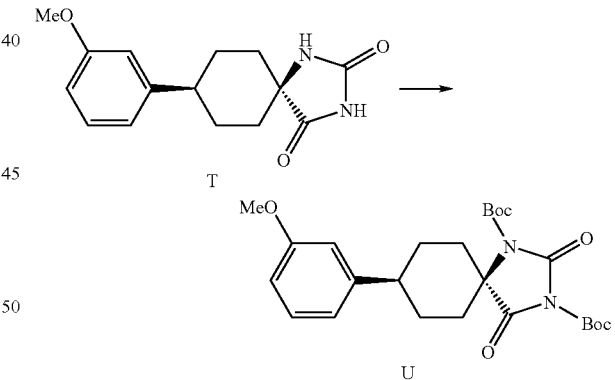

To a suspension of the hydantoin T (5.29 g, 19.30 mmol) in dry THF (250 mL) were added di-tert-butyl dicarbonate (10.5 g, 48.16 mmol, 2.5 equiv), triethylamine (3.0 mL, 2.17 g, 21.52 mmol, 1.1 equiv) and DMAP (235 mg, 1.92 mmol) in succession. The reaction turned into a clear yellow solution and was stirred overnight at room temperature. The reaction mixture was concentrated under reduced pressure to yield a solid that was then taken up in EtOAc (500 mL), washed with 1N HCl (3×50 mL), saturated aqueous Na$_2$CO$_3$ (2×50 mL) and brine (2×50 mL), dried over anhydrous Na$_2$SO$_4$ and concentrated under reduced pressure. The crude light yellow product was purified through flash chromatography (hexane/EtOAc, 80/20→60/40) to give the pure bis- Boc hydantoin U as a white solid (8.70 g, 95% yield). MS (electrospray) m/e 538 (M+MeCN+Na), Calcd for $C_{25}H_{34}N_2O_7$, 474.

Step 5:

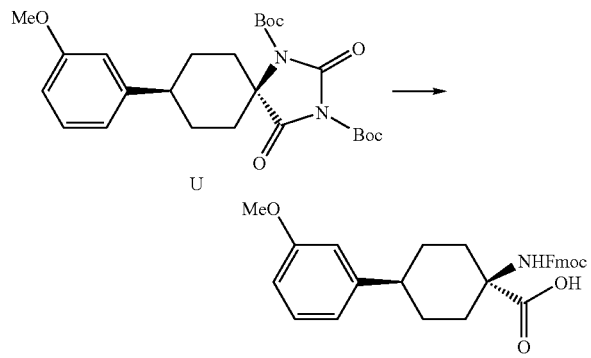

The bis-Boc hydantoin U (2.30 g, 4.84 mmol) was dissolved in DME (80 mL) to give a clear solution. To this solution was added 1N NaOH (44 mL, 44 mmol) and the reaction was stirred overnight at room temperature, giving a slightly cloudy mixture. HPLC showed completion of the reaction. The reaction mixture was concentrated under reduced pressure to remove DME and extracted with $Et_2O$. Without purification, the resulting aqueous layer containing 1-amino-4-(3-methoxyphenyl)cyclohexane carboxylic acid (3-MeOAPC) was treated with 6N HCl to adjust the pH to 11–12. To this solution (40 mL) were added dioxane (80 mL) and Fmoc-Cl (1.73 g, 6.76 mmol, 1.4 equiv) and the reaction was stirred overnight at room temperature. The reaction mixture was then concentrated under reduced pressure to remove DME, neutralized with 3N HCl and extracted with EtOAc. The combined organic extracts were washed with brine, dried over anhydrous $Na_2SO_4$ and concentrated. The crude product was purified by flash chromatography on silica gel ($CH_2Cl_2$/MeOH, 98/2→90/10) to give Fmoc-3-MeOAPC as a white solid (1.98 g, 87% yield from bis-Boc hydantoin U). $^1H$ NMR (DMSO-$d_6$), 7.88 (d, 2H), 7.75 (d, 2H), 7.40 (td, 2H), 7.30 (td, 2H), 7.21 (m, 1H), 6.71–6.80 (m, 3H), 3.72 (s, 31H); MS (electrospray) m/e 494 (M+Na), Calcd for $C_{29}H_{29}NO_5$, 471.

EXAMPLE 28

Preparation of Fmoc-(D,L)-5-bromo-2 aminotetraline-2-carboxylic acid (Fmoc-(D,L) 5-Br-Atc-OH)

Step 1:

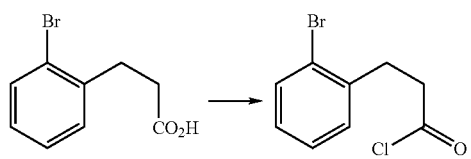

A mixture of 3-(2-bromophenyl)propanoic acid (prepared in 2 steps from 2-bromobenzyl bromide, 2.0 g, 8.73 mmole), oxalyl chloride (1.14 ml, 13.1 mmole) and methylene chloride (20 ml) was cooled in an ice bath and N,N-dimethylformamide (34 μL, 0.44 mmole) was added dropwise. The mixture was stirred at room temperature for 3 hours. Concentration in vacuo gave 3-(2-bromophenyl) propanoyl chloride which was taken up in methylene chloride and used in the next step as a crude.

Step 2:

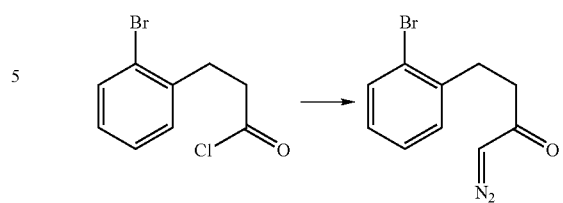

A solution of the above acid chloride (crude, 8.73 mmole) in methylene chloride was slowly added to a solution of diazomethane (generated from 5.70 g of 1-methyl-3-nitro-1-nitrosoguanidine) in ether (40 ml) cooled in an ice bath. The mixture was then warmed up to room temperature and stirred overnight. The mixture was concentrated in vacuo and purified by column chromatography (10→20% ethyl acetate/hexanes) to give 1-diazo-4-(2-bromophenyl)butan-2-one (1.88 g, 85% over 2 steps). $^1H$ NMR (CDCl$_3$) δ 7.50 (1H, d, phenyl), 7.24 (2H, m, phenyl), 7.06 (1H, m, phenyl), 5.21 (1H, broad s, diazo), 3.05 (2H, t, benzylic), 2.62 (2H, m).

Step 3:

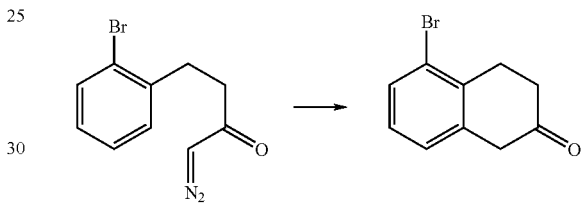

To a mixture of rhodium (II) acetate dimer (15 mg, 0.068 mmole) in methylene chloride (120 ml) under reflux was slowly added a solution of 1-diazo-4-(2-bromophenyl) butan-2-one (1.74 g, 6.85 mmole) in methylene chloride (30 ml). After the addition was complete, the mixture was refluxed for an extra twenty minutes. The mixture was cooled to room temperature, trifluoroacetic acid (1.5 ml) was added and the mixture was stirred at room temperature for an hour. The reaction was quenched with saturated sodium bicarbonate solution. The layers were separated and the methylene chloride layer was washed once more with saturated sodium bicarbonate solution. The combined aqueous layers were back-extracted with methylene chloride. The combined organic layers were dried over magnesium sulfate, filtered and concentrated in vacuo to give a brown oil. Purification by column chromatography (10→15% ethyl acetate/hexanes) gave 5-bromo-β-tetralone (1.18 g, 77% yield) as a colorless oil. $^1H$ NMR (CDCl$_3$) δ 7.46 (1H, t, phenyl), 7.05–7.09 (2H, m, phenyl), 3.58 (2H, s, benzylic), 3.22 (2H, t, benzylic), 2.54 (2H, t).

Step 4:

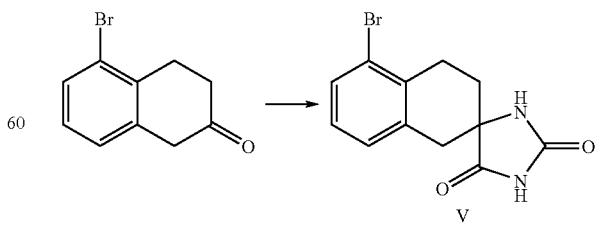

A mixture of 5-bromo-β-tetralone (1.18 g, 5.24 mmole), potassium cyanide (512 mg, 7.86 mmole), ammonium carbonate (3.0 g, 31.22 mmole), ethanol (25 ml) and water (5 ml) in a sealed, thick walled pressure flask was heated in a 80° C. oil bath for 4 days. After cooling to room temperature, the white slurry was poured into ice-water and stirred at room temperature for a couple of hours. Filtration followed by air-drying gave hydantoin V (1.31 g, 85%). $^1$H NMR (DMSO-$d_6$) δ 10.71 (1H, broad, NH), 8.28 (1H, broad s, NH), 7.0–7.5 (3H, m, phenyl). LRMS (Electrospray): $C_{12}H_{11}BrN_2O_2$, calc. 294; observed: 293 (M−H), 295 (M−H).

Step 5:

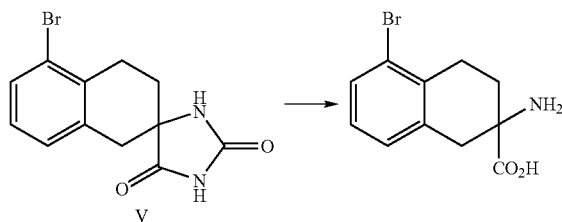

A mixture of hydantoin V (1.287 g, 4.36 mmole), Ba(OH)$_2$·H$_2$O (4.20 g, 22.2 mmole) in water (25 ml) in a sealed, thick walled pressure flask was heated in a 125° C. oil bath for 4 days. The reaction mixture was cooled to room temperature, acidified to ~pH 3 using 4N sulfuric acid while being stirred vigorously. The suspension was stirred in a boiling water bath for one hour and cooled to room temperature. The white suspension was filtered and the precipitates rinsed with water. The combined filtrate and washings were concentrated in vacuo to ~20 ml. Neutralization with concentrated ammonium hydroxide solution gave white precipitate which were filtered, washed with water and dried in vacuo overnight to give racemic 5-bromo-2-aminotetraline-2-carboxylic acid (893 mg, 76% yield). LRMS (Electrospray): $C_{11}H_{12}BrNO_2$, calc. 269; observed: 270 (M+H), 272 (M+H), 268 (M−H), 270 (M−H).

Step 6:

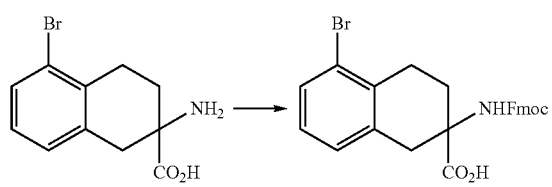

A mixture of racemic 5-bromo-2 aminotetraline-2-carboxylic acid (882 mg, 3.27 mmole), triethylamine (0.60 ml, 4.30 mmole), 9-fluorenylmethyl succinimidyl carbonate (Fmoc-OSu, 1.32 g, 3.91 mmole) in acetonitrile (30 ml) and water (30 ml) was stirred at room temperature overnight. TLC analysis of the reaction the next day indicated the presence of starting material amino acid. 9-fluorenylmethyl succinimidyl carbonate (0.25 g), triethylamine (0.6 ml) and acetonitrile (5 ml) was added and the mixture was stirred at room temperature for another day. The reaction mixture was concentrated in vacuo to remove most of the acetonitrile, acidified to pH ~3 with 10% aqueous citric acid solution, and the white emulsion extracted twice with methylene chloride. The combined organic layers were washed with water, brine, dried over magnesium sulfate. Filtration and concentration gave a crude oil which was purified by column chromatography (eluted with 2→5→10% methanol/methylene chloride) to give racemic Fmoc-5-bromo-2 aminotetraline-2-carboxylic acid (1.09 g, 68% yield) as a white solid. HRMS (FAB): $C_{26}H_{22}BrNNaO_4$ (M+Na) calc. 514.0630; observed: 514.0643.

EXAMPLE 10

Preparation of Fmoc-(D,L)-5-chloro-2 aminotetraline-2-carboxylic acid (Fmoc-(D,L) 5-ClAtc-OH)

Step 1:

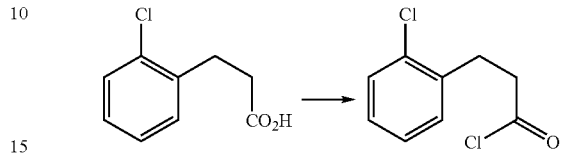

A mixture of 3-(2-chlorophenyl)propanoic acid (5.0 g, 27.1 mmole), thionyl chloride (10.9 ml, 149 mmole) and toluene (75 ml) was refluxed for two hours. Concentration in vacuo gave 3-(2-chlorophenyl)propanoyl chloride which was taken up in methylene chloride and used in the next step without further purification.

Step 2:

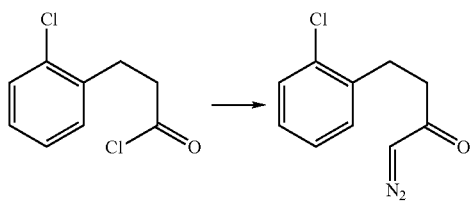

A solution of the above acid chloride (crude, 27.1 mmole) in methylene chloride was slowly added to a solution of diazomethane (generated from 17.8 g of 1-methyl-3-nitro-1-nitrosoguanidine) in ether (120 ml) cooled in an ice bath. The mixture was then warmed up to room temperature and stirred overnight. The mixture was concentrated in vacuo to give 1-diazo-4-(2-chlorophenyl)butan-2-one (5.87 g, >100% over 2 steps) as a bright yellow oil. The compound was used in the next step without further purification. $^1$H NMR (CDCl$_3$) δ 7.05–7.32 (4H, m, phenyl), 5.13 (1H, broad s, diazo), 3.00 (2H, t, benzylic), 2.57 (2H, m).

Step 3

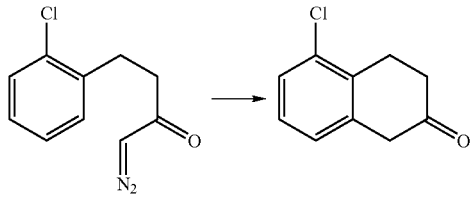

To a mixture of rhodium (II) acetate dimer (60 mg, 0.27 mmole) in methylene chloride (400 ml) under reflux was slowly added a solution of crude 1-diazo-4-(2-bromophenyl)butan-2-one (5.87 g, 27.1 mmole theoretical) in methylene chloride (50 ml). After the addition was complete, the mixture was refluxed for an extra twenty minutes. The mixture was cooled to room temperature, trifluoroacetic acid (6.0 ml) was added and the mixture was stirred at room temperature for two hours. The reaction was quenched with saturated sodium bicarbonate solution. The layers were separated and the methylene chloride layer was washed once more with saturated sodium bicarbonate solution. The combined aqueous layers were back-extracted with methylene chloride. The combined organic layers were dried over magnesium sulfate, filtered and concentrated in vacuo to give a brown oil. Purification by column chromatography (10→15% ethyl acetate/hexanes) gave 5-chloro-β-tetralone (3.32 g, 68% yield for steps 1 through 3) as a light brown oil. $^1$H NMR (CDCl$_3$) δ 7.30 (1H, m, phenyl), 7.15 (1H, t, phenyl), 7.05 (1H, d, phenyl), 3.60 (2H, s, benzylic), 3.22 (2H, t, benzylic), 2.56 (2H, t).

Step 4:

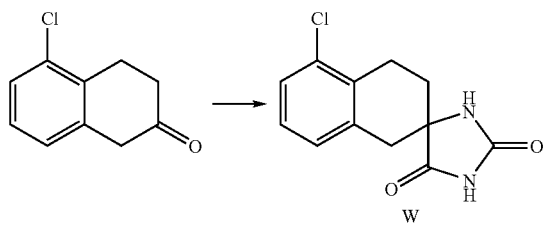

A mixture of 5-chloro-B-tetralone (880 mg, 4.87 mmole), potassium cyanide (500 mg, 7.67 mmole), ammonium carbonate (2.85 g, 29.7 mmole), ethanol (24 ml) and water (6 ml) in a sealed, thick walled pressure flask was heated in a 80° C. oil bath for 66 hours. After cooling to room temperature, the slurry was poured into ice-water and stirred at room temperature for a couple of hours. Filtration followed by air-drying gave hydantoin W (0.92 g, 75%) as a light beige solid. $^1$H NMR (DMSO-d$_6$) δ 10.70 (1H, broad, NH), 8.25 (1H, broad s, NH), 7.0–7.3 (3H, m, phenyl). LRMS (Electrospray): C$_{12}$H$_{11}$ClN$_2$O$_2$, calc. 250; observed: 249 (M−H), 251 (M−H).

Step 5:

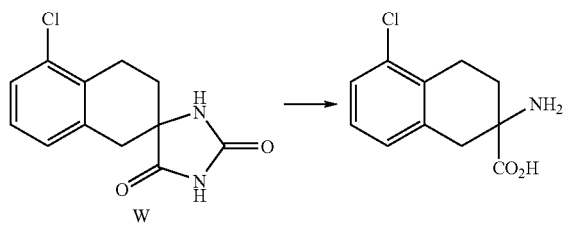

A mixture of hydantoin W (880 mg, 3.51 mmole), Ba(OH)$_2$. H$_2$O (3.40 g, 18.0 mmole) in water (50 ml, too dilute) in a sealed, thick walled pressure flask was heated in a 125° C. oil bath for 2 days. The reaction mixture was cooled to room temperature, acidified to ~pH 3 using 4N sulfuric acid while being stirred vigorously. The suspension was stirred in a boiling water bath for two hours and cooled to room temperature. The white suspension was filtered and the precipitates rinsed with water. The combined filtrate and washings were concentrated in vacuo to ~50 ml. Neutralization with concentrated ammonium hydroxide solution gave white precipitate which were filtered, washed with water and dried in vacuo overnight to give racemic 5-chloro-2-aminotetraline-2-carboxylic acid (788 mg, 99% yield). LRMS (Electrospray): C$_{11}$H$_{12}$ClNO$_2$, calc. 225; observed: 226 (M+H), 228 (M+H), 224 (M−H), 226 (M−H).

Step 6:

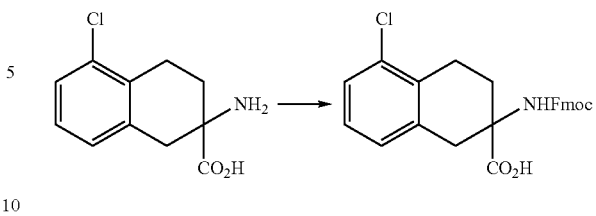

A mixture of racemic 5-chloro-2-aminotetraline-2-carboxylic acid (402 mg, 1.78 mmole), triethylamine (0.38 ml, 2.73 mmole), 9-fluorenylmethyl succinimidyl carbonate (Fmoc-OSu, 904 mg, 2.68 mmole) in acetonitrile (20 ml) and water (20 ml) was stirred at room temperature for two days. TLC analysis of the reaction after two days indicated the presence of starting material amino acid. 9-fluorenylmethyl succinimidyl carbonate (0.12 g) and triethylamine (0.1 ml) was added and the mixture was stirred at room temperature for another day. The reaction mixture was concentrated in vacuo to remove most of the acetonitrile, acidified to pH ~3 with 10% aqueous citric acid solution, and the white emulsion extracted three times with ethyl acetate. The combined organic layers were washed with water, brine, dried over magnesium sulfate. Filtration and concentration gave a crude oil which was purified by column chromatography (eluted with 3→6→8% methanol/methylene chloride) to give racemic Fmoc-5-chloro-2-aminotetraline-2-carboxylic acid (540 mg, 68% yield) as a white solid. HRMS (EI): C$_{26}$H$_{22}$ClNO$_4$ (M) calc. 447.1237; observed: 447.1234.

EXAMPLE 11

Preparation of Fmoc-(D,L)-5-methoxy-2-aminotetraline-2-carboxylic acid (Fmoc-(D,L) 5-MeOAtc-OH)

Step 1:

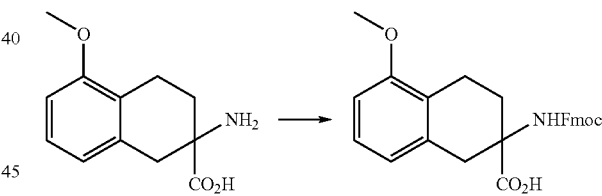

A mixture of racemic 5-methoxy-2-aminotetraline-2-carboxylic acid (prepared according to Obrecht, D. et. al. *Helv. Chim Acta*. 1992, 75, 1666) (802 mg, 3.62 mmole), triethylamine (0.62 ml, 4.45 mmole), 9-fluorenylmethyl succinimidyl carbonate (Fmoc-OSu, 1.47 g, 4.36 mmole) in acetonitrile (25 ml) and water (25 ml) was stirred at room temperature for 30 hours. TLC analysis of the reaction indicated the presence of starting material amino acid. 9-fluorenylmethyl succinimidyl carbonate (370 mg) and triethylamine (0.6 ml) were added and the mixture was stirred at room temperature for another 24 hours. The reaction mixture was concentrated in vacuo to remove most of the acetonitrile, acidified to pH 3 with 10% aqueous citric acid solution, and the white emulsion was extracted three times with ethyl acetate. The combined organic layers were washed with water, brine and dried over magnesium sulfate. Filtration and concentration gave a crude oil which was purified by column chromatography (eluted with 1→3→5→10% methanol/methylene chloride) to give racemic Fmoc-5-methoxy-2-aminotetraline-2-carboxylic acid (1.14 g, 71% yield) as an off-white solid. HRMS (FAB): $C_{27}H_{26}NO_5$ (M+H) calc. 444.1812; observed: 444.1814.

EXAMPLE 12

Preparation of Fmoc-(D,L)-5-ethoxy-2-aminotetraline-2-carboxylic acid (Fmoc-(D,L) 5-EtOAtc-OH)

Step 1:

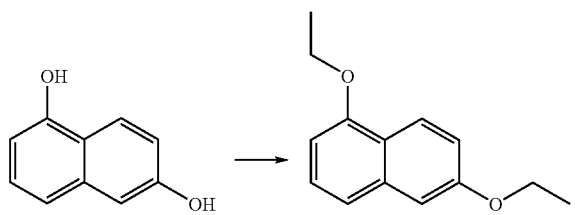

A mixture of 1,6-dihydroxynaphthalene (5.02 g, 31.3 mmole), anhydrous potassium carbonate (52.0 g, 376 mmole), N,N-dimethylformamide (50 ml) and iodoethane (15 ml, 188 mmole) was stirred in a 35° C. oil bath for 24 hours. The reaction mixture was filtered and the solid residue was rinsed thoroughly with ethyl ether. The filtrate and the washings were combined and concentrated in vacuo to remove most of the solvents. The brown residue was partitioned between water and ether and the layers were separated. The ether layer was washed with water. The combined aqueous layers were back extracted with ether. The ether extracts were combined, washed with brine and dried over magnesium sulfate. Filtration and concentration gave a crude brown solid (6.74 g, 99% yield). Recrystallization of the crude product from hot methanol gave 1,6-diethoxynaphthalene (4.36 g, 64% yield, first crop) as a light brown solid. $^1$H NMR (CDCl$_3$) δ 8.20 (1H, d, phenyl), 7.06–7.36 (4H, m, phenyl), 6.66 (1H, dd, phenyl), 4.10–4.23 (4H, 2 sets of q, 2 CH$_2$), 1.45–1.56 (6H, 2 sets of t, 2 CH$_3$).

Step 2:

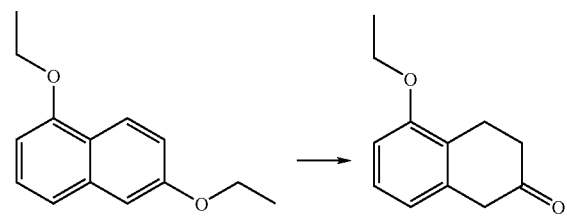

To a refluxing solution of 1,6-diethoxynaphthalene (4.15 g, 19.2 mmole) in absolute ethanol (100 ml) was carefully added small pieces of sodium metal (6.8 g, 296 mmole) over 60 minutes. The mixture was refluxed for another 90 minutes. TLC indicated the presence of unreacted starting material. Extra sodium metal (1.0 g, 43.5 mmole) was added and the reaction mixture was refluxed for another 60 minutes. The reaction was cooled to room temperature, quenched with water and acidified with concentrated hydrochloric acid. The mixture was concentrated in vacuo to remove most of the ethanol. The aqueous mixture was extracted three times with ether. The combined organic layers were washed with water and dried over sodium sulfate. Filtration and concentration gave a brown solid which was dissolved in 1:1 ethanol/water (200 ml), then p-toluenesulfonic acid (400 mg) was added. The mixture was refluxed for 210 minutes. Extra p-toluenesulfonic acid (100 mg) was added and the mixture was refluxed for another 60 minutes. After cooling to room temperature, most of the ethanol was removed under reduced pressure. The aqueous mixture was extracted three times with ether and the combined organic layers were washed with water, saturated sodium chloride solution and dried over sodium sulfate. Filtration and concentration gave a brown oil which was purified by column chromatography (7% ethyl acetate/hexanes) to give 5-ethoxy-β-tetralone (2.43 g, 67% yield) as a light yellow oil. $^1$H NMR (CDCl$_3$) δ 7.15 (1H, t, phenyl), 6.76 (1H, d, phenyl), 6.72 (1H, d, phenyl), 4.05 (2H, q, CH$_2$), 3.56 (2H, s, benzylic), 3.10 (2H, t, benzylic), 2.53 (2H, t), 1.44 (3H, t, CH$_3$).

Step 3:

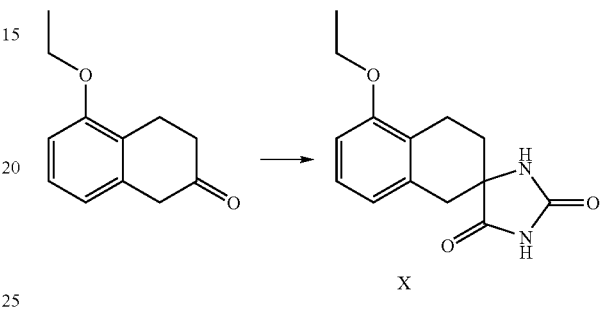

A mixture of 5-ethoxy-β-tetralone (2.23 g, 11.7 mmole), potassium cyanide (1.20 g, 18.4 mmole), ammonium carbonate (6.75 g, 70.2 mmole), ethanol (80 ml) and water (20 ml) in a sealed, thick walled pressure flask was heated in a 80° C. oil bath for 3 days. After cooling to room temperature, the slurry was poured into ice-water and stirred at room temperature for a couple of hours. Filtration followed by air-drying gave hydantoin X (2.69 g, 88%) as a beige solid. $^1$H NMR (DMSO-d$_6$) δ 10.65 (1H, broad s, NH), 8.22 (1H, broad s, NH), 7.06 (1H, t, phenyl), 6.75 (1H, d, phenyl), 6.65 (1H, d, phenyl), 3.98 (2H, q, CH$_2$), 1.32 (3H, t, CH$_3$). LRMS (Electrospray): $C_{14}H_{16}N_2O_3$, calc. 259; observed: 258 (M−H).

Step 4:

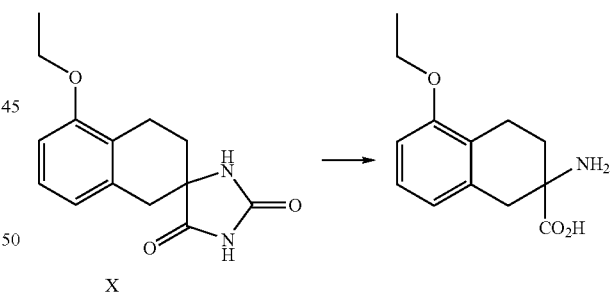

A mixture of hydantoin X (2.57 g, 9.87 mmole), Ba(OH)$_2$·H$_2$O (9.40 g, 49.6 mmole) in water (200 ml, too dilute) in a sealed, thick walled pressure flask was heated in a 105° C. oil bath for 39 hours. Extra Ba(OH)$_2$·H$_2$O (9.40 g, 49.6 mmole) was added and the mixture was heated in a 125° C. oil bath for an additional 21 hours. The reaction mixture was cooled to room temperature, acidified to ~pH 3 using 4N sulfuric acid while being stirred vigorously. The suspension was stirred in a boiling water bath for one hour and cooled to room temperature. The white suspension was filtered and the precipitates rinsed with water. The combined filtrate and washings were concentrated in vacuo to 75 ml. Neutralization with concentrated ammonium hydroxide solution gave white precipitate which were filtered, washed with water and air-dried to give racemic 5-ethoxy-2-aminotetraline-2-carboxylic acid (2.34 g, quantitative yield) as a light beige solid. LRMS (Electrospray): $C_{13}H_{17}NO_3$, calc. 235; observed: 236 (M+H), 234 (M–H).

Step 5:

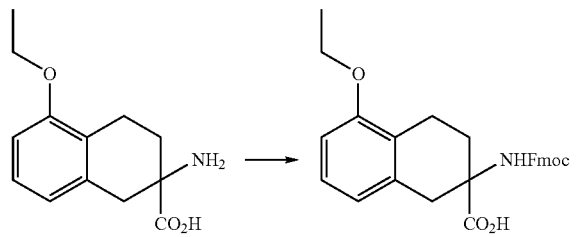

A mixture of racemic 5-ethoxy-2-aminotetraline-2-carboxylic acid (2.22 g, 9.44 mmole), triethylamine (2.00 ml, 14.3 mmole), 9-fluorenylmethyl succinimidyl carbonate (Fmoc-OSu, 4.81 g, 14.3 mmole) in acetonitrile (75 ml) and water (75 ml) was stirred at room temperature for two days. TLC analysis of the reaction indicated the presence of starting material amino acid. 9-fluorenylmethyl succinimidyl carbonate (645 mg) and triethylamine (1.0 ml) was added and the mixture was stirred at room temperature for another day. The reaction mixture was concentrated in vacuo to remove most of the acetonitrile, acidified to pH 3 with 10% aqueous citric acid solution, and the white emulsion extracted three times with ethyl acetate. The combined organic layers were washed with water, brine, dried over magnesium sulfate. Filtration and concentration gave a crude oil which was purified by column chromatography (eluted with 3→5→10% methanol/methylene chloride) to give racemic Fmoc-5-ethoxy-2-aminotetraline-2-carboxylic acid (4.66 g, >quantitative yield) as a white solid. HRMS (FAB): $C_{28}H_{28}NO_5$ (M+H) calc. 458.1967; observed: 458.1985.

EXAMPLE 13

Preparation of Fmoc-(D,L)-5-isopropoxy-2-aminotetraline-2-carboxylic acid (Fmoc-(D,L) 5-iPrOAtc-OH)

Step 1:

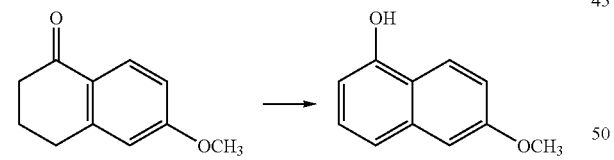

A mixture of 6-methoxy-1-tetralone (5.07 g, 28.8 mmole), 10% Pd/C (3.53 g, 3.32 mmole) in dry p-cymene (250 ml) was heated to reflux under argon for 38 hours. The reaction mixture was cooled to room temperature, filtered over celite and the residue rinsed thoroughly with p-cymene. The filtrate and the washings were combined and extracted twice with 1N sodium hydroxide solution (2×70 ml). The combined aqueous extracts were acidified with 6N hydrochloric acid to pH ~3 and extracted three times with ether. The combined organic layers were washed with water, dried over anhydrous sodium sulfate. Filtration and concentration gave crude 5-hydroxy-6-methoxynaphthalene (2.31 g, 46% yield) as a light brown solid which was used in the next step without further purification. LRMS (Electrospray): $C_{11}H_{10}O_2$, calc. 174; observed: 173 (M–H).

Step 2:

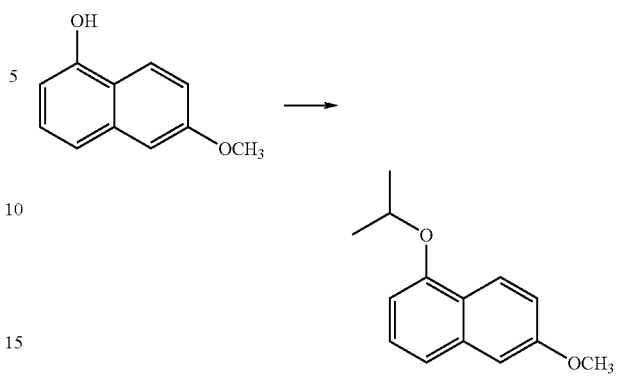

A mixture of 5-hydroxy-6-methoxynaphthalene (2.10 g, 12.1 mmole), cesium carbonate (19.7 g, 60.5 mmole), N,N-dimethylformamide (12 ml) and 2-bromopropane (3.50 ml, 36.9 mmole) was stirred in a 40° C. oil bath overnight. The reaction mixture was filtered and the solid residue was rinsed thoroughly with ethyl ether. The filtrate and the washings were combined and concentrated in vacuo to remove most of the solvents. The brown residue was partitioned between water and ether and the layers were separated. The ether layer was washed with water. The combined aqueous layers were back extracted with ether. The ether extracts were combined, washed with brine and dried over sodium sulfate. Filtration and concentration gave a crude which was purified by column chromatography (2.5→5% ethyl acetate/hexanes) to give 1-isopropoxy-6-methoxynaphthalene (2.23 g, 86% yield) as a light brown oil. $^1$H NMR (CDCl$_3$) δ 8.17 (1H, d, phenyl), 7.05–7.38 (4H, m, phenyl), 6.72 (1H, dd, phenyl), 4.73 (1H, m, CH of iPr), 3.92 (3H, s, OCH$_3$), 1.42 (6H, d, 2 CH$_3$ of iPr).

Step 3:

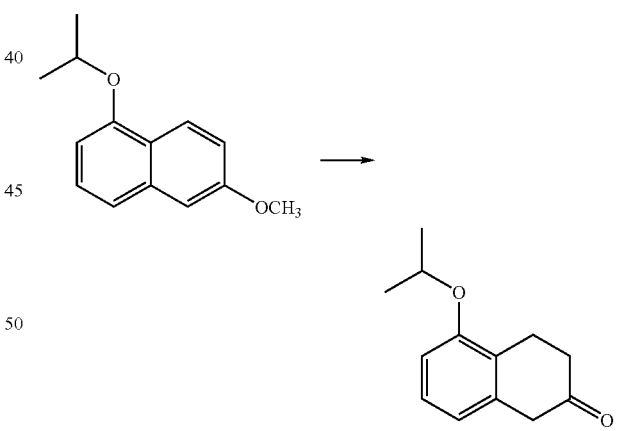

To a refluxing solution of 1-isopropoxy-6-methoxynaphthalene (2.23 g, 10.3 mmole) in absolute ethanol (50 ml) was carefully added small pieces of sodium metal (3.6 g, 157 mmole) over 45 minutes. The mixture was refluxed for a further 120 minutes. The reaction was cooled to room temperature, quenched with water and acidified with concentrated hydrochloric acid. The mixture was concentrated in vacuo to remove most of the ethanol. The aqueous mixture was extracted three times with ether. The combined organic layers were washed with water and dried over sodium sulfate. Filtration and concentration gave a reddish oil which was dissolved in 1:1 ethanol/water (90 ml), then p-toluenesulfonic acid (200 mg) was added. The mixture was refluxed for 60 minutes. After cooling to room temperature, most of the ethanol was removed under reduced pressure. The aqueous mixture was extracted twice with ether and the combined organic layers were washed with water, saturated sodium chloride solution and dried over sodium sulfate. Filtration and concentration gave a reddish oil which was purified by column chromatography (8→15% ethyl acetate/hexanes) to give 5-isopropoxy-β-tetralone (1.37 g, 65% yield) as a colorless oil. $^1$H NMR (CDCl$_3$) δ 7.16 (1H, t, phenyl), 6.78 (1H, d, phenyl), 6.71 (1H, d, phenyl), 4.53 (1H, m, CH of iPr), 3.56 (2H, s, benzylic), 3.08 (2H, t, benzylic), 2.50 (2H, t), 1.37 (6H, d, 2 CH$_3$ of iPr).

Step 4:

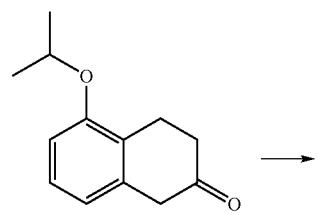

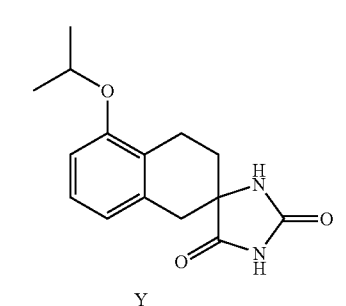

Y

A mixture of 5-isopropoxy-β-tetralone (1.37 g, 6.71 mmole), potassium cyanide (660 mg, 10.1 mmole), ammonium carbonate (3.87 g, 40.3 mmole), ethanol (44 ml) and water (9 ml) in a sealed, thick walled pressure flask was heated in a 80° C. oil bath for 42 hours. After cooling to room temperature, the slurry was poured into ice-water and stirred at room temperature for a couple of hours. Filtration followed by air-drying gave hydantoin Y (1.64 g, 89%).

Step 5:

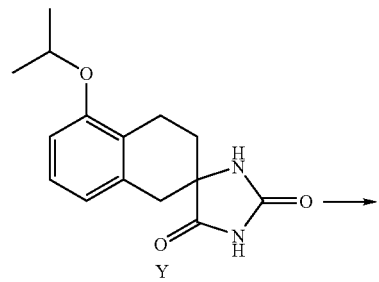

Y

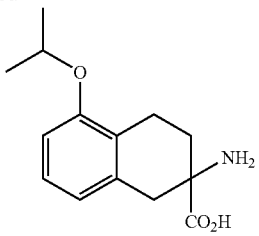

A mixture of hydantoin Y (1.64 g, 5.98 mmole), Ba(OH)$_2$·H$_2$O (5.66 g, 29.9 mmole) in water (25 ml) in a sealed, thick walled pressure flask was heated in a 100° C. oil bath for 70 hours. The reaction mixture was cooled to room temperature, neutralized to ~pH 7 using 4N sulfuric acid while being stirred vigorously. The suspension was stirred in a boiling water bath for one hour and cooled to room temperature. Basified with 1N sodium hydroxide solution and the white suspension was filtered and the precipitates rinsed with water. The combined filtrate and washings were concentrated in vacuo to ~75 ml. Neutralization with concentrated hydrochloric acid solution gave white precipitate which were filtered, washed with water and air-dried to give racemic 5-isopropoxy-2-aminotetraline-2-carboxylic acid (3.48 g, wet and containing inorganic salt, >quantitative yield). LRMS (Electrospray): C$_{14}$H$_{19}$NO$_3$, calc. 249; observed: 248 (M–H).

Step 6:

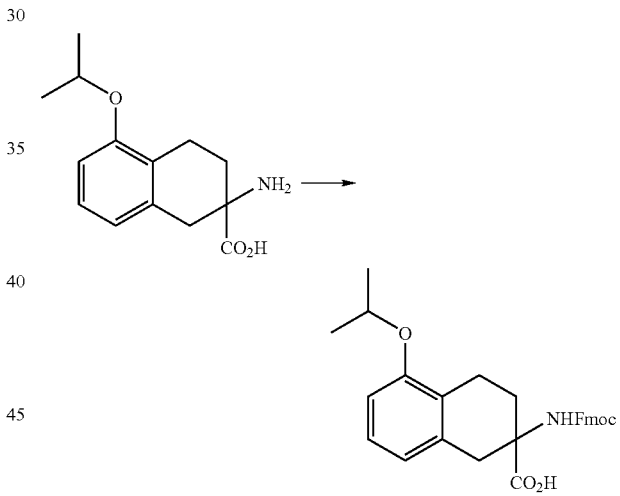

A mixture of racemic 5-isopropoxy-2-aminotetraline-2-carboxylic acid (3.48 g, 5.98 mmole theoretical), triethylamine (1.10 ml, 7.89 mmole), 9-fluorenylmethyl succinimidyl carbonate (Fmoc-OSu, 2.62 g, 7.77 mmole) in acetonitrile (30 ml) and water (30 ml) was stirred at room temperature for one day. TLC analysis of the reaction indicated the presence of starting material amino acid. 9-fluorenylmethyl succinimidyl carbonate (500 mg) was added and the mixture was stirred at room temperature for another day. The reaction mixture was concentrated in vacuo to remove most of the acetonitrile, acidified to pH ~3 with 10% aqueous citric acid solution, and the white emulsion extracted three times with methylene chloride. The combined organic layers were washed with water, brine, dried over magnesium sulfate. Filtration and concentration gave a crude oil which was purified by column chromatography (eluted with 1→2→5→8% methanol/methylene chloride) to give racemic Fmoc-5-isopropoxy-2-aminotetraline-2- carboxylic acid (0.50 g, 18% yield over 2 steps) as a white solid. HRMS (FAB): $C_{29}H_{30}NO_5$ (M+H) calc. 472.2124; observed: 472.2117.

EXAMPLE 14

Preparation of Fmoc-(D,L)-5-methyl-2-aminotetraline-2-carboxylic acid (Fmoc-(D,L) 5-MeAtc-OH)

Step 1:

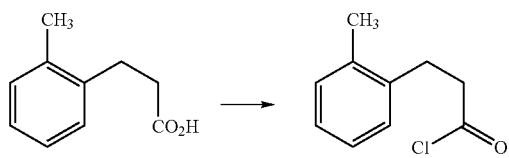

A mixture of 2-methylhydrocinnamic acid (3.0 g, 18.3 mmole), oxalyl chloride (3.19 ml, 36.6 mmole) and methylene chloride (30 ml) was cooled in an ice bath and N,N-dimethylformamide (0.14 ml, 1.81 mmole) was added dropwise. The mixture was stirred at room temperature overnight. Concentration in vacuo gave 3-(2-methylphenyl)propanoyl chloride which was taken up in methylene chloride and used in the next step as a crude.

Step 2:

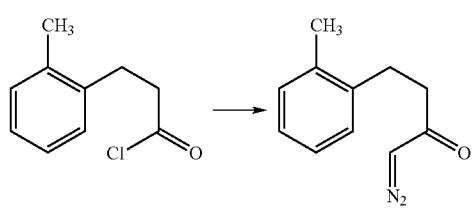

A solution of the above acid chloride (crude, 18.3 mmole) in methylene chloride was slowly added to a solution of diazomethane (generated from 11.9 g of 1-methyl-3-nitro-1-nitrosoguanidine) in ether (80 ml) cooled in an ice bath. The mixture was then warmed up to room temperature and stirred overnight. The mixture was concentrated in vacuo and purified by column chromatography (10→20% ethyl acetate/hexanes) to give 1-diazo-4-(2-methylphenyl)butan-2-one (2.08 g, 60% over 2 steps) as a bright yellow oil.

Step 3:

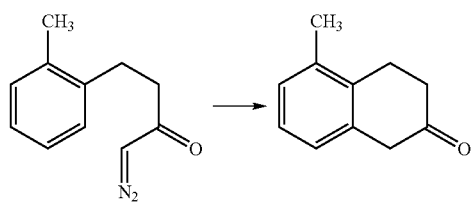

To a mixture of rhodium (11) acetate dimer (24 mg, 0.109 mmole) in methylene chloride (200 ml) under reflux was slowly added a solution of 1-diazo-4-(2-methylphenyl)butan-2-one (2.08 g, 11.1 mmole) in methylene chloride (50 ml) over 180 minutes. After the addition was complete, the mixture was refluxed for an extra twenty minutes. The mixture was cooled to room temperature, trifluoroacetic acid (2.40 ml) was added and the mixture was stirred at room temperature for an hour. The reaction was quenched with saturated sodium bicarbonate solution. The layers were separated and the methylene chloride layer was washed once more with saturated sodium bicarbonate solution. The combined aqueous layers were back-extracted with methylene chloride. The combined organic layers were dried over magnesium sulfate, filtered and concentrated in vacuo to give a crude brown oil. Purification by column chromatography (15% ethyl acetate/hexanes) gave 5-methyl-β-tetralone (1.48 g, 84% yield) as a light brown oil. $^1$H NMR (CDCl$_3$) δ 6.90–7.20 (3H, m, phenyl), 3.58 (2H, s, benzylic), 3.03 (2H, t, benzylic), 2.55 (2H, t), 2.34 (3H, s, CH$_3$).

Step 4:

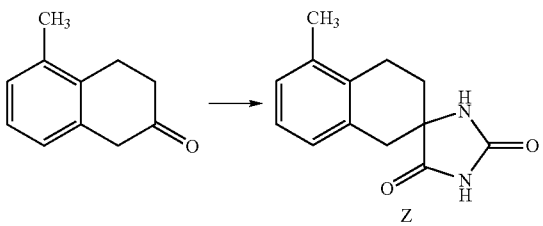

A mixture of 5-methyl-β-tetralone (1.48 g, 9.24 mmole), potassium cyanide (902 mg, 13.9 mmole), ammonium carbonate (5.33 g, 55.5 mmole), ethanol (45 ml) and water (9 ml) in a sealed, thick walled pressure flask was heated in a 80° C. oil bath for 3 days. After cooling to room temperature, the slurry was poured into ice-water and stirred at room temperature for a couple of hours. Filtration followed by air-drying gave crude hydantoin Z (1.81 g, 85% yield) as a beige solid. $^1$H NMR (DMSO-d$_6$) δ 10.66 (111, broad s, NH), 8.22 (11H, broad s, NH), 6.85–7.05 (3H, m, phenyl), 2.17 (3H, s, CH$_3$).

Step 5:

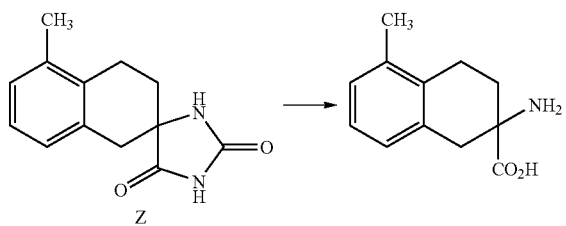

A mixture of hydantoin Z (1.80 g, 7.82 mmole), Ba(OH)$_2$·H$_2$O (7.40 g, 39.1 mmole) in water (28 ml) in a sealed, thick walled pressure flask was heated in a 125° C. oil bath for 88 hours. The reaction mixture was cooled to room temperature, acidified to ~pH 3 using 4N sulfuric acid while being stirred vigorously. The suspension was stirred in a boiling water bath for an hour and cooled to room temperature. The white suspension was filtered and the precipitates rinsed with water. The combined filtrate and washings were concentrated in vacuo to ~50 ml. Neutralization with concentrated ammonium hydroxide solution gave white precipitate which were filtered, washed with water and air-dried to give racemic 5-methyl-2-aminotetraline-2-carboxylic acid (1.05 g, 65% yield) as a beige solid. LRMS (Electrospray): $C_{12}H_{15}NO_2$, calc. 205; observed: 206 (M+H).

Step 6:

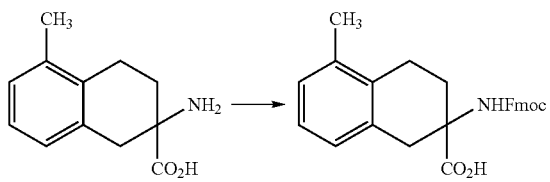

A mixture of racemic 5-methyl-2-aminotetraline-2-carboxylic acid (1.05 g, 5.12 mmole), triethylamine (0.93 ml, 6.67 mmole), 9-fluorenylmethyl succinimidyl carbonate (Fmoc-OSu, 2.24 g, 6.64 mmole) in acetonitrile (30 ml) and water (30 ml) was stirred at room temperature for 2 days. TLC analysis of the reaction indicated the presence of starting material amino acid. 9-fluorenylmethyl succinimidyl carbonate (520 mg) was added and the mixture was stirred at room temperature for another 24 hours. The reaction mixture was concentrated in vacuo to remove most of the acetonitrile, acidified to pH ~3 with 10% aqueous citric acid solution, and the white emulsion was extracted twice with methylene chloride. The combined organic layers were washed with water, brine and dried over magnesium sulfate. Filtration and concentration gave a crude oil which was purified by column chromatography (eluted with 2→5→8% methanol/methylene chloride) to give racemic Fmoc-5-methyl-2-aminotetraline-2-carboxylic acid (1.62 g, 74% yield) as an light brown solid. HRMS (FAB): $C_{27}H_{26}NO_4$ (M+H) calc. 428.1862; observed: 428.1844.

EXAMPLE 15

Preparation of Fmoc-(D,L)-5-ethyl-2 aminotetraline-2-carboxylic acid (Fmoc-(D,L) 5-EtAtc-OH)

Step 1:

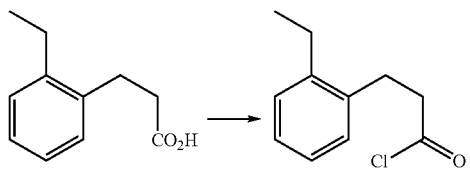

A mixture of 3-(2-ethylphenyl)propanoic acid (prepared in 3 steps from 1-ethyl-2-iodobenzene, 4.24 g, 23.8 mmole), thionyl chloride (9.50 ml, 130 mmole) and toluene (100 ml) was refluxed for 2 hours. Concentration in vacuo gave 3-(2-ethylphenyl)propanoyl chloride which was taken up in methylene chloride and used in the next step as a crude.

Step 2:

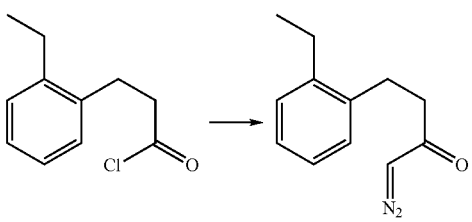

A solution of 3-(2-ethylphenyl)propanoyl chloride (crude, 23.8 mmole) in methylene chloride was slowly added to a solution of diazomethane (generated from 15.6 g of 1-methyl-3-nitro-1-nitrosoguanidine) in ether (100 ml) cooled in an ice bath. The mixture was then warmed up to room temperature and stirred overnight. The mixture was concentrated in vacuo and purified by column chromatography (10→20% ethyl acetate/hexanes) to give 1-diazo-4-(2-ethylphenyl)butan-2-one (3.47 g, 72% over 2 steps). $^1$H NMR (CDCl$_3$) δ 7.1–7.25 (4H, m, phenyl), 5.21 (1H, broad s, diazo), 2.97 (2H, m, CH$_2$ of ethyl), 1.20 (3H, t, CH$_3$).

Step 3:

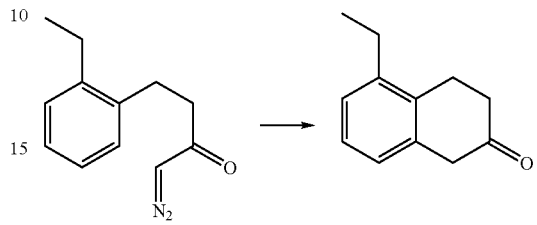

To a mixture of rhodium (II) acetate dimer (38 mg, 0.172 mmole) in methylene chloride (300 ml) under reflux was slowly added a solution of 1-diazo-4-(2-ethylphenyl)butan-2-one (3.47 g, 17.2 mmole) in methylene chloride (50 ml) over 90 minutes. After the addition was complete, the mixture was refluxed for an extra twenty minutes. The mixture was cooled to room temperature, trifluoroacetic acid (3.75 ml) was added and the mixture was stirred at room temperature for an hour. The reaction was quenched with saturated sodium bicarbonate solution. The layers were separated and the methylene chloride layer was washed once more with saturated sodium bicarbonate solution. The combined aqueous layers were back-extracted with methylene chloride. The combined organic layers were dried over magnesium sulfate, filtered and concentrated in vacuo to give crude 5-ethyl-β-tetralone (3.09 g, >quantitative yield) as a reddish-brown oil. The compound was used in the next step without further purification. $^1$H NMR (CDCl$_3$) δ 6.9–7.2 (3H, m, phenyl), 3.58 (2H, s, benzylic), 3.08 (2H, s, benzylic), 2.70 (2H, q, CH$_2$ of ethyl), 2.52 (2H, t, benzylic), 1.20 (3H, t, CH$_3$ of ethyl).

Step 4:

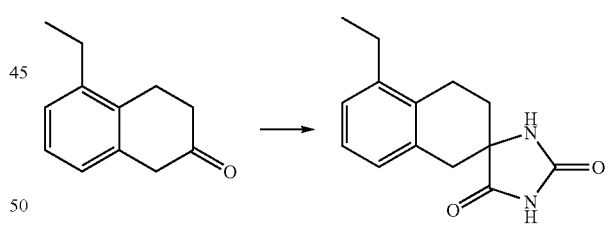

AA

A mixture of 5-ethyl-β-tetralone (3.09 g, 17.7 mmole), potassium cyanide (1.73 g, 26.6 mmole), ammonium carbonate (10.2 g, 106 mmole), ethanol (80 ml) and water (16 ml) in a sealed, thick walled pressure flask was heated in a 80° C. oil bath for 48 hours. After cooling to room temperature, the white slurry was poured into ice-water and stirred at room temperature for a couple of hours. Filtration followed by air-drying gave hydantoin AA (3.85 g, 92% yield over 2 steps) as a light beige solid. $^1$H NMR (DMSO-d$_6$) δ 10.67 (1H, broad s, NH), 8.26 (1H, broad s, NH), 6.8–7.1 (3H, m, phenyl), 1.13 (3H, t, CH$_3$). LRMS (Electrospray): $C_{14}H_{16}N_2O_2$, calc. 244; observed: 243 (M−H).

Step 5:

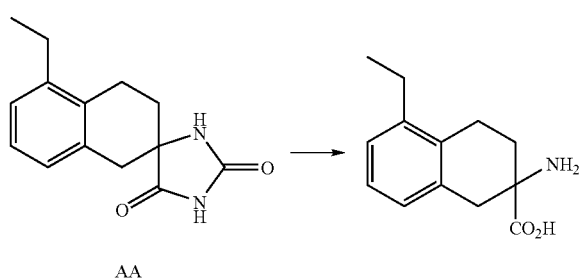

A mixture of hydatoin AA (1.00 g, 4.09 mmole), Ba(OH)$_2$·H$_2$O (4.00 g, 21.1 mmole) in water (20 ml) in a sealed, thick walled pressure flask was heated in a 125° C. oil bath for 48 hours. The reaction mixture was cooled to room temperature, acidified to ~pH 3 using 4N sulfuric acid while being stirred vigorously. The suspension was stirred in a boiling water bath for two hours and cooled to room temperature. The white suspension was filtered and the precipitates rinsed with water. The combined filtrate and washings were concentrated in vacuo to ~50 ml. Neutralization with concentrated ammonium hydroxide solution gave white precipitate which were filtered, washed with water and dried in vacuo overnight to give racemic 5-ethyl-2-aminotetraline-2-carboxylic acid (796 mg, 89% yield). LRMS (Electrospray): C$_{13}$H$_{17}$NO$_2$, calc. 219; observed: 220 (M+H).

Step 6:

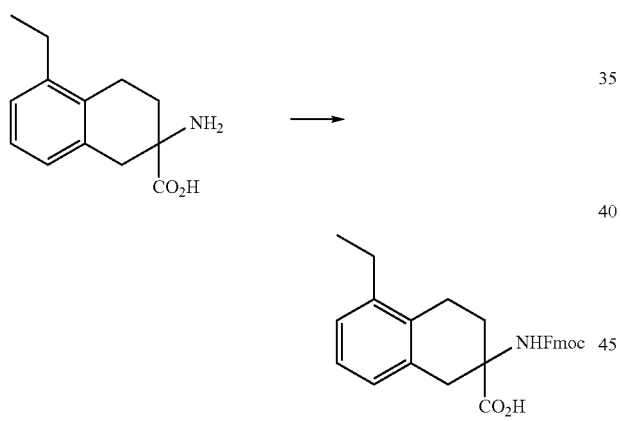

A mixture of racemic 5-ethyl-2-aminotetraline-2-carboxylic acid (765 mg, 3.49 mmole), triethylamine (1.0 ml, 7.17 mmole), 9-fluorenylmethyl succinimidyl carbonate (Fmoc-OSu, 1.79 g, 5.31 mmole) in acetonitrile (40 ml) and water (40 ml) was stirred at room temperature for 2 days. The reaction mixture was concentrated in vacuo to remove most of the acetonitrile, acidified to pH ~3 with 10% aqueous citric acid solution, and the white emulsion extracted twice with methylene chloride, twice with ethyl acetate. The methylene chloride extracts were washed with water, brine and dried over magnesium sulfate. The ethyl acetate extracts were washed with water, brine and dried over magnesium sulfate. Filtration and concentration gave a crude oil which was purified by column chromatography (eluted with 2→5→8% methanol/methylene chloride) to give racemic Fmoc-5-ethyl-2-aminotetraline-2-carboxylic acid (330 mg, 21% yield) as a white solid. HRMS (FAB): C$_{28}$H$_{28}$NO$_4$ (M+H) calc. 442.2018; observed: 442.2010.

EXAMPLE 16

Preparation of Fmoc-(D,L)-5-isopropyl-2-aminotetraline-2-carboxylic acid (Fmoc-(D,L) 5-iPrAtc-OH)

Step 1:

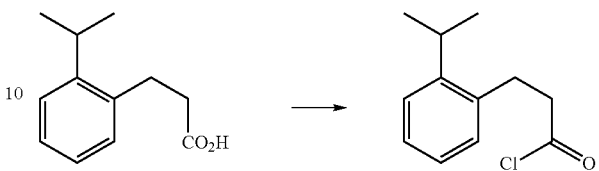

A mixture of 3-(2-isopropylphenyl)propanoic acid (prepared in 3 steps from 1-isopropyl-2-iodobenzene, 2.01 g, 10.5 mmole), thionyl chloride (4.30 ml, 59.0 mmole) and toluene (40 ml) was refluxed for 2 hours. Concentration in vacuo gave 3-(2-isopropylphenyl)propanoyl chloride which was taken up in methylene chloride and used in the next step as a crude.

Step 2:

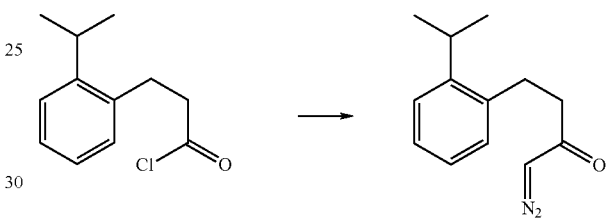

A solution of 3-(2-isopropylphenyl)propanoyl chloride (crude, 10.5 mmole) in methylene chloride was slowly added to a solution of diazomethane (generated from 6.95 g of 1-methyl-3-nitro-1-nitrosoguanidine) in ether (50 ml) cooled in an ice bath. The mixture was then warmed up to room temperature and stirred overnight. The mixture was concentrated in vacuo and purified by column chromatography (20% ethyl acetate/hexanes) to give 1-diazo-4-(2-isopropylphenyl)butan-2-one (1.87 g, 82% over 2 steps) as a bright yellow oil. $^1$H NMR (CDCl$_3$) δ 7.10–7.30 (4H, m, phenyl), 5.21 (1H, broad s, diazo), 3.15 (1H, m, CH of iPr), 3.00 (2H, t, benzylic), 2.57 (2H, m), 1.24 (6H, d, 2 CH$_3$ of iPr).

Step 3:

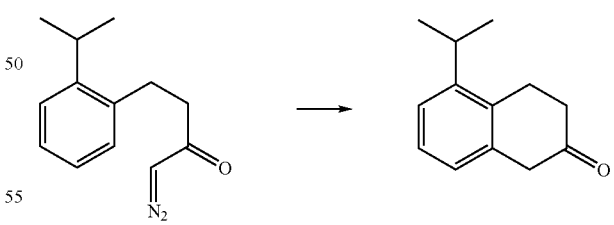

To a mixture of rhodium (II) acetate dimer (20 mg, 0.091 mmole) in methylene chloride (160 ml) under reflux was slowly added a solution of 1-diazo-4-(2-bromophenyl)butan-2-one (1.87 g, 8.65 mmole) in methylene chloride (25 ml) over 60 minutes. After the addition was complete, the mixture was refluxed for an extra fifteen minutes. The mixture was cooled to room temperature, trifluoroacetic acid (1.90 ml) was added and the mixture was stirred at room temperature for 45 minutes. The reaction was quenched with saturated sodium bicarbonate solution. The layers were separated and the methylene chloride layer was washed once more with saturated sodium bicarbonate solution. The combined aqueous layers were back-extracted with methylene chloride. The combined organic layers were dried over magnesium sulfate, filtered and concentrated in vacuo to give a crude brown oil. Purification by column chromatography (5% ethyl acetate/hexanes) gave 5-isopropyl-β-tetralone (1.57 g, 96% yield) as a light yellow oil. $^1$H NMR (CDCl$_3$) δ 6.93–7.22 (3H, m, phenyl), 3.59 (2H, s, benzylic), 3.24 (1H, m, CH of iPr), 3.12 (2H, t, benzylic), 2.52 (2H, t), 1.27 (6H, d, 2 CH$_3$ of iPr).

Step 4:

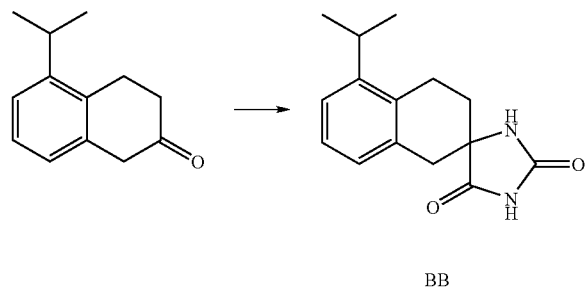

BB

A mixture of 5-isopropyl-β-tetralone (1.57 g, 8.34 mmole), potassium cyanide (0.82 g, 12.6 mmole), ammonium carbonate (4.81 g, 50.1 mmole), ethanol (40 ml) and water (10 ml) in a sealed, thick walled pressure flask was heated in a 80° C. oil bath for 48 hours. After cooling to room temperature, the brown slurry was poured into ice-water and stirred at room temperature for a couple of hours. Filtration followed by air-drying gave crude hydantoin BB as a beige solid which was used in the next step without further purification. $^1$H NMR (DMSO-d$_6$) δ 10.69 (1H, broad s, NH), 8.30 (1H, broad s, NH), 6.85–7.32 (3H, m, phenyl), 1.15 (6H, t, CH$_3$). LRMS (Electrospray): C$_{15}$H$_{18}$N$_2$O$_2$, calc. 258; observed: 539 (2M+Na).

Step 5:

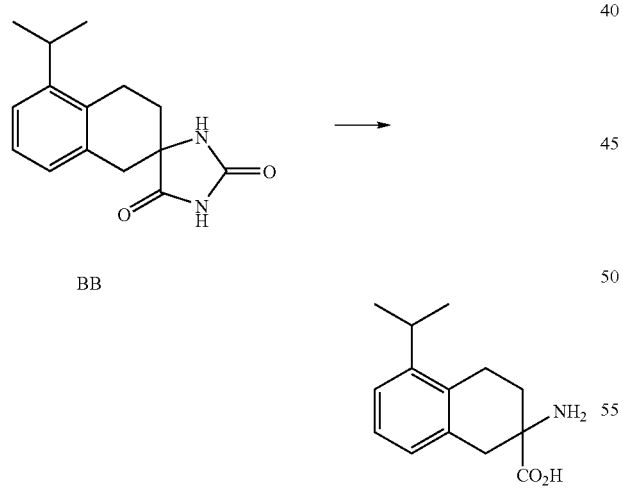

A mixture of hydantoin BB (crude, 8.34 mmole theoretical), Ba(OH)$_2$·H$_2$O (7.90 g, 41.7 mmole) in water (40 ml) in a sealed, thick walled pressure flask was heated in a 125° C. oil bath for 38 hours. The reaction mixture was cooled to room temperature, acidified to ~pH 3 using 4N sulfuric acid while being stirred vigorously. The suspension was stirred in a boiling water bath for two hours and cooled to room temperature. The white suspension was filtered and the precipitates rinsed with water. The combined filtrate and washings were concentrated in vacuo to ~50 ml. Neutralization with concentrated ammonium hydroxide solution gave white precipitate which were filtered, washed with water and dried in vacuo overnight to give racemic 5-isopropyl-2-aminotetraline-2-carboxylic acid (1.23 g, 63% yield over 2 steps) as a beige solid. LRMS (Electrospray): C$_{14}$H$_{19}$NO$_2$, calc. 233; observed: 232 (M−H).

Step 6:

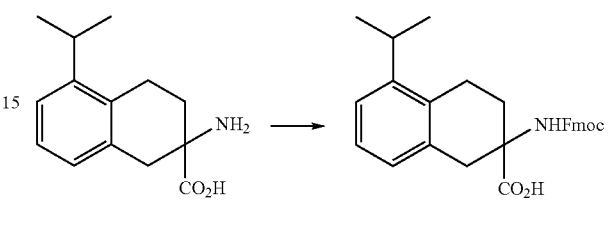

A mixture of racemic 5-isopropyl-2-aminotetraline-2-carboxylic acid (250 mg, 1.07 mmole), triethylamine (1.2 ml, 8.61 mmole), 9-fluorenylmethyl succinimidyl carbonate (Fmoc-OSu, 2.70 g, 8.00 mmole) in acetonitrile (30 ml) and water (30 ml) was stirred at room temperature for 2 days. The reaction mixture was concentrated in vacuo to remove most of the acetonitrile, acidified to pH 3 with 10% aqueous citric acid solution, and the white emulsion was extracted with ethyl acetate. The organic layer was washed with water, brine and dried over sodium sulfate. Filtration and concentration gave a crude oil which was purified by column chromatography (eluted with 2→5→8% methanol/methylene chloride) to give racemic Fmoc-5-isopropyl-2-aminotetraline-2-carboxylic acid (208 mg, 43% yield) as an off-white foam. HRMS (FAB): C$_{29}$H$_{30}$NO$_4$ (M+H) calc. 456.2175; observed: 456.2184.

EXAMPLE 17

Preparation of Fmoc-4-amino-1-phenylpiperidine-4-carboxylic acid (Fmoc-Appc-OH)

Step 1:

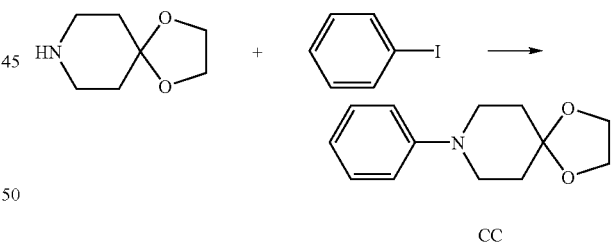

CC

To a solution of iodobenzene (6.37 g, 3.5 mL, 31.2 mmole), 1,4-dioxa-8-azaspiro[4.5]decane (10.32 g, 9.3 mL, 72.2 mmole, 2.3 equiv) and sodium tert-butoxide (8.0 g, 83.3 mmole, 2.7 equiv) in dry dioxane (120 mL) were added tris(dibenzylideneacetone)dipalladium(0) (91 mg, 0.1 mmol) and tri-o-tolylphosphine (180 mg, 0.591 mmol). The reaction was heated at 90° C. for 26 hrs. The resulting reaction mixture was concentrated to remove solvent. The residue was treated with water and extracted with EtOAc. The combined organic extracts were combined, washed with brine, dried over Na$_2$SO$_4$ and concentrated to give a brown oil. This crude product was purified on flash chromatography (hexane/EtOAc, 95/5 to 75/25) to provide the pure product CC as a slightly yellow solid (6.08 g, 89%). $^1$H NMR (CDCl$_3$), 7.25 (ddt, 2H), 6.95 (dd, 2H), 6.84 (t, 1H), 4.00 (s, 4H), 3.32 (t, 4H) and 1.84 (t, 4H); MS (electrospray) m/e 220 (M+H), Calcd for C$_{13}$H$_{17}$NO$_2$, 219.

Step 2:

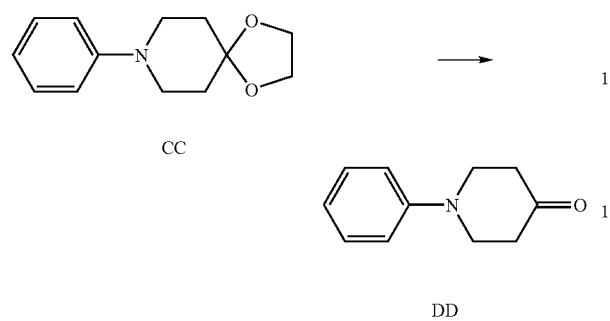

CC

DD

To a solution of the ketal CC (3.22 g, 15.16 mmol) in acetone (100 mL) was added 6N hydrochloric acid (50 mL) and the reaction was heated at reflux overnight. The resulting reaction mixture was concentrated to remove solvent. The residue was taken up in EtOAc and neutralized with aqueous 6N NaOH solution. The layers were separated and the aqueous layer was extracted with EtOAc. The combined organic extracts were washed with brine, dried over Na$_2$SO$_4$ and concentrated. The crude product was purified on flash chromatography (hexane/EtOAc, 80/20→60/40) to give the product DD as a yellow oil (2.58 g, 97%). MS (electrospray) m/e 176 (M+H), Calcd for C$_{11}$H$_{13}$NO, 175.

Step 3:

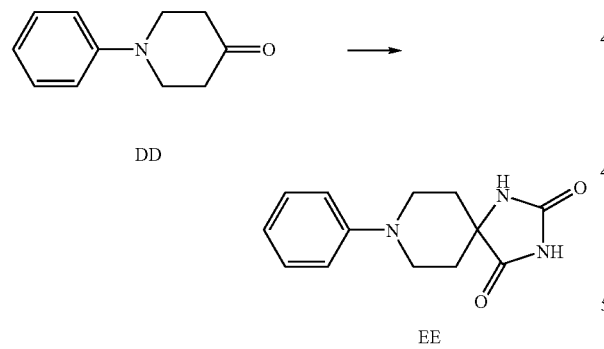

DD

EE

To a solution of the ketone DD (2.53 g, 14.46 mmol) in ethanol (75 mL) and water (25 mL) in a glass pressure bottle, were added ammonium carbonate (12.9 g, 134.3 mmole, 9 equiv.) and potassium cyanide (2.11 g, 32.5 mmol, 2 equiv.). The mixture was heated at 80–90° C. for 18 hrs. The cooled reaction mixture was concentrated in vacuo and the residue was treated with water, extracted with EtOAc (4×). The combined organic extracts were washed with water, dried over anhydrous Na$_2$SO$_4$ and concentrated to give the spectroscopically pure hydantoin EE as a white solid (3.36 g, 95% yield). MS (electrospray) m/e 246 (M+H), Calcd for C$_{13}$H$_{15}$N$_3$O$_2$, 245.

Step 4:

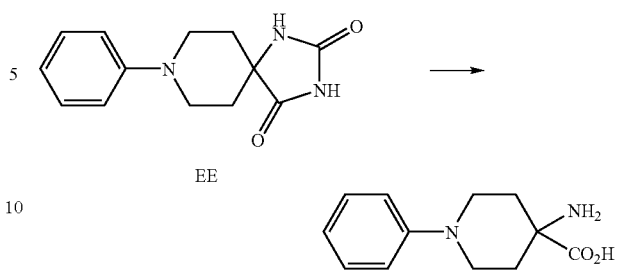

EE

The hydantoin EE (3.36 g) was suspended in aqueous NaOH (6N, 100 mL) and heated at 130° C. for 2–3 days. Upon completion (by HPLC) of the hydrolysis, the reaction mixture was neutralized with conc. HCl to slightly acidic (pH ~6). The resulting slurry was filtered, washed with water and dried to give 4-amino-1-phenylpiperidine-4-carboxylic acid (APPC) as a white solid (5.26 g, >100% yield, wet and contaminated with inorganic salt), which showed a single peak on HPLC and used directly for the next step. MS (electrospray) m/e 221 (M+H), Calcd for C$_{12}$H$_{16}$N$_2$O$_2$, 220.

Step 5:

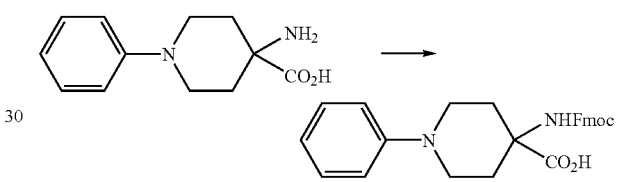

The crude 4-amino-1-phenylpiperidine-4-carboxylic acid (APPC) from the last step was suspended in dioxane (80 mL) and aqueous 10% Na$_2$CO$_3$ (40 ml), treated with Fmoc-Cl (5.3 g, 20.57 mmole, 1.5 equiv) and was stirred vigorously overnight. The reaction mixture was then concentrated to remove dioxane, neutralized with 6N HCl to slightly acidic (pH 6) and extracted with EtOAc. The combined organic extracts were washed with brine and dried over Na$_2$SO$_4$. Removal of the solvent gave the crude product which was purified on flash chromatography (hexane/EtOAc to CH$_2$Cl$_2$/MeOH) to give pure Fmoc-APPC (4.91 g, 81% overall yield for two steps). $^1$H NMR(DMSO-d$_6$), 7.88 (d, 2H), 7.74 (d, 2H), 7.19–7.42 (m, 8H), 4.20–4.31 (m, 3H); HRMS m/z 465.1788, Calcd for C$_{27}$H$_{26}$N$_2$O$_4$Na, 465.1791.

EXAMPLE 18

Preparation of Fmoc-4-amino-1-(4-methylphenyl) piperidine-4-carboxylic acid (Fmoc-4-MeAppc-OH)

Step 1:

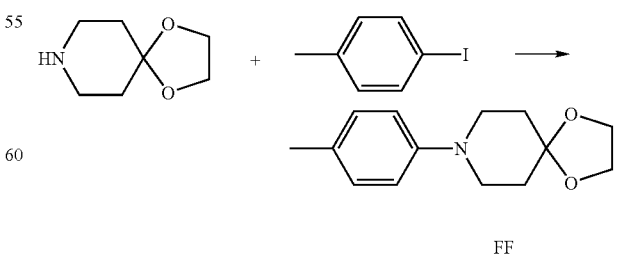

FF

To a solution of 4-iodotoluene (2.12 g, 9.7 mmol), 1,4-dioxa-8-azaspiro[4.5]decane (2.8 mL, 3.12 g, 21.82 mmol, 2.2 equiv) and sodium tert-butoxide (2.6 g, 27.08 mmol, 2.8 equiv) in dry dioxane (40 mL) were added tris(dibenzylideneacetone)dipalladium(0) (44.4 mg, 0.0485 mmol) and tri-o-tolylphosphine (59.0 mg, 0.194 mmol). The reaction was heated at 90° C. for 26 hrs. The resulting reaction mixture was concentrated to remove solvent. The residue was treated with water and extracted with EtOAc. The combined organic extracts were combined, washed with brine, dried over Na$_2$SO$_4$ and concentrated to give brown oil. This crude product was purified on flash chromatography (hexane/EtOAc, 95/5 to 75/25) to provide the pure product FF as a slightly yellow solid (1.937 g, 85%). $^1$H NMR (CDCl$_3$), 7.06 (d, 2H), 6.87 (d, 2H), 3.99 (s, 4H), 3.26 (t, 4H), 2.26 (s, 3H) and 1.85 (t, 4H).

Step 2:

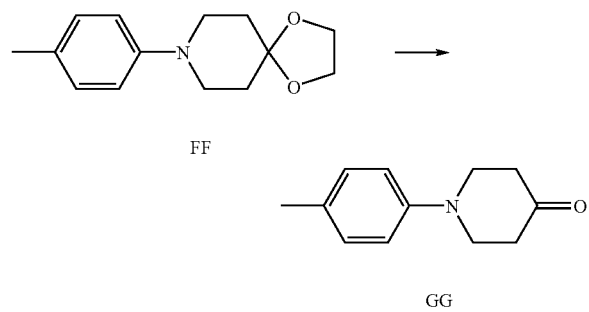

FF

GG

To a solution of the ketal FF (1.58 g, 6.79 mmol) in acetone (50 mL) was added 6N hydrochloric acid (25 mL) and the reaction was heated at reflux overnight. The resulting reaction mixture was concentrated to remove solvent. The residue was taken up in EtOAc and neutralized with aqueous 6N NaOH solution. The layers were separated and the aqueous layer was extracted with EtOAc. The combined organic extracts were washed with brine, dried over Na$_2$SO$_4$ and concentrated. The crude product was purified on flash chromatography (hexane/EtOAc, 90/10→70/30) to give the product GG as a yellow oil (1.27 g, 98%). MS (electrospray) m/e 190 (M+H), Calcd for C$_{12}$H$_{15}$NO, 189.

Step 3:

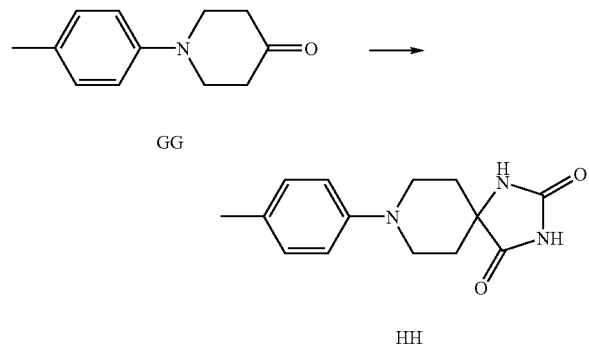

GG

HH

To a solution of the ketone GG (1.17 g, 6.18 mmol) in ethanol (60 mL) and water (20 mL) in a glass pressure bottle, were added ammonium carbonate (4.74 g, 49.44 mmole, 8 equiv.) and potassium cyanide (1.01 g, 15.54 mmol, 2.5 equiv.). The mixture was heated at 90° C. for 22 hrs. The cooled reaction mixture was concentrated in vacuo and the residue was treated with water, extracted with EtOAc (4×). The combined organic extracts were washed with water, dried over anhydrous Na$_2$SO$_4$ and concentrated to give the spectroscopically pure hydantoin HH as a white solid (1.554 g, 97% yield). MS (electrospray) m/e 260 (M+H), Calcd for C$_{14}$H$_{17}$N$_3$O$_2$, 259.

Step 4:

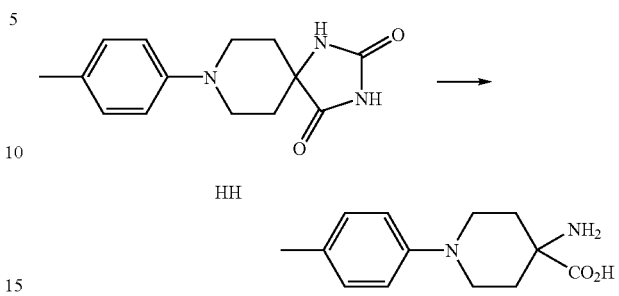

HH

The hydantoin HH (1.502 g) was suspended in aqueous NaOH (6N, 40 mL) and heated at 130° C. for 4 days. Upon completion (by HPLC) of the hydrolysis, the reaction mixture was neutralized with conc. HCl to slightly acidic (pH ~6). The resulting slurry was filtered, washed with water and dried to give 4-amino-1-(4-methylphenyl)piperidine-4-carboxylic acid (4-MeAPPC) as a white solid (2.10 g, >100% yield, wet and contaminated with inorganic salt), which showed a single peak on HPLC and used directly in the next step. MS (electrospray) m/e 235 (M+H), Calcd for C$_{13}$H$_{18}$N$_2$O$_2$, 234.

Step 5:

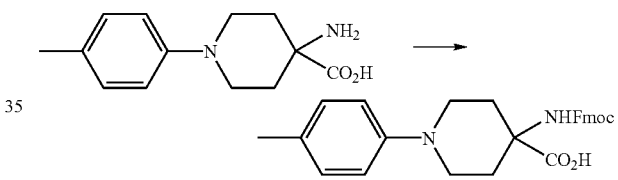

The crude 4-amino-1-(4-methylphenyl)piperidine-4-carboxylic acid (4-MeAPPC) from the last step was suspended in dioxane (80 mL) and aqueous 10% Na$_2$CO$_3$ (40 ml), treated with Fmoc-Cl (2.2 g, 8.59 mmole, 1.5 equiv) and was stirred vigorously overnight. The reaction mixture was then concentrated to remove dioxane, neutralized with 6N HCl to slightly acidic (pH 6) and extracted with EtOAc. The combined organic extracts were washed with brine and dried over Na$_2$SO$_4$. Removal of the solvent gave the crude product which was purified on flash chromatography (hexane/EtOAc to CH$_2$Cl$_2$/MeOH) to give pure Fmoc-4-MeAPPC (2.16 g, 82% overall yield for two steps). $^1$H NMR (DMSO-d$_6$): 7.88 (d, 2H), 7.72 (d, 2H), 7.39 (t, 2H), 7.30 (td, 2H), 6.99 (d, 2H), 6.82 (d, 2H), 2.18 (s, 3H); MS (electrospray) m/e 457 (M+H), Calcd for C$_{28}$H$_{28}$N$_2$O$_4$, 456.

EXAMPLE 19

Preparation of Fmoc-4-amino-1-(4-chlorophenyl)piperidine-4-carboxylic acid (Fmoc-4-ClAppc-OH)

Step 1:

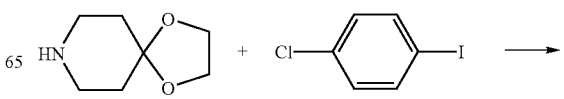

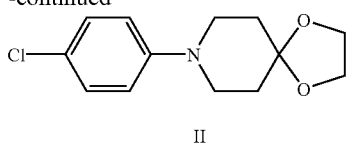

II

To a solution of 1-chloro-4-iodobenzene (2.38 g, 10.0 mmole), 1,4-dioxa-8-azaspiro[4.5]decane (3.1 mL, 3.44 g, 24.0 mmole, 2.4 equiv) and sodium tert-butoxide (2.68 g, 28.0 mmole, 2.8 equiv) in dry dioxane (40 mL) were added tris(dibenzylideneacetone)dipalladium(0) (45.5 mg, 0.0497 mmol) and tri-o-tolyl-phosphine (61 mg, 0.20 mmol). The reaction was heated at 90° C. for 9 hrs. The resulting reaction mixture was concentrated to remove solvent. The residue was treated with water and extracted with EtOAc. The combined organic extracts were combined, washed with brine, dried over Na2SO4 and concentrated to give a brown oil. This crude product was purified on flash chromatography (hexane/EtOAc, 95/5 to 75/25) to provide the pure product II as a slightly yellow solid (2.17 g, 86%). $^1$H NMR (CDCl$_3$), 7.18 (dt, 2H), 6.85 (dt, 2H), 3.98 (s, 4H), 3.28 (t, 4H) and 1.82 (t, 4H).

Step 2:

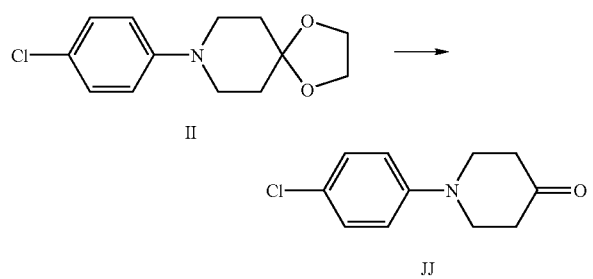

To a solution of the ketal 11 (2.123 g, 8.39 mmole) in acetone (75 mL) was added 6N hydrochloric acid (30 mL) and the reaction was heated at reflux overnight. The resulting reaction mixture was concentrated to remove solvent. The residue was taken up in EtOAc and neutralized with aqueous 6N NaOH solution. The layers were separated and the aqueous layer was extracted with EtOAc. The combined organic extracts were washed with brine, dried over Na$_2$SO$_4$ and concentrated. The crude product was purified on flash chromatography (hexane/EtOAc, 95/5→70/30) to give the product JJ as a yellow solid (1.515 g, 86%). MS (electrospray) m/e 210 (M+H), Calcd for C$_{11}$H$_{12}$ClNO, 209.

Step 3:

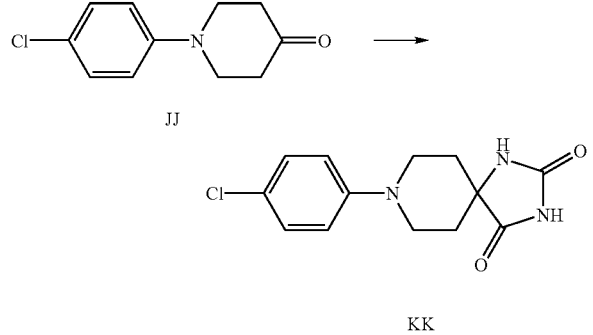

To a solution of the ketone JJ (1.465 g, 6.986 mmole) in ethanol (75 mL) and water (25 mL) in a glass pressure bottle, were added ammonium carbonate (5.36 g, 55.88 mmole, 8 equiv.) and potassium cyanide (1.135 g, 17.46 mmol, 2.5 equiv.). The mixture was heated at 80–90° C. for 18 hrs. The cooled reaction mixture was concentrated in vacuo and the residue was treated with water, extracted with EtOAc (4×). The combined organic extracts were washed with water, dried over anhydrous Na$_2$SO$_4$ and concentrated to give the spectroscopically pure hydantoin KK as a white solid (1.817 g, 93% yield). MS (electrospray) m/e 280 (M+H), Calcd for C$_{13}$H$_{14}$ClN$_3$O$_2$, 279.

Step 4:

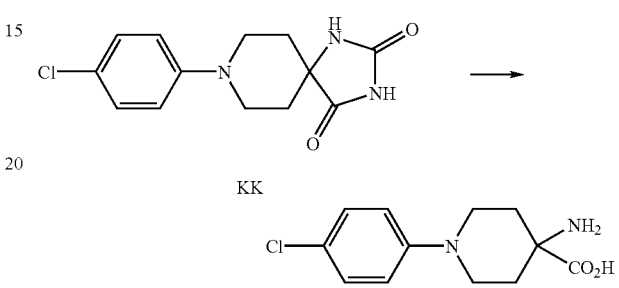

The hydantoin KK (1.768 g) was suspended in aqueous NaOH (6N, 50 mL) and heated at 130° C. for 4 days. Upon the completion (by HPLC) of the hydrolysis, the reaction mixture was neutralized with conc. HCl to slightly acidic (pH ~6). The resulting slurry was filtered, washed with water and dried to give 4-amino-1-(4-chlorophenyl)piperidine-4-carboxylic acid (4-ClAPPC) as a white solid (2.05 g, >100% yield, wet and contaminated with inorganic salt), which showed a single peak on HPLC and used directly for the next step. MS (electrospray) m/e 253 (M−H), Calcd for C$_{12}$H$_{15}$ClN$_2$O$_2$, 254.

Step 5:

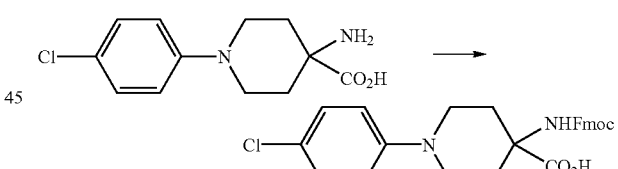

The crude 4-amino-1-(4-chlorophenyl)piperidine-4-carboxylic acid (4-ClAPPC) from the last step was suspended in dioxane (100 mL) and aqueous 10% Na$_2$CO$_3$ (50 ml), treated with Fmoc-Cl (2.0 g, 7.75 mmole, 1.2 equiv) and was stirred vigorously overnight. The reaction mixture was then concentrated to remove dioxane, neutralized with 6N HCl to slightly acidic (pH 6) and extracted with EtOAc. The combined organic extracts were washed with brine and dried over Na$_2$SO$_4$. Removal of the solvent gave the crude product which was purified on flash chromatography (hexane/EtOAc to CH$_2$Cl$_2$/MeOH) to give pure Fmoc-4-ClAPPC (1.18 g, 81% overall yield for two steps). $^1$H NMR (DMSO-d$_6$): 7.87 (d, 2H), 7.71 (d, 2H), 7.39 (td, 2H), 7.30 (td, 2H), 7.20 (d, 2H), 6.92 (d, 2H), 3.44 (d, 2H), 2.93 (t, 2H); MS (electrospray) m/e 477 (M+H), Calcd for C$_{27}$H$_{25}$N$_2$O$_4$, 476.

EXAMPLE 20

Preparation of Fmoc-4-amino-1-(4-phenoxyphenyl)piperidine-4-carboxylic acid (Fmoc-4-PhOAppc-OH)

Step 1:

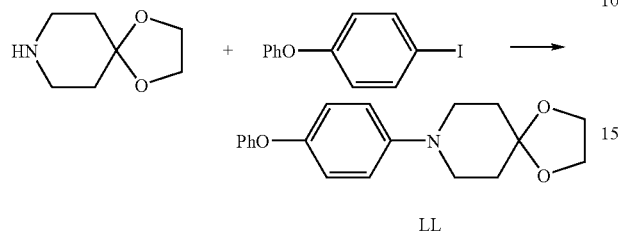

To a solution of 1-iodo-4-phenoxybenzene (3.15 g, 10.6 mmol), 1,4-dioxa-8-azaspiro[4.5]decane (3.3 mL, 3.66 g, 25.6 mmole, 2.4 equiv) and sodium tert-butoxide (2.85 g, 29.7 mmol, 2.8 equiv) in dry dioxane (40 mL) were added tris(dibenzylideneacetone)dipalladium(0) (48.5 mg, 0.053 mmol) and tri-o-tolyl-phosphine (64 mg, 0.4 mmol). The reaction was heated at 90° C. for 9 hrs. The resulting reaction mixture was concentrated to remove solvent. The residue was treated with water and extracted with EtOAc. The combined organic extracts were combined, washed with brine, dried over $Na_2SO_4$ and concentrated to give a brown oil. This crude product was purified on flash chromatography (hexane/EtOAc, 95/5 to 80/20) to provide the pure product LL as a slightly yellow solid (2.805, 85%). $^1$H NMR ($CDCl_3$), 7.26–7.32 (m, 2H), 7.03 (t, 1H), 6.92–6.97 (m, 6H), 4.00 (s, 4H), 3.26 (t, 4H), 1.86 (t, 4H).

Step 2:

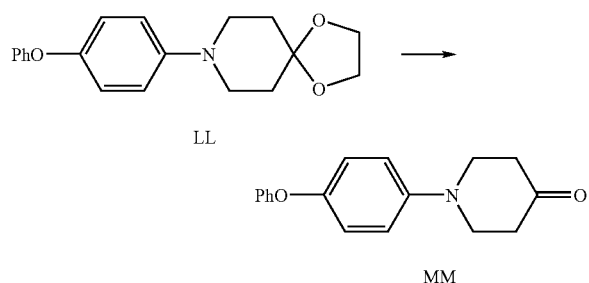

To a solution of the ketal LL (2.755 g, 8.86 mmol) in acetone (90 mL) was added 6N hydrochloric acid (45 mL) and the reaction was heated at reflux overnight. The resulting reaction mixture was concentrated to remove solvent. The residue was diluted with EtOAc and neutralized with aqueous 6N NaOH. The layers were separated and the aqueous layer was extracted with EtOAc. The combined organic extracts were washed with brine, dried over $Na_2SO_4$ and concentrated to give the crude product which was purified on flash chromatography (hexane/EtOAc, 90/10 to 70/30) to give the product MM as a yellow oil (2.21 g, 93%). MS (electrospray) m/e 268 (M+H), Calcd for $C_{17}H_{17}ClNO_2$, 267.

Step 3:

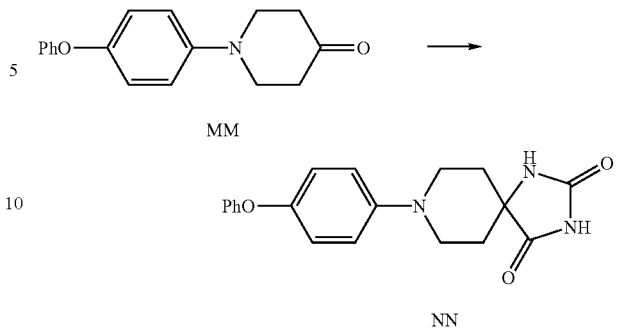

To a solution of the ketone MM (2.01 g, 7.52 mmol) in ethanol (80 mL) and water (25 mL) in a glass pressure bottle, were added ammonium carbonate (5.78 g, 60.0 mmol, 8 equiv.) and potassium cyanide (1.22 g, 18.80 mmol, 2.5 equiv.). The mixture was heated at 80–90° C. for 18 hrs. The cooled reaction mixture was concentrated in vacuo and the residue was treated with water, extracted with EtOAc (4×). The combined organic extracts were washed with water, dried over anhydrous $Na_2SO_4$ and concentrated to give the spectroscopically pure hydantoin NN as a white solid (2.34 g, 95% yield). MS (electrospray) m/e 338 (M+H), Calcd for $C_{19}H_{19}N_3O_3$, 337.

Step 4:

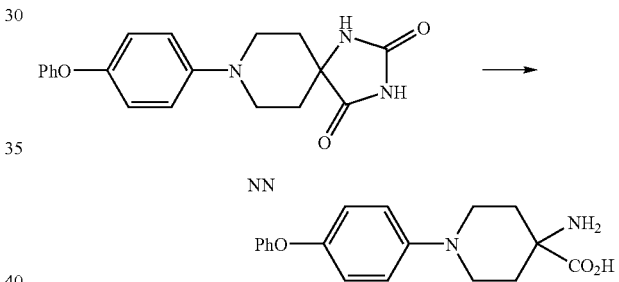

The hydantoin NN (2.28 g, 6.76 mmole) was suspended in aqueous NaOH (6N, 60 mL) and heated at 130° C. for 4 days. Upon completion (by HPLC) of the hydrolysis, the reaction mixture was neutralized with conc. HCl to slightly acidic (pH 6). The resulting slurry was filtered, washed with water and dried to give 4-amino-1-(4-phenoxyphenyl)piperidine-4-carboxylic acid (4-PhOAPPC) as a white solid (2.53 g, >100% yield, wet and contaminated with inorganic salt), which showed a single peak on HPLC and used directly for the next step. MS (electrospray) m/e 313 (M+H), Calcd for $C_{18}H_{20}N_2O_3$, 312.

Step 5:

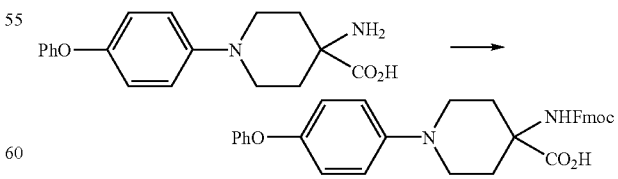

The crude 4-amino-1-(4-phenoxyphenyl)piperidine-4-carboxylic acid (4-PhOAPPC) from the last step was suspended in dioxane (50 L) and aqueous 10% $Na_2CO_3$ (50 ml) and stirred vigorously overnight. The reaction mixture was concentrated to remove dioxane, neutralized with 6N HCl to slightly acidic (pH 6) and extracted with EtOAc. The combined organic extracts were washed with brine and dried over Na₂SO₄. Removal of the solvent gave the crude product which was purified on flash chromatography (hexane/EtOAc to CH₂Cl₂/MeOH) to give pure Fmoc-4-PhOAPPC (2.18 g, 60% overall yield for two steps). ¹H NMR (DMSO-d₆): 7.87 (d, 2H), 7.72 (d, 2H), 7.38 (t, 2H), 7.30 (td, 4H), 7.02 (dt, 1H), 6.86–6.96 (m, 6H), 3.35 (m, 2H), 2.94 (t, 2H); MS (electrospray) m/e 535 (M+H), Calcd for C₃₃H₃₀N₂O₅, 534.

EXAMPLE 21

Preparation of Fmoc-4-amino-1-(2-methylphenyl) piperidine-4-carboxylic acid(Fmoc-2-MeAppc-OH)
Step 1:

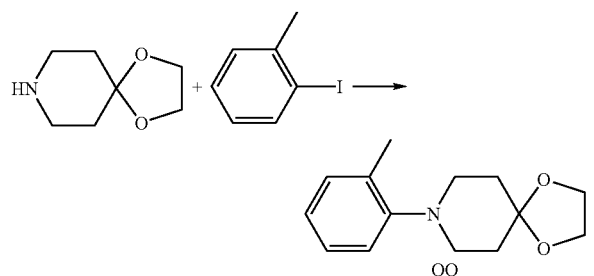

To a solution of 2-iodotoluene (4.36 g, 2.5 mL, 20.0 mmol), 1,4-dioxa-8-azaspiro[4.5]decane (6.88 g, 6.2 mL, 48.1 mmol, 2.4 equiv) and sodium tert-butoxide (5.3 g, 55.2 mmol, 2.8 equiv) in dry dioxane (80 mL) were added tris(dibenzylideneacetone)dipalladium(0) (91 mg, 0.1 mmol) and tri-o-tolylphosphine (122 mg, 0.4 mmol). The reaction was heated at 90° C. for 26 hrs. The resulting reaction mixture was concentrated to remove solvent. The residue was treated with water and extracted with EtOAc. The combined organic extracts were combined, washed with brine, dried over Na₂SO₄ and concentrated to give brown oil. This crude product was purified on flash chromatography (hexane/EtOAc, 95/5 to 75/25) to provide the pure product OO as a slightly yellow solid (2.66 g, 57%). ¹H NMR (CDCl₃), 7.12–7.18 (m, 2H), 6.94–7.06 (m, 2H), 4.01 (s, 4H), 2.98 (t, 4H) and 1.88 (t, 4H).
Step 2:

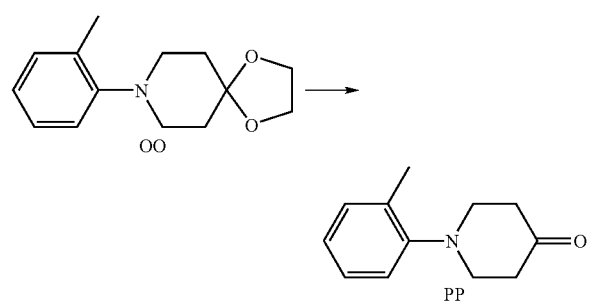

To a solution of the ketal OO (2.66 g, 11.4 mmol) in acetone (70 mL) was added 6N hydrochloric acid (35 mL) and the reaction was heated at 85° C. overnight. The resulting reaction was concentrated to remove solvent. The residue was diluted with EtOAc and neutralized with aqueous NaOH (6N). The layers were separated and the aqueous layer was extracted with EtOAc. The combined organic extracts was washed with brine, dried over Na₂SO₄ and concentrated. The crude product was purified on flash chromatography (hexane/EtOAc, 90/10 to 70/30) to give the product PP as a yellow oil (2.04 g, 95%). MS (electrospray) m/e 190 (M+H), Calcd for C₁₂H₁₅NO, 189.
Step 3:

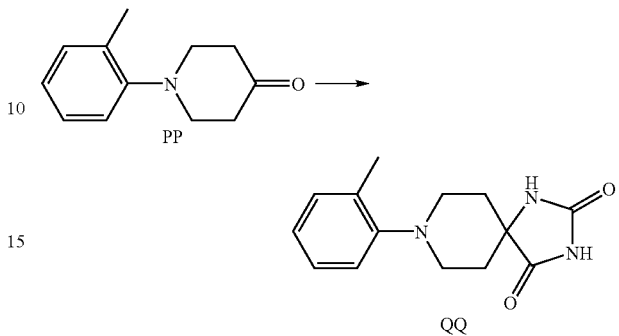

To a solution of the ketone PP (1.54 g, 8.15 mmol) in ethanol (60 mL) and water (20 mL) in a glass pressure bottle, were added ammonium carbonate (4.69 g, 48.9 mmol, 6 equiv.) and potassium cyanide (800 g, 12.2 mmol, 1.5 equiv.). The mixture was heated at 80–90° C. for 18 hrs. The cooled reaction mixture was added to icy water (300 ml) and stirred vigorously for 30 min. The resulting precipitate was suction filtered, washed thoroughly with water and dried to yield the hydantoin QQ as a white solid (2.01 g, 95% yield). MS (electrospray) m/e 260 (M+H), Calcd for C₁₄H₁₇N₃O₂, 259.
Step 4:

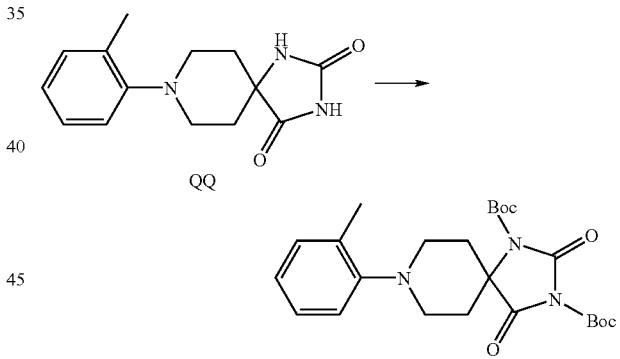

To a suspension of the hydantoin QQ (1.07 g, 4.13 mmol) in dry THF (25 mL) were added di-tert-butyl dicarbonate (2.25 g, 10.32 mmol, 2.5 equiv), triethylamine (0.63 mL, 460 mg, 4.54 mmol, 1.1 equiv) and DMAP (36 mg, 0.29 mmol) in succession. About 15 minutes after the addition, the reaction turned into a clear yellow solution and was stirred overnight at room temperature. The reaction mixture was concentrated under reduced pressure to yield a solid that was then taken up in EtOAc (300 mL), washed with 1N HCl (3×30 mL), saturated aqueous Na₂CO₃ (2×30 mL) and brine (2×30 mL), dried over anhydrous Na₂SO₄ and concentrated under reduced pressure. The crude light yellow product was purified through flash chromatography (hexane/EtOAc, 90/10→80/20) to give the pure bis-Boc hydantoin RR as a white solid (1.71 g, 90%). MS (electrospray) m/e 460 (M+H), Calcd for C₂₄H₃₃N₃O₆, 459.

Step 5:

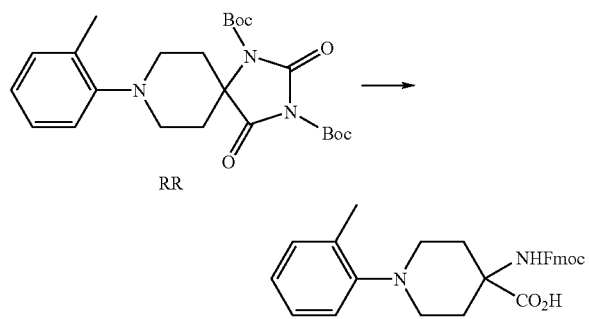

The bis-Boc hydantoin RR (1.71 g, 3.72 mmol) was dissolved in DME (23 mL) to give a clear solution. To this solution was added 1N NaOH (33 mL, 33 mmol) and the reaction was stirred overnight at room temperature, giving a fairly clear mixture. HPLC showed completion of the reaction. The reaction mixture was concentrated under reduced pressure to remove DME and extracted with Et$_2$O. Without purification, the resulting aqueous layer containing 4-amino-1-(2-methylphenyl)piperidine-4-carboxylic acid (2-MeAPPC) was treated with 6N HCl to adjust the pH to 11–12. This solution (30 mL) was then diluted with 1,4-dioxane (30 mL) and treated with Fmoc-Cl (1.28 g, 4.96 mmol, 1.3 equiv) and stirred overnight at room temperature. The reaction mixture was concentrated under reduced pressure to remove dioxane, neutralized with 1N HCl and extracted with EtOAc. The combined organic extracts were washed with brine, dried over anhydrous Na$_2$SO$_4$ and concentrated. The crude product was purified through flash chromatography (hexane/EtOAc4CH$_2$Cl$_2$/MeOH) to give the pure product Fmoc-2-MeAPPC as a white solid (1.09 g, 64% yield from the bis-Boc hydantoin RR). $^1$H NMR (DMSO-d$_6$): 7.87 (d, 2H), 7.74 (d, 2H), 7.40 (td, 2H), 7.31 (td, 2H), 7.12 (m, 2H), 6.97 (d, 1H), 6.92 (td, 1H), 2.72–2.88 (m, 4H) and 2.22 (s, 3H); MS (electrospray) m/e 457 (M+H), Calcd for C$_{28}$H$_{28}$N$_2$O$_4$, 456.

EXAMPLE 22

Preparation of Fmoc-4-amino-1-(2-isopropylphenyl)piperidine-4-carboxylic acid (Fmoc-2-iPrAppc-OH)

Step 1:

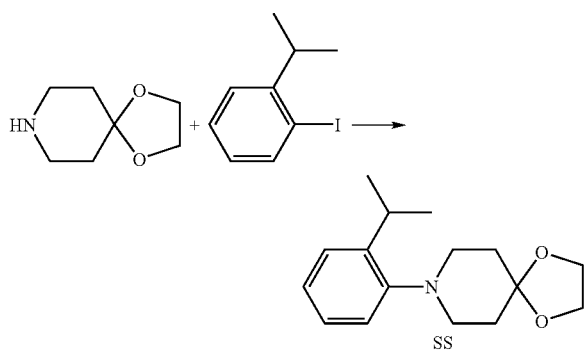

To a solution of 1-iodo-2-iso-propylbenzene (10.0 g, 40.7 mmol), 1,4-dioxa-8-azaspiro[4.5]decane (12.0 mL, 13.3 g, 93.0 mmol, 2.3 equiv) and sodium tert-butoxide (10.0 g, 104.2 mmol, 2.6 equiv) in dry dioxane (160 mL) were added tris(dibenzylideneacetone)dipalladium(0) (180 mg, 0.197 mmol) and tri-o-tolyl-phosphine (244 mg, 0.80 mmol) and the reaction was heated at 90° C. for 26 hrs. The resulting reaction mixture was concentrated to remove solvent, treated with water and extracted with EtOAc. The combined organic extracts were combined, washed with brine, dried over Na$_2$SO$_4$ and concentrated to give a brown oil. This crude product was purified on flash chromatography (hexane/EtOAc, 95/5→75/25) to provide the pure product SS as a slightly yellow solid (3.61 g, 35% yield). MS m/z 262 (M+H), Calcd for C$_{16}$H$_{23}$NO$_2$, 261.

Step 2:

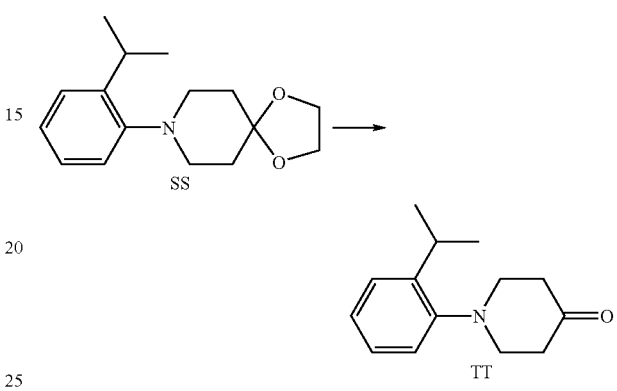

To a solution of the ketal SS (3.24 g, 12.4 mmol) in acetone (90 mL) was added 6N hydrochloric acid (45 mL) and the reaction was heated at reflux overnight. The resulting reaction mixture was concentrated to remove solvent and the residue was diluted with EtOAc, neutralized with aqueous NaOH (6N). The layers were separated and the aqueous layer was extracted with EtOAc. The combined organic extracts were washed with brine, dried over Na$_2$SO$_4$ and concentrated. The crude product was purified on flash chromatography (hexane/EtOAc, 90/10→70/30) to give the product TT as a yellow oil (2.42 g, 89%). $^1$H NMR (CDCl$_3$): 7.27 (m, 1H), 7.04–7.19 (m, 3H), 3.58 (m, 1H), 3.20 (t, 4H), 2.60 (t, 4H) and 1.25 (d, 6H); MS m/z 218 (M+H), Calcd for C$_{14}$H$_{19}$NO, 217.

Step 3:

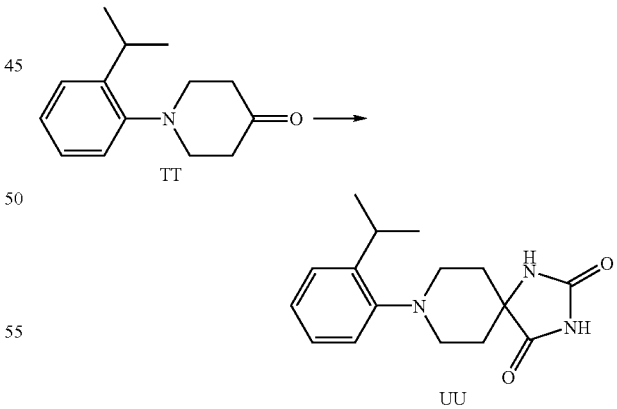

To a solution of the ketone TT (2.30 g, 10.6 mmol) in ethanol (90 mL) and water (20 mL) in a glass pressure bottle, were added ammonium carbonate (8.1 g, 84.3 mmol, 8 equiv) and potassium cyanide (1.72 g, 26.5 mmol, 2.5 equiv). The mixture was heated at 80–90° C. for 18 hrs. The cooled reaction mixture was added to icy water (400 ml) and stirred vigorously for 30 min. The resulting precipitate was suction filtered, washed thoroughly with water and dried to yield the hydantoin UU as a white solid (2.78 g, 91% yield). MS m/z 288 (M+H), Calcd for $C_{16}H_{21}N_3O_2$, 287.

Step 4:

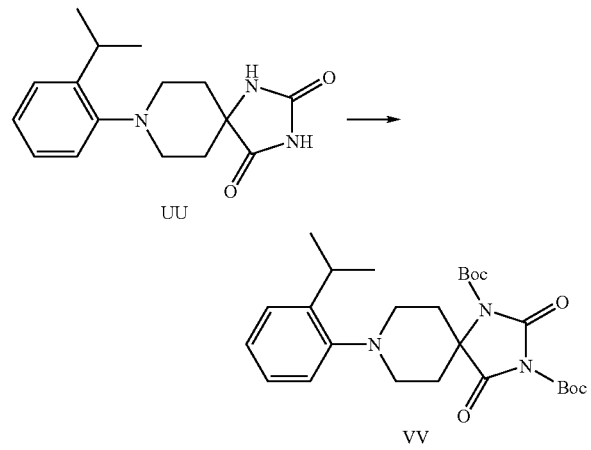

To a suspension of the hydantoin UU (2.74 g, 9.54 mmol) in dry THF (100 mL) were added di-tert-butyl dicarbonate (5.2 g, 24.24 mmol, 2.5 equiv), triethylamine (1.5 mL, 1.07 g, 10.5 mmol, 1.1 equiv) and DMAP (46 mg, 0.29 mmol) in succession. About 15 minutes after the addition, the reaction turned into a clear yellow solution and was stirred overnight at room temperature. The reaction mixture was concentrated under reduced pressure to yield a solid that was then taken up in EtOAc (300 mL), washed with brine (3×30 mL), dried over anhydrous $Na_2SO_4$ and concentrated under reduced pressure. The crude light yellow product was purified through flash chromatography (hexane/EtOAc, 90/10→80/20) to give the pure bis-Boc hydantoin VV as a white solid (4.39 g, 94% yield). MS m/z 488 (M+H), Calcd for $C_{26}H_{37}N_3O_6$, 487.

Step 5:

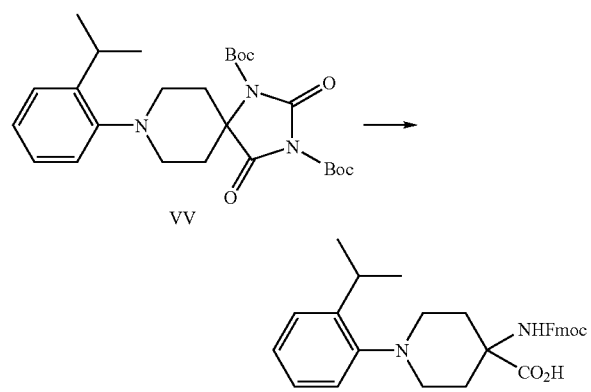

The bis-Boc hydantoin VV (2.34 g, 4.8 mmol) was dissolved in DME (30 mL) to give a clear solution. To this solution was added 1N NaOH (45 mL, 45 mmol) and the reaction was stirred overnight at room temperature, giving a fairly clear mixture. HPLC showed completion of the reaction. The reaction mixture was concentrated under reduced pressure to remove DME and extracted with $Et_2O$. Without purification, the resulting aqueous layer containing 4-amino-1-(2-isopropylphenyl)piperidine-4-carboxylic acid (2-iPrAPPC) was treated with 6N HCl to adjust the pH to 11–12. This solution (Q45 mL) was then diluted with 1,4-dioxane (45 mL) and treated with Fmoc-Cl (1.78 g, 6.89 mmol, 1.5 equiv) and stirred overnight at room temperature. The reaction mixture was concentrated under reduced pressure to remove dioxane, neutralized with 1N HCl and extracted with EtOAc. The combined organic extracts were washed with brine, dried over anhydrous $Na_2SO_4$ and concentrated. The crude product was purified through flash chromatography (hexane/EtOAc-$CH_2Cl_2$/MeOH) to give the pure product Fmoc-2-iPrAPPC as a white solid (1.46 g, 63% yield from the bis-Boc hydantoin). HRMS m/z 507.2263, Calcd for $C_{30}H_{32}N_2O_4Na$, 507.2260.

EXAMPLE 23

Preparation of Fmoc-4-amino-1-(3-methylphenyl) piperidine-4-carboxylic acid (Fmoc-3-MeAppc-OH)

Step 1:

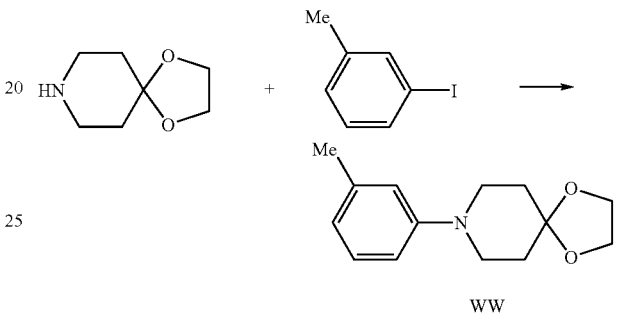

To a solution of 3-iodotoluene (4.36 g, 2.6 mL, 20.0 mmol), 1,4-dioxa-8-azaspiro[4.5]decane (6.88 g, 6.2 mL, 48.1 mmol, 2.4 equiv) and sodium tert-butoxide (5.3 g, 55.2 mmol, 2.8 equiv) in dry dioxane (80 mL) were added tris(dibenzylideneacetone)dipalladium(0) (91 mg, 0.1 mmol) and tri-o-tolylphosphine (122 mg, 0.4 mmol). The reaction was heated at 90° C. for 26 hrs. The resulting reaction mixture was concentrated to remove solvent. The residue was treated with water and extracted with EtOAc. The combined organic extracts were combined, washed with brine, dried over $Na_2SO_4$ and concentrated to give a brown oil. This crude product was purified on flash chromatography (hexane/EtOAc, 95/5 to 75/25) to provide the pure product WW as a slightly yellow solid (3.21 g, 69%).

Step 2:

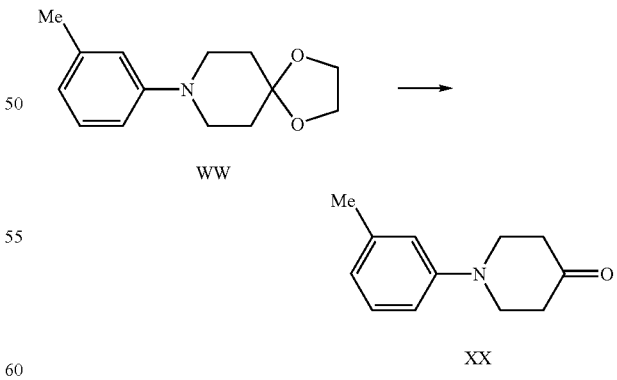

To a solution of the ketal WW (1.25 g, 5.36 mmol) in acetone (20 mL) was added 6N hydrochloric acid (10 mL) and the reaction was heated at reflux overnight. The resulting reaction was concentrated to remove solvent. The residue was diluted with EtOAc and neutralized with aqueous NaOH (6N). The layers were separated and the aqueous layer was extracted with EtOAc. The combined organic extracts were washed with brine, dried over $Na_2SO_4$ and concentrated. The crude product was purified on flash chromatography (hexane/EtOAc, 90/10 to 70/30) to give the product XX as a yellow oil (843 mg, 83% yield). MS m/z 190 (M+H), Calcd for $C_{12}H_{15}NO$, 189.

Step 3:

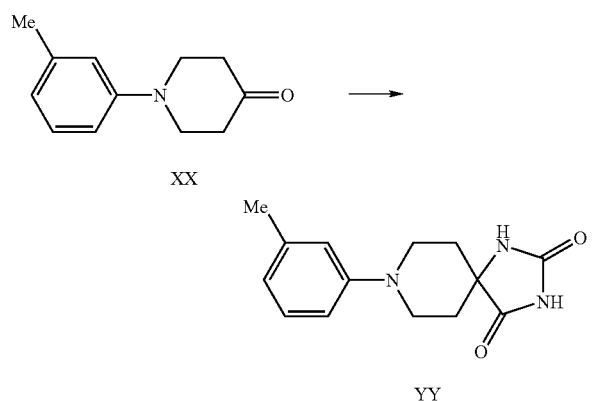

To a solution of the ketone XX (763 g, 4.03 mmol) in ethanol (45 mL) and water (15 mL) in a glass pressure bottle, were added ammonium carbonate (3.09 g, 32.21 mmol, 8 equiv) and potassium cyanide (675 mg, 10.38 mmol, 2.5 equiv). The mixture was heated at 80–90° C. for 18 hrs. The cooled reaction mixture was added to icy water (200 ml) and stirred vigorously for 30 min. The resulting precipitate was suction filtered, washed thoroughly with water and dried to yield the hydantoin YY as a white solid (930 mg, 89% yield). MS m/z 260 (M+H), Calcd for $C_{14}H_{17}N_3O_2$, 259.

Step 4:

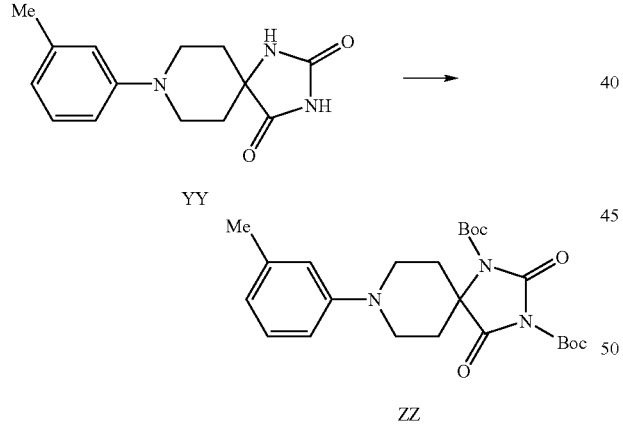

To a suspension of the hydantoin YY (780 mg, 3.012 mmol) in dry THF (22 mL) were added di-tert-butyl dicarbonate (1.64 g, 7.52 mmol, 2.5 equiv), triethylamine (0.42 mL, 305 mg, 3.01 mmol, 1.0 equiv) and DMAP (20 mg, 0.164 mmol) in succession. About 5 minutes after the addition, the reaction turned into a clear yellow solution and was stirred overnight at room temperature. The reaction mixture was concentrated under reduced pressure to yield a solid that was then taken up in EtOAc (300 mL), washed with brine (3×30 mL), dried over anhydrous $Na_2SO_4$ and concentrated under reduced pressure. The crude light yellow product was purified through flash chromatography (hexane/EtOAc, 90/10→80/20) to give the pure bis-Boc hydantoin ZZ as a white solid (1.37 g, quantitative). HRMS m/z 482.2261 (M+Na), Calcd. for $C_{24}H_{33}N_3O_6Na$, 482.2267.

Step 5:

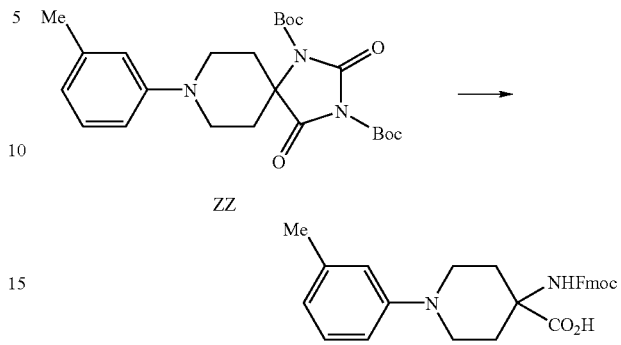

The bis-Boc hydantoin ZZ (1.29 g, 2.818 mmol) was dissolved in DME (20 mL) to give a clear solution. To this solution was added 1N NaOH (25 mL, 25 mmol) and the reaction was stirred overnight at room temperature, giving a fairly clear mixture. HPLC showed completion of the reaction. The reaction mixture was concentrated under reduced pressure to remove DME and extracted with $Et_2O$. Without purification, the resulting aqueous layer containing 4-amino-1-(3-methylphenyl)piperidine-4-carboxylic acid (3-MeAPPC) was treated with 6N HCl to adjust the pH to 11–12. This solution (30 mL) was then diluted with 1,4-dioxane (30 mL) and treated with Fmoc-Cl (1.46 mg, 5.65 mmol, 2.0 equiv) and stirred overnight at room temperature. The reaction mixture was concentrated under reduced pressure to remove dioxane, neutralized with 1N HCl and extracted with EtOAc. The combined organic extracts were washed with brine, dried over anhydrous $Na_2SO_4$ and concentrated. The crude product was purified through flash chromatography (hexane/EtOAc→$CH_2Cl_2$/MeOH) to give the pure product Fmoc-3-MeAPPC as a white solid (1.002 g, 78% yield from the bis-Boc hydantoin). HRMS m/z 479.1940 (M+Na), Calcd. for $C_{28}H_{28}N_2O_4Na$, 479.1947.

EXAMPLE 24

Preparation of Fmoc-4-amino-1-(3-methoxyphenyl) piperidine-4-carboxylic acid (Fmoc-3-MeOAppc-OH)

Step 1:

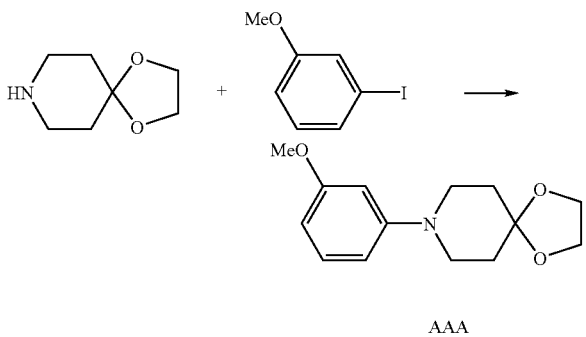

To a solution of 3-iodoanisole (4.68 g, 2.4 mL, 20.0 mmol), 1,4-dioxa-8-azaspiro[4.5]decane (6.2 mL, 6.88 g, 48.1 mmol, 2.4 equiv) and sodium tert-butoxide (5.3 g, 55.2 mmol, 2.8 equiv) in dry dioxane (80 mL) were added tris(dibenzylideneacetone)dipalladium(0) (91 mg, 0.1 mmol) and tri-o-tolylphosphine (122 mg, 0.4 mmol) and the reaction was heated at 90° C. for 26 hrs. The resulting reaction mixture was concentrated to remove solvent and the residue was treated with water and extracted with EtOAc. The combined organic extracts were combined, washed with brine, dried over Na₂SO₄ and concentrated to give brown oil. This crude product was purified on flash chromatography (hexane/EtOAc, 95/5 to 75/25) to provide the pure product AAA as a slightly yellow solid (3.10 g, 62% yield). MS m/z (M+H), 250 (M+H), Calcd for $C_{14}H_{19}NO_3$, 249.

Step 2:

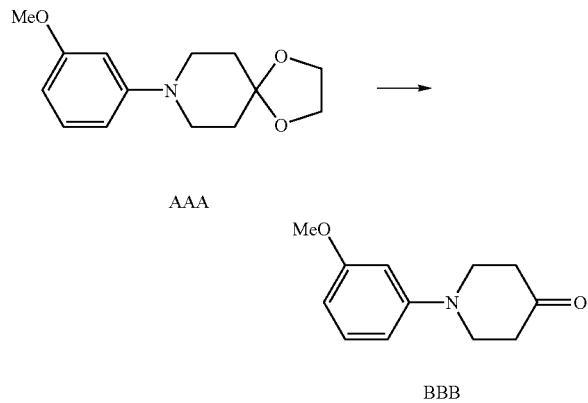

To a solution of the ketal AAA (3.10 g, 12.45 mmol) in acetone (90 mL) was added 6N hydrochloric acid (45 mL) and the reaction was heated at reflux overnight. The resulting reaction was concentrated to remove solvent. The residue was diluted with EtOAc and neutralized with aqueous NaOH (6N). The layers were separated and the aqueous layer was extracted with EtOAc. The combined organic extracts were washed with brine, dried over Na₂SO₄ and concentrated. The crude product was purified on flash chromatography (hexane/EtOAc, 90/10 to 70/30) to give the product BBB as a yellow oil (2.53 g, 99% yield). ¹H NMR (CDCl₃): 7.20 (m, 1H), 6.58 (d, 1H), 6.39–6.56 (m, 2H), 3.80 (s, 3H), 3.59 (m, 4H) and 2.58 (m, 4H).

Step 3:

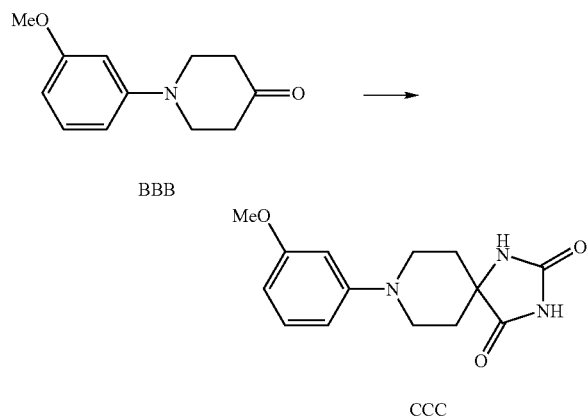

To a solution of the ketone BBB (1.81 g, 8.82 mmol) in ethanol (60 mL) and water (20 mL) in a glass pressure bottle, were added ammonium carbonate (6.77 g, 70.52 mmol, 8 equiv) and potassium cyanide (1.14 g, 17.6 mmol, 2.0 equiv). The mixture was heated at 80–90° C. for 18 hrs. The cooled reaction mixture was added to icy water (200 ml) and stirred vigorously for 30 min. The resulting precipitate was suction filtered, washed thoroughly with water and dried to yield the hydantoin CCC as a white solid (2.23 g, 92% yield). MS m/z 276 (M+H), Calcd for $C_{14}H_{17}N_3O_3$, 275.

Step 4:

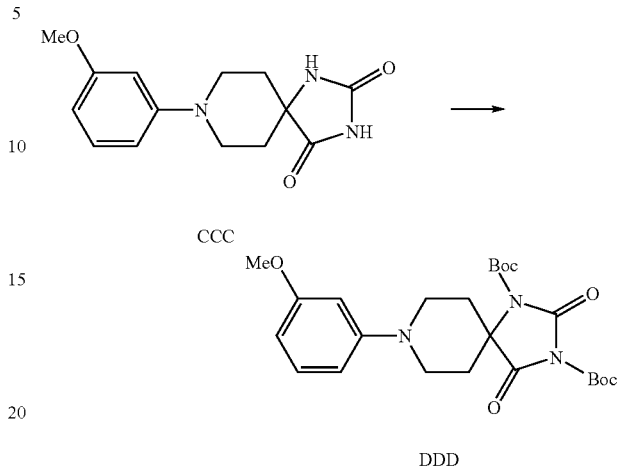

To a suspension of the hydantoin CCC (1.10 g, 4.00 mmol) in dry THF (50 mL) were added di-tert-butyl dicarbonate (2.18 g, 10.0 mmol, 2.5 equiv), triethylamine (0.62 mL, 4.4 mmol, 1.1 equiv) and DMAP (20 mg, 0.164 mmol) in succession. About 15 minutes after the addition, the reaction turned into a clear yellow solution and was stirred overnight at room temperature. The reaction mixture was concentrated under reduced pressure to yield a solid that was then taken up in EtOAc (300 mL), washed with brine (3×30 mL), dried over anhydrous Na₂SO₄ and concentrated under reduced pressure. The crude light yellow product was purified through flash chromatography (hexane/EtOAc, 90/10→80/20) to give the pure bis-Boc hydantoin DDD as a white solid (1.90 g, quantitative). ¹H NMR (CDCl₃): 7.16 (t, 1H), 6.57 (d, 1H), 6.24 (s, 1H), 6.19 (d, 1H), 3.77 (s, 3H), 1.58 (s, 9H), 1.42 (s, 9H); MS m/z 476 (M+H), Calcd for $C_{24}H_{33}N_3O_7$, 475.

Step 5:

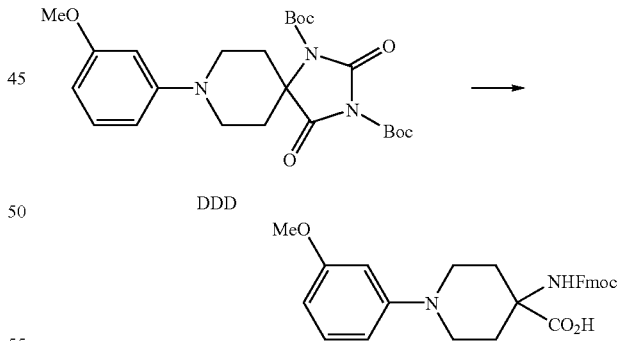

The bis-Boc hydantoin DDD (1.06 g, 2.23 mmol) was dissolved in DME (20 mL) to give a clear solution. To this solution was added 1N NaOH (20 mL, 20 mmol) and the reaction was stirred overnight at room temperature, giving a fairly clear mixture. HPLC showed completion of the reaction. The reaction mixture was concentrated under reduced pressure to remove DME and extracted with Et₂O. Without purification, the resulting aqueous layer containing 4-amino-1-(3-methoxyphenyl)piperidine-4-carboxylic acid (3-MeOAPPC) was treated with 6N HCl to adjust the pH to 11–12. This solution (35 mL) was then diluted with 1,4- dioxane (35 mL) and treated with Fmoc-Cl (755 mg, 2.93 mmol, 1.3 equiv) and stirred overnight at room temperature. The reaction mixture was concentrated under reduced pressure to remove dioxane, neutralized with 1N HCl and extracted with EtOAc. The combined organic extracts were washed with brine, dried over anhydrous $Na_2SO_4$ and concentrated. The crude product was purified through flash chromatography (hexane/EtOAc→$CH_2C_2$/1MeOH) to give the pure product Fmoc-3-MeOAPPC as a white solid (668 mg, 63% yield from the bis-Boc hydantoin DDD). $^1$H NMR ($CDCl_3$): 7.83 (d, 2H), 7.72 (d, 2H), 7.41 (td, 2H), 7.34 (dt, 2H), 7.16 (t, 1H), 6.52 (d, 1H), 6.42 (s, 1H), 6.36 (d, 1H), 4.25 (m, 3H), 3.68 (s, 3H), 3.23–3.40 (m, 2H), 2.96 (t, 2H) and 1.86–2.18 (m, 4H). HRMS m/z 495.1901 (M+Na), Calcd. for $C_{28}H_{28}N_2O_5Na$, 495.1896.

EXAMPLE 25

Preparation of Fmoc-1-amino-4-cyclohexylcyclohexane-1-carboxylic acid (Fmoc-Achc-OH)

Step 1:

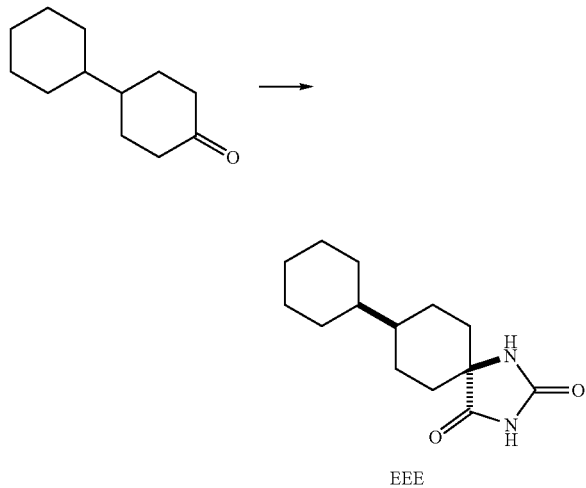

EEE

A mixture of 4-cyclohexylcyclohexanone (3.00 g, 16.6 mmole), potassium cyanide (1.63 g, 25.0 mmole), ammonium carbonate (9.59 g, 99.8 mmole), ethanol (75 ml) and water (15 ml) in a sealed, thick walled pressure flask was heated in a 80° C. oil bath for 15 hours. After cooling to room temperature, the white slurry was poured into ice-water and stirred at room temperature for a couple of hours. Filtration and air-drying gave hydantoin EEE (6.10 g, still wet, >100% yield) as a white solid. $^1$H NMR (DMSO-$d_6$) δ 10.52 (1H, broad, NH), 8.43 (1H, broad s, NH), 0.80–1.80 (20H, m). LRMS (APCI): $Cl_4H_{22}N_2O_2$, calc. 250; observed: 249 (M–H), 251 (M+H).

Step 2:

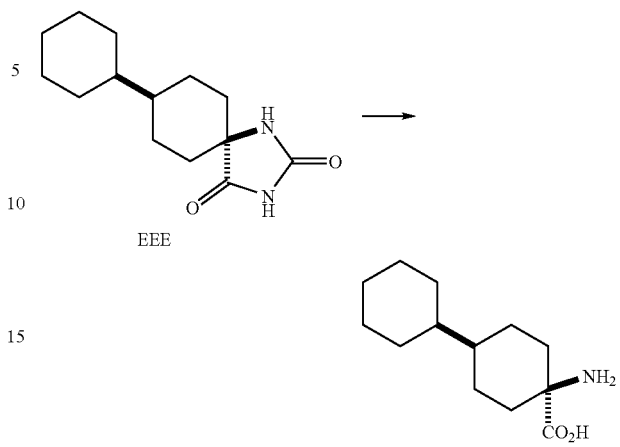

A mixture of hydantoin EEE (1.39 g, 5.55 mmole) and 6N sodium hydroxide solution (50 ml) in a sealed, thick walled pressure flask was heated in a 130° C. oil bath for 2 days. The reaction mixture was cooled in an ice bath, neutralized to ~pH 7 using concentrated hydrochloric acid. The white slurry was filtered and the precipitates rinsed with water to give crude 1-amino-4-cyclohexylcyclohexane-1-carboxylic acid (48.3 g, wet and containing inorganic salts, >100% yield). LRMS (Electrospray): $C_{13}H_{23}NO_2$, calc. 225; observed: 226 (M+H).

Step 3:

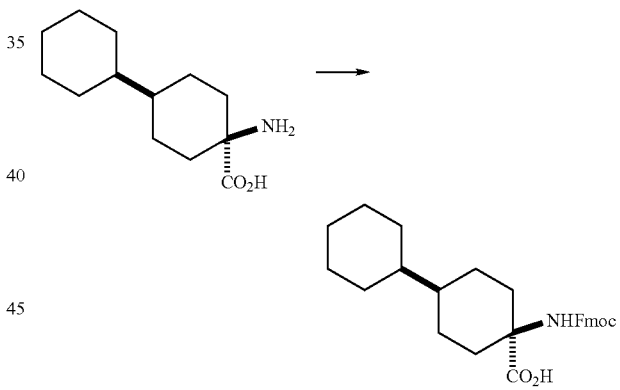

A mixture of crude 1-amino-4-cyclohexylcyclohexane-1-carboxylic acid (48.3 g, 5.55 mmole theoretical), triethylamine (1.0 ml, 7.17 mmole), 9-fluorenylmethyl succinimidyl carbonate (Fmoc-OSu, 2.43 g, 7.20 mmole) in acetonitrile (75 ml) and water (75 ml) was stirred at room temperature for 24 hours. The reaction mixture was concentrated in vacuo to remove most of the acetonitrile, acidified to pH ~3 with 10% aqueous citric acid solution, and the white emulsion extracted three times with methylene chloride. The combined organic layers were washed with water, brine, dried over magnesium sulfate. Filtration and concentration gave a crude oil which was purified by column chromatography (eluted with 1→5→8% methanol/methylene chloride) to give Fmoc-1-amino-4-trans-cyclohexylcyclohexane-1-carboxylic acid (250 mg, 10% yield for two steps). HRMS (FAB): $C_{28}H_{34}NO_4$ (M+H) calc. 448.2488; observed: 448.2497.

EXAMPLE 26

Preparation of Fmoc-1-amino-4,4-diphenylcyclohexane-1-carboxylic acid (Fmoc-Adpc-OH)

Step 1:

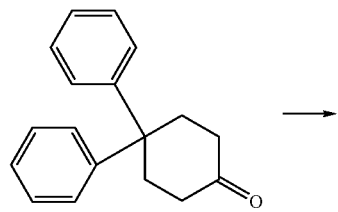

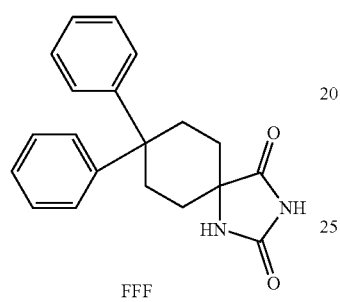

FFF

A mixture of 4,4-diphenylcyclohexanone (prepared by hydrogenation of 4,4-diphenylcyclohexenone according to the procedures of Freeman, P. K. et. al. *J. Org Chem.* 1989, 54, 782–789) (1.55 g, 6.19 mmole), potassium cyanide (0.65 g, 9.97 mmole), ammonium carbonate (3.60 g, 37.5 mmole), ethanol (48 ml) and water (12 ml) in a sealed, thick walled pressure flask was heated in a 80° C. oil bath for 24 hours. After cooling to room temperature, the white slurry was poured into ice-water and stirred at room temperature for a couple of hours. Filtration and air-drying gave hydantoin FFF (1.89 g, 95% yield) as a white solid. $^1$H NMR (DMSO-$d_6$) δ 10.57 (1H, broad, NH), 8.59 (1H, broad s, NH), 7.00–7.50 (1OH, m, phenyl). LRMS (Electrospray): $C_{20}H_{20}N_2O_2$, calc. 320; observed: 319 (M–H).

Step 2:

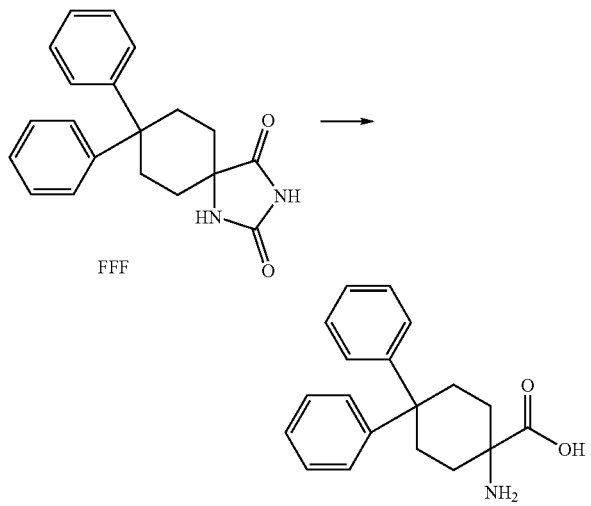

A mixture of hydantoin FFF (1.88 g, 5.87 mmole), barium hydroxide monohydrate (5.60 g, 29.6 mmole) and water (100 ml, too dilute!) in a sealed, thick walled pressure flask was heated in a 105° C. oil bath for 2 days. More barium hydroxide monohydrate (5.60 g, 29.6 mmole) was added and the mixture was heated in a 105° C. oil bath for another 24 hours. The reaction mixture was cooled to room temperature, acidified to pH 3 using 4N sulfuric acid while being stirred vigorously. The suspension was stirred in a boiling water bath for two hours and cooled to room temperature. The white suspension was filtered and the precipitates rinsed with water. The combined filtrate and washings were concentrated in vacuo to –30 ml. Neutralization with concentrated ammonium hydroxide solution gave white precipitates which were filtered, washed with water and dried in vacuo overnight to give crude 1-amino-4,4-diphenylcyclohexane-1-carboxylic acid (0.52 g, 30% yield) as a white solid. LRMS (Electrospray): $C_{19}H_{21}NO_2$, calc. 295; observed: 294 (M–H), 296 (M+H).

Step 3:

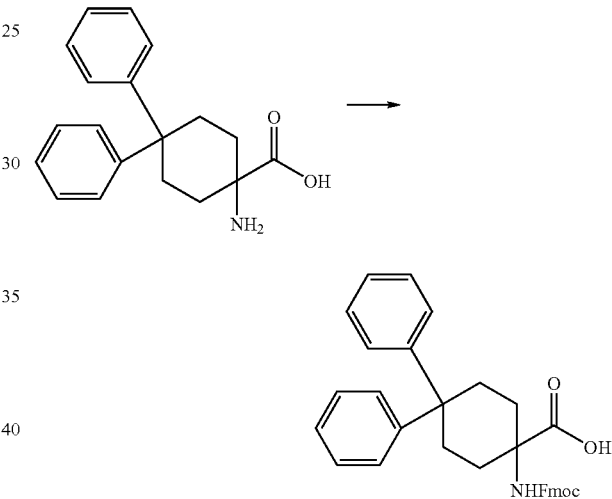

A mixture of crude 1-amino-4,4-diphenylcyclohexane-1-carboxylic acid (510 mg, 1.73 mmole), triethylamine (0.37 ml, 2.65 mmole), 9-fluorenylmethyl succinimidyl carbonate (Fmoc-OSu, 880 mg, 2.61 mmole) in acetonitrile (25 ml) and water (25 ml) was stirred at room temperature overnight. TLC analysis of the reaction indicated the presence of starting material amino acid. 9-fluorenylmethyl succinimidyl carbonate (200 mg) and acetonitrile (5 ml) were added and the mixture was stirred at room temperature for another 24 hours. The reaction mixture was concentrated in vacuo to remove most of the acetonitrile, acidified to pH 3 with 10% aqueous citric acid solution, and the white emulsion extracted three times with ethyl acetate. The combined organic layers were washed with water, brine, dried over sodium sulfate. Filtration and concentration gave a crude oil which was purified by column chromatography (eluted with 1→4→8% methanol/methylene chloride) to give Fmoc-1-amino-4,4-diphenylcyclohexane-1-carboxylic acid (350 mg, 39% yield) as a white solid. HRMS (FAB): $C_{34}H_{32}NO_4$ (M+H) calc. 518.2331; observed: 518.231

EXAMPLE 27

Preparation of Fmoc-1-amino-4-trans-t-butylcyclohexane-1-carboxylic acid (Fmoc-Abc-OH)

Step 1:

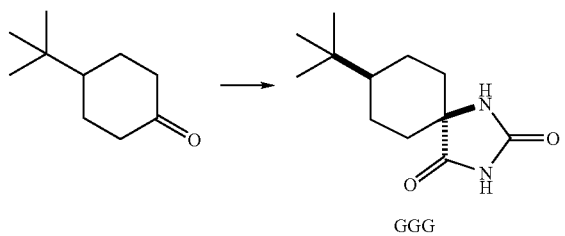

GGG

A mixture of 4-t-butylcyclohexanone (2.00 g, 13.0 mmole), potassium cyanide (1.27 g, 19.5 mmole), ammonium carbonate (7.48 g, 77.8 mmole), ethanol (60 ml) and water (12 ml) in a sealed, thick walled pressure flask was heated in a 80° C. oil bath for 15 hours. After cooling to room temperature, the white slurry was poured into ice-water and stirred at room temperature for a couple of hours. Filtration gave hydantoin GGG (2.78 g, 96% yield) as a white solid which was used in the next step as a crude. $^1$H NMR (DMSO-$d_6$) δ 10.52 (1H, broad, NH), 8.50 (1H, broad s, NH), 0.81 (9H, s, t-Bu).

Step 2:

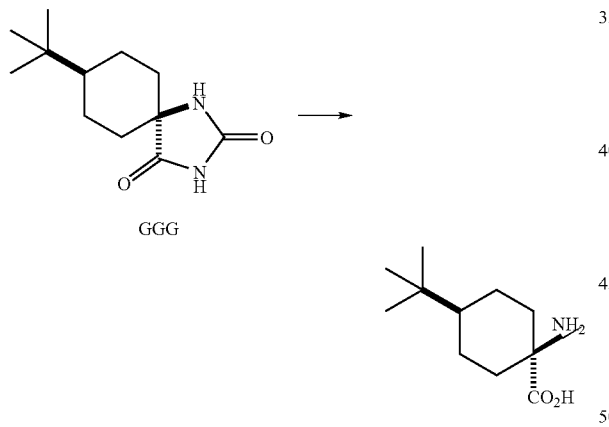

GGG

A mixture of hydantoin GGG (2.78 g, 12.4 mmole), barium hydroxide monohydrate (11.74 g, 62.0 mmole) and water (50 ml) in a sealed, thick walled pressure flask was heated in a 120° C. oil bath for 2 days. The reaction mixture was cooled to room temperature, acidified to ~pH 3 using 4N sulfuric acid while being stirred vigorously. The suspension was stirred in a boiling water bath for one hour and cooled to room temperature. The white suspension was filtered and the precipitates rinsed with water. The combined filtrate and washings were concentrated in vacuo to ~30 ml. Neutralization with concentrated ammonium hydroxide solution gave white precipitates which were filtered, washed with water and dried in vacuo overnight to give 1-amino-4-trans-t-butylcyclohexane-1-carboxylic acid (2.10 g, 85% yield) as a white solid.

Step 3:

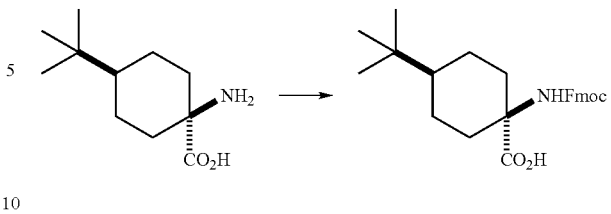

A mixture of crude 1-amino-4-trans-t-butylcyclohexyl-1-carboxylic acid (2.10 g, 10.54 mmole), 9-fluorenylmethyl succinimidyl carbonate (Fmoc-OSu, 6.33 g, 7.20 mmole) in dioxane (150 ml) and 10% sodium carbonate solution (120 ml) was stirred at room temperature for 24 hours. The reaction mixture was concentrated in vacuo to remove most of the dioxane, acidified to pH ~3 with 3N HCl, and the white emulsion extracted twice with methylene chloride. The combined organic layers were washed with water, brine, dried over magnesium sulfate. Filtration and concentration gave a crude which was purified by column chromatography (eluted with 1→4→5% methanol/methylene chloride) to give Fmoc-1-amino-4-trans-t-butylcyclohexane-1-carboxylic acid (1.42 g, 32% yield). HRMS (FAB): $C_{26}H_{32}NO_4$ (M+H) calc. 422.2331; observed: 422.23.

EXAMPLE 28

Preparation of 3S,2S-Fmoc-(L)-beta methyl(Nin-Mes)tryptophan, Fmoc-(L)-β-Me(Nin-Mes)Trp-OH)

Step 1:

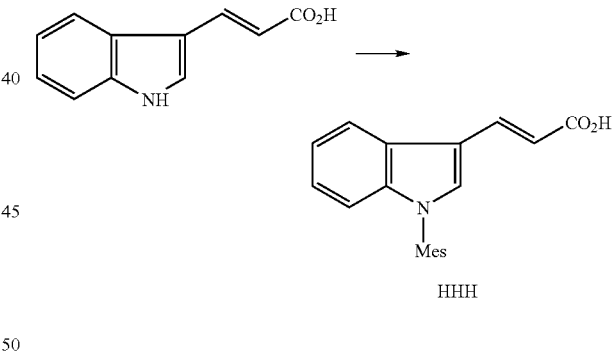

HHH

To a solution of trans-3-indolearylic acid (15.0 g, 0.08 mole) in 350 mL of dry THF at −78° C. was slowly added 125 mL of 1.6 M n-BuLi in hexane. The resulting suspension was stirred at −78° C. for 1 hr. Then, a solution of 2-mesitylenesulfonyl chloride (21.9 g, 0.1 mole) in 50 mL of dry THF was slowly added. The mixture was warmed to rt, and stirred overnight. The mixture was poured to a saturated aqueous NH$_4$Cl solution. The layers were separated and the aqueous layer was extracted with EtOAc. The combined organic layer was dried over sodium sulfate. Removal of solvents gave 14.1 g of crude product HHH which was used for the next step without further purification. $^1$H NMR analysis indicates that it contains 2.8 g of 2-mesitylenesulfonic acid. $^1$H NMR (CD$_3$OD) δ 7.57 (s, 1H), 7.42 (d, 1H), 7.15–7.30 (m, 3H), 7.02 (s, 2H), 6.54 (d, 1H), 6.36 (d, 1H), 2.52 (s, 9H), 2.30 (s, 3H).

Step 2:

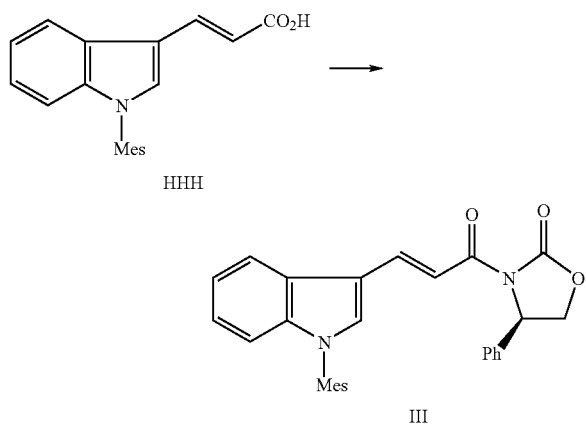

To a solution of N-2-mesitylenesulfonyl-trans-3-indolearylic acid (3.26 g, 8.8 mmole) in 140 mL of dry THF at −78° C. were added 3.7 mL (3 equiv.) of triethylamine and 2.17 mL (2 equiv.) of Me₃CCOCl. The resulting mixture was stirred at −78° C. for 15 min, and at 0° C. for 1.5 hr. The mixture was cooled down to −78° C., to which was added 5.5 mL of 1.6M n-BuLi in hexane, then added a mixture of (R)-4-phenyl-2-oxazolidinone and n-BuLi in THF (prepared by adding 11 mL of 1.6M n-BuLi in hexane to a solution of (R)-4-phenyl-2-oxazolidinone (2.87 g, 17.6 mmole) in 70 mL of dry THF at −78° C.) through a cannula. The resulting mixture was stirred at −78° C. for 2 hr, and at rt overnight. The reaction was quenched by NH₄Cl aqueous solution (100 mL). After removal of the organic solvents in vacuo, the aqueous residue was extracted with EtOAc. The combined organic layer was dried over sodium sulfate. Filtration and concentration gave a crude product which was purified by a flash chromatography (EtOAc/hexane, 1:4) to give the product III as light brown gum in 63% yield (2.86 g). LR-Electrospray: $C_{29}H_{26}N_2O_5S$, cal: 514 observed: m/z 515 (M+H).

Step 3:

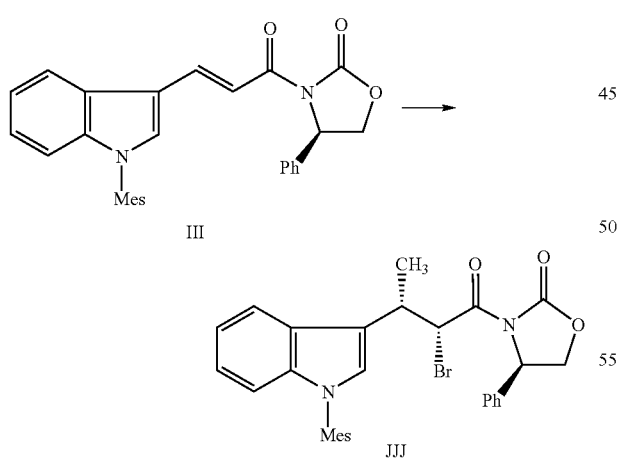

To a mixture of CuBr.Me₂S (0.84 g, 4.08 mmole) and 5 mL of dimethyl sulfide in 10 mL of dry THF at −4° C. was added 1.36 mL of 3M CH₃MgBr in ether. After stirring for 10 min, the above product (1.4 g, 2.72 mmole) in 8 mL of dry THF was added. The resulting mixture was stirred at −4° C. for 1 hr, and at rt for 6 hr. After cooling to −78° C., to the mixture was added 1.45 g (8.16 mmole) of N-bromosuccinimide in 15 mL of dry THF. The mixture was stirred at −78° C. for 30 min, and at rt overnight. The mixture was poured to 100 mL of brine, and extracted with EtOAc (2×100 mL). The organic layer was dried over sodium sulfate. Filtration and concentration gave a crude product which was purified by a flash chromatography (EtOAc/hexane, 1:4) to give the product JJJ as light brown gum in 46% yield (0.77 g). ¹H NMR (CDCl₃) δ 7.63 (d, 1H), 7.47 (s, 1H), 7.20–7.37 (m, 8H), 6.98 (s, 2H), 6.16 (d, 1H), 5.13 (dd, 1H), 4.49 (t, 1H), 4.17 (dd, 1H), 3.75 (dt, 1H), 2.54 (s, 9H), 2.31 (s, 3H), 1.59 (d, 3H).

Step 4:

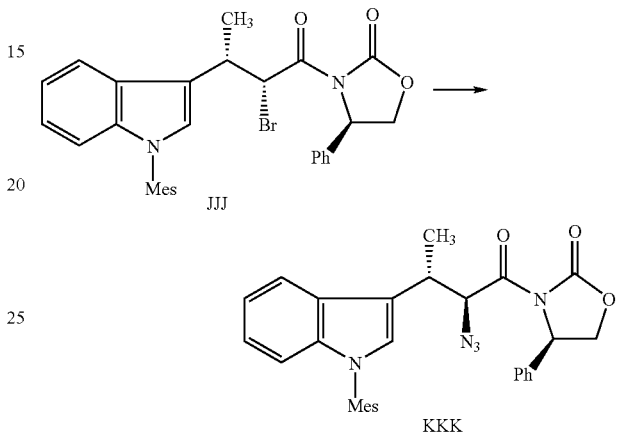

The above bromide JJJ (0.72 g, 1.18 mmole) was mixed with tetra-n-butylammonium azide (1.68 g, 5.9 mmole) and sodium azide (77 mg, 1.18 mmole) in 10 mL of acetonitrile, and stirred at rt for 6 hr. The mixture poured to 100 mL of NH₄Cl aqueous solution and extracted with EtOAc (2×100 mL). The organic layer was dried over sodium sulfate. Filtration and concentration gave a crude product which was purified by a flash chromatography (EtOAc/CH₂Cl₂/hexane, 1:2:5) to give the product KKK as light brown gum in 82% yield (0.55 g). ¹H NMR (CDCl3) δ 7.65 (d, 1H), 7.59 (s, 1H), 7.18–7.29 (m, 8H), 6.90 (s, 2H), 5.54 (d, 1H), 5.50 (dd, 1H), 4.78 (t, 1H), 4.35 (dd, 1H), 3.62 (quintet, 1H), 2.43 (s, 9H), 2.28 (s, 3H), 1.28 (d, 3H).

Step 5:

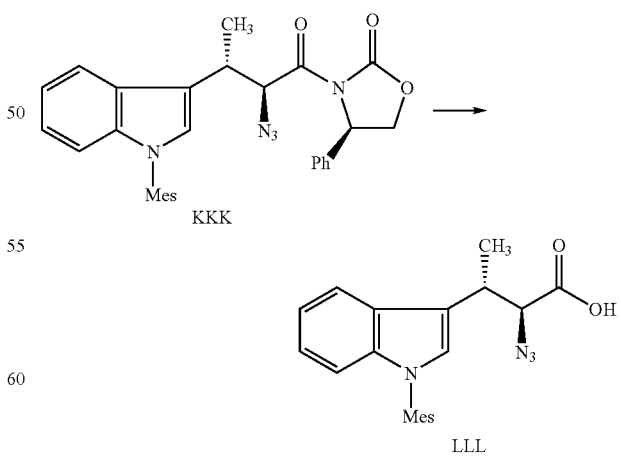

To a mixture of the above azide KKK (0.55 g, 0.96 mmole), water (4 mL) and THF (12 mL) at 0° C. was added 0.65 mL of 30% H₂O₂, then added 48 mg (2 equiv.) of LiOH in 1 mL water. The resulting mixture was stirred at 0° C. for 2 hr. The reaction was quenched with Na$_2$SO$_3$ (1 g) in 6 mL water. The mixture was stirred at rt for additional 30 min. After removal of the organic solvent, the aqueous solution was diluted with 10 mL of saturated NaHCO$_3$ solution and extracted with EtOAc (2×30 mL). Filtration and concentration gave a crude product which was purified by a flash chromatography (HOAc/MeOH/EtOAc, 1:10:100) to give the product LLL as off-white solid in 83% yield (0.34 g). LR-Electrospray: C$_{21}$H$_{22}$N$_4$O$_4$S, cal: 426 observed: m/z 425 (M−H).

Step 6:

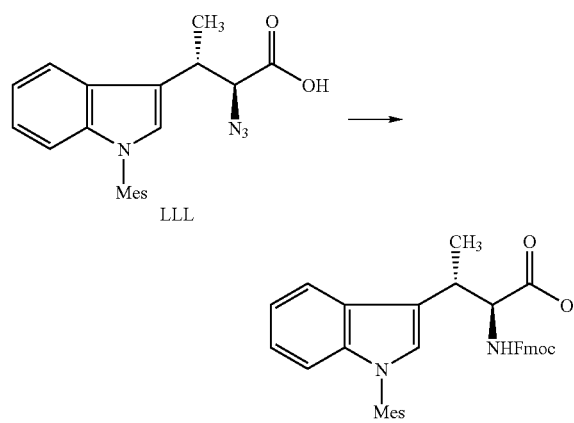

chromatography (HOAc/MeOH/EtOAc, 1:10:100) to give the product 3S,2S-Fmoc-(L)-beta methyl(Nin-Mes) tryptophan as off-white solid in 50% yield (0.25 g). LR-Electrospray: C$_{36}$H$_{34}$N$_2$O$_6$S, cal: 622 observed: m/z 621 (M−H).

EXAMPLE 29

Preparation of Fmoc-Linker-BHA Resin

Benzhydrylamine copolystyrene-1% divinylbenzene cross-linked resin (10.0 g, 9.3 mequiv, 100–200 ASTM mesh, Advanced ChemTech) was swelled in 100 mL CH$_2$Cl$_2$, filtered and washed successively with 100 ml each of CH$_2$Cl$_2$, 6% DIPEA/CH$_2$Cl$_2$ (two times), CH$_2$Cl$_2$ (two times). The resin was treated with p-[(R, S)-α-[1-(9H-fluoren-9-yl)-methoxyformamido]-2,4-dimethoxybenzyl]-phenoxyacetic acid (Fmoc-Linker) (7.01 g, 13.0 mmole), N-hydroxybenzotriazole (2.16 g, 16.0 mmole), and diisopropylcarbodiimide (2.04 ml, 13.0 mmol) in 100 mL 25% DMF/CH$_2$Cl$_2$ for 24 hours at room temperature. The resin was filtered and washed successively with 100 ml each of CH$_2$Cl$_2$ (two times), isopropanol (two times), DMF, and CH$_2$Cl$_2$ (three times). A Kaiser ninhydrin analysis was negative. The resin was dried under vacuum to yield 16.12 g of Fmoc-Linker-BHA resin. A portion of this resin (3.5 mg) was subjected to Fmoc deprotection and quantitative UV analysis indicated a loading of 0.56 mmol/g.

EXAMPLE 30

Preparation of Ac-Nle-Cyclo(Asp-Lys)-Asp-His-(D)Phe-Arg-Trp-Lys-NH$_2$

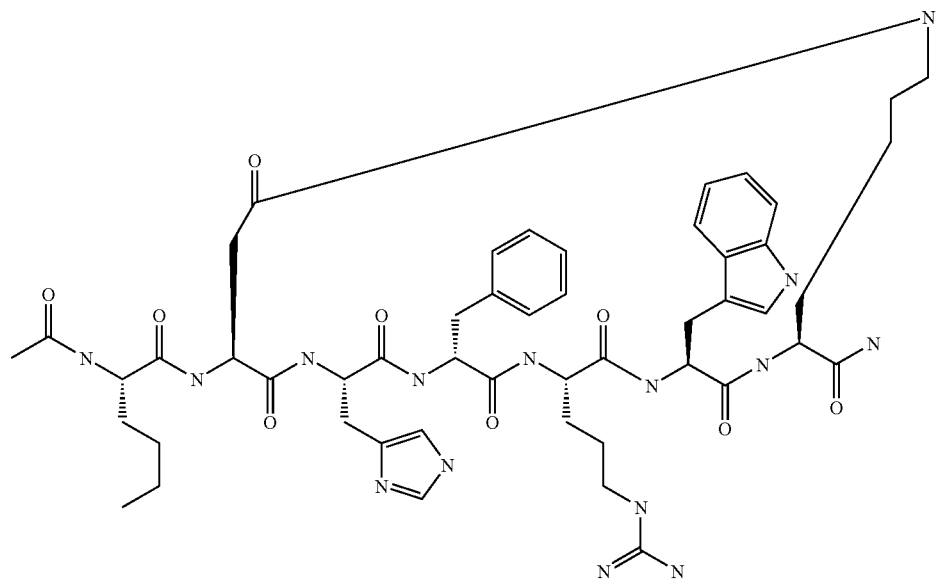

The above azido acid LLL (0.34 g, 0.8 mmole) was dissolved in 20 mL of methanol. To the solution was added 170 mg of 10% Pd on carbon. The resulting mixture was stirred at rt under H$_2$ (balloon) for 3 hr. After filtration and concentration, the crude was dissolved in a mixed solvent of THF (12 mL) and water (4 mL). To the mixture were added NaHCO$_3$ (254 mg, 3 mmole) and Fmoc-OSu (540 mg, 1.6 mmole). The resulting mixture was stirred at rt for 18 hr. Diluted with 30 mL of saturated NH$_4$Cl solution and extracted with EtOAc (2×30 mL). Filtration and concentration gave a crude product which was purified by a flash Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Seven coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-His (Trt) (600 mg 1.2 mmol) and HBTU (452 mg, 0.6 mmol), Fmoc-Asp (OBut) (500 mg, 1.2 mmol) and HBTU (452 mg, 1.2 mmol), Fmoc-Nle (430, 1.2 mmol) and HBTU (452 mg, 1.2 mmol). The peptide resin was carried through steps 1–5 of protocol 1, washed with $CH_2Cl_2$ (three times) and treated with 1 mL acetic anhydride in 6% DIPEA/$CH_2Cl_2$ for 30 minutes. The resin was filtered and washed successively with 50 ml each of $CH_2Cl_2$ (two times), isopropanol, and $CH_2Cl_2$ (three times). The resin was dried under vacuum to yield 1.2 g of Ac-Heptapeptide resin. The Ac-heptapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude linear product was dried under vacuum to yield 250 mg of an off-white solid. The crude peptide was subjected to cyclization without purification.

250 mg of the crude linear peptides was dissolved in 250 ml of DMF, 600 μL of N-methyl morpholine was added to have an apparent pH of 8.0. 300 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/$H_2O$, buffer B: 0.1% TFA/$CH_3CN$) in 90 min., flow rate 8 ml/min, detection 280 nm. The main peak was cut by analytical HPLC analysis of collected fractions, pooled and lyophilized to yield 60 mg (15%) of a white, amorphous powder. This compound was homogeneous by HPLC. LR-Electrospray $C_{50}H_{69}N_{15}O_9$ cal: 1024 observed: m/z (1025 M+H).

EXAMPLE 31

Preparation of Penta-cyclo(Asp-Lys)-Asp-Apc-(D)Phe-Arg-Trp-Lys-$NH_2$

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-Apc (550 mg 1.2 mmol) and HBTU (452 mg, 1.2 mmol), Fmoc-Asp (OBut) (500 mg, 1.2 mmol) and HBTU (452 mg, 1.2 mmol). The peptide resin was carried through steps 1–5 of protocol 1, washed with $CH_2Cl_2$ (three times) and treated with 2 mL valeric anhydride in 6% DIPEA/$CH_2Cl_2$ for 30 minutes. The resin was filtered and washed successively with 50 ml each of $CH_2Cl_2$ (two times), isopropanol, and $CH_2Cl_2$ (three times). The resin was dried under vacuum to yield 1.0 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude linear product was dried under vacuum to yield 220 mg of an off-white solid. The crude peptide was subjected to cyclization without purification. 220 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with

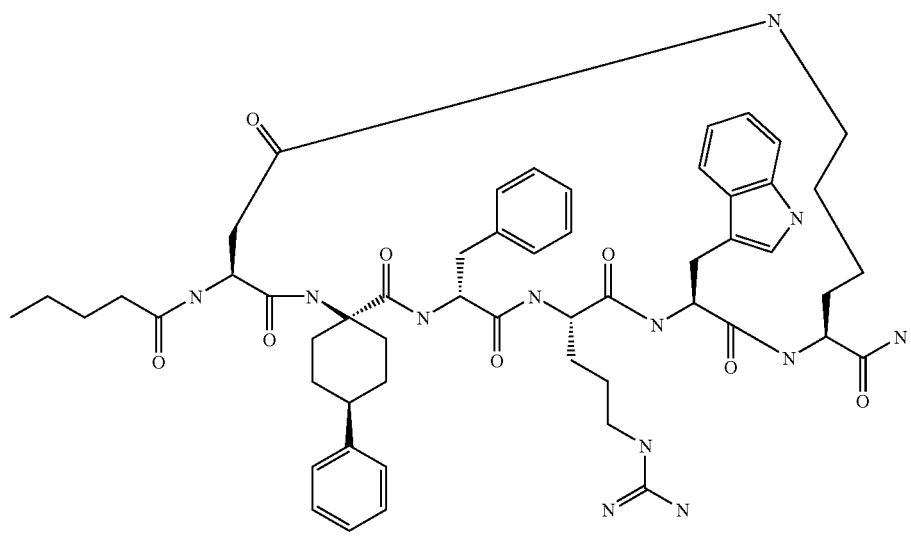

a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 53 mg (13%) of a white, amorphous powder. This compound was homogeneous by HPLC. LR-Electrospray C$_{54}$H$_{72}$N$_{12}$O$_8$ cal: 1017 observed: m/z (1018 M+H).

EXAMPLE 32

Preparation of Penta-cyclo(Asp-Lys)-Asp-Apc-(D)Phe-Arg-(2)Nal-Lys-NH$_2$

The Pentyl-hexapeptide resin was treated with 100 µL ethanedithiol, 100 µL dimethylsulfide, 250 µL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 220 mg of an off-white solid. The crude peptide was subjected to cyclization without purification.

240 mg of the crude linear peptides was dissolved in 220 ml of DMF, 500 µL of N-methyl morpholine was added to have an apparent pH of 8.0. 280 mg of BOP was added and the cyclization was monitored by HPLC. Typically the

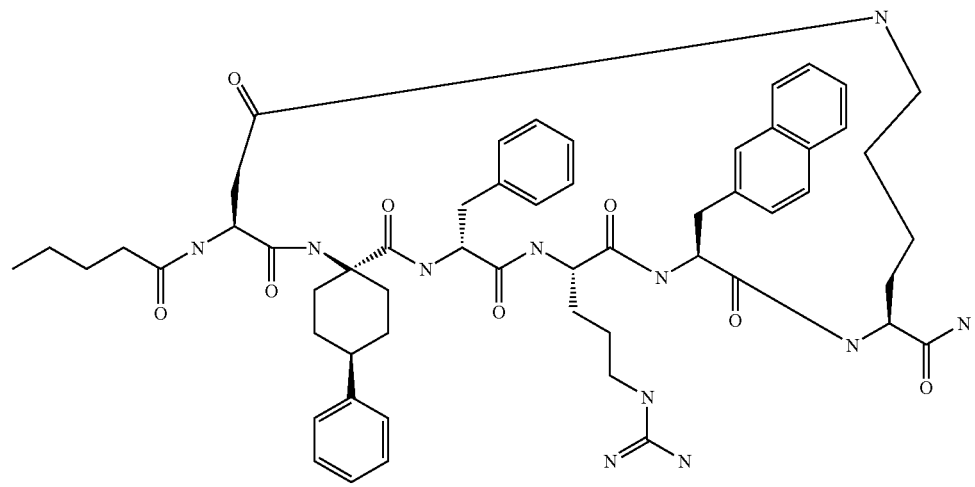

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-(2)Nal (530 mg, 1.2 mmol) and HBTU (452 mg, 1.2. mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-Apc (550 mg 1.2 mmol) and HBTU (452 mg, 1.2 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.1 g of Pentyl-hexapeptide resin.

cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 55 mg (14%) of a white, amorphous powder. This compound was homogeneous by HPLC. LR-Electrospray C$_{56}$H$_{73}$N$_{11}$O$_8$ cal: 1028 observed: m/z (1029 M+H).

EXAMPLE 33

Preparation of Penta-cyclo(Asp-Lys)-Asp-Apc-(D)Phe-Arg-N-methyl(2)Nal-Lys-NH$_2$

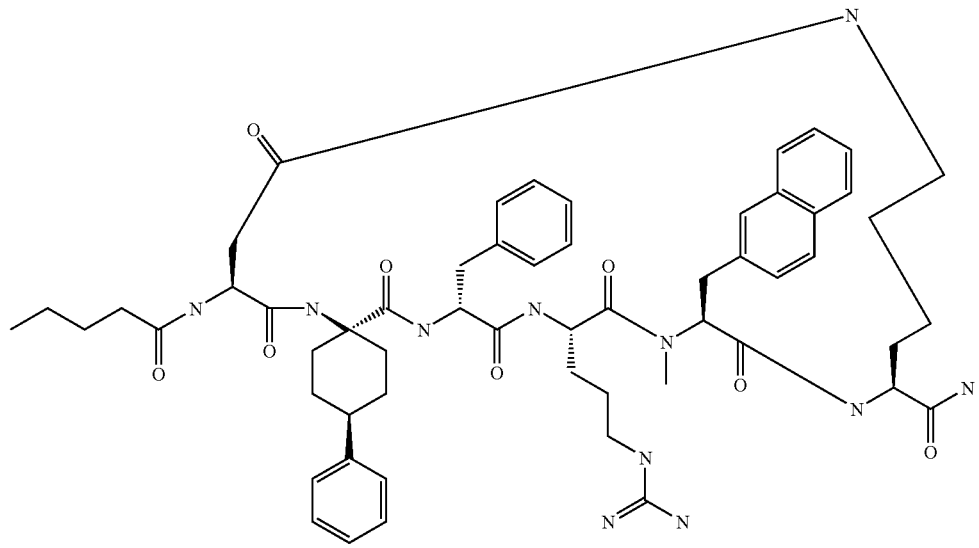

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Two coupling cycles were performed of one cycle each with Fmoc-Lys (Boc) (565 mg, 1.2 mmol) and HBTU (452 mg, 1.2 mmol), Fmoc-(2)Nal (530 mg, 1.2 mmol) and HBTU (452 mg, 1.2. mmol).

After Fmoc removal from 2-Nal residue, the resulting amine was converted to its 2-nitrobenzene sulfonyl derivative using 2-nitrobenzenesulfonyl chloride (5 eq., 426 mg, 1.93 mmol) and DIPEA (5 eq.) as the base in DMF. Washings were performed using DMF (6×30 ml) followed by CH$_2$Cl$_2$ (3×30 ml) and the resin was dried under vacuum. The sulfonamide obtained was subjected to methylation using triphenylphosphine (5 eq., 505 mg, 1.93 mmol), N,N-diethylazodicarboxylate (5 eq., 303 mL, 1.93 mmol) and methanol (10 eq. 156 µL, 3.85 mmol) in THF. Washings were performed using THF (6×30 ml) followed by CH$_2$Cl$_2$ (5×30 ml) and the resin was dried under vacuum. The 2-nitrobenzene sulfonyl group was then removed using 1,8-diazabicyclo [5.4.0] undec-7-ene (3 eq., 173 µL, 1.16 mmol), 2-mercaptoethanol (5 eq. 135 µL, 1.93 mmol) in DMF. Washings were performed using DMF (3×30 ml), isopropanol (3×30 ml) followed by ethyl ether (3×30 ml) and the resin was dried under vacuum. The resulting N-Me-2-Nal residue was subjected to four coupling cycles, one cycle each with Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-Apc (550 mg 1.2 mmol) and HBTU (452 mg, 1.2 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.2 g of Pentyl-hexapeptide resin.

The Pentyl-hexapeptide resin was treated with 100 µL ethanedithiol, 100 µL dimethylsulfide, 250 µL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 235 mg of an off-white solid. The crude peptide was subjected to cyclization without purification.

235 mg of the crude linear peptides was dissolved in 220 ml of DMF, 500 µL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 43 mg (10%) of a white, amorphous powder. This compound was homogeneous by HPLC. LR-Electrospray C$_{57}$H$_{75}$N$_{11}$O$_8$ cal: 1042 observed: m/z (1043 M+H).

EXAMPLE 34

Preparation of Cyclo(succinic acid-Lys)-succinic acid-Apc-(D)Phe-Arg-Trp-Lys-NH$_2$

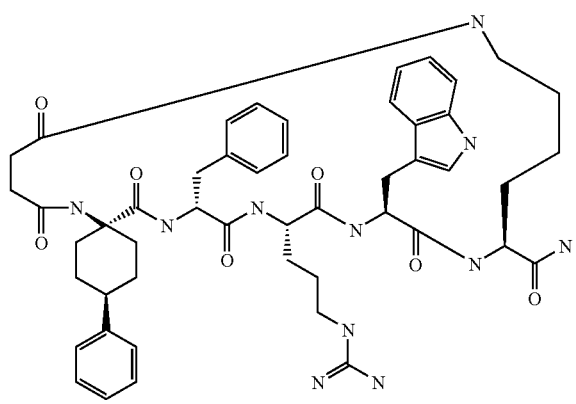

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 n-mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-Apc (550 mg 1.2 mmol) and HBTU (452 mg, 0.6 mmol), Succinic anhydride (600 mg, 6 mmol) in DMF with 1.1 ml of DIPEA.

The resin was filtered and washed successively with 50 ml each of CH$_2$Cl$_2$ (two times), isopropanol, and CH$_2$Cl$_2$ (three times). The resin was dried under vacuum to yield 1.0 g Pentapetide resin. The pentapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude 1 product was dried under vacuum to yield 220 mg of an off-white solid. The crude peptide was subjected to cyclization without purification.

220 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C$_{18}$-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 40 mg (11%) of a white, amorphous powder. This compound was homogeneous by HPLC. LR-Electrospray C$_{49}$H$_{63}$N$_{11}$O$_7$ cal: 918 observed: m/z (919 M+H).

EXAMPLE 35

Preparation of Cyclo(maleic acid-Lys)-maleic acid-Apc-(D)Phe-Arg-Trp-Lys-NH$_2$

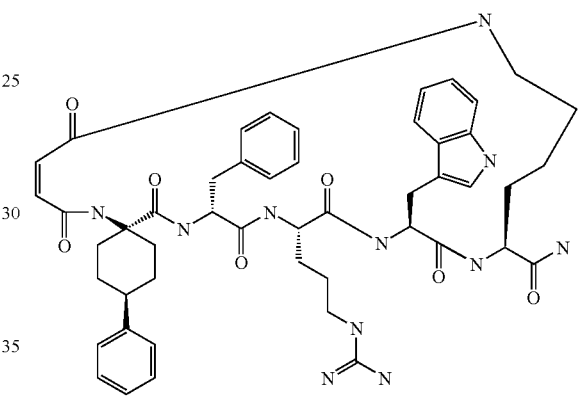

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-Apc (550 mg 1.2 mmol) and HBTU (452 mg, 0.6 mmol), Maleic anhydride (600 mg, 6 mmol) in DMF with the addition of HOBT (800 mg, 6 mmol), without DIPEA. The resin was filtered and washed successively with 50 ml each of CH$_2$Cl$_2$ (two times), isopropanol, and CH$_2$Cl$_2$ (three times). The resin was dried under vacuum to yield 1.0 g Pentapetide resin. The pentapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 230 mg of an off-white solid. The crude peptide was subjected to cyclization without purification.

230 mg of the crude linear peptides was dissolved in 220 ml of DMF, 500 µL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 38 mg (11%) of a white, amorphous powder. This compound was homogeneous by HPLC. LR-Electrospray C$_{49}$H$_{61}$N$_{11}$O$_7$ cal: 916 observed: m/z (917 M+H).

EXAMPLE 36

Preparation of Cyclo(phthalic acid-Lys)-phthalic acid-Apc-(D)Phe-Arg-Tip-Lys-NH$_2$ Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-Apc (550 mg 1.2 mmol) and HBTU (452 mg, 0.6 mmol), Phthalic anhydride (660 mg, 6 mmol) in DMF with 1.1 ml of DIPEA.

The resin was filtered and washed successively with 50 ml each of CH$_2$Cl$_2$ (two times), isopropanol, and CH$_2$Cl$_2$ (three times). The resin was dried under vacuum to yield 1.0 g Pentapetide resin. The pentapeptide resin was treated with 100 µL ethanedithiol, 100 µL dimethylsulfide, 250 µL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude 1 product was dried under vacuum to yield 220 mg of an off-white solid. The crude peptide was subjected to cyclization without purification.

220 mg of the crude linear peptides was dissolved in 220 ml of DMF, 500 µL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 35 mg (10%) of a white, amorphous powder. This compound was homogeneous by HPLC. LR-Electrospray C$_{53}$H$_{63}$N$_{11}$O$_7$ cal: 966 observed: m/z (967 M+H).

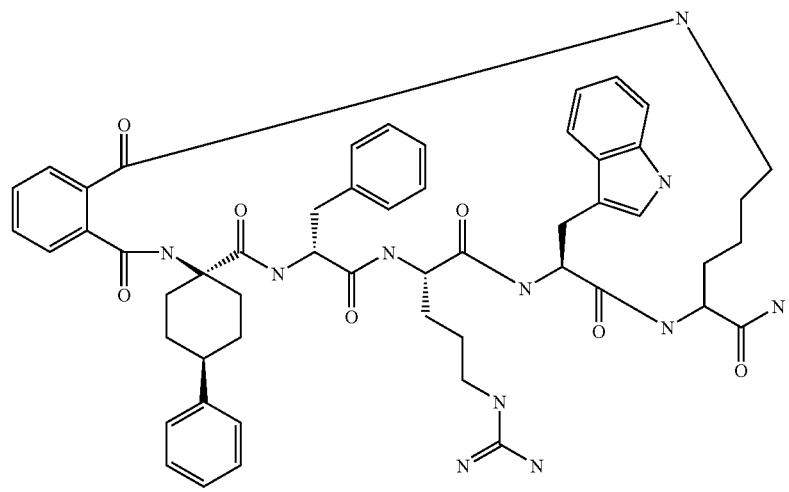

EXAMPLE 37

Preparation of Penta-cyclo(Asp-Lys)-Asp-4-OHApc-(D)Phe-Arg-Trp-Lys-NH$_2$

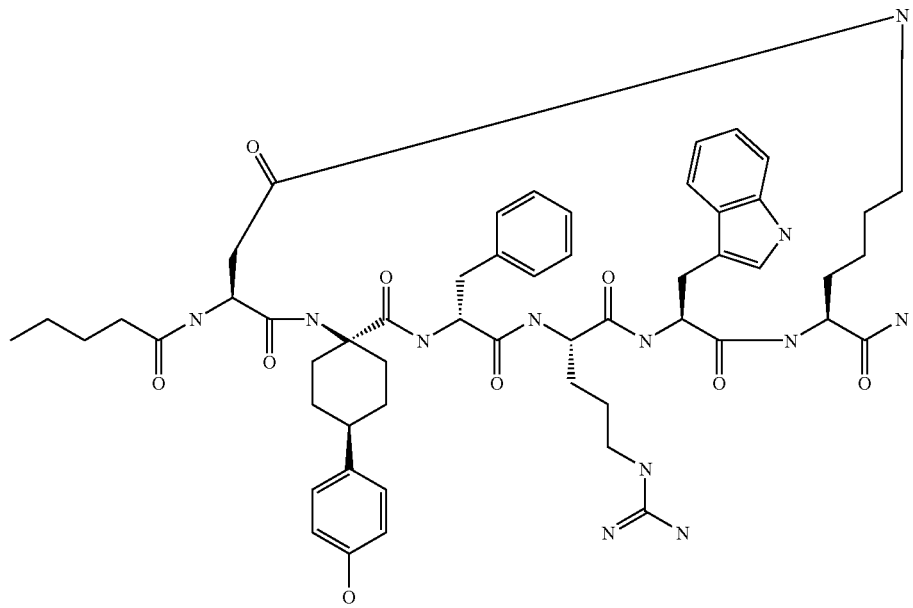

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-4-OHApc (565 mg 1.2 mmol) and HBTU (452 mg, 1.2 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.1 g of Pentyl-hexapeptide resin.

The Pentyl-hexapeptide resin was treated with 100 μLL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 225 mg of an off-white solid. The crude peptide was subjected to cyclization without purification.

225 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C$_{18}$-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 55 mg (13%) of a white, amorphous powder. This compound was homogeneous by HPLC. LR-Electrospray C$_{54}$H$_{72}$N$_{12}$O$_9$ cal: 1033 observed: m/z (1034 M+H).

EXAMPLE 38

Preparation of Penta-cyclo(Asp-Lys)-Asp-4-MeOApc-(D)Phe-Arg-Trp-Lys-NH$_2$

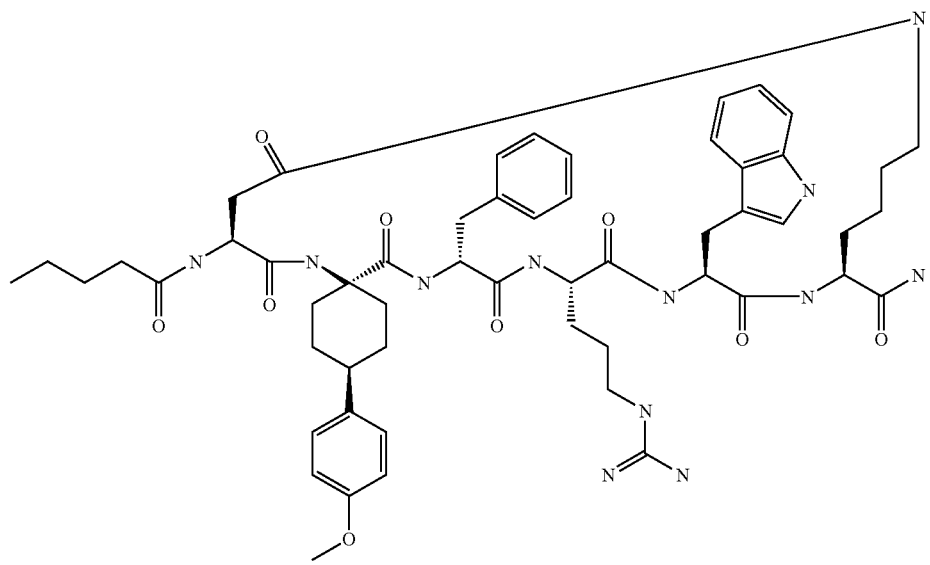

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-4-MeOApc (600 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.1 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 235 mg of an off-white solid. The crude peptide was subjected to cyclization without purification.

235 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 49 mg (12%) of a white, amorphous powder. This compound was homogeneous by HPLC. LR-Electrospray C$_{55}$H$_{74}$N$_{12}$O$_9$ cal: 1047 observed: m/z (1048 M+H).

EXAMPLE 39

Preparation of Penta-cyclo(Asp-Lys)-Asp-4-EtOApc-(D)Phe-Arg-Trp-Lys-NH₂

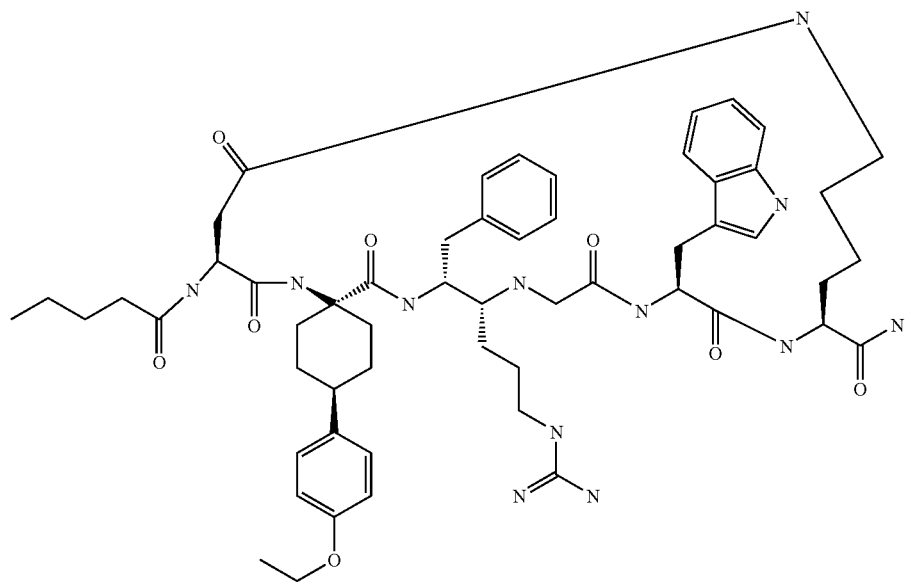

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-4-EtOApc (640 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with $CH_2Cl_2$ (three times) and treated with 2 mL valeric anhydride in 6% DIPEA/$CH_2Cl_2$ for 30 minutes. The resin was filtered and washed successively with 50 ml each of $CH_2Cl_2$ (two times), isopropanol, and $CH_2Cl_2$ (three times). The resin was dried under vacuum to yield 1.2 g of Pentyl-hexapeptide resin.

The Pentyl-hexapeptide resin was treated with 100 µL ethanedithiol, 100 µL dimethylsulfide, 250 µL anisole, and 10 mL trifluoroacetic acid at room temperature for 180 min. The resin was filtered off, washed with ~2 ml TFA, and the filtrates precipitated in chilled ethyl ether. The precipitates were centrifuged and the ether layer decanted. The residue was washed with two or three volumes of $Et_2O$ and recentrifuged and the crude linear product was dried under vacuum to yield 235 mg of an off-white solid. The crude peptide was subjected to cyclization without purification.

235 mg of the crude linear peptides was dissolved in 220 ml of DMF, 500 µL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/$H_2O$, buffer B: 0.1% TFA/$CH_3CN$) in 90 min., flow rate 8 ml/min, detection 280 nm. The main peak was cut by analytical HPLC analysis of collected fractions, pooled and lyophilized to yield 60 mg (14%) of a white, amorphous powder. This compound was homogeneous by HPLC. LR-Electrospray $C_{56}H_{76}N_{12}O_9$ cal: 1061 observed: m/z (1062 M+H).

EXAMPLE 40

Preparation of Penta-cyclo(Asp-Lys)-Asp-4-iPrOApc-(D)Phe-Arg-Trp-Lys-NH$_2$

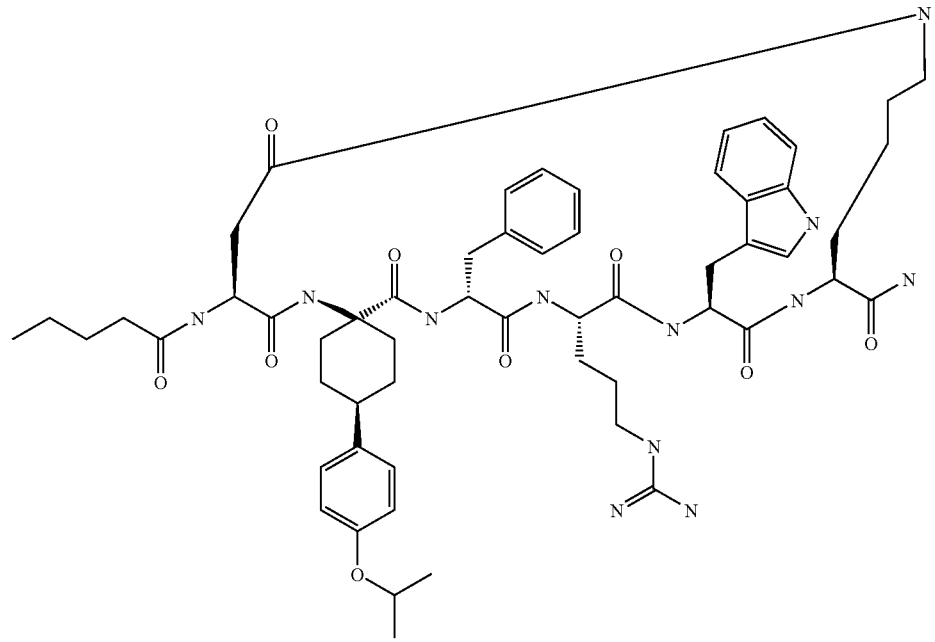

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv) as base. Six coupling cycles were performed of one cycle each with Fmoc-Lys (Bloc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and UBTU (452 mg, 1.2 mmol), Fmoc-4-iPrOApc (660 mg 1.2 mmol) and HBTU (452 mg, 0.6 mmol), Fmoc-Asp (OBut) (500 mg, 1.2 mmol) and 1HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.2 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 260 mg of an off-white solid. The crude peptide was subjected to cyclization without purification.

260 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 63 mg (15%) of a white, amorphous powder. This compound was homogeneous by HPLC. LR-Electrospray C$_{57}$H$_{78}$N$_{12}$O$_9$ cal: 1075 observed: m/z (1076 M+H).

EXAMPLE 41

Preparation of Penta-cyclo(Asp-Lys)-Asp-3-MeOApc-(D)Phe-Arg-Trp-Lys-NH$_2$

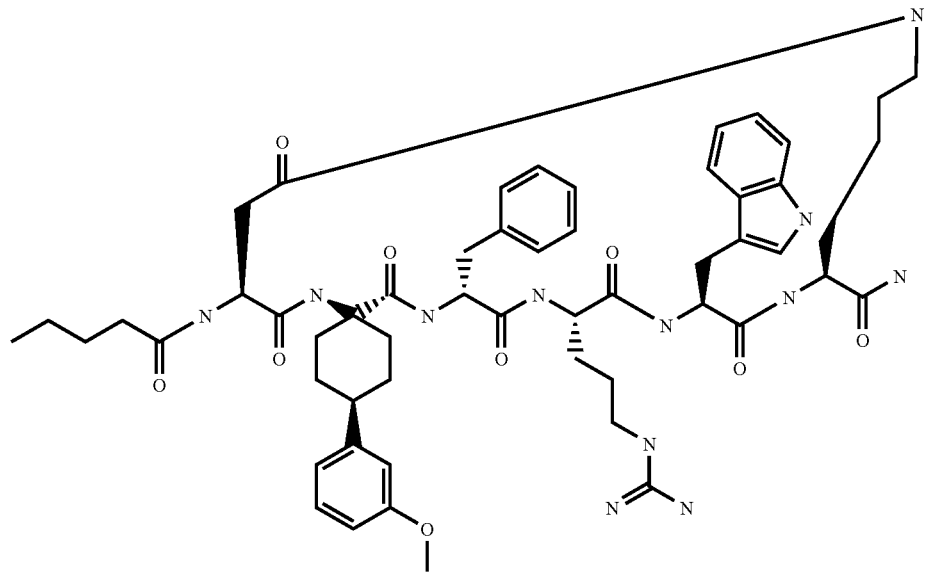

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-3-MeOApc (600 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.1 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 235 mg of an off-white solid. The crude peptide was subjected to cyclization without purification.

235 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C$_{18}$-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 49 mg (12%) of a white, amorphous powder. This compound was homogeneous by HPLC. LR-Electrospray C$_{55}$H$_{74}$N$_{12}$O$_9$ cal: 1047 observed: m/z (1048 M+H).

EXAMPLE 42

Preparation of Penta-cyclo(Asp-Lys)-Asp-4-ClApc-(D)Phe-Arg-Trp-Lys-NH₂

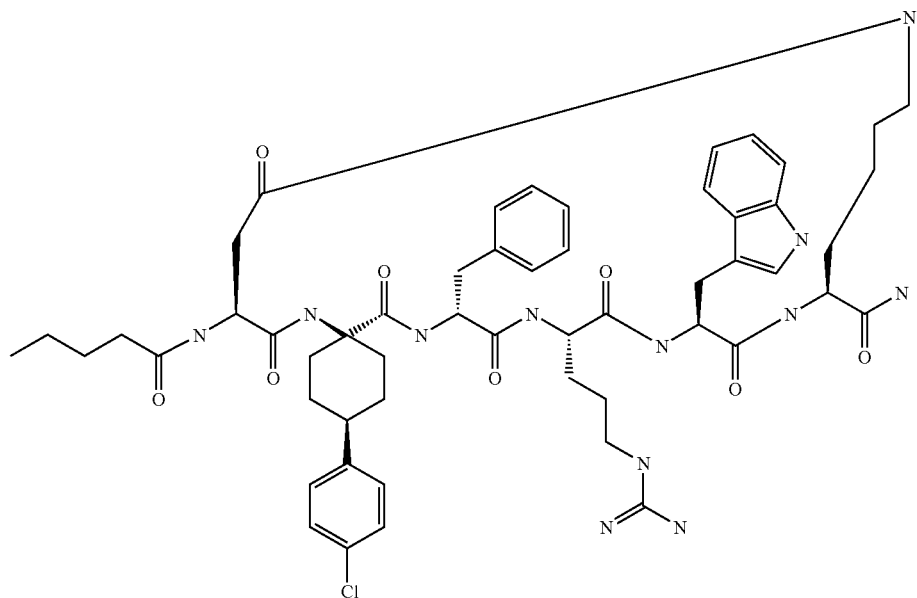

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-4-ClApc (560 mg 1.2 mmol) and HBTU (452 mg, 1.2 mmol), Fmoc-Asp (OBut) (500 mg, 1.2 mmol) and HBTU (452 mg, 1.2 mmol). The peptide resin was carried through steps 1–5 of protocol 1, washed with $CH_2Cl_2$ (three times) and treated with 2 mL valeric anhydride in 6% DIPEA/$CH_2Cl_2$ for 30 minutes. The resin was filtered and washed successively with 50 ml each of $CH_2Cl_2$ (two times), isopropanol, and $CH_2Cl_2$ (three times). The resin was dried under vacuum to yield 1.0 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude linear product was dried under vacuum to yield 230 mg of an off-white solid. The crude peptide was subjected to cyclization without purification.

230 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/$H_2O$, buffer B: 0.1% TFA/$CH_3CN$) in 90 min., flow rate 8 ml/min, detection 280 nm. The main peak was cut by analytical HPLC analysis of collected fractions, pooled and lyophilized to yield 49 mg (12%) of a white, amorphous powder. This compound was homogeneous by HPLC. LR-Electrospray $C_{54}H_{71}N_{12}O_8Cl$; cal: 1051 observed: m/z (1052 M+H).

EXAMPLE 43

Preparation of Penta-cyclo(Asp-Lys)-Asp-4-MeApc-(D)Phe-Arg-Trp-Lys-NH₂

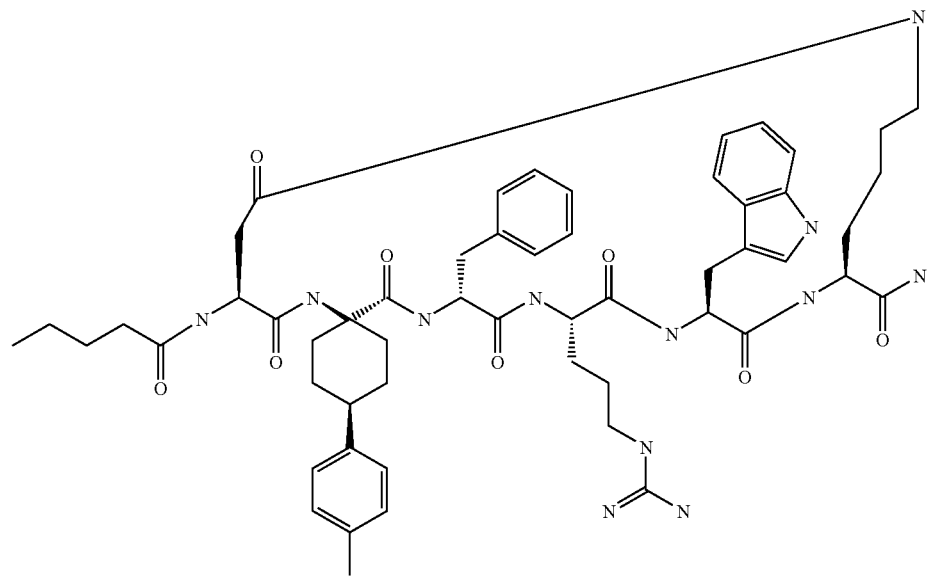

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-4-MeApc (590 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with $CH_2Cl_2$ (three times) and treated with 2 mL valeric anhydride in 6% DIPEA/$CH_2Cl_2$ for 30 minutes. The resin was filtered and washed successively with 50 ml each of $CH_2Cl_2$ (two times), isopropanol, and $CH_2Cl_2$ (three times). The resin was dried under vacuum to yield 1.2 g of Pentyl-hexapeptide resin.

The Pentyl-hexapeptide resin was treated with 100 µL ethanedithiol, 100 µL dimethylsulfide, 250 µL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et2O and recentrifuged and the crude linear product was dried under vacuum to yield 240 mg of an off-white solid. The crude peptide was subjected to cyclization without purification.

240 mg of the crude linear peptides was dissolved in 220 ml of DMF, 500 µL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/$H_2O$, buffer B: 0.1% TFA/$CH_3CN$) in 90 min., flow rate 8 ml/min, detection 280 nm. The main peak was cut by analytical HPLC analysis of collected fractions, pooled and lyophilized to yield 55 mg (14%) of a white, amorphous powder. This compound was homogeneous by HPLC. LR-Electrospray $C_{55}H_{74}N_{12}O_8$ cal: 1031 observed: m/z (1032 M+H).

EXAMPLE 44

Preparation of Penta-cyclo(Glu-Lys)-Glu-Apc-(D)Phe-Arg-Trp-Lys-NH$_2$

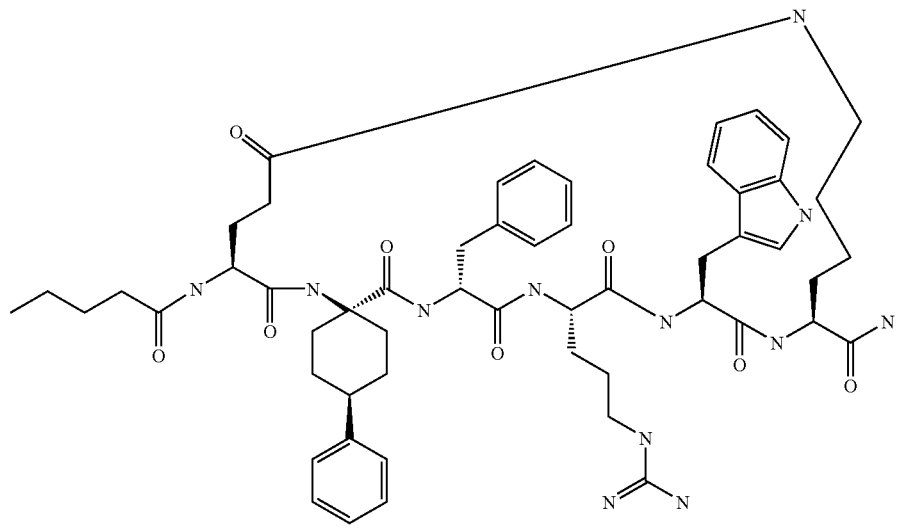

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-Apc (550 mg 1.2 mmol) and HBTU (452 mg, 0.6 mmol), Fmoc-Glu (OBut) (510 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.1 g of Pentyl-hexapeptide resin.

The Pentyl-hexapeptide resin was treated with 100 µL ethanedithiol, 100 µL dimethylsulfide, 250 µL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 255 mg of an off-white solid. The crude peptide was subjected to cyclization without purification.

255 mg of the crude linear peptides was dissolved in 220 ml of DMF, 500 µL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 60 mg (15%) of a white, amorphous powder. This compound was homogeneous by HPLC. LR-Electrospray C$_{55}$H$_{74}$N$_{12}$O$_8$ cal: 1031 observed: m/z (1032M+H).

EXAMPLE 45

Preparation of Penta-cyclo(Asp-Orn)-Asp-Apc-(D)Phe-Arg-Trp-Orn-NH$_2$

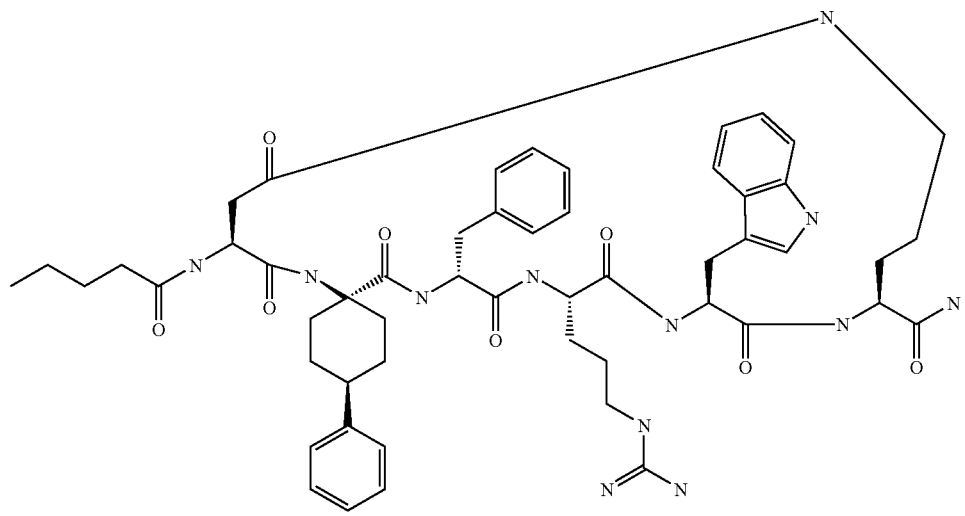

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Orn (Boc) (550 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-Apc (550 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.15 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 240 mg of an off-white solid. The crude peptide was subjected to cyclization without purification.

240 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacou, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 53 mg (13%) of a white, amorphous powder. This compound was homogeneous by HPLC. LR-Electrospray C$_{53}$H$_{70}$N$_{12}$O$_8$ cal: 1003 observed: m/z (1004 M+H).

EXAMPLE 46

Preparation of Penta-cyclo(Asp-Dbr)-Asp-Apc-(D)Phe-Arg-Trp-Dbr-NH$_2$

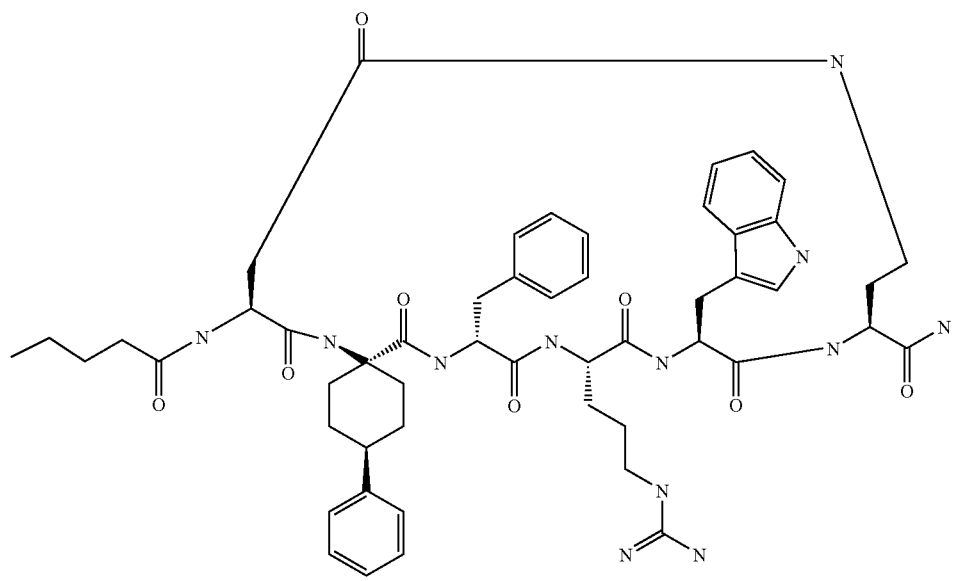

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Dbr (Boc) (540 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-Apc (550 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.10 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 220 mg of an off-white solid. The crude peptide was subjected to cyclization without purification.

220 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 35 mg (9%/o) of a white, amorphous powder. This compound was homogeneous by HPLC. LR-Electrospray C$_{52}$H$_{68}$N$_{12}$O$_8$ cal: 989 observed: m/z (990 M+H).

EXAMPLE 47

Preparation of Penta-cyclo(Asp-Dpr)-Asp-Apc-(D)Phe-Arg-Trp-Dpr-NH$_2$

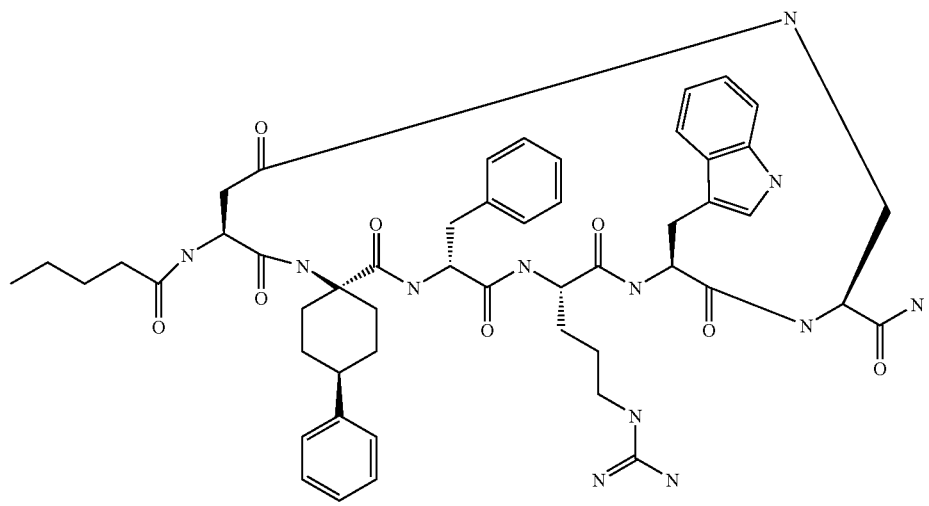

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Dpr (Boc) (530 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-Apc (550 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.0 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 200 mg of an off-white solid. The crude peptide was subjected to cyclization without purification.

200 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 30 mg (8%) of a white, amorphous powder. This compound was homogeneous by HPLC. LR-Electrospray C$_{51}$H$_{66}$N$_{12}$O$_8$ cal: 975 observed: m/z (976 M+H).

EXAMPLE 48

Preparation of Ac-cyclo(Asp-Dpr)-Asp-Apc-(D)Phe-Arg-Trp-Dpr-NH$_2$

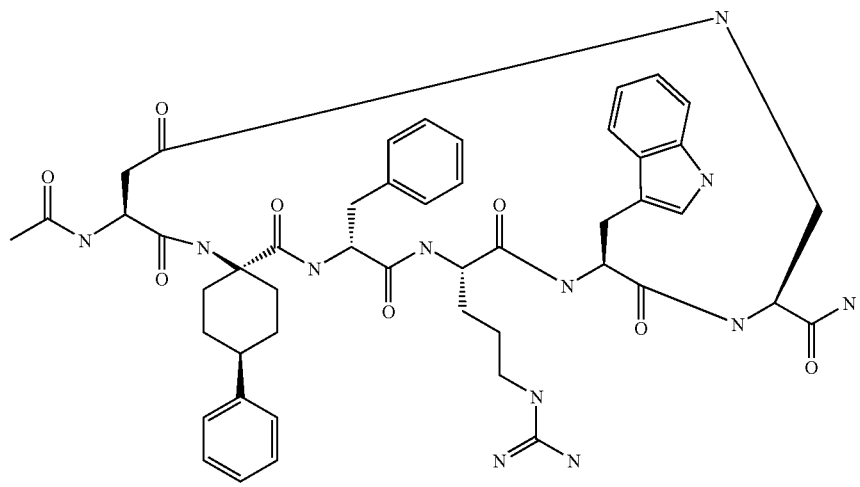

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Dpr (Boc) (530 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-Apc (550 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL acetic anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.1 g of Acetyl-hexapeptide resin.

The Acetyl-hexapeptide resin was treated with 100 µL ethanedithiol, 100 µL dimethylsulfide, 250 µL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 200 mg of an off-white solid. The crude peptide was subjected to cyclization without purification.

210 mg of the crude linear peptides was dissolved in 220 ml of DMF, 500 µL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 28 mg (8%) of a white, amorphous powder. This compound was homogeneous by HPLC. LR-Electrospray C$_{48}$H$_{60}$N$_{12}$O$_8$ cal: 933 observed: m/z (934 M+H).

EXAMPLE 49

Preparation of Cyclo(phthalic acid-Dpr)-phthalic acid-Apc-(D)Phe-Arg-Trp-Dpr-NH$_2$

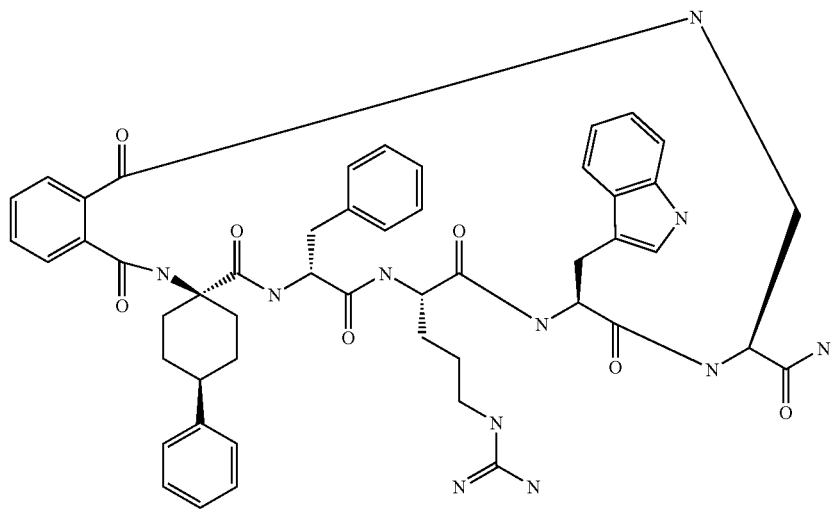

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Dpr (Boc) (530 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-Apc (550 mg 1.2 mmol) and HBTU (452 mg, 0.6 mmol), Phthalic anhydride (660 mg, 6 mmol) in DMF with 1.1 ml of DIPEA. The resin was filtered and washed successively with 50 ml each of CH$_2$Cl$_2$ (two times), isopropanol, and CH$_2$Cl$_2$ (three times). The resin was dried under vacuum to yield 1.0 g Pentapetide resin.

The pentapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude 1 product was dried under vacuum to yield 220 mg of an off-white solid. The crude peptide was subjected to cyclization without purification.

220 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C$_{18}$-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 30 mg (8%) of a white, amorphous powder. This compound was homogeneous by HPLC. LR-Electrospray C$_{50}$H$_{57}$N$_{11}$O$_7$ cal: 924 observed: m/z (925 M+H).

EXAMPLE 50

Preparation of Cyclo(succinic acid-Dpr)-succinic acid-Apc-(D)Phe-Arg-Trp-Dpr-NH$_2$

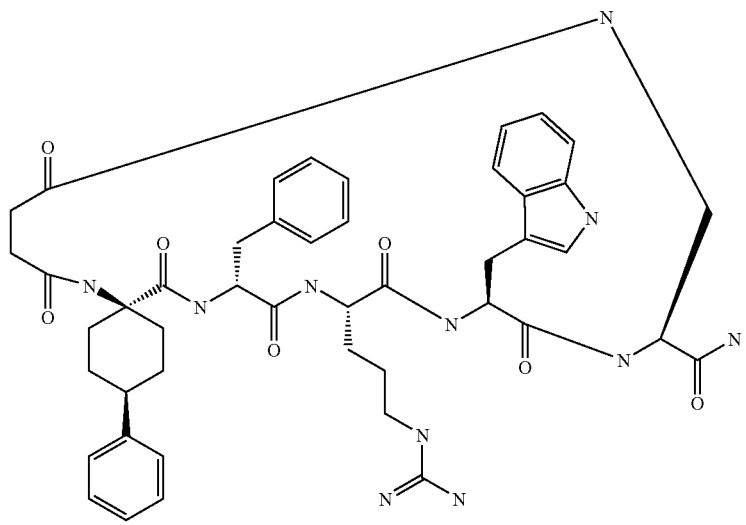

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Dpr (Boc) (530 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-Apc (550 mg 1.2 mmol) and HBTU (452 mg, 0.6 mmol), Succinic anhydride (600 mg, 6 mmol) in DMF with 1.1 ml of DIPEA. The resin was filtered and washed successively with 50 ml each of CH$_2$Cl$_2$ (two times), isopropanol, and CH$_2$Cl$_2$ (three times). The resin was dried under vacuum to yield 1.0 g Pentapeptide resin.

The pentapeptide resin was treated with 100 µL ethanedithiol, 100 µL dimethylsulfide, 250 µL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude 1 product was dried under vacuum to yield 220 mg of an off-white solid. The crude peptide was subjected to cyclization without purification.

220 mg of the crude linear peptides was dissolved in 220 ml of DMF, 500 µL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 31 mg (8%) of a white, amorphous powder. This compound was homogeneous by HPLC. LR-Electrospray C$_{46}$H$_{57}$N 10$_7$ cal: 876 observed: m/z (877 M+H).

EXAMPLE 51

Preparation of Cyclo(maleic acid-Dpr)-maleic acid-Apc-(D)Phe-Arg-Trp-Dpr-NH$_2$

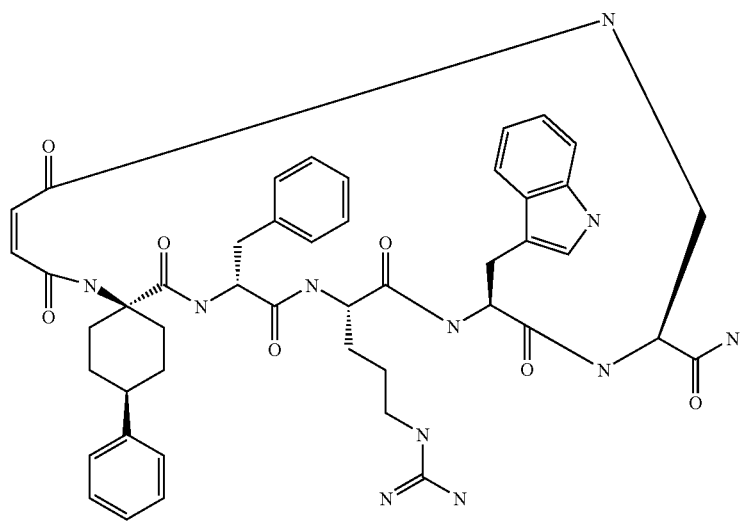

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Dpr (Boc) (530 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-Apc (550 mg 1.2 mmol) and HBTU (452 mg, 0.6 mmol), Maleic anhydride (600 mg, 6 mmol) in DMF with the addtion of HOBT (800 mg, 6 mmol), without DIPEA. The resin was filtered and washed successively with 50 ml each of CH$_2$Cl$_2$ (two times), isopropanol, and CH$_2$Cl$_2$ (three times). The resin was dried under vacuum to yield 1.0 g Pentapetide resin.

The pentapeptide resin was treated with 100 µL ethanedithiol, 100 µL dimethylsulfide, 250 µL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude product was dried under vacuum to yield 230 mg of an off-white solid. The crude peptide was subjected to cyclization without purification.

230 mg of the crude linear peptides was dissolved in 220 ml of DMF, 500 µL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 28 mg (8%) of a white, amorphous powder. This compound was homogeneous by HPLC. LR-Electrospray C$_{46}$H$_{55}$N, 107 cal: 874 observed: m/z (875 M+H).

EXAMPLE 52

Preparation of Penta-cyclo(Asp-Lys)-Asp-Apc-(D)Phe-Cit-Trp-Lys-NH$_2$

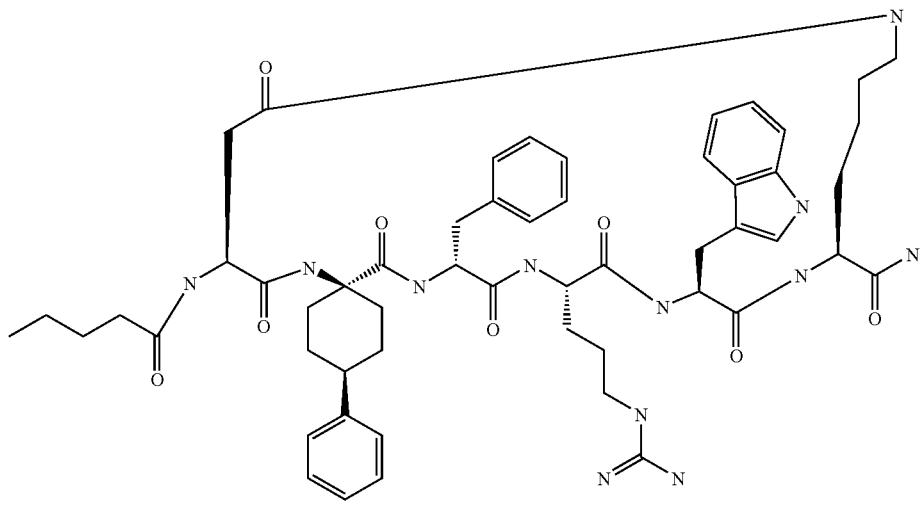

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Cit (480 mg, 1.2 mmol) and HBTU (452 mg, 1.2 mmol), Fmoc-(D)Phe (480 mg, 1.2 mmol) and HBTU (452 mg, 1.2 mmol), Fmoc-Apc (550 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.3 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 300 mg of an off-white solid. The crude peptide was subjected to cyclization without purification.

300 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 80 mg (20%) of a white, amorphous powder. This compound was homogeneous by HPLC. LR-Electrospray C$_{54}$H$_{71}$N$_{11}$O$_9$ cal: 1018 observed: m/z (1019 M+H).

EXAMPLE 53

Preparation of Penta-cyclo(Asp-Lys)-Asp-Apc-(D)Phe-Ala-Trp-Lys-NH₂

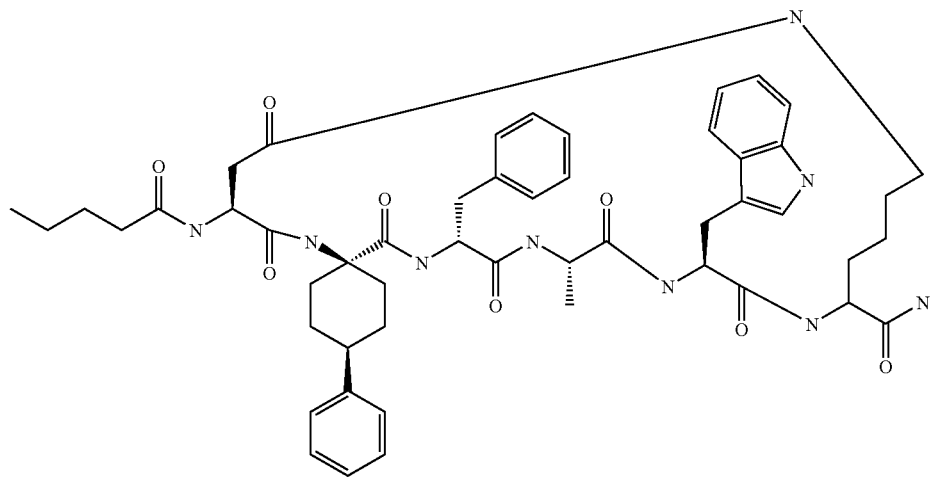

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Ala (380 mg, 1.2 mmol) and HBTU (452 mg, 1.2 mmol), Fmoc-(D)Phe (480 mg, 1.2 mmol) and HBTU (452 mg, 1.2 mmol), Fmoc-Apc (550 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with $CH_2Cl_2$ (three times) and treated with 2 mL valeric anhydride in 6% DIPEA/$CH_2Cl_2$ for 30 minutes. The resin was filtered and washed successively with 50 ml each of $CH_2Cl_2$ (two times), isopropanol, and $CH_2Cl_2$ (three times). The resin was dried under vacuum to yield 1.4 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude linear product was dried under vacuum to yield 330 mg of an off-white solid. The crude peptide was subjected to cyclization without purification.

330 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/$H_2O$, buffer B: 0.1% TFA/$CH_3CN$) in 90 min., flow rate 8 ml/min, detection 280 nm. The main peak was cut by analytical HPLC analysis of collected fractions, pooled and lyophilized to yield 87 mg (20%) of a white, amorphous powder. This compound was homogeneous by HPLC. LR-Electrospray $C_{51}H_{65}N_9O_8$ cal: 932 observed: m/z (933 M+H).

EXAMPLE 54

Preparation of Ac-Nle-cyclo(Cys-Cys)-Cys-Apc-(D)Phe-Arg-Trp-Cys-NH$_2$

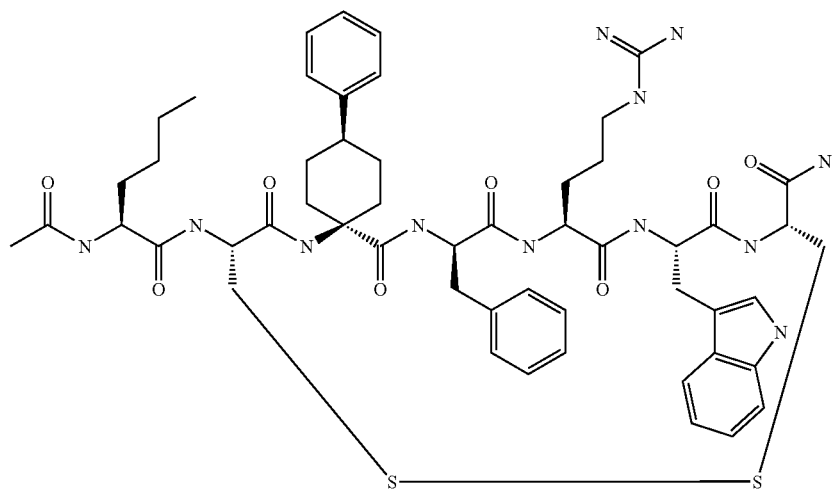

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Seven coupling cycles were performed of one cycle each with Fmoc-Cys (Trt) (710 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-Apc (550 mg 1.2 mmol) and HBTU (452 mg, 0.6 mmol), Fmoc-Cys (Trt) (710 mg, 1.2 mmol) and HBTU (452 mg, 1.2 mmol), Fmoc-Nle (430, 1.2 mmol) and HBTU (452 mg, 1.2 mmol). The peptide resin was carried through steps 1–5 of protocol 1, washed with CH$_2$Cl$_2$ (three times) and treated with 1 mL acetic anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.2 g of Ac-Heptapeptide resin.

The Ac-heptapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 250 mg of an off-white solid.

This crude linear peptide was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 45 mg of purified linear peptide.

The purified linear peptide was dissolved in 2 ml of DMSO, diluted with 500 ml of water and the pH was adjusted to pH 8.0 with NH$_4$OH. O$_2$ was bubbled into the solution and the cyclization was monitored by HPLC. Typically the cyclization was completed within 24–48 hours. The solution was lyophilized and the material dissolved in CH$_3$COOH and was subjected to preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 20 mg (4.7%) of purified cyclic peptide. This compound was homogeneous by HPLC. LR-Electrospray C$_{53}$H$_{70}$N$_{12}$O$_8$S$_2$ cal: 1067 observed: m/z (1068 M+H).

EXAMPLE 55

Preparation of Penta-cyclo(Asp-Lys)-Asp-(D,L)-Atc-(D)Phe-Arg-Trp-Lys-NH$_2$

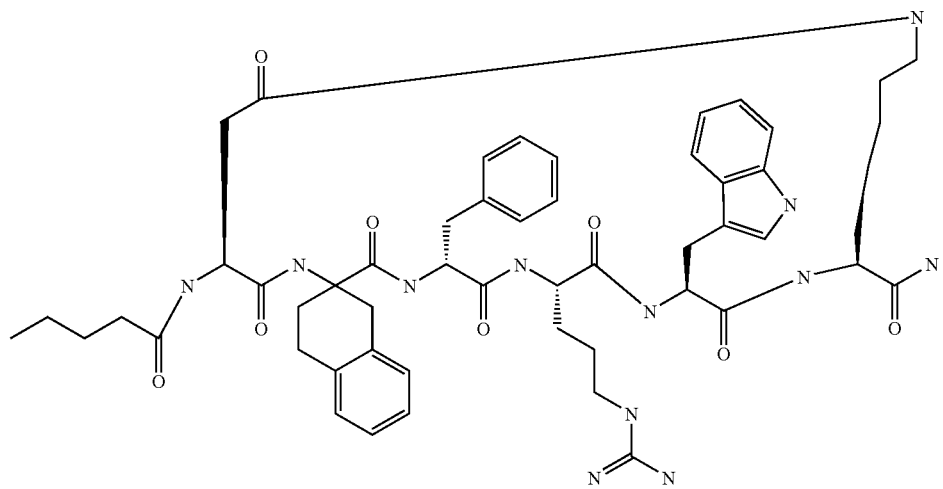

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-(D,L)-Atc (510 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.15 g of Pentyl-hexapeptide resin.

The Pentyl-hexapeptide resin was treated with 100)L ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 245 mg of an off-white solid. The crude peptide was subjected to cyclization without purification.

250 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C$_{18}$-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 55 mg (14%) of a white, amorphous powder. This compound was homogeneous by HPLC. LR-Electrospray C$_{52}$H$_{68}$N$_{12}$O$_8$ cal: 989 observed: m/z (990 M+H).

EXAMPLE 56

Preparation of Penta-(Asp-Lys)-Asp-5-BrAtc-(D)Phe-Arg-Trp-Lys-NH₂ (peak 1)

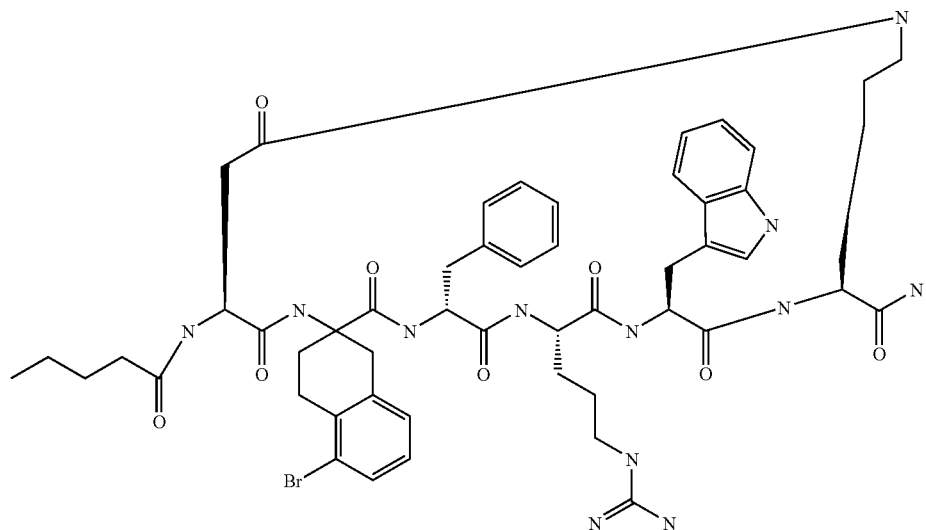

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-5-Br-(D,L)Atc (620 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH₂Cl₂ (three times) and treated with 2 mL valeric anhydride in 6% DIPEA/CH₂Cl₂ for 30 minutes. The resin was filtered and washed successively with 50 ml each of CH₂Cl₂ (two times), isopropanol, and CH₂Cl₂ (three times). The resin was dried under vacuum to yield 1.1 g of Pentyl-hexapeptide resin.

The Pentyl-hexapeptide resin was treated with 100 μL ethanedithiol, 100 μL dimethylsulfide, 240 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et₂O and recentrifuged and the crude linear product was dried under vacuum to yield 240 mg of an off-white solid. The crude peptide was subjected to cyclization without purification.

240 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H₂O, buffer B: 0.1% TFA/CH3CN) in 90 min., flow rate 8 ml/min, detection 280 nm. The first main peak was cut by analytical HPLC analysis of collected fractions, pooled and lyophilized to yield 26 mg (6%) of a white, amorphous powder. This compound was homogeneous by HPLC. LR-Electrospray $C_{52}H_{67}N_{12}O_8Br$ cal: 1068 observed: m/z (1069 M+H).

EXAMPLE 57

Preparation of Penta-(Asp-Lys)-Asp-5-BrAtc-(D)Phe-Arg-Trp-Lys-NH$_2$ (peak 2)

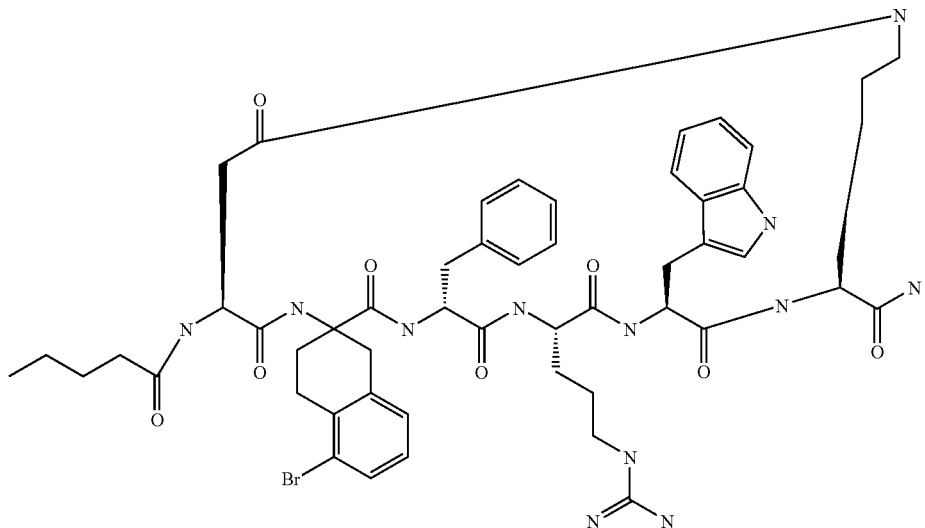

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-5-Br-(D,L)Atc (620 mg 1.2 mmol) and HBTU (452 mg, 0.6 mmol), Fmoc-Asp (OBut) (500 mg$_3$ 1.2 mmol) protocol 1, washed with CH$_2$Cl$_2$ (three times) and treated with 2 mL valeric anhydride in 6% DIPEA/CH$_2$Cl$_2$ for 30 minutes. The resin was filtered and washed successively with o50 ml each of CH$_2$G2 (two times), isopropanol, and CH$_2$Cao (three times). The resin was dried under vacuum to yield 1.1 g of Pentyl-hexapeptide resin.

The Pentyl-hexapeptide resin was treated with 100 μL ethanedithiol, 100 μL dimethylsulfide, 240 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 240 mg of an off-white solid. The crude peptide was subjected to cyclization without purification.

240 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The second main peak was cut by analytical HPLC analysis of collected fractions, pooled and lyophilized to yield 20 mg (5%) of a white, amorphous powder. This compound was homogeneous by HPLC. LR-Electrospray C$_{52}$H$_{67}$N$_{12}$O8Br cal: 1068 observed: m/z (1069 M+H).

EXAMPLE 58

Preparation of Penta-(Asp-Lys)-Asp-5-ClAtc-(D)Phe-Arg-Trp-Lys-NH$_2$ (peak 1)

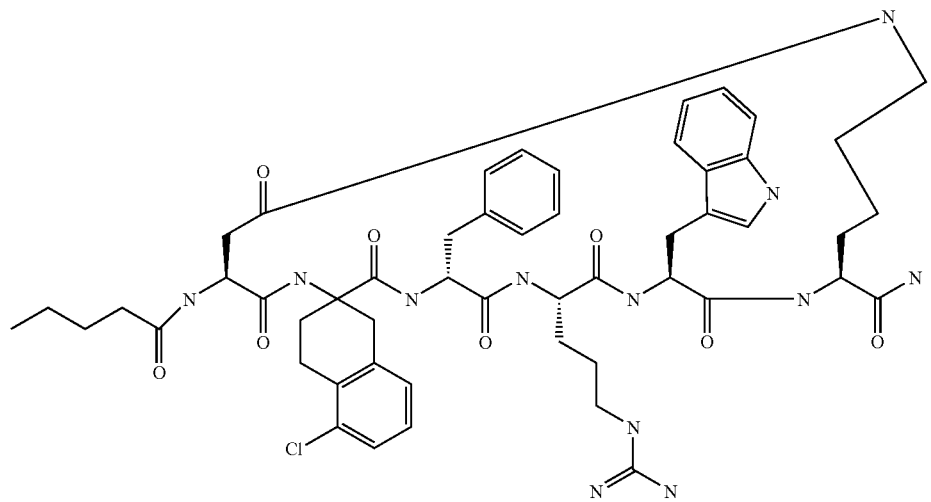

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-5-Cl(D,L)Atc (560 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.2 g of Pentyl-hexapeptide resin.

The Pentyl-hexapeptide resin was treated with 100 μL ethanedithiol, 100 μL dimethylsulfide, 250 μL anisole, and 10 μL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 250 mg of an off-white solid. The crude peptide was subjected to cyclization without purification.

250 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The first main peak was cut by analytical HPLC analysis of collected fractions, pooled and lyophilized to yield 24 mg (6%) of a white, amorphous powder. This compound was homogeneous by HPLC. LR-Electrospray C$_{52}$H$_{67}$N$_{12}$O$_8$Cl cal: 1024 observed: m/z (1025 M+H).

EXAMPLE 59

Preparation of Penta-(Asp-Lys)-Asp-5-ClAtc-(D)
Phe-Arg-Trp-Lys-NH₂ (peak 2)

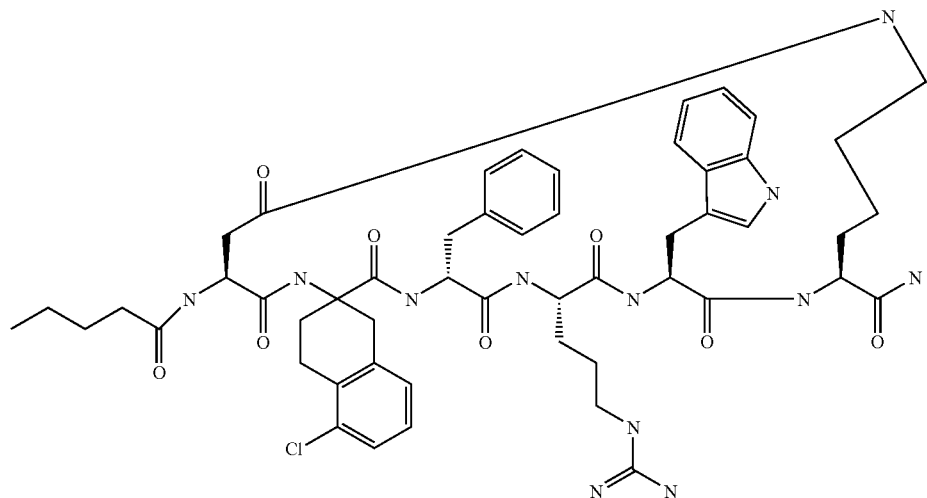

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-5-Cl-(D,L)Atc (560 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with $CH_2Cl_2$ (three times) and treated with 2 mL valeric anhydride in 6% DIPEA/$CH_2Cl_2$ for 30 minutes. The resin was filtered and washed successively with 50 ml each of $CH_2Cl_2$ (two times), isopropanol, and $CH_2Cl_2$ (three times). The resin was dried under vacuum to yield 1.2 g of Pentyl-hexapeptide resin. The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude linear product was dried under vacuum to yield 250 mg of an off-white solid. The crude peptide was subjected to cyclization without purification.

250 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/$H_2O$, buffer B: 0.1% TFA/$CH_3CN$) in 90 min., flow rate 8 ml/min, detection 280 nm. The second main peak was cut by analytical HPLC analysis of collected fractions, pooled and lyophilized to yield 20 mg (4%) of a white, amorphous powder. This compound was homogeneous by HPLC. LR-Electrospray $C_{52}H_{67}N_{12}O_8Cl$ cal: 1024 observed: m/z (1025 M+H).

EXAMPLE 60

Preparation of Penta-(Asp-Lys)-Asp-5-MeO-(D,L) Atc-(D)Phe-Arg-Trp-Lys-NH$_2$

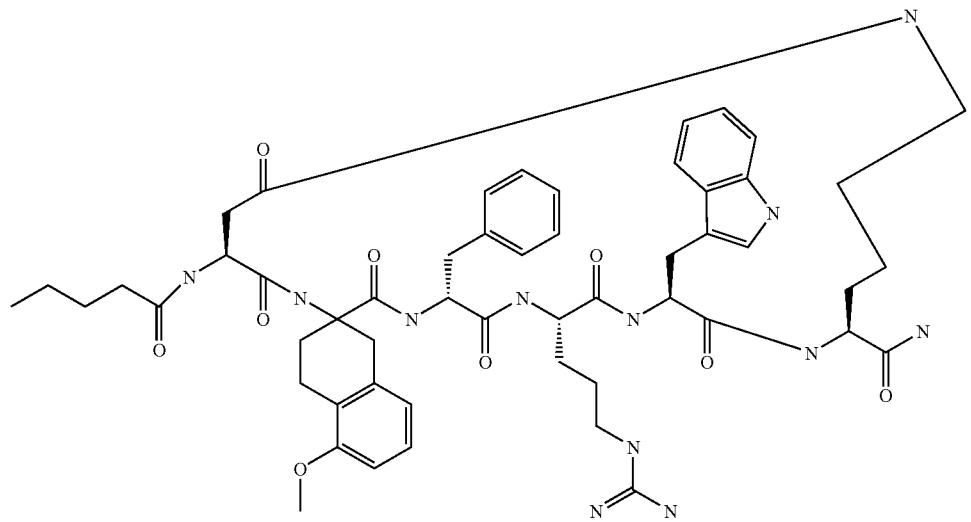

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-5-MeO-(D),L)Atc (600 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.2 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 250 mg of an off-white solid. The crude peptide was subjected to cyclization without purification.

250 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 55 mg (13%) of a white, amorphous powder. This compound was homogeneous by HPLC. LR-Electrospray C$_{53}$H$_{70}$N$_{12}$O$_9$ cal: 1019 observed: m/z (1020 M+H).

EXAMPLE 61

Preparation of Penta-(Asp-Lys)-Asp-5-EtO-(D,L) Atc-(D)Phe-Arg-Trp-Lys-NH$_2$

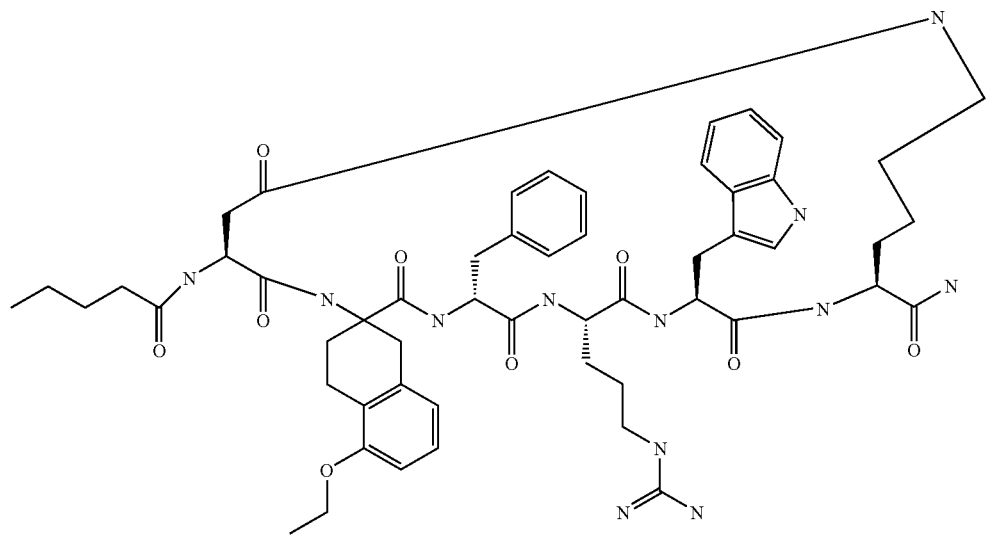

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-5-EtO-(D,L)Atc (620 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.3 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 260 mg of an off-white solid. The crude peptide was subjected to cyclization without purification.

260 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 58 mg (13%) of a white, amorphous powder. This compound was homogeneous by HPLC. LR-Electrospray C$_{54}$H$_{72}$N$_{12}$O$_9$ cal: 1033 observed: m/z (1034 M+H).

EXAMPLE 62

Preparation of Penta-(Asp-Lys)-Asp-5-iPrO-(D,L)Atc-(D)Phe-Arg-Trp-Lys-NH$_2$

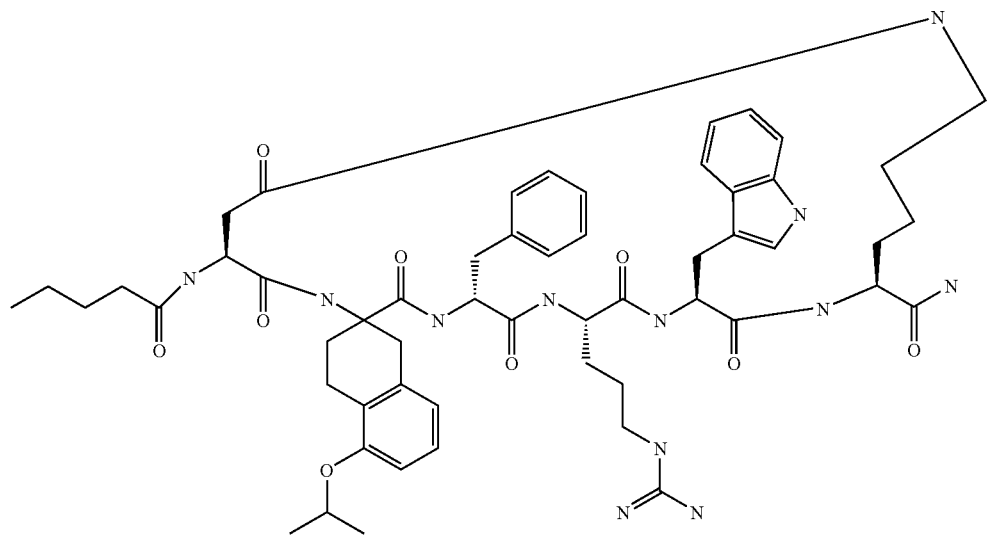

Fmoc-Linker-BHA resin (720 mg, 0.4 mmol) from Example 29 were subjected to solid phase synthesis using Protocol 1 described above. All couplings were performed a using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-5-iPrO-(D,L)Atc (620 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.2 g of Pentyl-hexapeptide resin.

The Pentyl-hexapeptide resin was treated with 100 µL ethanedithiol, 100 µL dimethylsulfide, 250 µL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 250 mg of an off-white solid. The crude peptide was subjected to cyclization without purification.

250 mg of the crude linear peptides was dissolved in 220 ml of DMF, 500 µL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 58 mg (13%) of a white, amorphous powder. This compound was homogeneous by HPLC. LR-Electrospray C$_{55}$H$_{74}$N$_{12}$O$_9$ cal: 1047 observed: m/z (1048 M+H).

EXAMPLE 63

Preparation of Penta-(Asp-Lys)-Asp-5-Me-(D,L) Atc-(D)Phe-Arg-Trp-Lys-NH$_2$

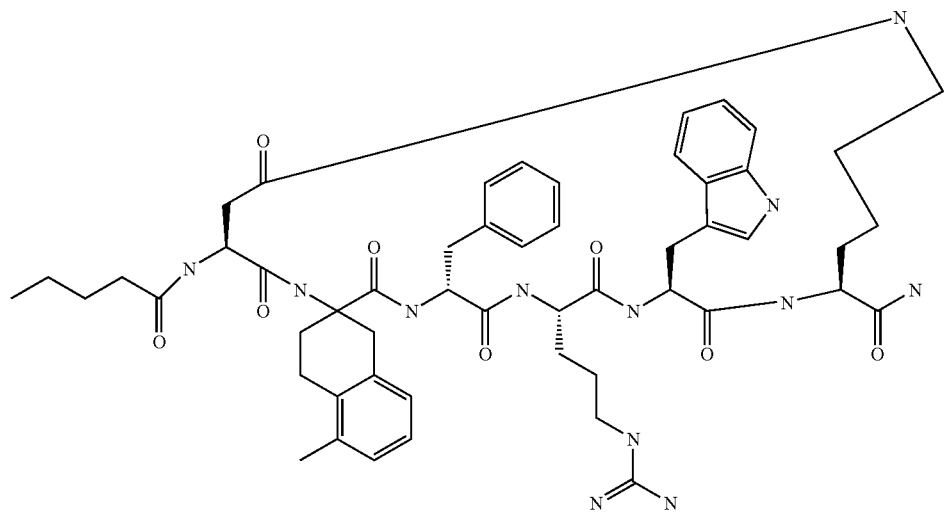

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-5-Me-(D,L)Atc (590 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.2 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 260 mg of an off-white solid. The crude peptide was subjected to cyclization without purification.

260 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 62 mg (13%) of a white, amorphous powder. This compound was homogeneous by HPLC. LR-Electrospray C$_{53}$H$_{70}$N$_{12}$O$_8$ cal: 1003 observed: m/z (1004 M+H).

EXAMPLE 64

Preparation of Penta-(Asp-Lys)-Asp-5-Et-(D,L)Atc-(D)Phe-Arg-Trp-Lys-NH₂

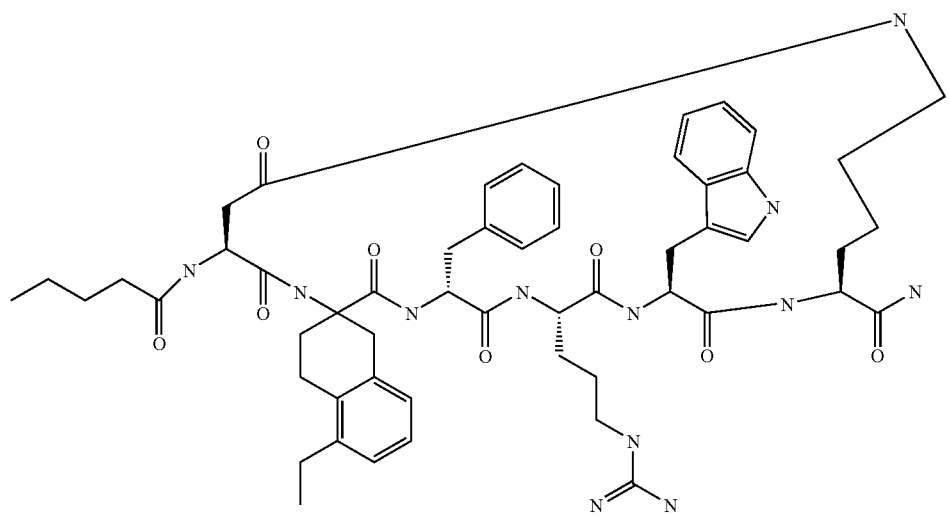

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-5-Et-(D,L)Atc (600 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH₂Cl₂ (three times) and treated with 2 mL valeric anhydride in 6% DIPEA/CH₂Cl₂ for 30 minutes. The resin was filtered and washed successively with 50 ml each of CH₂Cl₂ (two times), isopropanol, and CH₂Cl₂ (three times). The resin was dried under vacuum to yield 1.3 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et₂O and recentrifuged and the crude linear product was dried under vacuum to yield 245 mg of an off-white solid. The crude peptide was subjected to cyclization without purification.

245 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H₂O, buffer B: 0.1% TFA/CH₃CN) in 90 min., flow rate 8 ml/min, detection 280 nm. The main peak was cut by analytical HPLC analysis of collected fractions, pooled and lyophilized to yield 55 mg (12%) of a white, amorphous powder. This compound was homogeneous by HPLC. LR-Electrospray $C_{54}H_{72}N_{12}O_8$ cal: 1017 observed: m/z (1018 M+H).

EXAMPLE 65

Preparation of Penta-(Asp-Lys)-Asp-5-iPr-(D,L)Atc-(D)Phe-Arg-Trp-Lys-NH₂

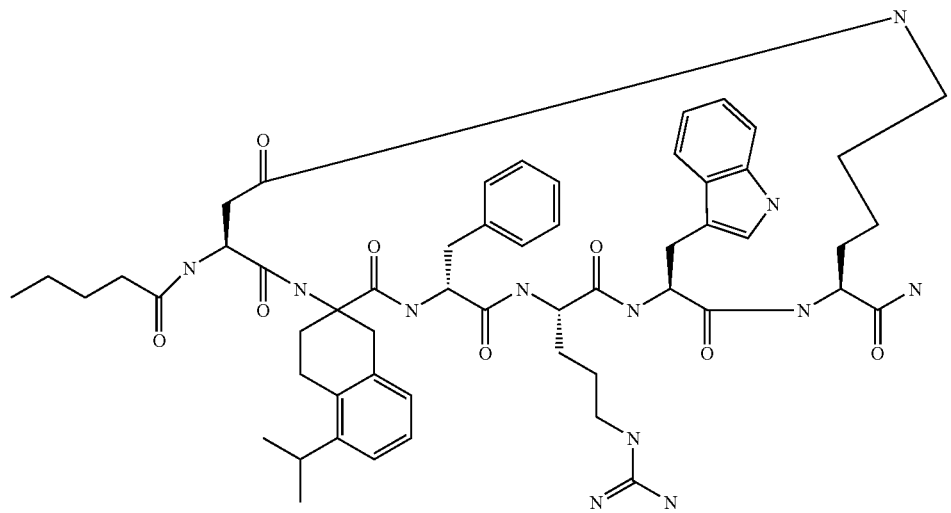

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-5-iPr-(D,L)Atc (600 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with $CH_2Cl_2$ (three times) and treated with 2 mL valeric anhydride in 6% DIPEA/$CH_2Cl_2$ for 30 minutes. The resin was filtered and washed successively with 50 ml each of $CH_2Cl_2$ (two times), isopropanol, and $CH_2Cl_2$ (three times). The resin was dried under vacuum to yield 1.2 g of Pentyl-hexapeptide resin.

The Pentyl-hexapeptide resin was treated with 100 μL ethanedithiol, 100 μL dimethylsulfide, 250 μL anisole, and 10 μL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude linear product was dried under vacuum to yield 245 mg of an off-white solid. The crude peptide was subjected to cyclization without purification.

245 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/$H_2O$, buffer B: 0.1% TFA/$CH_3CN$) in 90 min., flow rate 8 ml/min, detection 280 nm. The main peak was cut by analytical HPLC analysis of collected fractions, pooled and lyophilized to yield 54 mg (13%) of a white, amorphous powder. This compound was homogeneous by HPLC. LR-Electrospray $C_{55}H_{74}N_{12}O_8$ cal: 1031 observed: m/z (1032 M+H).

EXAMPLE 66

Preparation of Penta-(Asp-Lys)-Asp-5-BrAtc-(D)Phe-Cit-Trp-Lys-NH₂ (peak 1)

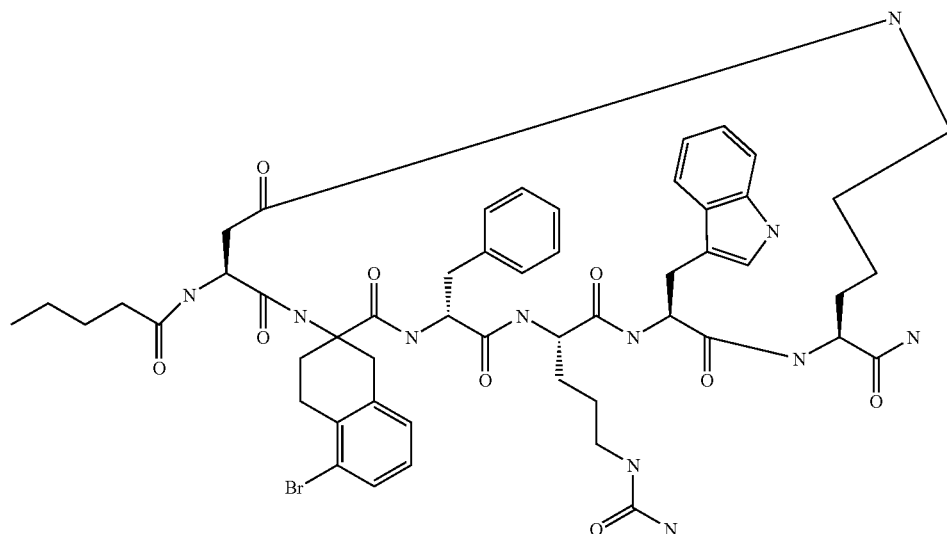

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Cit (480 mg, 1.2 mmol) and HBTU (452 mg, 1.2 mmol), Fmoc-(D)Phe (480 mg, 1.2 mmol) and HBTU (452 mg, 1.2 mmol), Fmoc-5-Br-(D,L)Atc (620 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH₂Cl₂ (three times) and treated with 2 mL valeric anhydride in 6% DIPEA/CH₂Cl₂ for 30 minutes. The resin was filtered and washed successively with 50 ml each of CH₂Cl₂ (two times), isopropanol, and CH₂Cl₂ (three times). The resin was dried under vacuum to yield 1.2 g of Pentyl-hexapeptide resin.

The Pentyl-hexapeptide resin was treated with 100 μL L ethanedithiol, 100 μL dimethylsulfide, 240 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et₂O and recentrifuged and the crude linear product was dried under vacuum to yield 260 mg of an off-white solid. The crude peptide was subjected to cyclization without purification.

240 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H₂O, buffer B: 0.1% TFA/CH₃CN) in 90 min., flow rate 8 ml/min, detection 280 nm. The first main peak was cut by analytical HPLC analysis of collected fractions, pooled and lyophilized to yield 24 mg (5,6%) of a white, amorphous powder. This compound was homogeneous by HPLC. LR-Electrospray $C_{52}H_{66}NH_{11}O_9Br$ cal: 1069 observed: m/z (1070 M+H).

EXAMPLE 67

Preparation of Penta-(Asp-Lys)-Asp-5-BrAtc-(D)Phe-Cit-Trp-Lys-NH$_2$ (peak 2)

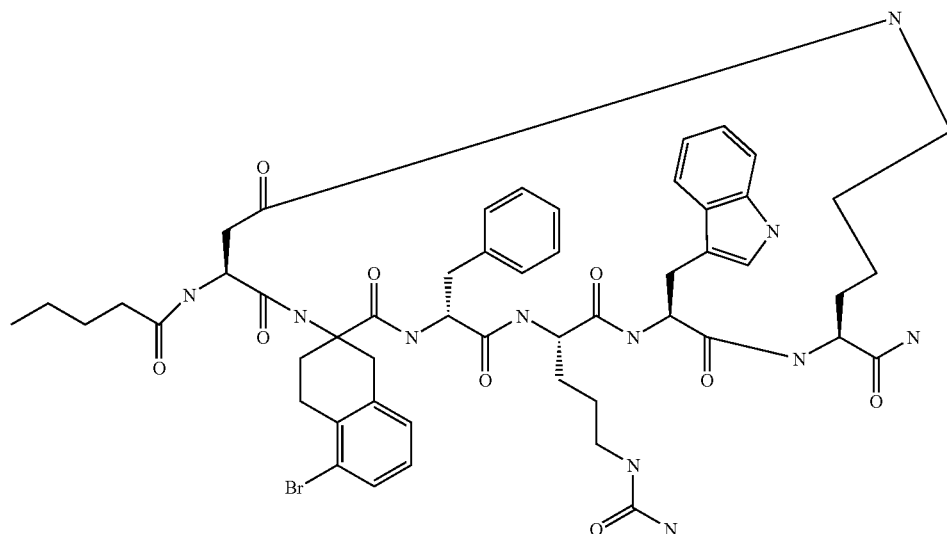

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Cit (480 mg, 1.2 mmol) and HBTU (452 mg, 1.2 mmol), Fmoc-(D)Phe (480 mg, 1.2 mmol) and HBTU (452 mg, 1.2 mmol), Fmoc-5-Br-(D,L)Atc (620 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.1 g of Pentyl-hexapeptide resin.

The Pentyl-hexapeptide resin was treated with 100 μL ethanedithiol, 100 μL dimethylsulfide, 240 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 240 mg of an off-white solid. The crude peptide was subjected to cyclization without purification.

240 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The second main peak was cut by analytical HPLC analysis of collected fractions, pooled and lyophilized to yield 22 mg (4.8%) of a white, amorphous powder. This compound was homogeneous by HPLC. LR-Electrospray C$_{52}$H$_{66}$N$_{11}$O$_9$Br cal: 1069 observed: m/z (1070 M+H).

EXAMPLE 68

Preparation of Penta-(Asp-Lys)-Asp-5-ClAtc-(D)Phe-Cit-Trp-Lys-NH$_2$ (peak 1)

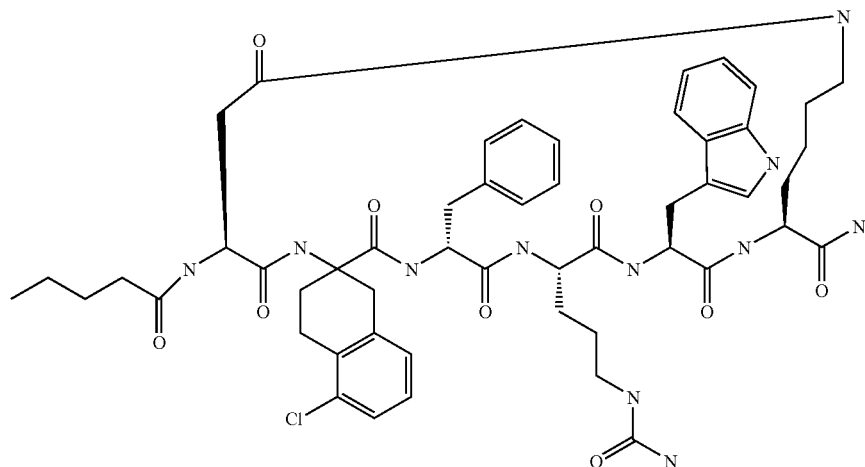

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Cit (480 mg, 1.2 mmol) and HBTU (452 mg, 1.2 mmol), Fmoc-(D)Phe (480 mg, 1.2 mmol) and HBTU (452 mg, 1.2 mmol), Fmoc-5-Cl-(D,L)Atc (560 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.2 g of Pentyl-hexapeptide resin.

The Pentyl-hexapeptide resin was treated with 100 λL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 245 mg of an off-white solid. The crude peptide was subjected to cyclization without purification.

245 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C$_{18}$-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The first main peak was cut by analytical HPLC analysis of collected fractions, pooled and lyophilized to yield 22 mg (5.8%) of a white, amorphous powder. This compound was homogeneous by HPLC. LR-Electrospray C$_{52}$H$_{66}$N$_{11}$O$_9$Cl cal: 1024 observed: m/z (1025 M+H).

EXAMPLE 69

Preparation of Penta-(Asp-Lys)-Asp-5-ClAtc-(D)
Phe-Cit-Trp-Lys-NH$_2$ (peak 2)

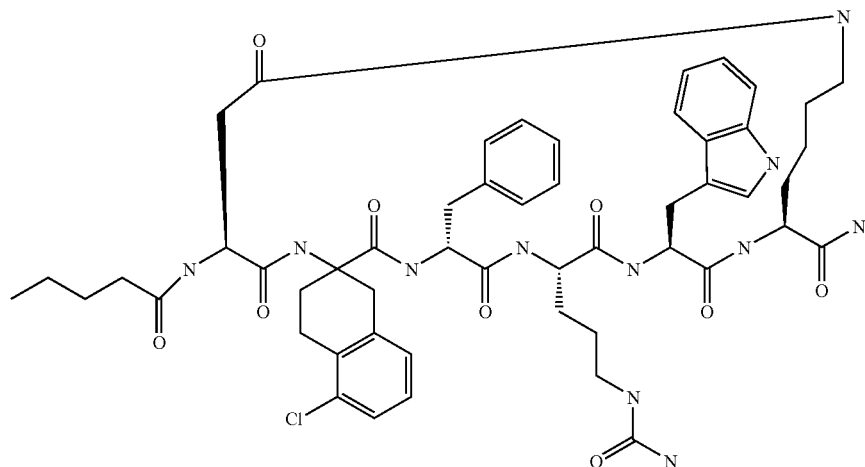

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Cit (480 mg, 1.2 mmol) and HBTU (452 mg, 1.2 mmol), Fmoc-(D)Phe (480 mg, 1.2 mmol) and HBTU (452 mg, 1.2 mmol), Fmoc-5-Cl-(D,L)Atc (560 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.2 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 250 mg of an off-white solid. The crude peptide was subjected to cyclization without purification.

250 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The second main peak was cut by analytical HPLC analysis of collected fractions, pooled and lyophilized to yield 20 mg (5.4%) of a white, amorphous powder. This compound was homogeneous by HPLC. LR-Electrospray C$_{52}$H$_{66}$N$_{11}$O$_9$Cl cal: 1024 observed: m/z (1025 M+H).

EXAMPLE 70

Preparation of Ac-Nle-cyclo(Cys-Cys)-Cys-(D,L) Atc-(D)Phe-Arg-Trp-Cys-NH$_2$

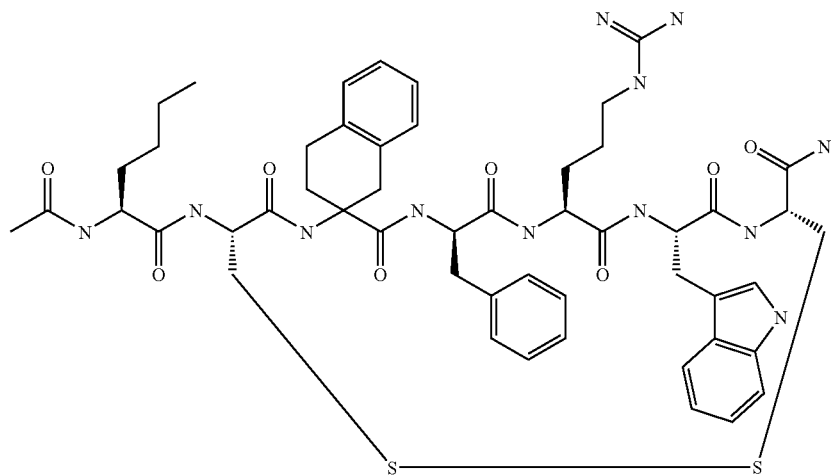

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Seven coupling cycles were performed of one cycle each with Fmoc-Cys (Trt) (710 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-(D,L)Atc (550 mg 1.2 mmol) and HBTU (452 mg, 0.6 mmol), Fmoc-Cys (Trt) (710 mg, 1.2 mmol) and HBTU (452 mg, 1.2 mmol), Fmoc-Nle(430 mg, 1.2 mmol) and HBTU (452 mg, 1.2 mmol). The peptide resin was carried through steps 1–5 of protocol 1, washed with CH$_2$Cl$_2$ (three times) and treated with 1 mL acetic anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.0 g of Ac-Heptapeptide resin.

The Acetyl-hepta peptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA, and the filtrates precipitated in chilled ethyl ether. The precipitates were centrifuged and the ether layer decanted. The residue was washed with two or three volumes of Et$_2$O and recentrifuged and the crude linear product was dried under vacuum to yield 240 mg of an off-white solid.

This crude linear peptide was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 55 mg of purified linear peptide.

The purified linear peptide was dissolved in 2 ml of DMSO, diluted with 500 ml of water and the pH was adjusted to pH 8.0 with NH$_4$OH. O$_2$ was bubbled into the solution and the cyclization was monitored by HPLC. Typically the cyclization was completed within 24–48 hours. The solution was lyophilized and the material dissolved in CH$_3$COOH and was subjected to preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 20 mg (5.0%) of purified cyclic peptide. This compound was homogeneous by HPLC. LR-Electrospray C$_{51}$H$_{66}$N$_{12}$O$_8$S$_2$ cal: 1039 observed: m/z (1040 M+H).

EXAMPLE 71

Preparation of Penta-cyclo(Cys-Cys)-Cys-5-Br(D,L)Atc-(D)Phe-Arg-Trp-Cys-NH$_2$

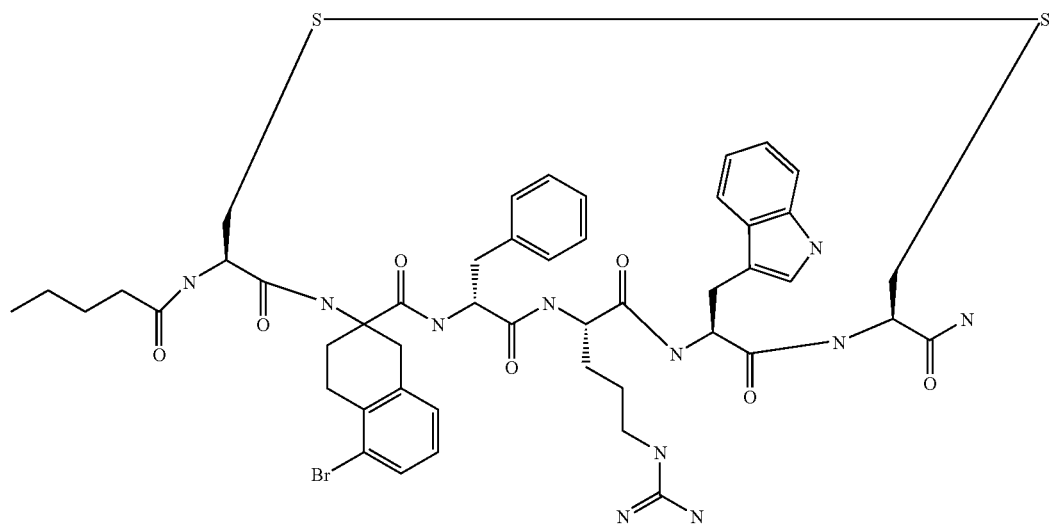

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Seven coupling cycles were performed of one cycle each with Fmoc-Cys (Trt) (710 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-5-BrAtc (620 mg 1.2 mmol) and HBTU (452 mg, 0.6 mmol), Fmoc-Cys (Trt) (710 mg, 1.2 mmol) and HBTU (452 mg, 1.2 mmol). The peptide resin was carried through steps 1–5 of protocol 1, washed with CH$_2$Cl$_2$ (three times) and treated with 1 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.1 g of Ac-Heptapeptide resin.

The pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA, and the filtrates precipitated in chilled ethyl ether. The precipitates were centrifuged and the ether layer decanted. The residue was washed with two or three volumes of Et$_2$O and recentrifuged and the crude linear product was dried under vacuum to yield 240 mg of an off-white solid.

This crude linear peptide was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 50 mg of purified linear peptide.

The purified linear peptide was dissolved in 2 ml of DMSO, diluted with 500 ml of water and the pH was adjusted to pH 8.0 with NH$_4$OH. O$_2$ was bubbled into the solution and the cyclization was monitored by HPLC. Typically the cyclization was completed within 24–48 hours. The solution was lyophilized and the material dissolved in CH$_3$COOH and was subjected to preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 22 mg (5.2%) of purified cyclic peptide. This compound was homogeneous by HPLC. LR-Electrospray C$_{48}$H$_{60}$N$_{11}$O$_7$S$_2$Br cal: 1047 observed: m/z (1048 M+H).

EXAMPLE 72

Preparation of Penta-cyclo(Asp-Lys)-Asp-Appc-(D)Phe-Arg-Trp-Lys-NH$_2$

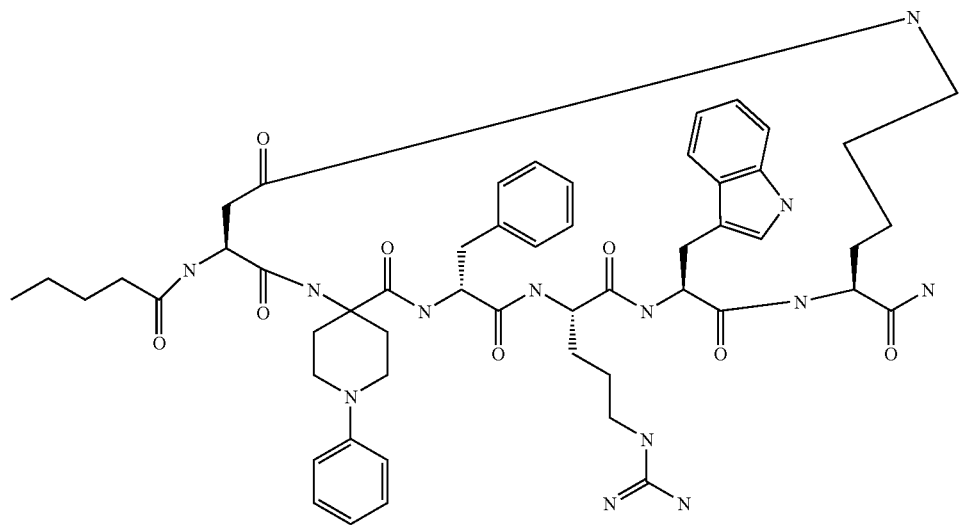

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-Appc (550 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.2 g of Pentyl-hexapeptide resin.

The Pentyl-hexapeptide resin was treated with 100 μLL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 245 mg of an off-white solid. The crude peptide was subjected to cyclization without purification.

245 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 57 mg (14%) of a white, amorphous powder. This compound was homogeneous by HPLC. LR-Electrospray: C$_{53}$H$_{71}$N$_{13}$O$_8$ cal: 1018 observed: m/z (1019 M+H).

EXAMPLE 73

Preparation of Penta-cyclo(Asp-Lys)-Asp-2-MeAppc-(D)Phe-Arg-Trp-Lys-NH₂

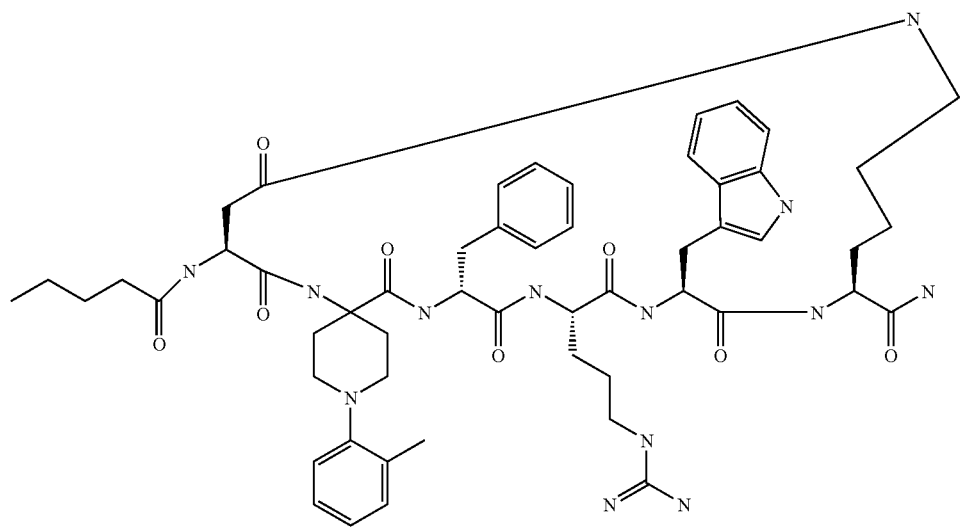

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-2-MeAppc (570 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with $CH_2Cl_2$ (three times) and treated with 2 mL valeric anhydride in 6% DIPEA/$CH_2Cl_2$ for 30 minutes. The resin was filtered and washed successively with 50 ml each of $CH_2Cl_2$ (two times), isopropanol, and $CH_2Cl_2$ (three times). The resin was dried under vacuum to yield 1.2 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude linear product was dried under vacuum to yield 250 mg of an off-white solid. The crude peptide was subjected to cyclization without purification.

250 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/$H_2O$, buffer B: 0.1% TFA/$CH_3CN$) in 90 min., flow rate 8 ml/min, detection 280 run. The main peak was cut by analytical HPLC analysis of collected fractions, pooled and lyophilized to yield 61 mg (15%) of a white, amorphous powder. This compound was homogeneous by HPLC. LR-Electrospray: $C_{54}H_{73}N_{13}O_8$ cal: 1032 observed: m/z (1033M+H).

EXAMPLE 74

Preparation of Penta-cyclo(Asp-Lys)-Asp-2-iPrAppc-(D)Phe-Arg-Trp-Lys-NH$_2$

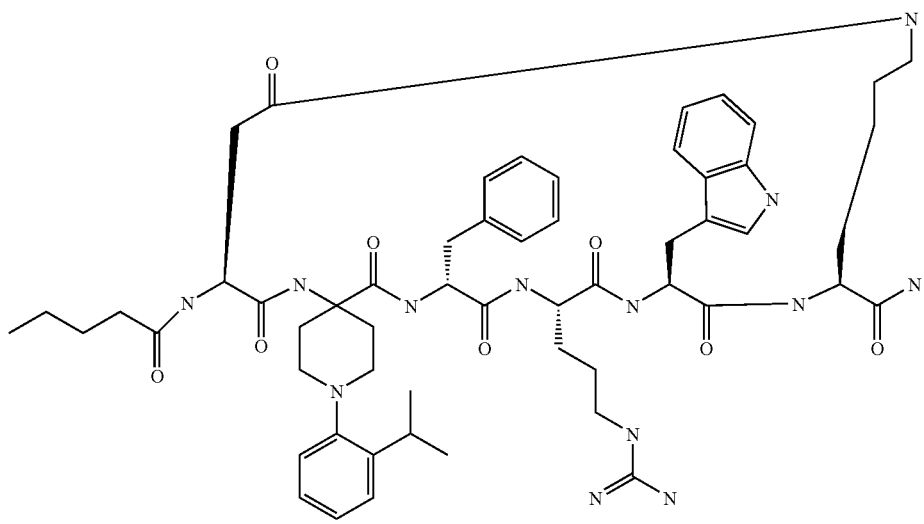

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-2-iPrAppc (600 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.2 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 245 mg of an off-white solid. The crude peptide was subjected to cyclization without purification.

245 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 mn. The main peak was cut by analytical HPLC analysis of collected fractions, pooled and lyophilized to yield 52 mg (14%) of a white, amorphous powder. This compound was homogeneous by HPLC. LR-Electrospray: C$_{56}$H$_{77}$N$_{13}$O$_8$ cal: 1060 observed: m/z (1061 M+H).

EXAMPLE 75

Preparation of Penta-cyclo(Asp-Lys)-Asp-3-MeAppc-(D)Phe-Arg-Trp-Lys-NH$_2$

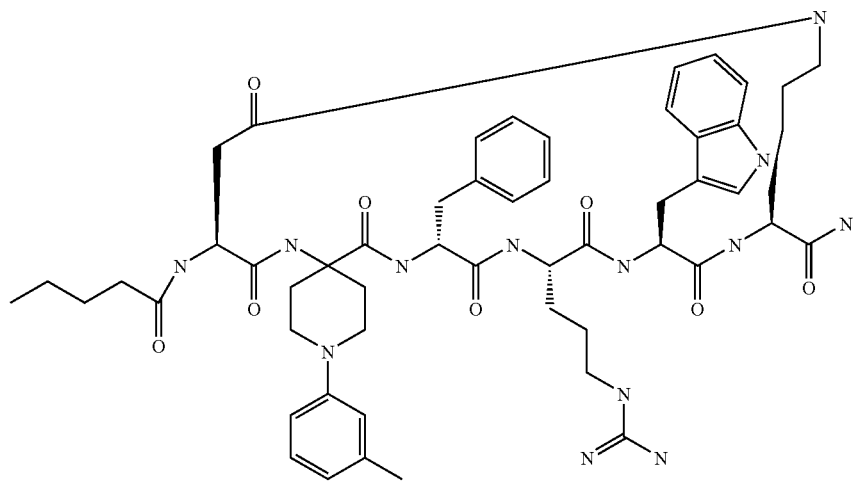

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-3-MeAppc (570 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.2 g of Pentyl-hexapeptide resin.

The Pentyl-hexapeptide resin was treated with 100 µL ethanedithiol, 100 µL dimethylsulfide, 250 µL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 248 mg of an off-white solid. The crude peptide was subjected to cyclization without purification.

248 mg of the crude linear peptides was dissolved in 220 ml of DMF, 500 µL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C$_{18}$-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 55 mg (14%) of a white, amorphous powder. This compound was homogeneous by HPLC. LR-Electrospray: C$_{54}$H$_{73}$N$_{13}$O$_8$ cal: 1032 observed: m/z (1033 M+H).

EXAMPLE 6

Preparation of Penta-cyclo(Asp-Lys)-Asp-4-MeAppc-(D)Phe-Arg-Trp-Lys-NH$_2$

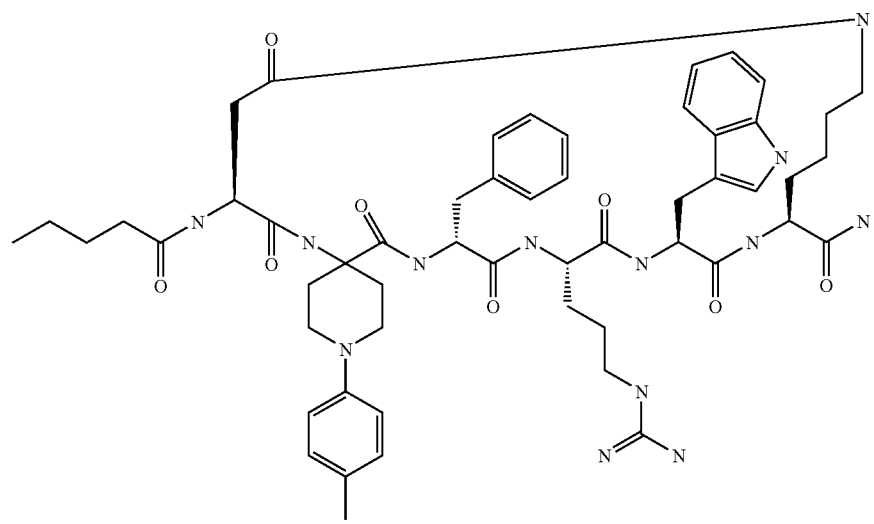

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 a;mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-4-MeAppc (570 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.2 g of Pentyl-hexapeptide resin.

The Pentyl-hexapeptide resin was treated with 100 µL ethanedithiol, 100 µL dimethylsulfide, 250 µL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 254 mg of an off-white solid. The crude peptide was subjected to cyclization without purification.

254 mg of the crude linear peptides was dissolved in 220 ml of DMF, 500 µL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C$_{18}$-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 57 mg (14%) of a white, amorphous powder. This compound was homogeneous by HPLC. LR-Electrospray: C$_{54}$H$_{73}$N$_{13}$O$_8$ cal: 1032 observed: m/z (1033 M+H).

EXAMPLE 77

Preparation of Penta-cyclo(Asp-Lys)-Asp-4-ClAppc-(D)Phe-Arg-Trp-Lys-NH$_2$

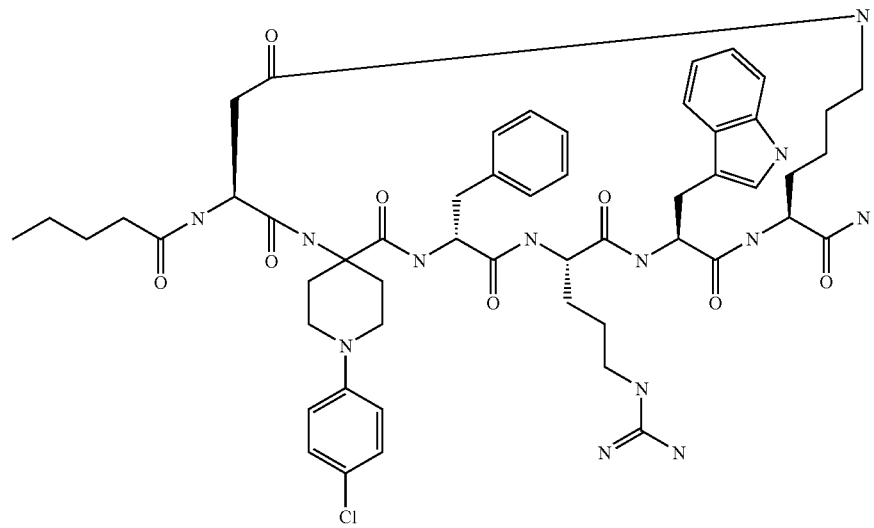

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-4-ClAppc (580 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.2 g of Pentyl-hexapeptide resin.

The Pentyl-hexapeptide resin was treated with 100 µL ethanedithiol, 100 µL dimethylsulfide, 250 µL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 250 mg of an off-white solid. The crude peptide was subjected to cyclization without purification.

250 mg of the crude linear peptides was dissolved in 220 ml of DMF, 500 µL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 55 mg (14%) of a white, amorphous powder. This compound was homogeneous by HPLC. LR-Electrospray: C$_{53}$H$_{70}$N$_{13}$O$_8$Cl cal: 1032 observed: m/z (1033 M+H).

EXAMPLE 78

Preparation of Penta-cyclo(Asp-Lys)-Asp-4-PhOAppc-(D)Phe-Arg-Trp-Lys-NH$_2$

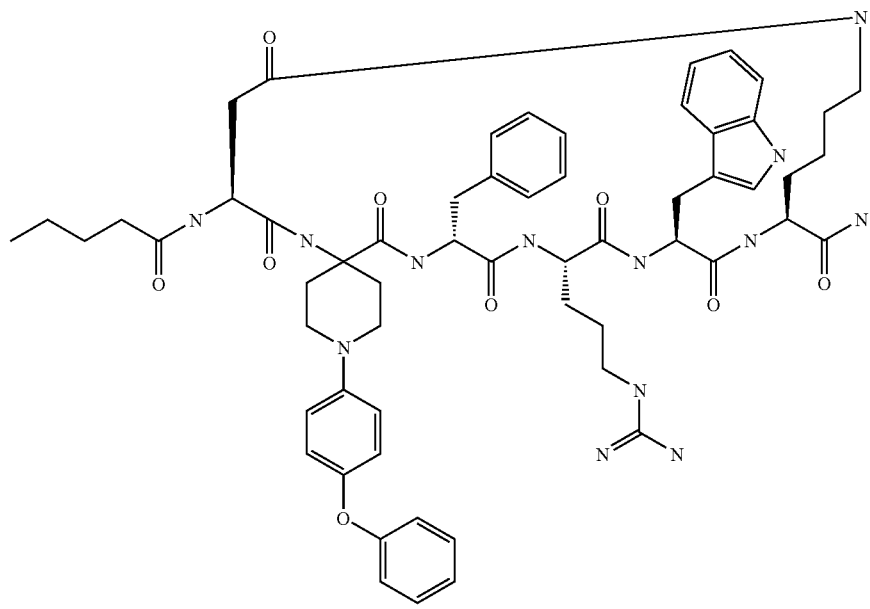

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-4-PhOAppc (650 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.2 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 270 mg of an off-white solid. The crude peptide was subjected to cyclization without purification.

270 mg of the crude linear peptides was dissolved in 220 ml of DMF, 500)L of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main pa peak was cut by analytical HPLC analysis of collected fractions, pooled and lyophilized to yield 58 mg (13%) of a white, amorphous powder. This compound was homogeneous by HPLC. LR-Electrospray: C$_{59}$H$_{75}$N$_{13}$O$_9$ cal: 1110 observed: m/z (1111 M+H).

EXAMPLE 79

Preparation of Penta-(Asp-Lys)-Asp-3-MeO-Appc-(D)Phe-Arg-Trp-Lys-NH₂

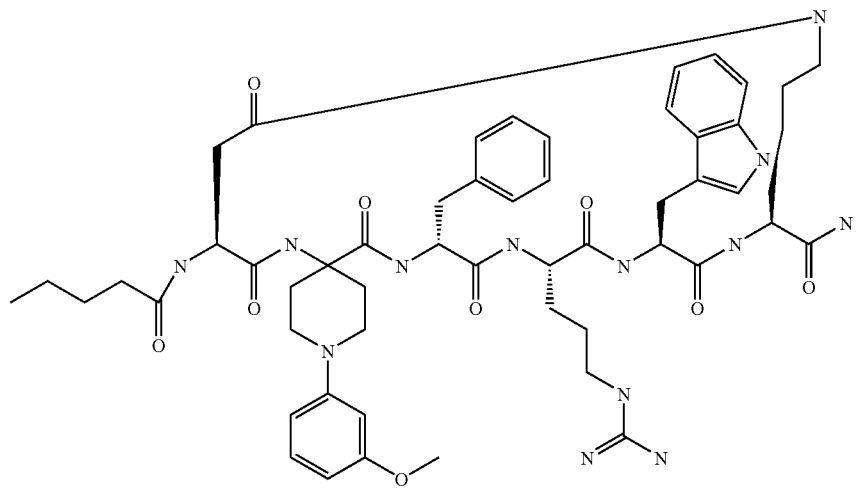

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-3-MeOAppc (580 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with $CH_2Cl_2$ (three times) and treated with 2 mL valeric anhydride in 6% DIPEA/$CH_2Cl_2$ for 30 minutes. The resin was filtered and washed successively with 50 ml each of $CH_2Cl_2$ (two times), isopropanol, and $CH_2Cl_2$ (three times). The resin was dried under vacuum to yield 1.2 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude linear product was dried under vacuum to yield 250 mg of an off-white solid. The crude peptide was subjected to cyclization without purification.

250 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/$H_2O$, buffer B: 0.1% TFA/$CH_3CN$) in 90 min., flow rate 8 ml/min, detection 280 nm. The main peak was cut by analytical HPLC analysis of collected fractions, pooled and lyophilized to yield 54 mg (13%) of a white, amorphous powder. This compound was homogeneous by HPLC. LR-Electrospray: $C_{54}H_{73}N_{13}O_9$ cal: 1048 observed: m/z (1049 M+H).

EXAMPLE 80

Preparation of Penta-cyclo(Asp-Lys)-Asp-4-Adpc-(D)Phe-Arg-Trp-Lys-NH₂

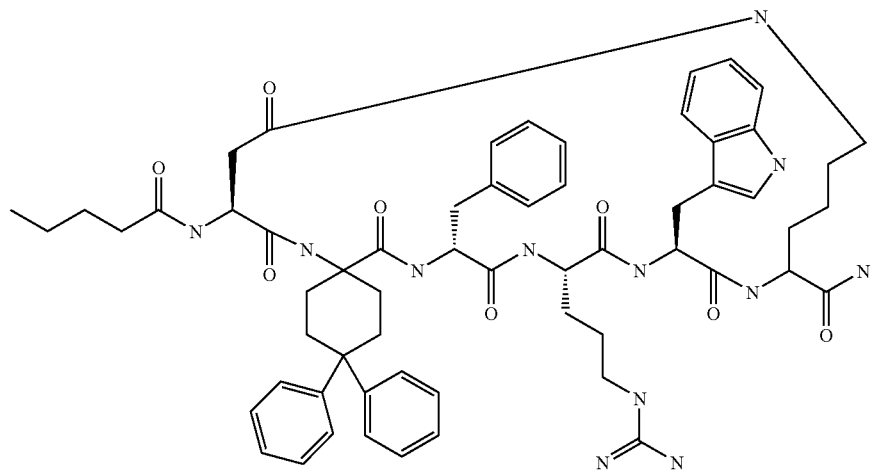

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-Adpc (620 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with $CH_2Cl_2$ (three times) and treated with 2 mL valeric anhydride in 6% DIPEA/$CH_2Cl_2$ for 30 minutes. The resin was filtered and washed successively with 50 ml each of $CH_2Cl_2$ (two times), isopropanol, and $CH_2Cl_2$ (three times). The resin was dried under vacuum to yield 1.1 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of $Et_2O$ and recentrifuged and the crude linear product was dried under vacuum to yield 242 mg of an off-white solid. The crude peptide was subjected to cyclization without purification.

242 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/$H_2O$, buffer B: 0.1% TFA/$CH_3CN$) in 90 min., flow rate 8 ml/min, detection 280 nm. The main peak was cut by analytical HPLC analysis of collected fractions, pooled and lyophilized to yield 48 mg (11%) of a white, amorphous powder. This compound was homogeneous by HPLC. LR-Electrospray: $C_{60}H_{76}N_{12}O_8$ cal: 1093 observed: m/z (1094 M+H).

EXAMPLE 81

Preparation of Penta-cyclo(Asp-Lys)-Asp-Achc-(D)Phe-Arg-Trp-Lys-NH$_2$

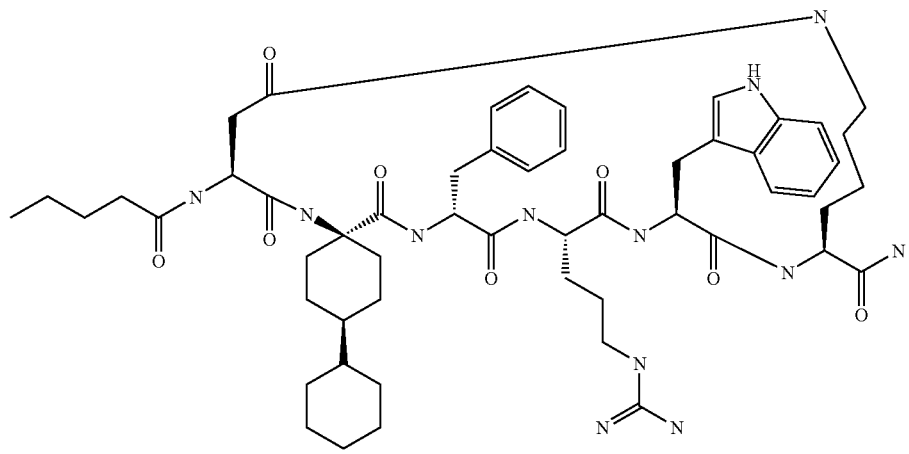

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling ;-═cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-Achc (560 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.1 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 250 mg of an off-white solid. The crude peptide was subjected to cyclization without purification.

250 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 52 mg (13%) of a white, amorphous powder. This compound was homogeneous by HPLC. LR-Electrospray: C$_{54}$H$_{78}$N$_{12}$O$_8$ cal: 1023 observed: m/z (1024 M+H).

EXAMPLE 82

Preparation of Penta-cyclo(Asp-Lys)-Asp-Abc-(D)Phe-Arg-Trp-Lys-NH$_2$

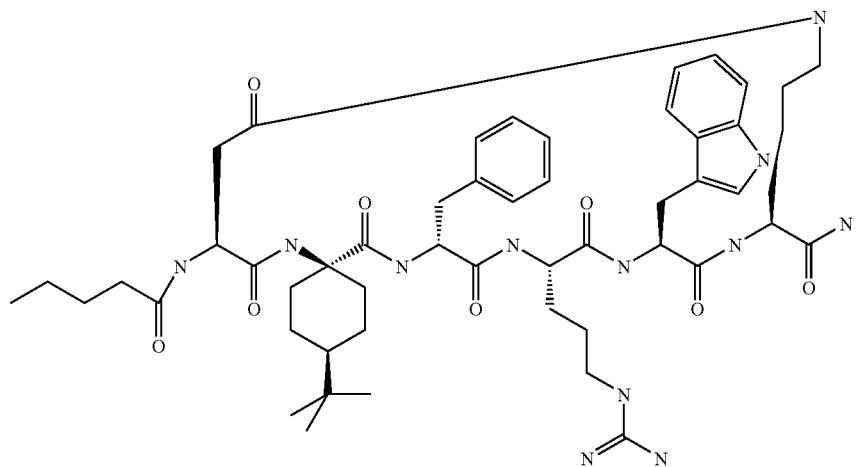

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-Trp (520 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-Abc (530 mg 1.2 mmol) and HBTU (452 mg, 0.6 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 13 g of Pentyl-hexapeptide resin.

The Pentyl-hexapeptide resin was treated with 100 μL ethanedithiol, 100 μL dimethylsulfide, 250 μL anisole, and 10 mL trifluoroacetic acid at room temperature for 180 min. The resin was filtered off, washed with ~2 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 255 mg of an off-white solid. The crude peptide was subjected to cyclization without purification.

255 mg of the crude linear peptides was dissolved in 220 ml of DMF, 500 μL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 58 mg (14%) of a white, amorphous powder. This compound was homogeneous by HPLC. LR-Electrospray C$_{52}$H$_{76}$N$_{12}$O$_8$ cal: 997 observed: m/z (998 M+H).

EXAMPLE 83

Preparation of Penta-cyclo(Asp-Lys)-Asp-Apc-(D) Phe-Arg-(2S,3S) beta methyl-Trp-Lys-NH$_2$

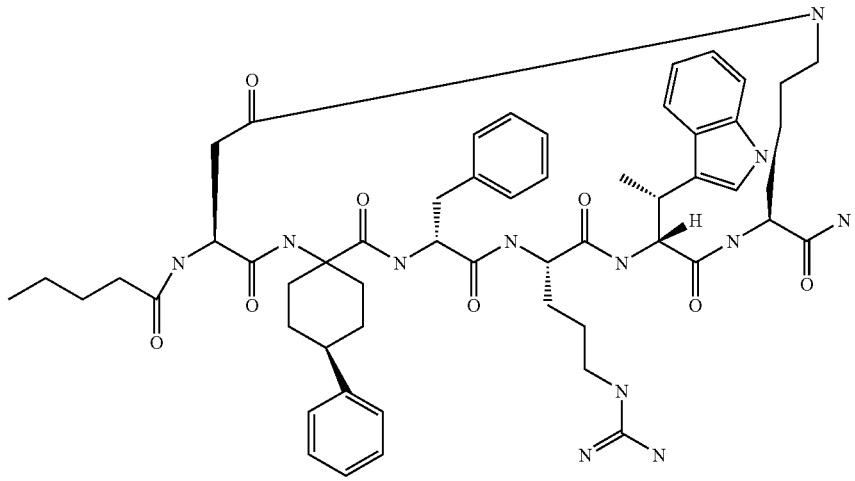

Fmoc-Linker-BHA resin (720 mg, 0.4 mmol) from Example 29 were subjected to solid phase synthesis using Protocol 1 described above. All couplings were performed using HBTU in DMF as the coupling agent and DIPEA (3 equiv.) as base. Six coupling cycles were performed of one cycle each with Fmoc-Lys (Boc) (565 mg, 1.2 mmol) and HBTU (452 mg, 1.2 mmol), Fmoc-(2S,3S) beta methyl (nMes)Trp (616 mg, 1.2 mmol) and HBTU (452 mg, 1.2 mmol), Fmoc-Arg (Pmc) (800 mg, 1.2 mmol) and HBTU (452 mg, 1.2 mmol), Fmoc-(D)Phe (480 mg, 1.2 mmol) and HBTU (452 mg, 1.2 mmol), Fmoc-Apc (550 mg 1.2 mmol) and HBTU (452 mg, 1.2 mmol), Fmoc-Asp (OBut) (500 mg, 1.2 mmol) and HBTU (452 mg, 1.2 mmol). The peptide resin was carried through steps 1–5 of protocol 1, washed with CH$_2$Cl$_2$ (three times) and treated with 2 mL valeric anhydride in 6% DIPEA/CH$_2$Cl$_2$ for 30 minutes. The resin was filtered and washed successively with 50 ml each of CH$_2$Cl$_2$ (two times), isopropanol, and CH$_2$Cl$_2$ (three times). The resin was dried under vacuum to yield 1.0 g of Pentyl-hexapeptide resin.

The Pentyl-hexapeptide resin was treated with 100 µL ethanedithiol, 100 µL dimethylsulfide, 250 µL anisole, and 10 mL HF at 0 C for 60 min. HF was evaporated, and the resin was washed with ethylacetae filtered off, washed with ~5 ml TFA and the filtrates precipitated in chilled ethyl ether. The precipitates were centrifuged and the ether layer decanted. The residue was washed with two or three volumes of Et$_2$O and recentrifuged and the crude linear product was dried under vacuum to yield 180 mg of an off-white solid. The crude peptide was subjected to cyclization without purification.

180 mg of the crude linear peptides was dissolved in 220 ml of DMF, 500 µL of N-methyl morpholine was added to have an apparent pH of 8.0. 280 mg of BOP was added and the cyclization was monitored by HPLC. Typically the cyclization was completed within 18–24 hours. 10 ml of water was added to stop the reaction, DMF was evaporated in vacuum, and the resulting reaction mixture was purified by HPLC.

This crude cyclic material was purified by preparative HPLC on a Vydac C18-column (2.5×20 cm) and eluted with a linear gradient of 20–60% B (buffer A: 0.1% TFA/H$_2$O, buffer B: 0.1% TFA/CH$_3$CN) in 90 min., flow rate 8 ml/min, detection 280 nm. The main peak was cut by analytical HPLC analysis of collected fractions, pooled and lyophilized to yield 40 mg (10%) of a white, amorphous powder. This compound was homogeneous by HPLC. LR-Electrospray C$_{55}$H$_{74}$N$_{12}$O$_8$ cal: 1031 observed: m/z (1032 M+H).

BIOLOGICAL ACTIVITY EXAMPLE

Example A: Agonist Assay

Method

Description: HEK 293 cells transfected with either the MC-4 receptor or MC-1 receptor were grown in 96 well plates. The cells were stimulated with either 100 nM NDP-αMSH or screening compounds. Cyclic AMP was extracted from the cells and concentrations were determined using a Biotrak-cAMP SPA assay. Agonists were identified as those compounds causing an increase in cAMP.

Cell Culture: HEK 293 cells transfected with either the MC-4 receptor or MC-1 receptor were cultured in 75 cm$^2$ flasks in D-MEM supplemented with 10% FCS and 500 µg/ml G418. Cells were trypsinized and split 1:3 into 96 well flat-bottom tissue culture treated plates. Cells were stimulated at confluence (day 2–4).

cAMP Response: Compounds serially diluted in 100% DMSO were further diluted 1:200 (2.5 μl compound dilution +500 μl media) in D-MEM containing 10% FBS and 0.1 mM IBMX. For unstimulated cells, 2.5 μl of DMSO was added to 500 μl of media. For NDP-αMSH stimulated cells, 2.5 μl of 20μM NDP-αMSH in 100% DMSO was added to 500μl of media (final conc. 100 nM). Final concentration of DMSO in all wells was 0.5%.

Note: Each sample was run in duplicate on separate plates.

Culture medium was removed from confluent 96 well culture plates and replaced with 200 μof above dilutions into the appropriate wells. The plates were incubated for 1 hr at RT. The media was removed, and the plates were washed 1× with 200 μl well of PBS. CAMP was extracted by the addition of 60 μl 70% ethanol (stored in the refrigerator). After a 30 min extraction period, 10 μl ethanol extract was transferred to the cAMP assay plate or samples were stored at −20° C. until the cAMP assay was performed.

cAMP Assay: The extracted samples and all reagents included in the kit were brought to room temperature. To a 96 well OptiPlate, 10 μl ethanol extract, 40 μl assay buffer, 50 μl [125I]cAMP, 50 μl antiserum and 50 μl SPA beads were added. The total well volume after addition was 200 μl. The plates were sealed and incubated for 15–20 hr at room temperature. [125I]cAMP binding to the SPA beads was determined by counting each plate for 2 minutes on a Packard TopCount™.

Note: Each plate contained samples of controls for unstimulated cells and NDP-αMSH for stimulated cells.

What is claimed is:

1. A compound of the formula:
wherein

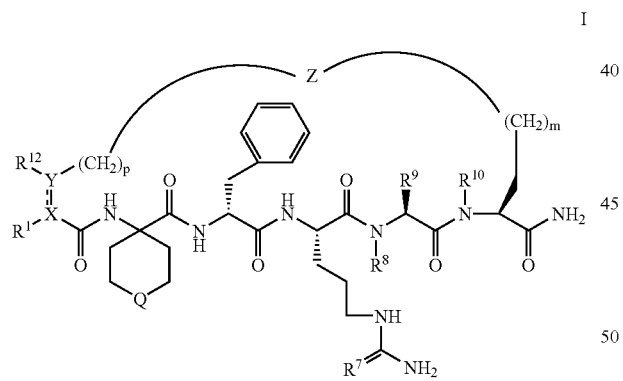

$R^1$ and $R^{12}$ together with X and Y form a phenyl ring and X is C and Y is C, or
$R^1$ is hydrogen,

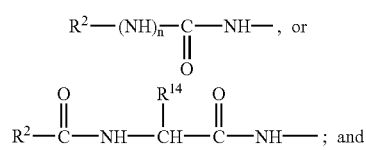

$R^{12}$ is hydrogen, with either X and Y being each C and the bond between X and Y being a double bond, or with X and Y being each CH and the bond between X and Y being a single bond;

$R^2$ is alkyl having from 1 to 5 carbon atoms, alkenyl having from 2 to 5 carbon atoms, or alkynyl having from 2 to 5 carbon atoms;

$R^{14}$ is alkyl having from 1 to 5 carbon atoms;

n is 0 or 1; and

Q is

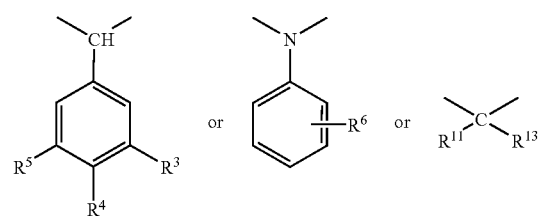

wherein $R^3$, $R^4$ and $R^5$ are independently hydrogen, halo, alkyl having from 1 to 4 carbon atoms, hydroxy or alkoxy having from 1 to 4 carbon atoms, wherein when $R^4$ is not hydrogen, $R^3$ and $R^5$ are both hydrogen; and $R^6$ is hydrogen, alkyl having from 1 to 3 carbon atoms, alkoxy having from 1 to 3 carbon atoms, phenoxy, or halo;

$R^{11}$ and $R^{13}$ are each independently hydrogen, alkyl having 3 or 4 carbons, cycloalkyl having 5 or 6 carbon atoms, or $R^{11}$ and $R^{13}$ are both phenyl;

$R^7$ is O or NH;

$R^8$ is hydrogen or methyl;

$R^9$ is

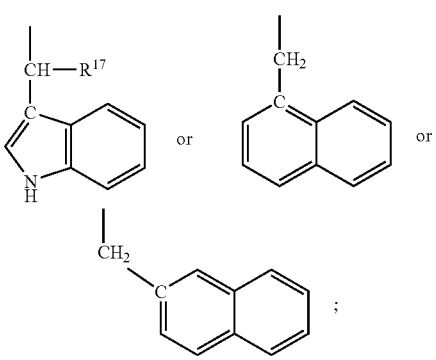

$R^{10}$ is hydrogen or methyl;

p is 0 or 1;

m is 0, 1, 2, or 3; and

Z is

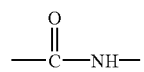

or —S—S—; and $R^{17}$ is hydrogen or lower alkyl.

2. A compound of the formula:

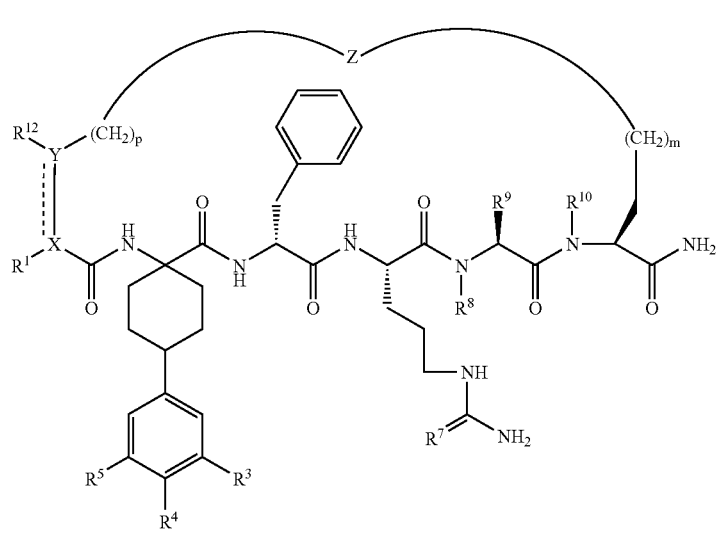

IA wherein
R¹ and R¹² together with X and Y form a phenyl ring and X is C and Y is C, or
R¹ is hydrogen,

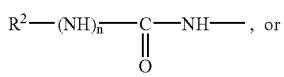, or

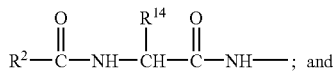; and

R¹² is hydrogen, with either X and Y being each C and the bond between X and Y being a double bond, or with X and Y being each CH and the bond between X and Y being a single bond;
R² is alkyl having from 1 to 5 carbon atoms, alkenyl having from 2 to 5 carbon atoms, or alkynyl having from 2 to 5 carbon atoms;
R¹⁴ is alkyl having from 1 to 5 carbon atoms;
n is 0 or 1;
R³, R⁴ and R⁵ are independently hydrogen, halo, alkyl having from 1 to 4 carbon atoms, hydroxy, or alkoxy having from 1 to 4 carbon atoms; wherein when R⁴ is not hydrogen, R³ and R⁵ are both hydrogen;
R⁷ is O or NH;
R⁸ is hydrogen or methyl;
R⁹ is

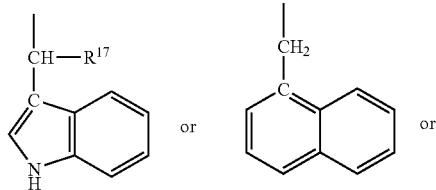

-continued

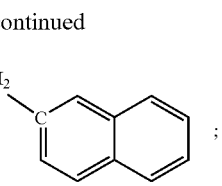;

R¹⁰ is hydrogen or methyl;
p is 0 or 1;
m is 0, 1, 2, or 3; and
Z is

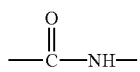

or —S—S—; and

R¹⁷ is hydrogen or lower alkyl.

3. The compound of claim 2, wherein X and Y are each CH and the bond between X and Y is a single bond; Z is

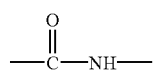

R⁷ is O;
R¹ is

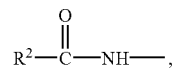,

R² is alkyl; and
R¹⁰ and R¹² are both hydrogen.

4. The compound of claim 3, Penta-cyclo(Asp-Lys)-Asp-Apc-(D)Phe-Cit-Trp-Lys-NH₂.

5. The compound of claim 2, wherein Z is

R⁷ is NH;
R¹ is hydrogen,

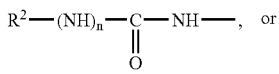, or

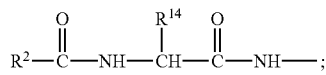;

R² is alkyl; and
R¹⁰ and R¹² are both hydrogen;
R¹⁴ is alkyl having from 1 to 5 carbon atoms: and
n is 0 or 1.

6. The compound of claim 5, wherein X and Y are each CH and the bond between X and Y is a single bond; n is 0; and R⁹ is

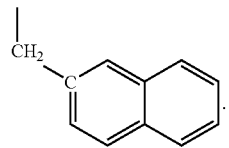

7. The compound of claim 6, Penta-cyclo(Asp-Lys)-Asp-Apc-(D)Phe-Arg-(2)Nal-Lys-NH₂.

8. The compound of claim 6, penta-cyclo(Asp-Lys)-Asp-Apc-(D)Phe-Arg-N-methyl(2)Nal-Lys-NH₂.

9. The compound of claim 5, wherein R⁹ is

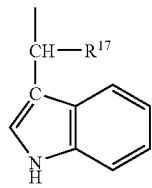

and R¹⁷ is as hydrogen or lower alkyl.

10. The compound of claim 9, wherein X and Y are each CH and the bond between X and Y is a single bond; and one of R³, R⁴ and R⁵ is hydrogen, halo or alkyl and the remainder are hydrogen.

11. The compound of claim 10, Penta-cyclo(Asp-Lys)-Asp-Apc-(D)Phe-Arg-Trp-Lys-NH₂.

12. The compound of claim 10, Penta-cyclo(Asp-Lys)-Asp-4-MeApc-(D)Phe-Arg-Trp-Lys-NH₂.

13. The compound of claim 10, Penta-cyclo(Glu-Lys)-Glu-Apc-(D)Phe-Arg-Trp-Lys-NH₂.

14. The compound of claim 10, Penta-cyclo(Asp-Orn)-Asp-Apc-(D)Phe-Arg-Trp-Orn-NH₂.

15. The compound of claim 10, Penta-cyclo(Asp-Dbr)-Asp-Apc-(D)Phe-Arg-Trp-Dbr-NH₂.

16. The compound of claim 10, Penta-cyclo(Asp-Dpr)-Asp-Apc-(D)Phe-Arg-Trp-Dpr-NH₂.

17. The compound of claim 10, Ac-cyclo(Asp-Dpr)-Asp-Apc-(D)Phe-Arg-Trp-Dpr-NH₂.

18. The compound of claim 9, wherein X and Y are each CH and the bond between X and Y is a single bond; one of R³, R⁴ and R⁵ is alkoxy, and the remainder are hydrogen; and n is 0.

19. The compound of claim 18, Penta-cyclo(Asp-Lys)-Asp-4-MeOApc-(D)Phe-Arg-Trp-Lys-NH₂.

20. The compound of claim 18, Penta-cyclo(Asp-Lys)-Asp-4-EtOApc-(D)Phe-Arg-Trp-Lys-NH₂.

21. The compound of claim 18, Penta-cyclo(Asp-Lys)-Asp-4-iPrOApc-(D)Phe-Arg-Trp-Lys-NH₂.

22. The compound of claim 18, Penta-cyclo(Asp-Lys)-Asp-3-MeOApc-(D)Phe-Arg-Trp-Lys-NH₂.

23. The compound of claim 9, Penta-cyclo(Asp-Lys)-Asp-4-OHApc-(D)Phe-Arg-Trp-Lys-NH₂.

24. The compound of claim 9, Penta-cyclo(Asp-Lys)-Asp-4-ClApc-(D)Phe-Arg-Trp-Lys-NH₂.

25. The compound of claim 9, wherein each of R¹, R³, R⁴, R⁵, R⁸ and R¹⁰ is hydrogen;

R⁷ is NH;
R⁹ is

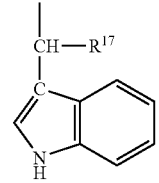

p is 0; and R¹⁷ is hydrogen or a lower alkyl.

26. The compound of claim 25, Cyclo(succinic acid-Lys)-succinic acid-Apc-(D)Phe-Arg-Trp-Lys-NH₂.

27. The compound of claim 25, Cyclo(maleic acid-Lys)-maleic acid-Apc-(D)Phe-Arg-Trp-Lys-NH₂.

28. The compound of claim 25, Cyclo(succinic acid-Dpr)-succinic acid-Apc-(D)Phe-Arg-Trp-Dpr-NH₂.

29. The compound of claim 25, Cyclo(maleic acid-Dpr)-maleic acid-Apc-(D)Phe-Arg-Trp-Dpr-NH₂.

30. The compound of claim 2, wherein R¹ and R¹² together with X and Y form a phenyl ring.

31. The compound of claim 30, Cyclo(phthalic acid-Lys)-phthalic acid-Apc-(D)Phe-Arg-Trp-Lys-NH₂.

32. The compound of claim 30, Cyclo(phthalic acid-Dpr)-phthalic acid-Apc-(D)Phe-Arg-Trp-Dpr-NH₂.

33. The compound of claim 2, Ac-Nle-cyclo(Cys-Cys)-Cys-Apc-(D)Phe-Arg-Trp-Cys-NH₂.

34. A compound of the formula:

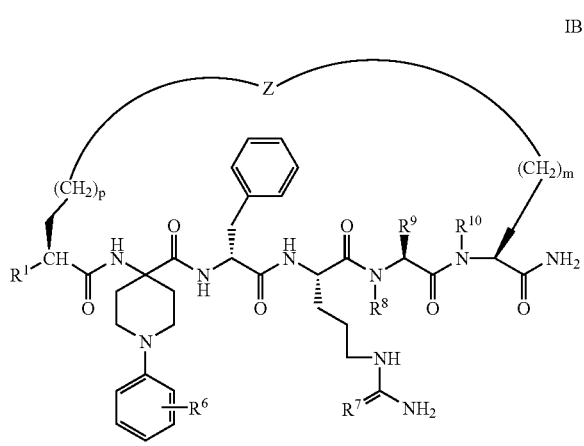

wherein $R^1$ is hydrogen,

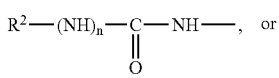, or

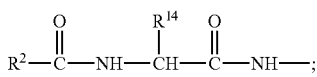;

$R^2$ is alkyl having from 1 to 5 carbon atoms, alkenyl having from 2 to 5 carbon atoms, or alkynyl having from 2 to 5 carbon atoms;

$R^{14}$ is alkyl having from 1 to 5 carbon atoms;

n is 0 or 1;

$R^6$ is hydrogen, alkyl having from 1 to 3 carbons, alkoxy having from 1 to 3 carbons, phenoxy, or halo;

$R^7$ is O or NH;

$R^8$ is hydrogen or methyl;

$R^9$ is

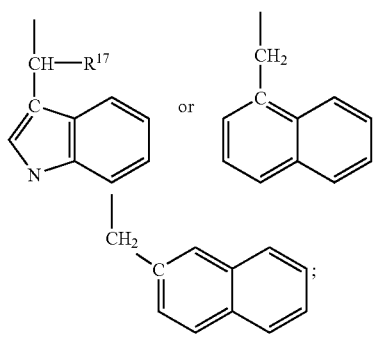

$R^{10}$ is hydrogen or methyl;

p is 0 or 1;

m is 0, 1, 2, or 3; and

Z is

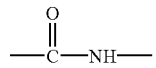

or —S—S—;

and $R^{17}$ is hydrogen or lower alkyl.

35. The compound of claim 34, wherein Z is

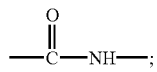;

$R^7$ is NH;

$R^1$ is

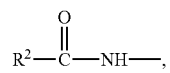, $R^2$ is alkyl;

$R^8$ and $R^{10}$ are each hydrogen; and $R^9$ is

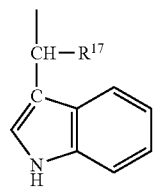

and $R^{17}$ is as above.

36. The compound of claim 35, wherein $R^6$ is hydrogen or alkyl.

37. The compound of claim 36, Penta-cyclo(Asp-Lys)-Asp-Appc-(D)Phe-Arg-Trp-Lys-$NH_2$.

38. The compound of claim 36, Penta-cyclo(Asp-Lys)-Asp-2-MeAppc-(D)Phe-Arg-Trp-Lys-$NH_2$.

39. The compound of claim 36, Penta-cyclo(Asp-Lys)-Asp-2-iPrAppc-(D)Phe-Arg-Trp-Lys-$NH_2$.

40. The compound of claim 36, Penta-cyclo(Asp-Lys)-Asp-3-MeAppc-(D)Phe-Arg-Trp-Lys-$NH_2$.

41. The compound of claim 36, Penta-cyclo(Asp-Lys)-Asp-4-MeAppc-(D)Phe-Arg-Trp-Lys-$NH_2$.

42. The compound of claim 35, wherein $R^6$ is halo.

43. The compound of claim 42, Penta-cyclo(Asp-Lys)-Asp-4-ClAppc-(D)Phe-Arg-Trp-Lys-$NH_2$.

44. The compound of claim 35, wherein $R^6$ is alkoxy or phenoxy.

45. The compound of claim 44, Penta-cyclo(Asp-Lys)-Asp-4-PhOAppc-(D)Phe-Arg-Trp-Lys-$NH_2$.

46. The compound of claim 44, Penta-cyclo (Asp-Lys)-Asp-3-MeO-Appc-(D)Phe-Arg-Trp-Lys-$NH_2$.

47. A compound of the formula:

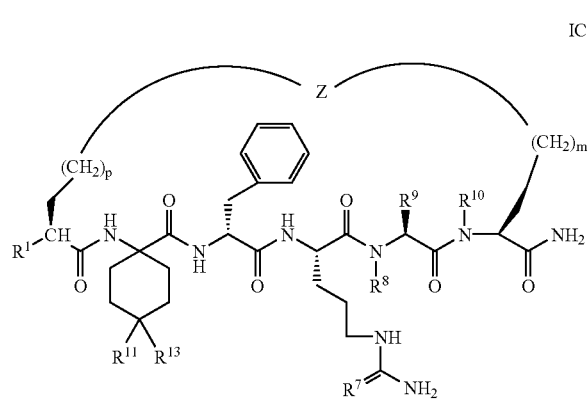

wherein
R¹ is hydrogen,

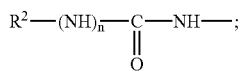

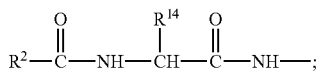

R² is alkyl having from 1 to 5 carbon atoms, alkenyl having from 2 to 5 carbon atoms, or alkynyl having from 2 to 5 carbon atoms;

R¹⁴ is alkyl having from 1 to 5 carbon atoms;

n is 0 or 1;

R¹¹ and R¹³ are each independently hydrogen, alkyl having 3 or 4 carbon atoms, or cycloalkyl having 5 or 6 carbon atoms or R¹¹ and R¹³ are both phenyl;

R⁷ is O or NH;

R⁸ is hydrogen or methyl;

R⁹ is

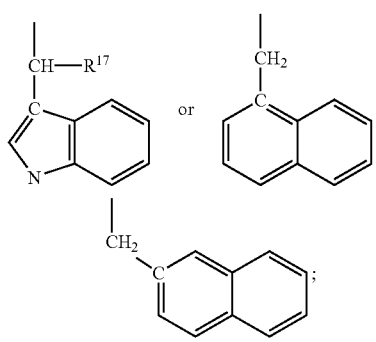

R¹⁰ is hydrogen or methyl;

p is 0 or 1;

m is 0, 1, 2, or 3; and

Z is

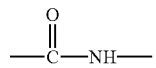

or —S—S—;

R¹⁷ is hydrogen or lower alkyl.

48. The compound of claim 47, wherein Z is

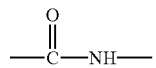

R⁷ is NH;

R¹ is

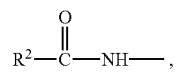

R² is alkyl;

R⁸ and R¹⁰ are each hydrogen; and

R⁹ is

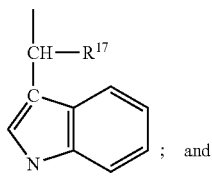; and

R¹⁷ is hydrogen or lower alkyl.

49. The compound of claim 48, wherein one of R¹¹ and R¹³ is alkyl or cycloalkyl and the other is hydrogen.

50. The compound of claim 49, penta-cyclo(Asp-Lys)-Asp-Achc-(D)Phe-Arg-Trp-Lys-NH₂.

51. The compound of claim 49, penta-cyclo(Asp-Lys)-Asp-Abc-(D) Phe-Arg-Trp-Lys-NH₂.

52. The compound of claim 48, wherein R¹¹ and R¹³ are phenyl.

53. The compound of claim 52, penta-cyclo(Asp-Lys)-Asp-4-Adpc-(D)Phe-Arg-Trp-Lys-NH₂.

54. A compound of the formula:

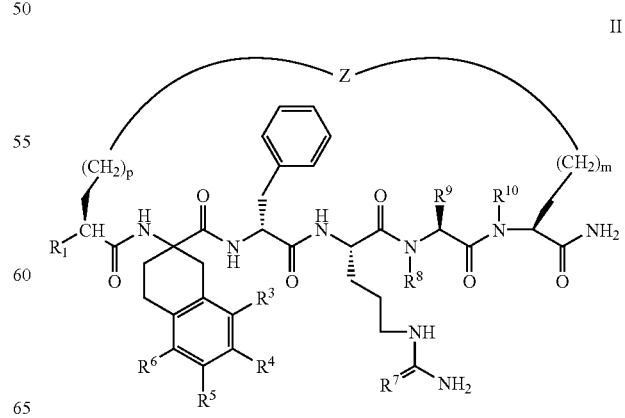

wherein
R¹ is hydrogen,

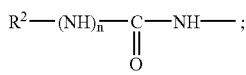

or

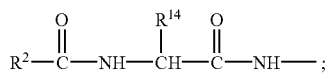

R² is alkyl having from 1 to 5 carbon atoms, alkenyl having from 2 to 5 carbon atoms, or alkynyl having from 2 to 5 carbon atoms;
R¹⁴ is alkyl having from 1 to 5 carbon atoms;
n is 0 or 1;
one of R³, R⁴, R⁵ and R⁶ is hydrogen, halo, alkyl having from 1 to 3 carbon atoms, or alkoxy having from 1 to 3 carbon atoms, and the remainder are hydrogen;
R⁷ is O or NH;
R⁸ is hydrogen or methyl;
R⁹ is

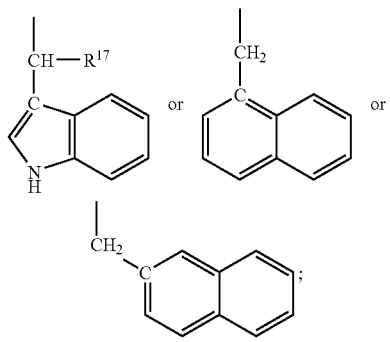

R¹⁰ is hydrogen or methyl;
p is 0 or 1;
m is 0, 1, 2, or 3; and
Z is

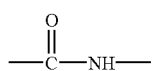

or —S—S—; and
R¹⁷ is hydrogen or lower alkyl.
55. The compound of claim 54, wherein Z is

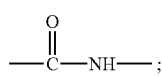

R¹ is

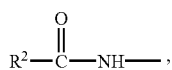

R² is alkyl;
R³, R⁴, R⁵, R⁸ and R¹⁰ are each hydrogen;

R⁶ is hydrogen, halo, alkyl having from 1 to 3 carbon atoms, or alkoxy having from 1 to 3 carbon atoms; and
R⁹ is

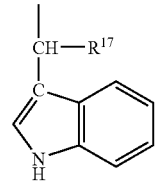

and R¹⁷ is hydrogen or lower alkyl.
56. The compound of claim 55, wherein R⁷ is NH.
57. The compound of claim 56, wherein R⁶ is hydrogen or alkyl.
58. The compound of claim 57, penta-cyclo(Asp-Lys)-Asp-(D,L)-Atc-(D)Phe-Arg-Trp-Lys-NH₂.
59. The compound of claim 57, penta-cyclo(Asp-Lys)-Asp-5-Me-(D,L)Atc-(D)Phe-Arg-Trp-Lys-NH₂.
60. The compound of claim 57, penta-cyclo(Asp-Lys)-Asp-5-Et-(D,L)Atc-(D)Phe-Arg-Trp-Lys-NH₂.
61. The compound of claim 57, penta-cyclo(Asp-Lys)-Asp-5-iPr-(D,L)Atc-(D)Phe-Arg-Trp-Lys-NH₂.
62. The compound of claim 52, wherein R⁶ is halo.
63. The compound of claim 62, penta-cyclo(Asp-Lys)-Asp-5-BrAtc-(D)Phe-Arg-Trp-Lys-NH₂.
64. The compound of claim 62, penta-cyclo(Asp-Lys)-Asp-5-ClAtc-(D)Phe-Arg-Trp-Lys-NH₂.
65. The compound of claim 52, wherein R⁶ is alkoxy.
66. The compound of claim 65, penta-cyclo(Asp-Lys)-Asp-5-MeO-(D,L)Atc-(D)Phe-Arg-Trp-Lys-NH₂.
67. The compound of claim 65, penta-cyclo(Asp-Lys)-Asp-5-EtO-(D,L)Atc-(D)Phe-Arg-Trp-Lys-NH₂.
68. The compound of claim 65, penta-cyclo(Asp-Lys)-Asp-5-iPrO-(D,L)Atc-(D)Phe-Arg-Trp-Lys-NH₂.
69. The compound of claim 56, wherein R⁷ is O and R⁶ is halo.
70. The compound of claim 69, penta-cyclo(Asp-Lys)-Asp-5-BrAtc-(D)Phe-Cit-Trp-Lys-NH₂.
71. The compound of claim 69, penta-cyclo(Asp-Lys)-Asp-5-GlAtc-(D)Phe-Cit-Trp-Lys-NH₂.
72. The compound of claim 54, wherein Z is —S—S—;
R¹ is

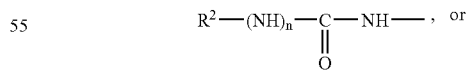

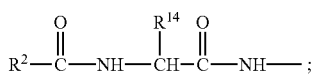

R³, R⁴, R⁵, R⁸ and R¹⁰ are hydrogen;
R⁶ is hydrogen or halo;
R⁷ is NH;

$R^9$ is
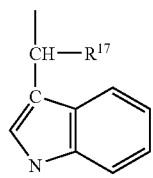
wherein $R^{17}$ is hydrogen or lower alkyl.
73. The compound of claim 72, Ac-Nle-cyclo(Cys-Cys)-Cys-(D,L)Atc-(D)Phe-Arg-Trp-Cys-NH$_2$.
74. The compound of claim 72, penta-cyclo(Cys-Cys)-Cys-5-Br(D,L)Atc-(D)Phe-Arg-Trp-Cys-NH$_2$.
75. A compound, penta-cyclo(Asp-Lys)-Asp-Apc-(D)Phe-Ala-Trp-Lys-NH$_2$.
76. A compound, Penta-cyclo(Asp-Lys)-Asp-Apc-(D)Phe-Arg-(2S,3 S) beta methyl-Trp-Lys-NH$_2$.
* * * * *

UNITED STATES PATENT AND TRADEMARK OFFICE
CERTIFICATE OF CORRECTION

PATENT NO.       : 7,045,591 B2
APPLICATION NO.  : 09/939966
DATED            : May 16, 2006
INVENTOR(S)      : Li Chen et al.

It is certified that error appears in the above-identified patent and that said Letters Patent is hereby corrected as shown below:

Col. 265, Line 55

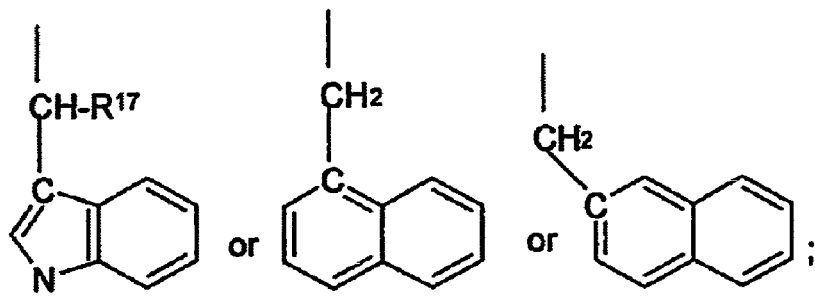

should be:

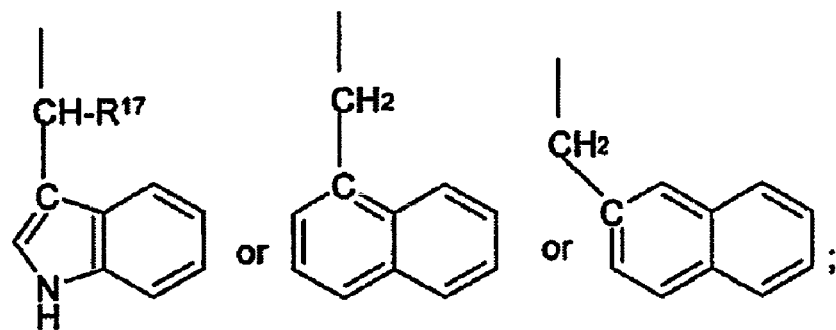

UNITED STATES PATENT AND TRADEMARK OFFICE
CERTIFICATE OF CORRECTION

PATENT NO.       : 7,045,591 B2                                              Page 2 of 2
APPLICATION NO.  : 09/939966
DATED            : May 16, 2006
INVENTOR(S)      : Li Chen et al.

It is certified that error appears in the above-identified patent and that said Letters Patent is hereby corrected as shown below:

Col. 267, Line 25

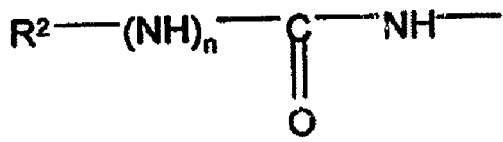

should be

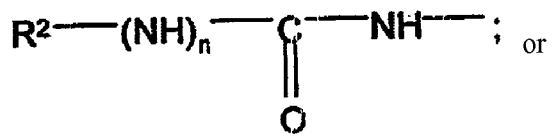 ; or

Col. 270, Line 50

71.     "...Asp-5-GIAtc-(D)Phe-Cit-Trp-Lys-NH$_2$.

Should be

71.     "...Asp-5-ClAtc-(D)Phe-Cit-Trp-Lys-NH$_2$.

Signed and Sealed this

Twenty-eighth Day of November, 2006

JON W. DUDAS
*Director of the United States Patent and Trademark Office*